US011591610B2

United States Patent
(12) United States Patent
Suzuki et al.

(10) Patent No.: US 11,591,610 B2
(45) Date of Patent: Feb. 28, 2023

(54) TOBACCO PLANT AND PRODUCTION METHOD THEREOF

(71) Applicant: JAPAN TOBACCO INC., Tokyo (JP)

(72) Inventors: Shoichi Suzuki, Tokyo (JP); Kaori Hamano, Tokyo (JP); Ayako Nomura, Tokyo (JP); Mai Tsukahara, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/569,326

(22) Filed: Sep. 12, 2019

(65) Prior Publication Data

US 2020/0002708 A1 Jan. 2, 2020

Related U.S. Application Data

(63) Continuation of application No. PCT/JP2017/032870, filed on Sep. 12, 2017.

(30) Foreign Application Priority Data

Mar. 16, 2017 (JP) ............................ JP2017-051974

(51) Int. Cl.

| | |
|---|---|
| ***C12N 15/82*** | (2006.01) |
| ***C12Q 1/6895*** | (2018.01) |
| ***C12N 15/113*** | (2010.01) |

(52) U.S. Cl.

CPC .......... *C12N 15/827* (2013.01); *C12N 15/113* (2013.01); *C12Q 1/6895* (2013.01); *C12Q 2600/13* (2013.01); *C12Q 2600/156* (2013.01)

(58) Field of Classification Search

None

See application file for complete search history.

(56) References Cited

U.S. PATENT DOCUMENTS

2009/0249518 A1 10/2009 Thomas et al.
2012/0017337 A1 1/2012 Trillo et al.

FOREIGN PATENT DOCUMENTS

CN 102823449 A 12/2012
WO WO 2010/081917 A1 7/2010
WO WO 2016/057515 A2 4/2016

OTHER PUBLICATIONS

Sequence Accession BCP72428, Jun. 2, 2016, attached to the office action (Year: 2016).*
"Nicotiana tabacum cultivar SR1 homeobox-leucine zipper protein revoulta (REV) mRNA, complete cds", Acc. JQ686937, 2014, Genbank.
Aida et al., "Genes Involved in Organ Separation in *Arabidopsis:* An Analysis of the cup-shaped cotyledon Mutant", The Plant Cell, Jun. 1997, vol. 9, pp. 841-857.
Allowance for JP 2018-505498 dated Jul. 24, 2018.
Busch et al., "Shoot branching and leaf dissection in tomato are regulated by homologous gene modules", The Plant Cell, Oct. 2011, vol. 23, pp. 3595-3609.
Database GenPept, [online], Accession No. XP_009800575, Oct. 21, 2014, <https://www.ncbi.nlm.nih.gov/protein/XP_009800575.1>.
English Translation of International Preliminary Report on Patentability for PCT/JP2017/013115 dated Oct. 2, 2018.
Greb et al., "Molecular analysis of the Lateral Suppressor gene in *Arabidopsis* reveals a conserved control mechanism for axillary meristem formation", Genes & Development, 2003, vol. 17, pp. 1175-1187.
Hibara et al., "*Arabidopsis* Cup-Shaped Cotyledon3 regulates postembryonic shoot meristem and organ boundary formation", The Plant Cell, Nov. 2006, Vo. 18, pp. 2946-2957.
Huh et al., "Inhibition of Chrysanthemum Axillary Buds via Transformation with the Antisense Tomato Lateral Suppressor Gene is Season Dependent", Horticulture, Environment and Biotechnology, Jun. 2013, vol. 54, No. 3, pp. 280-287.
International Search Report for PCT/JP2017/013115 dated Jul. 4, 2017.
International Search Report for PCT/JP2017/032870 dated Dec. 19, 2017.
Tajima et al., "Construction of Mutant Panel in Nicotiana tabacum L", Japanese Journal of Phytopathology, Aug. 2011, vol. 77, No. 3, total 2 pages.
Jeifetz et al., "CaBLIND regulates axillary meristem initiation and transition to flowering in pepper", Planta, 2011, vol. 234, pp. 1227-1236.
Keller et al., "Arabidopsis Regulator of Axillary Meristems1 controls of leaf axil stem cell niche and modulates vegetative development", The Plant Cell, Mar. 2006, vol. 18, pp. 598-611.
Li et al., "Multiplex and homologous recombination-mediated genome editing in *Arabidopsis* and Nicotiana benthamiana using guide RNA and Cas9", Nature Biotechnology, Aug. 2013, vol. 31, No. 8, pp. 688-691.
Li et al., "Control of tillering in rice", Nature, Apr. 10, 2003, vol. 422, pp. 618-621.
Mapelli et al., "A comparative auxin and cytokinin study in normal and to-2 mutant tomato plants", Plant and Cell Physiology, Jul. 1982, vol. 23, No. 5, pp. 751-757.
Marshallsay et al., "Amplification of plant U3 and U6 snRNA gene sequences using primers specific for an upstream promoter element and conserved intragenic regions", Nucleic Acids Research, 1990, vol. 18, No. 12, pp. 3459-3466.
Muller et al., "Blind Homologous R2R3 Myb Genes Control the Pattern of Lateral Meristem Initiation in Arabidopsis", The Plant Cell, Mar. 2006, vol. 18, pp. 586-597, total 20 pages.

(Continued)

*Primary Examiner* — Elizabeth F McElwain
(74) *Attorney, Agent, or Firm* — Birch, Stewart, Kolasch & Birch, LLP

(57) ABSTRACT

Provided are (i) a tobacco plant which is suitable for cultivation for harvesting leaf tobaccos, (ii) a method of obtaining the tobacco plant, (iii) a harvest from the tobacco plant, and (iv) a processed product of the harvest. The present invention encompasses (i) a tobacco plant into which a mutation for suppressing the development of primary axillary buds is introduced, (ii) a method of obtaining the tobacco plant, (iii) a harvest from the tobacco plant, and (iv) a processed product of the harvest.

21 Claims, 6 Drawing Sheets

Specification includes a Sequence Listing.

(56) References Cited

OTHER PUBLICATIONS

Office Action for U.S. Appl. No. 16/144,479 dated Apr. 30, 2019.
Office Action for U.S. Appl. No. 16/144,479 dated Aug. 7, 2019.
Office Action for JP 2018-505498 dated Jun. 12, 2018.
Office Action for JP 2018-505498 dated Mar. 20, 2018.
Office Action for JP 2018-505498 dated May 15, 2018.
Otsuga et al., "Revoluta regulates meristem initiation at lateral positions", The Plant Journal, 2001, vol. 25, No. 2, pp. 223-236.
Raman et al., "Interplay of miR164, Cup-Shaped Cotyledon genes and Lateralsuppressor controls axillary meristem formation in *Arabidopsis thaliana*", The Plant Journal, 2008, vol. 55, pp. 65-76.
Reddy et al., "Development of Tilling by sequencing platform towards enhanced leaf yield in tobacco", Industrial Crops and Products, Nov. 2012, vol. 40, pp. 324-335.
Schmitz et al., "The tomato Blind gene encodes a MYB transcription factor that controls the formation of lateral meristems", Proc. Natl. Acad. Sci. USA, Jan. 22, 2002, vol. 99, No. 2, pp. 1064-1069.
Schumacher et al., "The Lateral suppressor (Ls) gene of tomato encodes a new member of the VHIID protein family", Proc. Natl. Acad. Sci. USA, Jan. 1999, vol. 96, pp. 290-295.
Sun et al., "Inhibition of tobacco axillary bud differentiation by silencing Cup-Shaped Cotyledon 3", African Journal of Biotechnology, Feb. 23, 2012, vol. 11, No. 16, pp. 3919-3927.
Takada et al., "The Cup-Shaped COTYLEDON1 gene of Arabidopsis regulates shoot apical meristem formation", Development, 2001, vol. 128, pp. 1127-1135.
Takahashi et al., "A method for obtaining high quality RNA from paraffin sections of plant tissues by laser microdissection", J Plant Res, 2010, vol. 123, pp. 807-813.
Talbert et al., "The Revoluta gene is necessary for apical meristem development and for limiting cell divisions in the leaves and stems of *Arabidopsis thaliana*", Development, 1995, vol. 121, pp. 2723-2735.
UniProt, [online], Accession No. B5M4A5, <http://www.uniprot.org/uniprot/B5M4A5.txt?version=15>, Feb. 17, 2016 uploaded, [retrieved on Jun. 16, 2017].
UniProt, [online], Accession No. V9LXH8, <http://www.uniprot.org/uniprot/V9LXH8.txt?version=11>, Mar. 16, 2016 uploaded, [retrieved on Jun. 16, 2017].
Vroemen et al., "The Cup-Shaped Cotyledon3 gene is required for Boundary and Shoot Meristem Formation in Arabidopsis", The Plant Cell, Jul. 2003, vol. 15, No. 7, pp. 1563-1577.
Waibel et al., "U6 snRNAgenes of *Arabidopsis* are transcribed by RNA polymerase III but contain the same two upstream promoter elements as RNA polymerase II-transcribed U-snRNAgenes", Nucleic Acids Research, 1990, vol. 18, No. 12, pp. 3451-3458.
Wang et al., "Construction of RNAi Vector of NtLS Gene and its Transformation in Tobacco", Chinese Tobacco Science, 2011, vol. 32, No. 4, pp. 31-35, total 6 pages.
Written Opinion of the International Searching Authority for PCT/JP2017/032870 (PCT/ISA/237) dated Dec. 19, 2017.
Yang et al., "The bHLH protein ROX acts in concert with RAX1 and LAS to modulate axillary meristem formation in *Arabidopsis*", The Plant Journal, 2012, vol. 71, pp. 61-70.
Zhong et al., "Disruption of interfascicular fiber differentiation in an *Arabidopsis* mutant", The Plant Cell, Dec. 1997, vol. 9, pp. 2159-2170.
Zhong et al., "IFL1, a gene regulating interfascicular fiber differentiation in *Arabidopsis*, encodes a homeodomain-leucine zipper protein", The Plant Cell, Nov. 1999, vol. 11, pp. 2139-2152.
Extended European Search Report dated Sep. 18, 2019, in European Patent Application No. 17775330.8.
Yang, M. and Y. Jiao, "Regulation of Axillary Meristem Initiation by Transcription Factors and Plant Hormones," Frontiers in Plant Science (Feb. 18, 2016), vol. 7; No. 18, pp. 1-5.
Office Action dated Jan. 28, 2021, in Indian Patent Application No. 201847040146.

* cited by examiner

TOBACCO PLANT AND PRODUCTION METHOD THEREOF

CROSS-REFERENCE TO RELATED APPLICATIONS

This application is a Continuation of PCT International Application No. PCT/JP2017/032870 filed in Japan on Sep. 12, 2017, which claims the benefit of Patent Applications No. 2017-051974 filed in Japan on Mar. 16, 2017, the entire contents of which are hereby incorporated by reference.

TECHNICAL FIELD

The present invention relates to (i) a tobacco plant which is suitable for cultivation for harvesting leaf tobaccos, (ii) a method of obtaining the tobacco plant, (iii) a harvest from the tobacco plant, and (iv) a processed product of the harvest.

BACKGROUND ART

In the process of the growth of seed plants, embryos in seeds develop so as to form cotyledons and apical meristems (shoot apical meristems). Cell division of the apical meristem (shoot apical meristem) causes leaf primordia to be sequentially formed, and causes axillary meristems to be formed on an adaxial side of the leaf primordia. The axillary meristems then serve as apical meristems (shoot apical meristems) and result in axillary buds. During vegetative growth of a plant, usually, the development of axillary buds is temporarily in a dormant state (suppressed). In a case where apical meristems (shoot apical meristems) of a primary shoot is transitioned from a vegetative growth state to a reproductive growth state, or in a case where the apical meristems (shoot apical meristems) die, the development of the axillary buds is no longer in a dormant state and is promoted. With respect to the development of axillary buds, there are a plurality of research reports on solanaceous plants (e.g., tomatoes and tobaccos) and on other plants (e.g., rice and *Arabidopsis thaliana*).

A tobacco plant, which is cultivated for harvesting leaves, is subjected to topping (cutting off a stem of an apical portion with a flower) during cultivation, for the purpose of enhancing the quality and quantity of leaves to be harvested (e.g., for the purpose of accumulating composition of the leaves and maturing and expanding leaves). Topping causes axillary buds of the tobacco plant to start vigorously developing from, bases of leaves (leaf axil). The development of axillary buds naturally consumes nutrients, and therefore causes a relative decrease in nutrient which are supplied to leaves to be harvested. Therefore, the development and outgrowth of axillary buds leads to a decrease in quality and yield of leaves to be harvested. Therefore, in cultivating a tobacco plant for harvesting tobacco leaves, axillary buds are subjected to, for example, control such as removal or developmental suppression.

Examples of a method of removing an axillary bud encompass a method in which an axillary bud is picked by hand or by machine. Picking an axillary bud by hand involves (i) a large amount of work (and accordingly an increase in labor costs) and (ii) a problem of low efficiency. Picking an axillary bud by machine is less accurate than picking by hand, and therefore brings a problem of damaging a plant. Examples of a method of suppressing the development of an axillary bud encompass a method in which an agrochemical is used. The use of agrochemicals involves problems such as repeated application for maintaining an effect, an impact on the growth of a plant, an impact on leaves to be harvested due to agrochemicals residue, and an increase in inspection cost for agrochemicals residue.

Patent Literatures 1, 2, and 3 and Non-Patent Literatures 1 through 13 disclose matters in regard to development of axillary buds. Patent Literatures 1 through 3 disclose techniques for suppressing the development of axillary buds.

With reference to Non-Patent Literatures 1 through 13, genes involved in the formation of axillary meristem will be described below.

A plurality of genes from plants other than tobacco plants have been reported as genes involved in the formation of axillary meristem. Representative examples of such a gene encompass LATERAL SUPPLESSOR (LS), Blind (B1), and REVOLUTA (REV).

It has been reported that LS is isolated from *Arabidopsis thaliana* (Non-Patent Literature 1), tomato (Non-Patent Literature 2), and rice (Non-Patent Literature 3), and is a gene necessary for the formation of an axillary meristem. In a mutant of LS gene of *Arabidopsis thaliana*, while axillary buds of cauline leaves were normal, axillary buds of rosette leaves other than two topmost rosette leaves were hardly observed (Non-Patent Literature 1). In a mutant of LS gene of a tomato, while axillary buds during a vegetative stage were not present, axillary buds were formed at two topmost parts during a reproductive stage (Non-Patent Literature 2). In a mutant of LS gene of rice (moc1), no tillers, which are equivalent to axillary buds of rice, were observed at all during both a tillering stage and a heading stage (Non-Patent Literature 3). Regarding tobaccos, the cDNA sequence predicted as an LS orthologue gene is published (Accession number: EU0935581.1, and Patent Literature 3). However, the function of the gene having the cDNA sequence is unknown. It has been reported that in the case of tobacco in which the function of the gene is deleted by a genome editing technique, axillary buds after decapitation are formed as in the case of wild-type plants (CORESTA Congress 2016 IG02 High efficiency precision editing of the tobacco genome DEWEY R. E.; MATSUBAY.; SMITH W. A. North Carolina State University, Dept. of Crop Science, Raleigh, N.C., U.S.A.).

B1 gene is isolated from *Arabidopsis thaliana* (Non-Patent Literatures 4 and 5) and tomato (Non-Patent Literature 6). In tomatoes, even in a case where topping had been performed, axillary buds were hardly formed regardless of leaf position, due to a mutant of one gene (Non-Patent Literatures 6 and 7). Regarding *Arabidopsis thaliana*, at least three genes which are redundant and B1 orthologue (REGULATOR OF AXILLARY MERISTEM (RAX) 1, 2, and 3) have been reported. While RAX1 single mutant showed suppression of axillary buds, in RAX1, 2, 3 triple mutants, axillary buds of rosette leaves were hardly formed and those of cauline leaves were largely reduced (Non-Patent Literatures 4 and 5). In the RAX1 single mutants, even after topping, the outgrowth of axillary buds from bottom rosette leaves where no formation of axillary buds was observed before topping was not observed. Based on homology comparison between (i) the putative amino acid sequences predicted from the RAX gene sequence of *Arabidopsis thaliana* and (ii) the putative amino acid sequence predicted from genome sequences of grape and tomato, it was predicted that tomato orthologous genes of RAX1 of *Arabidopsis thaliana* include C gene other than B1. However, the C gene was not relevant to the formation of axillary buds, but was relevant to morphogenesis of leaves (Non- Patent Literature 8). Although Patent Literature 3 discloses a cDNA sequence which is believed to be orthologous genes of tobacco of RAX1, Patent Literature 3 does not disclose analysis of function of the orthologous genes in a tobacco plant.

REV gene was isolated from *Arabidopsis thaliana* (Non-Patent Literatures 10 and 11). In a mutant of REV, the formation of axillary buds was decreased at both rosette leaves and cauline leaves, and promotion of the formation of an axillary meristem by decapitation was not observed (Non-Patent Literatures 9, 10, and 12). Although there has not been any report on a cDNA sequence of REV orthologous gene in tobaccos, putative amino acid sequence predicted from an EST sequence identical by 79% on an amino acid level to *Arabidopsis thaliana* REV has been published (Accession number: FG135778.1). In addition, a full-length cDNA sequence predicted as REV orthologous gene in a tobacco (variety: SR-1) has been published (Accession number: JQ686937). However, there has not been any report on the function of these genes, in a tobacco, which is highly homologous to the REV.

There have been reports below concerning the enhancement of the effect of the combinations of mutations in a plurality of genes, on reduction of axillary buds. In double mutants of *Arabidopsis thaliana*, which have mutations in RAX1 and LS, axillary buds of rosette leaves and cauline leaves were further reduced in comparison with the single mutants of RAX1 or LS (Non-Patent Literatures 5 and 13). In double mutants of tomato, which have mutations in B1 and LS, the above-described effects were additively enhanced in comparison with the single mutants of B1 or LS (Non-Patent Literature 6). In two double mutants of *Arabidopsis thaliana* ((i) RAX1 and ROX and (ii) LS and ROX), axillary buds of rosette leaves and cauline leaves were further reduced in comparison with the single mutant of each gene (Non-Patent Literature 13).

CITATION LIST

Patent Literature

[Patent Literature 1]
US Patent Application Publication No. 2009/0249518 (Publication Date: Oct. 1, 2009)
[Patent Literature 2]
Pamphlet of International Publication No. WO 2010/081917 (Publication Date: Jul. 22, 2010)
[Patent Literature 3]
Pamphlet of International Publication No. WO 2016/057515 (Publication Date: Apr. 14, 2016)

Non-Patent Literature

[Non-patent Literature 1]
Greb T, Clarenz O, Schafer E, Muller D, Herrero R, Schmitz G, Theres K (2003) Molecular analysis of the LATERAL SUPPRESSOR gene in *Arabidopsis* reveals a conserved control mechanism for axillary meristem formation. Genes Dev. 17: 1175-1187
[Non-patent Literature 2]
Schumacher K, Schmitt T, Rossberg M, Schmitz G, Theres K (1999) The Lateral suppressor (Ls) gene of tomato encodes a new member of the VHIID protein family. Proc Natl Acad Sci USA 96: 290-295
[Non-patent Literature 3]
Xueyong L, Qian Q, Zhiming F, Yonghong W, Guosheng X, Dali Z, Xiaoqun W, Xinfang L, Sheng T, Fujimoto H, Ming Y, Da L, Bin H & Jiayang L (2003) Control of tillering in rice. Nature 402(10): 618-621
[Non-patent Literature 4]
Keller, T., Abbott, J., Moritz, T., and Doerner, P (2006) *Arabidopsis* REGULATOR OF AXILLARY MERISTEMS1 controls a leaf axil stem cell niche and modulates vegetative development. The Plant Cell 18: 598-611
[Non-patent Literature 5]
Muller D, Schmitz G, Theres K (2006) Blind homologous R2R3 Myb genes control the pattern of lateral meristem initiation in *Arabidopsis*. The Plant Cell 18: 586-597
[Non-patent Literature 6]
Schmitz G, Tillman E, Carriero F, Fiore C, Cellini F, TheresK (2002) The tomato Blind gene encodes a MYB transcription factor that controls the formation of lateral meristems. Proc Natl Acad Sci USA 99: 1064-1069
[Non-patent Literature 7]
Mapelli S C, Lombardi L (1982) A comparative auxin and cytokinin study in normal and to—2 mutant tomato plants. Plant Cell Physiol. 23: 751-757
[Non-patent Literature 8]
Busch B L, Schmitz G, Rossmann S, Piron F, Ding J, BendahmaneA, Theres K (2011) Shoot branching and leaf dissection in totamto are regulated by homologous gene modules. The Plant Cell 23: 3595-3609
[Non-patent Literature 9]
Talbert P B, Adler H T, Parks D W, Comai L (1995) The REVOLUTA gene is necessary for apical meristem development and for limiting cell divisions in the leaves and stems of *Arabidopsis thaliana*. Development 121: 2723-2735.
[Non-patent Literature 10]
Otsuga D, DeGuzman B, Prigge M J, Drews G N, Clark S E (2001) REVOLUTA regulates meristem initiation at lateral positions. The Plant Journal 25: 223-236
[Non-patent Literature 11]
Zhong R, Ye Z H (1999) IFL1, a gene regulating interfascicular fiber differentiation in Arabiodpsis, encodes a homeodomain-leucine zipper protein. The Plant Cell 11: 2139-2152
[Non-patent Literature 12]
Zhong R, Taylor J J, Ye Z H (1997) Disruption of interfascicular fiber differentiation in an *Arabidopsis* mutant. The Plant Cell 9: 2159-2170
[Non-patent Literature 13]
Yang F, Wang Q, Schmitz G, Muller D, Theres K (2012) The bHLH protein ROX acts in concert with RAX1 and LAS to modulate axillary meristem formation in *Arabidopsis*. The Plant Journal 71 (1): 61-70

SUMMARY OF INVENTION

Technical Problem

However, what can be known from the above literature is merely that axillary buds can be reduced in plants other than tobacco plants. Therefore, it is still unclear how to obtain a tobacco plant in which the problems resulting from the development of axillary buds are resolved or reduced and which is to be cultivated for harvesting leaf tobaccos.

An object of the present invention is to provide (i) a tobacco plant which is suitable for cultivation for harvesting leaf tobaccos, (ii) a method of obtaining the tobacco plant, (iii) a harvest from the tobacco plant, and (iv) a processed product of the harvest.

Solution to Problem

In view of the problems above, the inventors of the present invention identified a gene which is expected to be involved in the development of axillary buds in tobacco plants, and then searched for an advantageous effect which can be obtained by suppressing the function of the gene in a tobacco plant. This led to the completion of the present invention.

Specifically, in order to attain the object, a tobacco plant in accordance with one aspect of the present invention is a tobacco plant in which a mutation causing functional suppression of at least two genes of the following genes (1) through (3) is introduced into a genome:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A tobacco plant production method in accordance with one aspect of the present invention is a method of producing a tobacco plant, including the step of:

(A) introducing, into a genome of a tobacco plant, a mutation causing functional suppression of at least two genes of the following genes (1) through (3):

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A determining method in accordance with one aspect of the present invention is a method of determining a tobacco plant in which development of primary axillary buds is suppressed, the method including the steps of:

(A) obtaining a sample by collecting a part of a tobacco plant;

(B) detecting, from a genome included in the sample, a mutation causing functional suppression of at least two genes of the following genes (1) through (3) on the genomic DNA:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l); and (C) determining that a tobacco plant, in which the mutation has been detected, is a tobacco plant in which the development of the primary axillary buds is suppressed, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

Advantageous Effects of Invention

The present invention can advantageously provide (i) a tobacco plant which is suitable for cultivation for harvesting leaf tobaccos, (ii) a method of obtaining the tobacco plant, (iii) a harvest from the tobacco plant, and (iv) a processed product of the harvest.

DESCRIPTION OF EMBODIMENTS

[1. Tobacco Plant]

Figure 1:
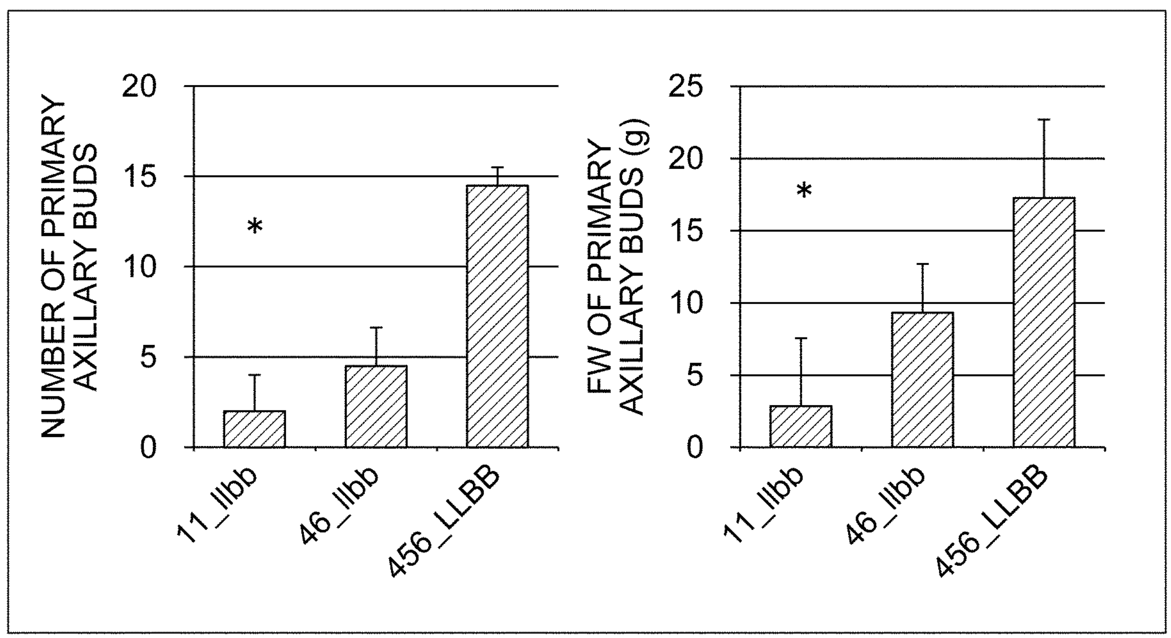
FIG. 1 is a view showing the results of evaluation of effects of suppressing primary axillary buds in a tobacco plant in accordance with an example of the present invention.

An embodiment of the present invention provides a tobacco plant in which a mutation is introduced into genome, which mutation causes suppression of functions of at least two genes of specific three genes. It should be noted that the above functional suppression is to suppress the development of primary axillary buds.

Concrete examples of the specific three genes encompass (1) through (3) below.

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l). Note that the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

In comparison with wild-type plants, the tobacco plant either exhibits (i) primary axillary buds which are decreased in number or weight (e.g., not more than ½ of wild-type plants) or (ii) no primary axillary bud (see Examples described later). Specifically, a process of removing axillary buds from the tobacco plant is necessary merely a single time or is unnecessary. This allows the amount of labor, which is involved in control of axillary buds in cultivation of a tobacco plant for harvesting leaf tobaccos, to be less than a fraction of the amount of labor involved in such a conventional control of axillary buds.

As used herein, "tobacco plant" and "tobacco" encompass (i) an entire individual (such as a mature plant, a seedling, and a seed), (ii) tissue (such as a leaf, a stem, a flower, a root, a reproductive organ, an embryo, and a part of any of these), and (iii) a dried product of any of these.

As used herein, "axillary bud" refers to both (i) a bud which is generated from an axillary meristem formed at a leaf axil of a leaf primordia and (ii) a shoot obtained as a result of the development of the bud. After topping, axillary buds develop in an order of primary axillary buds, secondary axillary buds, and then tertiary axillary buds, at a base of the same leaf. First, after topping, the primary axillary buds develop. After the primary axillary buds are removed, the secondary axillary buds develop. The "development" of an axillary bud means that the axillary bud, which remained as differentiated tissues from the axillary meristem, starts vigorous development due to, for example, removal of a shoot apex (topping), so that the axillary bud grows and extends.

The "number or weight" of axillary buds means the number or a total weight (fresh weight) of primary axillary buds which have developed in one individual or have been collected. The "number or weight", mainly of primary axillary buds, is herein measured.

As used herein, "sequence identity (of an amino acid sequence)" means a percentage ratio at which a concerned (amino acid) sequence matches a reference (amino acid) sequence. Note that a part of the sequence, which part does not match, is a part at which an amino acid residue is substituted, added, deleted, or inserted.

Note that the term "polypeptide having a sequence identity of 90% or higher with an amino acid sequence represented by [ . . . ]", which specifies the polypeptide with use of an amino acid sequence listed in a sequence listing, means a wild-type polypeptide. The wild-type polypeptide means a polypeptide which is typically present in a *Nicotiana* plant described later. As used herein, the terms "polypeptide" and "protein" have substantially the same meaning, and can therefore be used interchangeably.

Therefore, a polypeptide, which is decreased in abundance in the tobacco plant, need only be a polypeptide having a sequence identity of 90% or higher with each of the amino acid sequences listed in the sequence listing. A higher sequence identity is more preferable (e.g., 91%, 92%, 93%, 94%, 95%, 96%, 97%, 98%, or 99% or higher).

The "decrease in abundance" of a polypeptide means the presence of the polypeptide in an amount of 70% or lower, 60% or lower, 50% or lower, 40% or lower, 30% or lower, 20% or lower, 10% or lower, 5% or lower, or 1% or lower, relative to the abundance of a wild-type polypeptide as a reference. The abundance of the polypeptide relative to that of the wild-type polypeptide as a reference can be selected as appropriate from the above values which result in a decrease in the number or weight of primary axillary buds.

It is preferable that the above-described decrease in abundance of a polypeptide in the tobacco plant is, with stability, genetically inherited by cultured cell, callus, protoplast, seed, and offspring, any of which is obtained from the tobacco plant. Therefore, the tobacco plant can be an individual developed from cultured cell, callus, protoplast, seed, or offspring, any of which is produced through artificial operation. In addition, these materials, from which the individual develops, are also encompassed in the scope of the present invention.

The scope of the tobacco plant can further encompass bred progeny obtained by crossing. Breeding with use of mutants has been done in many plant species. Representative examples of such plant species encompass rice, wheat, barley, and soybean. For example, a mutant isolated from a mutant population treated with use of a mutagen has multiple mutations other than at a region of a target gene. In general, therefore, backcrossing is to be performed to remove excess mutations. In this crossing, a desired character (suppressed development of primary axillary buds) of the mutant can be introduced into an existing cultivar by crossing the mutant with the cultivar having excellent character. A bred progeny thus obtained can be a variety obtained by adding high values to an existing cultivar.

Note that the desired character of the mutant is derived from mutations introduced into a plurality of positions (e.g., a plurality of genes) on a genome. For efficient backcrossing, it is therefore necessary to select, in advance, individuals having the mutations. In the selection of the individuals, it is advantageous to be able to easily detect (i) whether or not the mutations are present in the individuals and (ii) whether the mutations are homozygous or heterozygous. The mutations can be detected by a method (described later) for detecting mutations in genes. Apart from the perspective above, it is preferable that lines having a high cultivar-return-rate (i.e., the proportion of a cultivar-derived genomic region to the entire genomic region) is obtained with the fewer times of crossing. Even fewer times of crossing can be achieved by, for example, Marker Assisted Selection (MAS) which uses a background marker indicative of a polymorphism between the mutant and the existing cultivar. The background marker indicative of a polymorphism can be, for example, SNP or Simple Sequence Repeat (SSR) each of which is known in tobacco. Other than the existing marker, examples of a new marker encompass the following differences (a) and (b) which are identified by determining respective genome sequences of the mutant and the existing cultivar for use in crossing and then making a comparison between the genome sequences: (a) a difference in nucleotide sequence and (b) a difference in the number of repeat sequences on a genome.

Gene and genome will be described below by taking *Nicotiana tabacum* (*N. tabacum*) as a reference. *Nicotiana tabacum* (*N. tabacum*), which serves as a reference in the description below, is an amphidiploid and has both an S genome and a T genome derived from *Nicotiana sylvestris* and *Nicotiana tomentosiformis*, respectively, each of which is an ancestor species thereof. In *N. tabacum*, in most cases, genes indicated by an identical name are present in each of an S genome and a T genome. The three genes described above each include two alleles in an S genome and two alleles in a T genome (i.e., the total of 4 alleles on the genome of *N. tabacum*).

Note that in a coding region of a tobacco plant, a nucleotide sequence of part (not the whole) of genes encoding polypeptides, which possesses the substantially same function between species, may have (i) 1% to several % difference between cultivars and (ii) approximately 10% or lower difference between a cultivar and wild species.

A polypeptide having an amino acid sequence represented by SEQ ID NO: 1 is encoded by, for example, a polynucleotide having a nucleotide sequence represented by SEQ ID NO: 7. A polypeptide having an amino acid sequence represented by SEQ ID NO: 2 is encoded by, for example, a polynucleotide having a nucleotide sequence represented by SEQ ID NO: 8. These polynucleotides are each cDNA of NtB11 gene demonstrated in Examples described later. SEQ ID NO: 7 represents a cDNA sequence of NtB11 gene of an S genome. SEQ ID NO: 8 represents a cDNA sequence of NtB11 gene of a T genome. SEQ ID NOs: 13 and 14 represent nucleotide sequences of an S genome and a T genome, respectively, of NtB11 gene.

A polypeptide having an amino acid sequence represented by SEQ ID NO: 3 is encoded by, for example, a polynucleotide having a nucleotide sequence represented by SEQ ID NO: 9. A polypeptide having an amino acid sequence represented by SEQ ID NO: 4 is encoded by, for example, a polynucleotide having a nucleotide sequence represented by SEQ ID NO: 10. These polynucleotides are each cDNA of NtLS gene demonstrated in Examples described later. SEQ ID NO: 9 represents a cDNA sequence of NtLS gene of an S genome. SEQ ID NO: 10 represents a cDNA sequence of NtLS gene of a T genome. SEQ ID NOs: 15 and 16 represent nucleotide sequences of an S genome and a T genome, respectively, of NtLS gene.

A polypeptide having an amino acid sequence represented by SEQ ID NO: 5 is encoded by, for example, a polynucleotide having a nucleotide sequence represented by SEQ ID NO: 11. A polypeptide having an amino acid sequence represented by SEQ ID NO: 6 is encoded by, for example, a polynucleotide having a nucleotide sequence represented by SEQ ID NO: 12. These polynucleotides are each cDNA of NtREV gene demonstrated in Examples described later. SEQ ID NO: 11 represents a cDNA sequence of NtREV gene of an S genome. SEQ ID NO: 12 represents a cDNA sequence of NtREV gene of a T genome. SEQ ID NOs: 17 and 18 represent nucleotide sequences of an S genome and a T genome, respectively, of NtREV gene.

There are methods for isolating orthologous genes. Examples of such methods well-known to those skilled in the art encompass a hybridization technique (Southern, E. M., Journal of Molecular Biology, Vol. 98, 503, 1975) and a polymerase chain reaction (PCR) technique (Saiki, R. K., et al. Science, vol. 230, 1350-1354, 1985, Saiki, R. K. et al. Science, vol. 239, 487-491, 1988). Therefore, those skilled in the art can easily isolate an orthologous gene of the gene (1) from various plants while, for example, (i) a polynucleotide having a nucleotide sequence shown in SEQ ID NO: 7 or a part of the polynucleotide is serving as a probe or (ii) oligonucleotide hybridizing with the polynucleotide under stringent conditions is serving as a primer. Likewise, those skilled in the art can easily isolate an orthologous gene of the gene (1) from various plants with use of (i) a polynucleotide having a nucleotide sequence shown in SEQ ID NO: 8 or (ii) a part of the polynucleotide. Skilled persons who read these descriptions can easily (i) isolate an orthologous gene of the gene (2) based on the nucleotide sequence of SEQ ID NO: 9 or SEQ ID NO: 10 (or on a part of the nucleotide sequence and (ii) isolate an orthologous gene from the gene (3) based on the nucleotide sequence of SEQ ID NO: 11 or SEQ ID NO: 12 (or on a part of the nucleotide sequence).

Note that the stringent conditions means, in general, conditions under which (i) a double-stranded polynucleotide specific to a nucleotide sequence is formed and (ii) the formation of a non-specific double-stranded polynucleotide is markedly suppressed. In other words, the stringent conditions can be expressed as conditions under which hybridization is carried out at a temperature in a range from (i) a melting temperature (Tm) of a hybrid of nucleic acids which are highly homologous to each other (e.g., a double-stranded polynucleotide perfectly-matched to a probe) to (ii) 15° C. lower than the melting temperature (Tm), preferably 10° C. lower than the melting temperature (Tm), more preferably 5° C. lower than the melting temperature (Tm). Examples of the stringent conditions encompass conditions under which hybridization is carried out with use of a common buffer solution for hybridization, at a temperature of 68° C., and for a period of 20 hours. In one example, hybridization can be carried out in a buffer solution (consisting of 0.25M Na2HPO4, pH 7.2, 7% SDS, 1 mM EDTA, and 1×Denhardt's solution) for 16 hours to 24 hours at a temperature in a range from 60° C. to 68° C., preferably at 65° C., further preferably at 68° C., and then washing can be carried out twice in a buffer solution (consisting of 20 mM Na2HPO4, pH 7.2, 1% SDS, and 1 mM EDTA) for 15 minutes at a temperature in a range from 60° C. to 68° C., preferably at 65° C., further preferably at 68° C. In another example, prehybridization is carried out overnight at 42° C. in a hybridization solution (including 25% formamide or 50% formamide (for a stringent condition), 4×SSC (sodium chloride/sodium citrate), 50 mM Hepes pH 7.0, 10×Denhardt's solution, and 20 μg/ml denatured salmon sperm DNA), and then hybridization is carried out by adding a labeled probe thereto and keeping a resulting solution at 42° C. overnight. In washing following the hybridization, conditions for a washing solution and a temperature are approximately "1×SSC, 0.1% SDS, 37° C.", approximately "0.5×SSC, 0.1% SDS, 42° C." for a more stringent condition, approximately "0.2×SSC, 0.1% SDS, 65° C." for a further severer condition. It can be thus expected that as the conditions for the washing following the hybridization become more stringent, DNA having higher homology to a sequence of a probe is isolated. However, the above-indicated combinations of conditions on SSC, SDS, and temperature are merely examples. Those skilled in the art can achieve a stringency similar to the above by appropriately combining the above-described or other elements (e.g., a probe concentration, a probe length, and a time period for a hybridization reaction) that determine the stringency of hybridization. For example, those skilled in the art can easily obtain such genes by referring to Molecular Cloning (Sambrook, J. et al., Molecular Cloning: a Laboratory Manual 2nd ed., Cold Spring Harbor Laboratory Press, 10 Skyline Drive Plainview, N.Y. (1989)).

The term "at least one of (former) . . . gene and (latter) . . . gene" as used herein to specify a gene refers to any one of the following genes and a combination thereof:

a (former) gene (gene on S genome);

a (latter) gene (gene on T genome); and a combination of the (former) gene (gene on S genome) and the (latter) gene (gene on T genome).

In a specific embodiment in which mutations are introduced into two genes, the tobacco plant has the above-described mutations in one or more alleles, per gene, selected from (i) at least one (one or two) of two alleles in S genome and (ii) at least one (one or two) of two alleles in T genome. Specifically, the tobacco plant has the mutations in two genes selected from NtB11 gene, NtLS gene, and NtREV gene which are on the genome.

As described above, a tobacco plant in many cases has one set of genes (i.e., two genes) in each of a T genome and an S genome. Therefore, in order for the functions of the genes to completely disappear, it is necessary to introduce the mutations into all of the (four) genes in the T genome and the S genome. Note, however, that in a tobacco plant in which the function of one gene has completely disappeared due to the mutation, the development of primary axillary buds is not suppressed (see Comparative Examples described later).

Note that the tobacco plant in accordance with an embodiment of the present invention preferably has mutations in at least two genes, and more preferably has mutations in two genes. In a more preferable tobacco plant, the number of alleles into which mutations are to be introduced is 8. In a preferable tobacco plant, it is unnecessary for the mutation to be introduced into all of the 8 alleles. This is because the suppression of the development of primary axillary buds can be observed in, for example, a tobacco plant in which the mutations are introduced into 6 or more (i.e., 6 or 7) alleles out of 8 alleles.

As described later in Examples, two genes of the tobacco plant, into which the mutations are introduced, are preferably a combination of (i) NtB11 gene and (ii) NtLS gene or NtREV gene. In an embodiment of the combination of these genes, the tobacco plant has mutations in 6 alleles and no mutations in 2 alleles, out of 2 genes. In the embodiment, the tobacco plant has mutations in: 4 alleles of the NtB11 gene and 2 alleles of the NtLS gene or the NtREV gene; 3 alleles of the NtB11 gene and 3 alleles of the NtLS gene or the NtREV gene; or 2 alleles of the NtB11 gene and 4 alleles of the NtLS gene or the NtREV gene.

In another embodiment of the combination of the genes, the tobacco plant has mutations in 7 alleles and has no mutation in 1 allele, out of 2 genes. In the another embodiment, the tobacco plant has mutations in: 4 alleles of the NtB11 gene and 3 alleles of the NtLS gene or the NtREV gene; or 3 alleles of the NtB11 gene and 4 alleles of the NtLS gene or the NtREV gene.

As used herein, "functional suppression of a gene" means a state in which the gene on a genome is not fulfilling its original function. Therefore, "functional suppression of a gene" is a term encompassing (i) "gene disruption", (ii) "gene mutation", and (iii) "suppressed expression of gene" by another gene (including an exogenous gene).

"Gene disruption" means that (i) a gene, which is originally present on a genome, is not present on the genome or (ii) a transcribed product is not produced from a gene on a genome. "Gene mutation" means, for example, (i) a mutation of a gene (i.e., decrease or impairment of the function) such that an original functional polypeptide is not produced, (ii) a mutation of the gene such that although a functional polypeptide is produced, the amount of the functional polypeptide produced is decreased, or (iii) a mutation of the gene such that although a functional polypeptide is produced, the stability of the functional polypeptide is decreased. "Suppressed expression of gene" means, for example, a state in which although no change has occurred to the nucleotide of the gene, the transcriptional or translational function of the gene (from transcription into mRNA to subsequent translation into polypeptide) is modified through another factor so that (i) the amount of protein produced is decreased or (ii) no polypeptide is produced. "Suppressed expression of gene" may occur as a result of, for example, degradation of mRNA which is transcribed from the gene.

As used herein, "mutation" has the meaning ordinarily understood in the technical field to which the present application belongs, and means, for example, any change in a nucleotide on a wild-type genome or any change in an amino acid residue in a wild-type polypeptide (examples of the change encompass substitution, deletion, insertion, addition, duplication, inversion, or translocation). "Gene mutation" means, for example, (i) a mutation of a gene such that an original functional polypeptide is not produced, (ii) a mutation of the gene such that although a polypeptide is produced, the amount of the polypeptide produced is decreased, (iii) a mutation of the gene such that although a polypeptide is produced, the stability of the polypeptide is decreased, or (iv) a mutation of the gene such that the gene (a coding region or a full length including an untranslated region) is lost, or that transcription from the gene is suppressed (e.g., a transcription-regulating region or a transcription-initiating region is deleted).

In a case where the functions are impaired by substitution, the substitution can be present in at least one of the following: a promoter sequence (such as a sequence upstream (5' end) and a sequence downstream (3' end) with the coding region as a reference), a 5' untranslated region and a 3' untranslated region, a conserved sequence (5'GT-AG3') present at both ends of an intron, and a coding region.

For example, in a case where substitution in nucleotide sequences (a promoter sequence, a 5' untranslated region, and a 3' untranslated region of a gene), which are important for regulating gene expression, leads to a decrease in transcriptional activity of the gene expression or to a decrease in stability of a transcribed product. Any of these decreases may lead to a reduction in transcribed product from the gene. This may lead to a reduction in translation product. Substitution in a conserved sequence leads to splicing abnormality of mRNA. This results in abnormal mRNA into which an unnecessary intron is added or inserted. The abnormal mRNA either generates an abnormal translation product or does not terminate translation, due to, for example, frame shifting.

Substitution in a coding region may lead to a translation product which has an incomplete length or to a translation product which does not maintain an original function. The translation product having an incomplete length is derived from conversion, by the substitution, of a codon, which is encoding an amino acid, into a stop codon (i.e., nonsense mutation). In comparison with the original translation product, the translation product having an incomplete length is such that one or more consecutive amino acid residues including an amino acid residue at a C-terminus are deleted. The nonsense mutation occurs to any codon on located upstream of the original stop codon, and is preferably located upstream of the original stop codon with one or more codons therebetween. A translation product having lost the original function can occur due to substitution of an amino acid. The translation product has, therein, a change in tertiary structure, deterioration of a function as a functional domain, or the like. The substitution of the amino acid is preferably a non-conservative substitution with a high possibility of changing the function of the translation product. Examples of the non-conservative substitution encompass (i) substitution of an amino acid by another amino acid having a different electric charge or a different hydrophobicity (e.g., substitution of a basic amino acid by an acidic amino acid or substitution of a polar amino acid by a non-polar amino acid) and (ii) substitution of an amino acid by another amino acid having a side chain of a different bulk (three-dimensional size).

In a case where mutations (deletion, insertion, or the like) other than substitution, occur within a promoter sequence, a 5' untranslated region, and a 3' untranslated region, a decrease may occur in transcriptional activity or stability as in the case of the substitution, so that (i) the amount of transcribed product may decrease and (ii) the amount of polypeptide may decrease. In addition, a mutation other than substitution into a conserved sequence of an intron, as in the case of the substitution, leads to translation of polypeptide having an amino acid sequence different from that of the original amino acid sequence. The mutation, which is other than substitution into a coding region, causes polypeptide, which have amino acid sequences different from original sequences, to be generated by the translation, the difference in amino acid sequences occurring due to (i) deletion or insertion of an amino acid residue (caused by deletion or insertion of consecutive nucleotides which are multiples of 3) or (ii) frame shifting. In a case of a large deletion of the entire gene itself or an insertion of a large fragment into the gene, the expression of the gene may be lost.

An individual, which was generated as a result of the gene mutation or gene disruption, is herein called a mutant (hereinafter simply referred to as "mutant") of a tobacco plant. The mutant can have the mutation in any of an S genome or a T genome, and preferably has the mutation in both the S genome and the T genome. Note that (i) a single mutation or a plurality of mutations can occur in a single gene and (ii) the kind of mutation to impair a function is not limited. The total of four alleles, which include two alleles in an S genome and two alleles in a T genome, can have identical mutations or different mutations.

Examples of suppressed expression of a gene encompass (i) suppression of transcription from the gene to an mRNA, (ii) suppression (e.g., degradation of the mRNA) of translation from the gene into a polypeptide through an mRNA and (iii) suppression of the function of the polypeptide which is generated by the translation. The suppression of the transcription can be achieved by, for example, (i) inhibition of a transcription factor which promotes the transcription from the gene or (ii) inhibition of access of a transcription initiation factor to the gene. The suppression of the translation can be achieved by use of an antisense RNA molecule, an RNAi molecule, or a co-suppression molecule. The functional suppression of the polypeptide can be achieved by a molecule which inhibits the function of a functional polypeptide by binding to the functional polypeptide. Examples of such a molecule encompass decoy nucleic acid, ribozyme, antibody, and inhibitory peptide.

The above-described suppression (of the transcription, translation, and polypeptide function) can be achieved by, for example, (i) directly introducing molecules for achieving the suppression into a plant or (ii) introducing, into a plant, nucleic acid molecules encoding the molecules (i.e., transformation of the plant). As a result of the transformation of the plant, the nucleic acid molecules are incorporated into one or more of any regions of genomes of the plant. Provided that the suppression is achieved, it is unnecessary for the nucleic acid molecules to be incorporated into both S genome and T genome as a result of the transformation of the plant.

In the tobacco plant, the functional suppression is preferably a decrease, as compared with a wild-type plant, in abundance of the polypeptides which are expression products of the at least two genes. Specifically, the abundance is decreased through mutation which leads to function suppression of a gene encoding the wild-type polypeptide.

A polypeptide, which has a sequence identity of 90% or higher with an amino acid sequence represented by SEQ ID NO: 1, 2, 3, 4, 5, or 6, is a polypeptide which is present in a wild-type plant (or a variant thereof). Therefore, the abundance of the polypeptide in the tobacco plant is decreased in comparison with that of a wild-type plant. This causes the tobacco plant to be inferior to the wild-type plant in terms of the function. Examples of the function encompass a function of a wild-type plant, such as (i) a function to form axillary meristem, (ii) a function to differentiate an axillary bud from axillary meristem, or (iii) a function to maintain or promote the capability of the development of an axillary bud.

In the tobacco plant, the functional suppression is preferably a decrease, as compared with a wild-type plant, in an amount of translation of the polypeptides which are expression products of the at least two genes. The translation of the polypeptide is based on (i) a decrease in mRNA (due to, for example, the abundance of mRNA, such as the instability of the mRNA itself, promoted degradation of the mRNA, or suppression of the transcription of the mRNA) or (ii) a decrease in an amount of translation from mRNA (due to, for example, lack of elements (tRNA and ribosome) constituting translation, inhibition of recruit, or functional impairment).

In the tobacco plant, the functional suppression is preferably a decrease, as compared with a wild-type plant, in an amount of transcription from the at least two genes to mRNA. The decrease in the amount of the transcription occurs due to, for example, suppression of transcription from a gene to mRNA. The suppression of the transcription can be achieved by, for example, inhibition of access of a transcription initiation factor to the gene, which occurs as a result of introducing a mutation into the gene.

In the tobacco plant, the functional suppression is preferably promotion of degradation of mRNAs transcribed from the at least two genes. The degradation of the mRNA may be caused by, for example, (i) the presence of an exogenous factor leading to the degradation of the mRNA, (ii) activation of an endogenous constituent element leading to the degradation of the mRNA, or (iii) the presence of a sequence for promoting the degradation of the mRNA.

In the tobacco plant, the mutation is preferably insertion, into an outside of a region in which the at least two genes are present, of a polynucleotide expressing a factor which promotes the degradation of the mRNAs transcribed from the at least two genes.

The factor is preferably an antisense RNA molecule, an RNAi molecule, or a co-suppression molecule.

In the tobacco plant, the mutations or disruption of the at least two genes occurs as a result of, for example, spontaneous mutation, mutagen treatment, gene recombination, genome editing, or gene knockout. The spontaneous mutation of the at least two genes generally occurs due to (i) replication errors and (ii) damage to the gene. The cause of the damage is, for example, exposure to publicly-known, naturally-occurring mutagens or publicly-known mutagens which have been artificially produced and then remaining in a natural environment (for example, radiation, ultraviolet rays, or mutation-inducing substances (such as EMS)). The at least two genes can be subjected to a mutagen treatment by artificially causing the mutagen to take effect on a tobacco plant (as necessary, in combination with suppression of a gene repair function). Recombination of the at least two genes can be performed by homologous recombination of all or part of a target gene with a recombinant sequence according to a publicly-known genetic recombination method. Genome editing of the gene can be performed by a publicly-known technique (for example, zinc-finger nucleases: ZFN, transcription activator-like effector nucleases: TALEN, and CRISPR/Cas9 system). The gene knockout can be performed by, for example, (i) transfer of the gene by use of a publicly-known transposase or (ii) introduction of T-DNA.

The various mutations described above can be easily introduced into a tobacco plant by those skilled in the art who have referred to, for example, genome sequences of genes represented by SEQ ID NOs: 13 through 18, 23, and 24. Specifically, based on these pieces of sequence information, it is possible to appropriately determine a region which is present in a genome of any of various tobacco plants encompassed in the scope of the present invention and at which a mutation should be introduced.

The tobacco plant is not limited to any particular one provided that the tobacco plant is a *Nicotiana* plant which is not limited to any particular one provided that the *Nicotiana* plant is a plant belonging to *Nicotiana*. Examples of the tobacco plant encompass *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and a hybrid of *Nicotiana* plants. Among these *Nicotiana* plants, *Nicotiana benthamiana, Nicotiana rustica*, and *Nicotiana tabacum* are more preferable. *Nicotiana rustica* and *Nicotiana tabacum*, which are used as materials to produce leaf tobacco, are particularly preferable.

[2. Method of Producing Tobacco Plant]

In one aspect, the present invention provides a method of producing the tobacco plant. The production method includes the step of introducing, into a genome of the tobacco plant, a mutation which causes functional suppression of at least two genes of the above-described three genes.

This introducing step results in the suppression of the development of primary axillary buds through the functional suppression of the at least two genes. The suppression of the development of primary axillary buds through the functional suppression of the genes is performed as outlined above. Therefore, as concrete examples of carrying out the introducing step, the following description will discuss introduction of a mutation into the at least two genes, which is performed by use of a genome editing technique. Examples of the usable genome editing technique encompass CRISPR/Cas9 system, TALEN, and ZFN. According to the CRISPR/Cas9 system, the genome editing is possible if guide RNAs and a Cas9 protein is present in a target cell. According to TALEN and ZFN, the genome editing is possible if a fusion protein (in which DNA-binding domains and nuclease are fused) is present in a target cell. Therefore, the guide RNAs, the Cas9 proteins, and the fusion proteins can be directly introduced into a target cell. Examples of a method of directly introducing any of these into a target cell encompass a PEG method, an electroporation method, and a particle bombardment method.

According to the CRISPR/Cas9 system, (i) a sequence, which is complementary to a nucleotide sequence located immediately upstream of XGG on a genome, forms a base pair with part of a guide RNA and (ii) a double stranded genomic DNA is cut by Cas9 in the nucleotide sequence. Examples of the nucleotide sequence encompass a part of (i) a polynucleotide (which can have a substitution of 0.1% to 1%) encoding a polypeptide having an amino acid sequence represented by SEQ ID NO: 1, 2, 3, 4, 5, or 6 or (ii) a polynucleotide (which can have a substitution of 0.1% to 1%) having SEQ ID NO: 7, 8, 9, 10, 11, or 12, which part is 10 or more consecutive bases (e.g., 15 or more consecutive bases, preferably 17 or more consecutive bases, more preferably 18 or more consecutive bases, still more preferably 19 or more consecutive bases, and most preferably 20 or more consecutive bases) located immediately upstream of XGG.

According to the TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The nucleotide sequence is present at one and the other strands of double stranded genomic DNA. Therefore, one of the pair of DNA-binding domains binds to the one strand, and the other of the pair of DNA-binding domains binds to the other strand. The DNA binding domain is composed of a repeating unit (module) which include 33 to 34 amino acid residues. The number of modules corresponds to the number of nucleotides to which the DNA bind domain bind. Provided that 33 to 34 amino acid residues serve as a repeating unit (module), the DNA-binding domain contains modules, the number of which corresponds to the number of nucleotides to bind to. The nucleotide sequence to which the DNA-binding domain binds is 10 or more consecutive bases, preferably 14 or more consecutive bases, and more preferably 18 or more consecutive bases, which are present at each terminus of a FokI cleavage domain so as to be away from the terminus by a spacer of 5 to 20 bases and which are (i) a part of a polynucleotide (which can have a substitution of 0.1% to 1%) encoding a polypeptide having an amino acid sequence represented by SEQ ID NO: 1, 2, 3, 4, 5, or 6, or a polynucleotide (which can have a substitution of 0.1% to 1%) having SEQ ID NO: 7, 8, 9, 10, 11, or 12 and (ii) a part of a polynucleotide forming complementary strand with the above polynucleotide.

According to ZFN, as in the case of TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The DNA-binding domain contains a plurality of zinc finger modules. The nucleotide sequence is 9 or more consecutive bases, preferably 12 or more consecutive bases, and more preferably 18 or more consecutive bases, which are present at respective termini of a FokI cleavage domain with a spacer of 5 to 20 bases therebetween and which are (i) a part of a polynucleotide (which can have a substitution of 0.1% to 1%) encoding a polypeptide having an amino acid sequence represented by SEQ ID NO: 1, 2, 3, 4, 5, or 6, or a polynucleotide (which can have a substitution of 0.1% to 1%) having SEQ ID NO: 7, 8, 9, 10, 11, or 12 and (ii) a part of a polynucleotide forming complementary strand with the above polynucleotide.

The descriptions of CRISPR/Cas9 system, TALEN, and ZFN, and RNAi (described later) can each be read so that, according to the description of each detail, the polypeptide having an amino acid sequence represented by SEQ ID NO: 1, 2, 3, 4, 5, or 6 is replaced with an orthologous polypeptide which (i) has a sequence identity of 90% or higher with the polypeptide and (ii) is present in another kind included in *Nicotiana* plant. Likewise, the description of the previous paragraph can be read so that a polynucleotide having SEQ ID NO: 7, 8, 9, 10, 11, or 12 is replaced with a polynucleotide of orthologous gene, which (i) has a sequence identity of 90% or higher with the polynucleotide and (ii) is present in another kind included in *Nicotiana* plant.

As described above, the mutation, which causes functional suppression of the at least two genes and which is introduced in the tobacco plant, is preferably genetically inherited. However, an exogenous polynucleotide introduced in a tobacco plant by genome editing is preferably eliminated from the tobacco plant after it is confirmed that a desired mutation is introduced in the tobacco plant. In a case where the exogenous polynucleotide is retained in the tobacco plant, an undesired mutation may (continue to) be introduced. This may cause a desired character (such as suppression of primary axillary buds) to be lost, or may threaten the survival of the tobacco plant.

The introduction of the mutation into the at least two genes of a tobacco plant or the disruption of the at least two genes of the tobacco plant can be achieved through another biotechnological method (e.g., a method in which transposon or *Agrobacterium* is utilized). Concrete examples of the method encompass a method in which a tobacco plant is introduced with (i) retrotransposon tnt1 of tobacco or transposon of another plant or (ii) T-DNA of T1 plasmid of *Agrobacterium.*

Alternatively, the introduction or the disruption can be achieved through another method (mutagen treatment of a tobacco plant). Examples of a source of the mutation encompass small molecule compounds (such as ethyl methane sulfonate (EMS), N-ethyl-N-nitrosourea (ENU), sodium azide) and radiations (such as gamma rays, heavy ion beams, X-rays, neutron beams, and ultraviolet rays).

A mutation can be introduced into any regenerable tobacco plant. Examples of the tobacco plant encompass seeds, roots, leaves, flowers, reproductive organs, and embryos. A preferable example is seeds.

What can be obtained by the methods above can be a mutant population of a plant which has various mutations (or no mutation). Therefore, an individual exhibiting a desired phenotype can be further selected from the mutant population. As an example of the selection of an individual, the following description will discuss a procedure for selecting a desired individual from a mutant population (panel) which is obtained in a case where tobacco is treated with use of a mutagen.

A tobacco mutant, which is functionally impaired due to mutations in the total of 4 alleles of both T genome and S genome for one gene or due to disruption of the total of 4 alleles for one gene, can be obtained by, for example, a method described below. A tobacco plant is treated with a mutagen as described above to prepare a population (panel) of tobacco mutants with mutations in the whole tobacco genome, and genomic DNAs are extracted. By utilizing gene-specific primers of each of the S genome and the T genome, target genes (polynucleotide) are amplified from the genomic DNAs of the panel. Subsequently, nucleotide sequences of resulting products are determined, and a line having a mutation is then selected. From an M2 individual group of a selected line, an M2 individual having a homozygous mutation in an S genome and an M2 individual having a homozygous mutation in a T genome are prepared and then crossed to obtain $F_1$ individuals. Subsequently, a selfed progeny ($F_2$) is cultivated from the $F_1$ individuals. From the selfed progeny ($F_2$), individuals having homozygous mutations in both an S genome and a T genome are obtained (such individuals are obtained at a probability of 1/16 since two elements are recessive). The tobacco mutants, which have been thus obtained and which have the mutations in different genes, are further crossed so that a tobacco mutant having mutations in two genes can be obtained.

Alternatively, the tobacco mutant having mutations in the two genes can be obtained by (i) further subjecting, to a mutagen treatment, the tobacco mutant, having the mutation in one gene, which has been obtained by the method described above or (ii) selecting, from the above-described mutant population, the tobacco mutant having the mutations in the two genes. In a case where the method of introducing the mutation is to be changed, it is sufficient to replace the method described above concerning the mutagen with another method (e.g., a method of introducing a mutation into a tobacco plant with use of genome editing or gene knockout, or a method of carrying out transformation of a tobacco plant with use of a vector described later).

Specifically, through, for example, stages (1) through (4) below, any of the following tobacco plants can be obtained: (i) a tobacco plant having mutations in two genes (first and second genes), (ii) a tobacco plant in which two genes are disrupted, and (iii) a tobacco plant which has a mutation in a first gene and in which a second gene is disrupted. Note that the stages (3) and (4) can be omitted by, for example, introducing the mutations into the two genes simultaneously in the stage (1), and then selecting, in the stage (2), a tobacco mutant having the mutations in the two genes.

(1) The mutant population is produced by use of any method of introducing a mutation (e.g., spontaneous mutation, mutagen treatment, gene recombination, genome editing, gene knockout, transformation, or a combination of any of these methods).

(2) A first tobacco mutant, which has the mutation in the first gene (or in which the first gene is disrupted), is selected from the tobacco mutant produced in the stage (1).

(3) A second tobacco mutant, which has the mutation in the second gene (or in which the second gene is disrupted), is prepared by repeating the stages (1) and (2).

(4) The first and second tobacco plants are crossed.

Another example of carrying out the introducing step is suppressed expression of the gene and introduction of the mutation into the gene, which are performed through transformation of a tobacco plant with use of a vector.

The vector to be used for the transformation of a tobacco plant for the purpose of the suppressed expression of the gene or the introduction of the mutation into the gene is not limited to any particular one, provided that a polynucleotide inserted into the vector can be expressed in a plant cell. Examples of a suitable vector encompass pBI, pPZP, and pSMA vectors each of which allows introduction of a target polynucleotide into a plant cell via *Agrobacterium*. In particular, plasmids of binary vectors (e.g., pBIG, pBIN19, pBI101, pBI121, pBI221, and pPZP202) are preferable.

In a case where the suppressed expression of the gene is achieved by RNAi, a trigger sequence, which is used by the RNAi to suppress the expression of the target gene, is inserted into the vector. Examples of the trigger sequence encompass (i) a polynucleotide (sense RNA portion) which is (a) a part of a polynucleotide (which can have a substitution of 0.1% to 1%) encoding a polypeptide having an amino acid sequence represented by SEQ ID NO: 1, 2, 3, 4, 5, or 6 or a part of a polynucleotide (which can have a substitution of 0.1% to 1%) having SEQ ID NO: 7, 8, 9, 10, 11, or 12 and (b) represented by a nucleotide sequence of at least 21 to 30 consecutive bases (e.g., 21 or more bases, 22 or more bases, 23 or more bases, 24 or more bases, 25 or more bases, 26 or more bases, 27 or more bases, 28 or more bases, 29 or more bases, and 30 or more bases) and (ii) a polynucleotide (antisense RNA portion) represented by a nucleotide sequence which is complementary to the polynucleotide (i). More specifically, the nucleotide sequence of the "at least 21 to 30 consecutive bases" described above means a nucleotide sequence of 21 or more consecutive bases, 23 or more consecutive bases, 25 or more consecutive bases, 30 or more consecutive bases, 35 or more consecutive bases, 40 or more consecutive bases, 45 or more consecutive bases, 50 or more consecutive bases, 60 or more consecutive bases, 70 or more consecutive bases, 80 or more consecutive bases, 90 or more consecutive bases, or 100 or more consecutive bases.

As described above, the suppressed expression of the gene in the tobacco plant is preferably genetically inherited. Therefore, the trigger sequence is preferably incorporated with a genome of the tobacco plant.

A tobacco plant, in which expression of a plurality of genes is simultaneously suppressed, can be obtained by crossing two tobacco plants in which expression of differing genes is suppressed. In addition, a tobacco plant, in which expression of a plurality of genes is simultaneously suppressed, can be obtained by (i) performing transformation which may cause expression of a plurality of differing genes to be simultaneously suppressed and then (ii) selecting the tobacco plant in which expression of a plurality of genes is simultaneously suppressed.

Note that in a case where a tobacco plant in which a plurality of genes are functionally suppressed is to be obtained by use of crossing, (i) one of tobacco plants to be crossed can be prepared by mutation or disruption of a gene and (ii) the other one of the tobacco plants to be crossed can be prepared by suppressed expression of a gene by transformation.

The method of producing the tobacco plant further includes the step of selecting, from the tobacco plants produced by the above producing step, an individual in which the number or weight of primary axillary buds is decreased to ½ or lower in comparison with a wild-type plant. This selecting step is carried out based on, for example, mutation, disruption, or suppressed expression of the at least two genes described above.

The mutation or disruption of the at least two genes is determined by identifying the presence/absence of a mutation of the gene. A method of identifying the mutation of the gene needs to allow the determination of the presence/absence of the mutation. Examples of the method encompass (1) a method in which a DNA sequence is directly decoded with use of a commercially available sequencer, (2) a method in which a difference in sequence is detected by a difference in distance of electrophoresis with use of the Single Strand Conformation Polymorphism (SSCP) method, (3) a method in which Single Nucleotide Polymorphism (SNP) is detected by the Cycleave PCR method, (4) a method in which the presence/absence of a mutation is identified by cleaving a mismatch site(s) with use of T7 EndonucleaseI or the like, (5) a Cleaved Amplified Polymorphic Sequence (CAPS) method in which the presence/absence of a mutation can be determined by the presence/absence of cleavage by a restriction enzyme treatment, (6) a derived CAPS (dCAPS) method in which a set of primers including a mismatch is intentionally used so that the presence/absence of a mutation can be determined by the presence/absence of cleavage by restriction enzymes, (7) a method (e.g., a PCR method in which a TaqMan probe is used, MassARRAY analysis) in which the presence/absence of a mutation is determined by identifying, by use of a probe which specifically hybridizes to a mutant sequence, whether or not a probe is hybridized, and (8) a method in which, in a case where the mutation is deletion or insertion, the mutation is detected by a difference in mobility of electrophoresis. Alternatively, the mutation of a gene can be determined by detection (e.g., Western blotting) of (i) a polypeptide which results from modification of the gene or (ii) an expression level of a wild-type polypeptide.

Prior to the above-described step of introducing a mutation, procedures (1 and 2) described below are carried out as necessary so as to determine a gene which leads to functional suppression.

1. Isolation of Tobacco Gene which is Predicted to Regulate Development of Axillary Bud A gene, which possibly regulates axillary buds, can be obtained from genes of tobacco by (i) selecting a gene from other plants based on a prior art document (e.g., Non-Patent Literature in which a relationship between a gene and an axillary bud is confirmed) and (ii) using, as an index, identity of nucleotide sequence and identity of amino acid sequence of the selected genes. For example, a nucleotide sequence and an amino acid sequence of a publicly-known tobacco gene or a gene of a plant species (e.g., tomato) which is closely related to tobacco can be obtained by conducting a search in sequences registered in a publicly-known database with use of Basic Local Alignment Search Tool (blast). In a case where a publicly-known sequence is of a partial length, a full-length cDNA can be obtained from known sequence information by a common method such as (i) screening from a cDNA library or (ii) Rapid amplification of cDNA ends (Race) method.

A novel gene, which possibly regulates the development of an axillary bud, can be obtained by, for example, selecting a gene which is expressed according to a target tissue or a treatment. The target tissue or the treatment can be selected based on information listed below. It is known that (i) a gene, which is involved in the formation of an axillary meristem, is expressed prior to the formation of the axillary meristem and (ii) a gene, which is involved in maintenance or growth of an axillary meristem, is expressed at the axillary meristem (e.g., LS, Blind gene). It is known that a gene, which is involved in dormancy or development of an axillary bud, is expressed in an increased or decreased amount, depending on the dormancy or non-dormancy of the axillary bud (e.g., BRANCHED1). It is also known that some plant hormones are involved in the regulating of axillary buds. Auxin is involved in apical dominance. Strigolactone is involved in suppression of the development of axillary buds. Cytokinin is involved in outgrowth of axillary buds. Abscisic acid is involved in dormancy.

New selection of a gene which possibly regulates the development of an axillary bud can be performed by a common method in which expression specificity is utilized. The following (1) through (3) are examples of the method. (1) Methods such as (a) a method in which gene expression profiling data is obtained from a nucleotide sequence of cDNA, (b) a method in which a cDNA library of genes that are expressed in a subject tissue is prepared and then a terminal sequence is sequenced, and (c) a Serial Analysis of Gene Expression (SAGE) method in which restriction fragments are connected in series and sequenced. (2) A method in which gene expression profiling data is obtained by differential hybridization. Macro arrays and DNA chips are well known. (3) Genes (Differentially Expressed Genes: DEGs) which differ in expression level between a plurality of samples can be obtained by a differential display method. Examples encompass a method in which the amounts of PCR amplification fragments are compared.

Amplification of Isolated Genes

Amplification of a polynucleotide can be performed by Polymerase Chain Reaction (PCR), but alternatively can be performed by, for example, Ligase Chain Reaction (LCR) or Loop-Mediated Isothermal Amplification (LAMP).

A primer for amplifying a polynucleotide only needs to be a primer which enables specific amplification of a target gene of each genome from tobacco genomes in which genes of an S genome and a T genome are mixed. Provided that the target gene can be specifically amplified, one or more substitutions, deletions, insertions, and additions can be included. In addition, as necessary, the primer can be labeled with, for example, a fluorescent substance or a radiation.

Extraction of genomic DNA to be used as a template of the amplification can be performed by a publicly-known method, and can be performed by using a commercially available extraction kit. Genomic DNA can be a partially purified one obtained through simple extraction or can be a purified one obtained through a purification step.

2. Identification of Gene which is Expected to be Involved in Development of Axillary Bud Effects of a target gene can be confirmed by (i) preparing recombinants and mutants in which expressions and functions of the target gene are suppressed and (ii) cultivating the recombinants and the mutants in a greenhouse, a phytotron, a semi-containment greenhouse, or a field. By comparing the number and weight of developed axillary buds with the controls, it is possible to confirm effects of the outgrowth and development of axillary buds. While the number and weight of the axillary buds can be performed without performing topping, the number and weight of the axillary buds is preferably performed while (i) the axillary buds are in a non-dormancy state due to topping and (ii) the development of the axillary buds are therefore promoted. Examination of the number and weight of the axillary buds can be performed once or more than once in any season. In a case where the examinations are performed a plurality of times, it is preferable to perform examinations at intervals. For example, it is possible to carry out the following method once each week: to count the number of primary axillary buds, collect the primary axillary buds, and examine the weight of the primary axillary buds.

The examination can be performed with the focus only on specific axillary buds (e.g., primary axillary buds), or the examination can be performed such that examination with the focus only on the number of axillary buds and examination with the focus only on the weight are separately performed. In such a case, it is preferable that a suitable number of times of examinations and suitable intervals between the examinations are determined according to each examination.

[3. Other Remarks]

Another aspect of the present invention provides a method of determining a tobacco plant in which the development of primary axillary buds is suppressed. The suppression of the primary axillary buds is caused by introducing a mutation which causes functional suppression of the above-described at least two genes in a tobacco plant. It should be noted that the above functional suppression is to suppress the development of primary axillary buds. That is, the determining method can be used for, for example, a method of producing a tobacco plant. Therefore, for details of the determining method, a reference can be made to the previous descriptions regarding the method of producing the tobacco plant.

In addition, other aspects of the present invention provide (1) a leaf tobacco harvested from (i) the tobacco plant, (ii) a tobacco plant obtained by the production method described above; (iii) a tobacco plant determined by the determining method described above; (iv) a tobacco plant obtained by the breeding method; or (v) the offspring or the bred progeny described above, (2) a cured tobacco obtained from the leaf tobacco, and (3) a tobacco product obtained from the cured tobacco. Therefore, reference can be made to the previous descriptions for the details of the tobacco plant and the tobacco plant production method for obtaining (1) the leaf tobacco, (2) the cured tobacco, and (3) the tobacco product.

(Recap)

With the above embodiments considered together, the present invention can be summarized as follows.

Specifically,

[1] A tobacco plant in which a mutation causing functional suppression of at least two genes of the following genes (1) through (3) is introduced into a genome:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

In the tobacco plant, the functional suppression preferably causes the number or weight of the primary axillary buds to decrease to not more than ½ of that of a wild-type plant.

In the tobacco plant, the functional suppression is preferably a decrease, as compared with a wild-type plant, in abundance of the polypeptides which are expression products of the at least two genes.

In the tobacco plant, the functional suppression is preferably a decrease, as compared with a wild-type plant, in an amount of translation of the polypeptides which are expression products of the at least two genes.

In the tobacco plant, the functional suppression is preferably a decrease, as compared with a wild-type plant, in an amount of transcription from the at least two genes to mRNA.

In the tobacco plant, the functional suppression is preferably promotion of degradation of mRNAs transcribed from the gene.

In the tobacco plant, the mutation is preferably introduced into each of the at least two genes.

In the tobacco plant, the mutation is preferably introduced by spontaneous mutation, mutagen treatment, gene recombination, genome editing, or gene knockout.

In the plant, the mutation is preferably insertion, into an outside of a region in which the at least two genes are present, of a polynucleotide expressing a factor which promotes the degradation of the mRNA.

In the tobacco plant, the factor is preferably an antisense RNA molecule, an RNAi molecule, or a co-suppression molecule.

In the tobacco plant, the tobacco plant preferably belongs to *Nicotiana tabacum* or *Nicotiana rustica.*

A method of producing a tobacco plant, including the step of:

(A) introducing, into a genome of a tobacco plant, a mutation causing functional suppression of at least two genes of the following genes (1) through (3):

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

The tobacco plant production method preferably further includes the step of: (B) selecting, from individuals produced by the step (A), an individual in which development of the primary axillary buds is suppressed.

According to the tobacco plant production method, in the step (B), an individual, in which the number or weight of the primary axillary buds is decreased in comparison with that of a wild-type plant, is preferably selected.

According to the tobacco plant production method, in the step (A) preferably includes introducing the mutation into each of the at least two genes.

According to the tobacco plant production method, the step (A) is preferably carried out by spontaneous mutation, mutagen treatment, gene recombination, genome editing, or gene knockout.

According to the tobacco plant production method, the step (A) preferably includes inserting, into an outside of a region in which the at least two genes are present, a polynucleotide expressing a factor which promotes the degradation of the mRNAs transcribed from the at least two genes.

According to the tobacco plant production method, the factor is preferably an antisense RNA molecule, an RNAi molecule, or a co-suppression molecule.

A method of determining a tobacco plant in which development of primary axillary buds is suppressed, the method including the steps of:

(A) obtaining a sample by collecting a part of a tobacco plant;

(B) detecting, from a genome included in the sample, a mutation causing functional suppression of at least two genes of the following genes (1) through (3) on the genomic DNA:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l); and (C) determining that a tobacco plant, in which the mutation has been detected, is a tobacco plant in which the development of the primary axillary buds is suppressed, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A method of breeding a tobacco plant, including the step of: crossing the tobacco plants which are determined by the determining method as tobacco plants in which development of primary axillary buds is suppressed.

An offspring or a bred progeny, in which: the offspring is of (i) the tobacco plant, (ii) the tobacco plant produced by the production method; (iii) the tobacco plant determined by the determining method; or (iv) the tobacco plant bred by the breeding method; and the bred progeny is obtained by crossing (i) the tobacco plant, (ii) the tobacco plant produced by the production method; (iii) the tobacco plant determined by the determining method; or (iv) the tobacco plant bred by the breeding method.

A leaf tobacco harvested from (i) the tobacco plant, (ii) the tobacco plant produced by the production method; (iii) the tobacco plant determined by the determining method; (iv) the tobacco plant obtained by the breeding method; or (v) the offspring or the bred progeny.

A cured tobacco obtained from the leaf tobacco.

A tobacco product obtained from the cured tobacco.

The following description will discuss details of the embodiment of the present invention with reference to Examples. The present invention is of course not limited to the Examples below and particulars can have various aspects. Further, the present invention is not limited to the embodiments, but can be altered by those skilled person in the art within the scope of the claims. An embodiment derived from a proper combination of technical means disclosed in respective different embodiments is also encompassed in the technical scope of the present invention. Moreover, all the literatures described in this specification are hereby incorporated by reference.

EXAMPLES

Example 1: Candidate Gene Involved in Development of Axillary Buds of Tobacco Plant Candidate genes of tobacco orthologue of a plurality of genes (Revolutla (REV) of *Arabidopsis thaliana*, Lateral suppressor (LS) of tomato, and Blind (B1) of tomato) involved in the development of axillary buds of other plants were determined by Basic Local Alignment Search Tool (blast) analysis. The genes, which were obtained based on the analyses and the results of the analyses, will be described below.

(a) Blast Analysis

With an amino acid sequence of REV gene of *Arabidopsis thaliana* serving as a query, tblastn search was conducted on a web page of NCBI (http://blast.ncbi.nlm.nih.gov/Blast.cgi). As a result, REV homologous gene sequences of tomato having a high amino acid sequence identity of 80% were obtained. With an amino acid sequence of REV homologous gene of tomato serving as a query, tblastn search was conducted with respect to the results of analysis of Expressed Sequence Tag (EST) of cDNA library (derived from a mixture of leaves, shoot apex, and roots of Tsukuba No. 1). As a result, putative REV cDNA clones of tobacco were selected.

cDNA sequence of tobacco having an amino acid sequence identity of 87% with LS gene of tomato was registered in public DB (Accession number: EU935581). Furthermore, a tobacco EST sequence (Accession number: AM848584) having a high identity with EU935581 was registered in public DB.

With an amino acid sequence of B1 gene of tomato serving as a query, tblastn search was conducted with respect to the results of analysis of EST of cDNA library (derived from a mixture of leaves, shoot apex, and roots of Tsukuba No. 1). As a result, putative B1 clones of tobacco were selected.

(b) Preparation of Individual-Derived Genomic DNA Fragments and cDNA (Total RNA-Derived)

Genomic DNA fragments were extracted from leaves of tobacco (Tsukuba No. 1 or Petit Havana SR-1 (SR-1)) according to a simple extraction method or a CTAB method. The CTAB method is publicly known, and therefore will not be described in detail. The simple extraction method was carried out according to the following procedure. A leaf segment, which was placed in 0.3 ml to 0.5 ml of extraction buffer (0.2 M Tris-HCl pH 8.0, 0.4 M NaCl, 25 mM EDTA, and 0.5% SDS), was ground (2500 rpm, 1 minute) with use of Multi Beads Shocker (Yasui Kikai Corporation). A supernatant is taken from a homogenate after the grinding. Then, genomic DNA fragments are purified from the supernatant through ethanol precipitation.

Total RNA was extracted as follows. A shoot apex, a seedling, and an axillary bud of tobacco were each immersed in RNAlater (Ambion), and then cryopreserved. Then, these samples were thawed, and then 0.5 ml of an RTL buffer (QIAGEN), to which 20 μl of 1 M DTT had been added, was added to the thawed sample. A resultant mixture was ground (2500 rpm, 1 minute) with use of Multi Beads Shocker (Yasui Kikai Corporation). The homogenate after the grinding was subjected to centrifugal separation (15000 rpm, 10 minutes), so that a supernatant was obtained. From the supernatant, total RNA was purified with use of Magtration (Precision System Science Co., Ltd.) or RNeasy Kit (QIAGEN), in the presence of DNase.

From the total RNA, cDNA was prepared with use of any one of the following kits according to the manual included in the kit.

PrimeScript II 1st strand cDNA Synthesis Kit (Takara-Bio Inc.)

PrimeScript RT reagent kit with gDNA Eraser (Takara-Bio Inc.)

(c) Production of Candidate Genes

By RT-PCR in which the cDNA obtained in (b) was used as a template, three genes were amplified. In a case where PrimeSTAR Max DNA Polymerase (Takara-Bio Inc.) was used as an enzyme, the reaction conditions were set as follows.

30 seconds at 94° C.

30 cycles to 40 cycles while each cycle includes 10 seconds at 98° C., 5 seconds at 55° C., and 10 seconds at 72° C.

10 seconds at 72° C.*

An extension reaction at 72° C. was set to 10 seconds per kb of the length of an amplification fragment.

In a case where Tks Gflex DNA Polymerase (Takara-Bio Inc.) was used as an enzyme, the reaction conditions were set as follows.

30 seconds at 94° C.

30 cycles to 40 cycles while each cycle includes 10 seconds at 98° C., 15 seconds at 55° C., and 60 seconds at 68° C.

60 seconds at 68° C.*

An extension reaction at 68° C. was set to 60 seconds per kb of the length of an amplification fragment.

Combinations of a target gene and a primer for RT-PCR are as follows.

```
(Set 1: NtLS, T genome, seedling of Tsukuba No. 1)
Combination of LS_Tom_F1:
                                        (SEQ ID NO: 50)
AGGTTCTTCTTCCTTAATATTGAGTC,
and

NtLS_qRV1:
                                        (SEQ ID NO: 51)
ATCTAAGGCCTAAAGAGTGAGCAAAT
```

-continued

```
Combination of LS2_F2:
                                        (SEQ ID NO: 52)
ACACCTAATGCATCATCTAATGTT,
and

LS_Syl_R1:
                                        (SEQ ID NO: 53)
CAAATAAAGATTAAGTTCAGGATCTG

(Set 2: NtLS, S genome, seedling of Tsukuba No. 1)
Combination of LS_F2_seq:
                                        (SEQ ID NO: 54)
ATTTCCCCTCCTCCATCATTG,
and

NtLS_qRV1:
                                        (SEQ ID NO: 51)
ATCTAAGGCCTAAAGAGTGAGCAAAT

Combination of LS1_F2:
                                        (SEQ ID NO: 55)
CTTGACACCATCTAATGTTGTTG,
and

LS_Tom_R1:
                                        (SEQ ID NO: 53)
CAAATAAAGATTAAGTTCAGGATCTG

(Set 3: NtREV, T genome, seedling of Tsukuba
No. 1)
Combination of REV_RT_F2:
                                        (SEQ ID NO: 56)
AAGCTGTTTGCAGGGAATATATC,
and

G053330_RV3:
                                        (SEQ ID NO: 57)
TCTCTGGCTAAATGTTCGAAG

Combination of REV_RT_F3:
                                        (SEQ ID NO: 58)
GTAAGTTGTGAGTCTGTGGTAACTAC,
and

REV_RT_R1:
                                        (SEQ ID NO: 59)
GGAAACAAACATCTGCACTCAA

(Set 4: NtB11, S genome, seedling of Tsukuba
No. 1)
Combination of B11_F1seq2:
                                        (SEQ ID NO: 60)
GTCCATCTGTCTATATAGGTAGAATG,
and

B11-2_RT_R1:
                                        (SEQ ID NO: 61)
TGAATCTTCTTGGCAACCCCC
```

By genomic PCR in which the genomic DNA fragment obtained in (b) was used as a template, three genes were amplified. Since the enzymes used and the reaction conditions for the enzymes are similar to those in the RT-PCR, combinations of a target gene and a primer are as follows.

```
(Set 1: NtREV, S genome, leaves of Tsukuba No. 1)
Combination of REV_F3:
                                        (SEQ ID NO: 62)
TCTCAAAGCTGGCTGTTTTATGTAT,
and

REV_R14:
                                        (SEQ ID NO: 63)
TACCATTCTCCAGGGTGGTTGTGTAT

Combination of Ns_in4_F1:
                                        (SEQ ID NO: 64)
GAAAATTCAGTATTGCCATGTC,
```

-continued and

G053330_RV2: (SEQ ID NO: 65)

GCAAAAACTAGTTCAGAACA

Combination of NtREV_TrFW2: (SEQ ID NO: 66)

CACCGCCTATGTAGCTTCGTCAATG, and

NtREV_RT-R1: (SEQ ID NO: 59)

GGAAACAAACATCTGCACTCAA (Set 2: NtREV, T genome, leaves of Tsukuba No. 1)
Combination of REV_F3: (SEQ ID NO: 62)

TCTCAAAGCTGGCTGTTTTATGTAT, and

REV_R14: (SEQ ID NO: 63)

TACCATTCTCCAGGGTGGTTGTGTAT

Combination of Nt_in4_F1: (SEQ ID NO: 67)

AAAAAAATTCAGTATTGCCACGTGC, and

G053330_RV2: (SEQ ID NO: 65)

GCAAAAACTAGTTCAGAACA

Combination of NtREV_TrFW2: (SEQ ID NO: 66)

CACCGCCTATGTAGCTTCGTCAATG, and

NtREV_RT-R1: (SEQ ID NO: 59)

GGAAACAAACATCTGCACTCAA (Set 3: NtLS, S genome, leaves of Tsukuba No. 1)
Combination of LS_F1_seq: (SEQ ID NO: 50)

AGGTTCTTCTTCCTTAATATTGAGTC, and

LS_TRV_R3: (SEQ ID NO: 68)

TCGCTTGATTAGCAGTCAGC

Combination of LS_F1_seq: (SEQ ID NO: 50)

AGGTTCTTCTTCCTTAATATTGAGTC, and

NtLS_QPCR_RV1: (SEQ ID NO: 51)

ATCTAAGGCCTAAAGAGTGAGCAAAT

Combination of LS_TRV_F3: (SEQ ID NO: 69)

CACCGAAGAAACTGATGATCAACGG, and

LS_TRV_R2: (SEQ ID NO: 70)

GAAGACCTCTTTGTCCTTCACCATGCAG (Set 4: NtLS, T genome, leaves of Tsukuba No. 1)
Combination of LS_F2_seq: (SEQ ID NO: 54)

ATTTCCCCTCCTCCATCATTG, and

NtLS_QPCR_RV1: (SEQ ID NO: 51)

ATCTAAGGCCTAAAGAGTGAGCAAAT

-continued

Combination of LS_TRV_F3: (SEQ ID NO: 69)

CACCGAAGAAACTGATGATCAACGG, and

LS_TRV_R2: (SEQ ID NO: 70)

GAAGACCTCTTTGTCCTTCACCATGCAG (Set 5: NtB11, S genome, leaves of Tsukuba No. 1 and SR-1)
Combination of B11_F1seq2: (SEQ ID NO: 60)

GTCCATCTGTCTATATAGGTAGAATG, and

B11_R1seq: (SEQ ID NO: 71)

CACCATGTTTGATATTAGGCCTTA

Combination of B11_F3seq2: (SEQ ID NO: 72)

TGATGAGATTTATGTTGGGAACTG, and

B11_R2seq: (SEQ ID NO: 73)

TCTCATCATTGAACACGAACATACT (Set 6: NtB11, T genome, leaves of Tsukuba No. 1 and SR-1)
Combination of B11_F1seq1: (SEQ ID NO: 74)

CCACTTGTCTATATAGCAAGAAAGA, and

B11_R1seq: (SEQ ID NO: 71)

CACCATGTTTGATATTAGGCCTTA

Combination of B11_F2seq: (SEQ ID NO: 75)

CTAAGGCCTAATATCAAACATGGT, and

B11_R2seq: (SEQ ID NO: 73)

TCTCATCATTGAACACGAACATACT.

(d) Determination of Sequence of Genes Obtained

Each of the PCR products, which were obtained by amplifying the three genes, were cloned with use of Zero Blunt TOPO PCR Cloning Kit for Sequencing Kit (Life Technologies Corporation). As necessary, the PCR products were purified before the cloning by a common method in which agarose gel electrophoresis and MiniElute column (QIAGEN) were combined. The respective nucleotide sequences of the cloned genes were determined by a capillary sequencer 3730×1 DNA Analyzer (ABI) with use of BigDye (registered trademark) Terminator v3.1 Cycle Sequencing Kit (ABI).

Tobacco orthologous genes of B1, LS, and REV, which were determined as described above, were named NtB11 gene, NtLS gene, and NtREV gene.

(e) Determination of 5' Upstream Region and 3' Downstream Region

By genomic PCR in which the genomic DNA fragment obtained in (b) was used as a template, the full lengths of the three genes were amplified. Since the enzymes used and the reaction conditions for the enzymes are similar to those in the RT-PCR, combinations of a target gene and a primer are as follows.

(Set 1: NtREV, S genome, leaves of Tsukuba No. 1)
5' upstream Combination of REV_Sg_FW1:
(SEQ ID NO: 76)
AAGAACATTGGCTTTAGTCCTCTAA
and Ns_ex1_R1:
(SEQ ID NO: 77)
ACCATCACTCATCTAACTTATCCCAT 3' downstream Combination of REV_3Tg_F1:
(SEQ ID NO: 78)
AGACAGGAACACAGTTGAACGGA
and REV_Sg_RV1:
(SEQ ID NO: 79)
CTTGACAAACACTCTGATTCTACAC
or REV_Sg_RV2:
(SEQ ID NO: 80)
TTGAGATAGCTTGTATATTATGCATGC (Set 2: NtREV, T genome, leaves of Tsukuba No. 1)
5' upstream Combination of REV_Tg_FW1:
(SEQ ID NO: 81)
TTGTACCCATTGAAGGATGACTACT
and Nt_ex1_R1:
(SEQ ID NO: 82)
TCCATCACTGATCTAACTAATCCAAG 3' downstream Combination of REV_3Tg_F1:
(SEQ ID NO: 78)
AGACAGGAACACAGTTGAACGGA
and REV_Tg_RV2:
(SEQ ID NO: 83)
CACGGGCGTTACCTCCACTAGTAT (Set 3: NtLS, S genome, leaves of Tsukuba No. 1)
5' upstream Combination of LS_Sg_FW1:
(SEQ ID NO: 84)
AAGGTCATTAGAATATGCGGAGC
and

LS2-R1:
(SEQ ID NO: 85)
AACATTAGATGATGCATTAGGTGT

3' downstream Combination of LS1,2-F4:
(SEQ ID NO: 86)
GTGGAGGCTTTGGATTATTATG
and LS_Sg_RV1:
(SEQ ID NO: 87)
CGTCAGAACTTCGGATTAATTACTTC (Set 4: NtLS, T genome, leaves of Tsukuba No. 1)
5' upstream Combination of LS_Tg_Fw1:
(SEQ ID NO: 88)
AAATGAGGCCTGAGCACAAG
and

LS1-R1:
(SEQ ID NO: 89)
CAACAACATTAGATGGTGTCAAG

3' downstream Combination of LS1,2-F4:
(SEQ ID NO: 86)
GTGGAGGCTTTGGATTATTATG
and LS_Tg_Rv1:
(SEQ ID NO: 90)
TTATGGGATTTGATGATGCAGAG -continued (Set 5: NtB11, S genome, leaves of Tsukuba No. 1)
5' upstream Combination of B1_Sg_FW1:
(SEQ ID NO: 91)
ATATAGAAGGATGAGACATAGTAACATACC
and

B11-2_R1:
(SEQ ID NO: 92)
CTTTGTCCCTTCGATTCATGA

3' downstream Combination of B11-2_F4:
(SEQ ID NO: 93)
AGGCCTAAATCATCAGTCCA
and

B1_Sg_RV1:
(SEQ ID NO: 94)
GCTGGTGTCGATAATTGCTATTTAG (Set 6: NtB11, T genome, leaves of Tsukuba No. 1)
5' upstream Combination of B1_Tg_FW2:
(SEQ ID NO: 95)
GGCAGGATACTATTCTACCACTAGG
and

B11-1_R1:
(SEQ ID NO: 96)
CGCTTCGATTCTGGGAATAAG

3' downstream Combination of B11-1_F4:
(SEQ ID NO: 97)
TACAGGCCTAAATCAGTCCA
and

B1_Tg_RV2:
(SEQ ID NO: 98)
ATGTGAAGACAATGAATTCCGC (Set 7: NtB11, S genome, and leaves of SR-1)
5' upstream Combination of B1_Sg_FW3:
(SEQ ID NO: 99)
GCTCTCCTCTGATACATGGCTAT
and

B11-1,2_R1:
(SEQ ID NO: 100)
TGTTTCAGTCTCAAATTCAT

3' downstream Combination of B11-2_F4:
(SEQ ID NO: 93)
AGGCCTAAATCATCAGTCCA
and

B1_Sg_RV1:
(SEQ ID NO: 94)
GCTGGTGTCGATAATTGCTATTTAG
(Set 8: NtB11, T genome, and leaves of SR-1)

5' upstream Combination of B1_Tg_FW2:
(SEQ ID NO: 95)
GGCAGGATACTATTCTACCACTAGG
and

B11-1_R1:
(SEQ ID NO: 96)
CGCTTCGATTCTGGGAATAAG

3' downstream Combination of B11-1_F4:
(SEQ ID NO: 97)
TACAGGCCTAAATCAGTCCA
and

B1_Tg_RV2:
(SEQ ID NO: 98)
ATGTGAAGACAATGAATTCCGC

As described in the item (d) above, the sequences of 5' upstream region and 3' downstream region of the three genes were determined. The genome sequence of each gene in Tsukuba No. 1 and SR-1 was determined by combining, with termini of the sequence of each gene determined in the item (d) above, the respective sequences of 5' upstream region and 3' downstream region determined in the item (d) above (SEQ ID NOs: 13 through 18, 23, and 24).

Example 2: Effect of Mutations Simultaneously Introduced into Two Genes on Development of Primary Axillary Buds Tobacco plants, in which mutations were simultaneously introduced into two (instead of one) of the NtB11 gene, the NtLS gene, and the NtREV gene, were prepared according to (1) through (3) below.

(1. Preparation of Single Mutants of NtB11 Gene)

Single mutants of the NtB11 gene were prepared by CRISPR/Cas9 system. The procedures of the preparation will be described below.

(a) Preparation for Transformation

As a transformation vector for *Agrobacterium*, a binary vector pRI-201-AN (Takara-Bio Inc.) was used. Between NdeI-SalI of pRI-201-AN, pcoCas9 (Reference 1) which had been subjected to codon optimization for plants was introduced. Between KpnI-BamHI, a sgRNA expression cassette was introduced. As a promoter for guide sequence $GN_{20}GG$, AtU6-1 (Reference 2) was used. As a promoter for guide sequence $AN_{20}GG$, AtU3B (Reference 3) was used. As a scaffold-polyT sequence, the sequence reported in Reference 1 was used. Specifically, the sgRNA expression cassette was designed so that the guide sequence excluding PAM sequence (NGG) at 3' end is inserted between the promoter and the scaffold-polyT sequence. Life Technologies Corporation was entrusted with synthesis, through GeneArt (registered trademark) Strings (trademark) DNA Fragments, of sgRNA expression cassette in which KpnI site and BamHI site are added to 5' end and 3' end, respectively (Chem. 1). Cas9, in which NdeI site and SalI are added to 5' end and 3' end, respectively, was obtained through entrusting Takara-Bio Inc. with synthesis of the Cas9 (Chems. 2 and 3).

[Chem. 1]

(SEQ ID NO: 101)

aattggtaccTTTACTTTAAATTTTTTCTTATGCAGCCTGTGATGGATAA

CTGAATCAAACAAATGGCGTCTGGGTTTAAGAAGATCTGTTTTGGCTATG

TTGGACGAAACAAGTGAACTTTTAGGATCAACTTCAGTTTATATATGGAG

CTTATATCGAGCAATAAGATAAGTGGGCTTTTTATGTAATTTAATGGGCT

ATCGTCCATAGATTCACTAATACCCATGCCCAGTACCCATGTATGCGTTT

CATATAAGCTCCTAATTTCTCCCACATCGCTCAAATCTAAACAAATCTTG

TTGTATATATAACACTGAGGGAGCAACATTGGTCacaatgatatcaagaa ttacGTTTTAGAGCTAGAAATAGCAAGTTAAAATAAGGCTAGTCCGTTAT CAACTTGAAAAAGTGGCACCGAGTCGGTGCTTTTTTTggatccaatt The underlined portion indicates the guide sequence. The portion upstream to the underlined portion indicates the AtU3B promoter sequence. The portion downstream to the underlined portion indicates the scaffold-polyT sequence. The lower case letters at the terminus indicate restriction enzyme sequences of KpnI and BamHI.

[Chem. 2]

Cas9 sequence (SEQ ID NO: 102)

catATGGATTACAAGGATGATGATGATAAGGATTACAAGGATGATGATGA

TAAGATGGCTCCAAAGAAGAAGAGAAAGGTTGGAATCCACGGAGTTCCAG

-continued

CTGCTGATAAGAAGTACTCTATCGGACTTGACATCGGAACCAACTCTGTT

GGATGGGCTGTTATCACCGATGAGTACAAGGTTCCATCTAAGAAGTTCAA

GGTTCTTGGAAACACCGATAGACACTCTATCAAGAAGAACCTTATCGGTG

CTCTTCTTTTCGATTCTGGAGAGACCGCTGAGGCTACCAGATTGAAGAGA

ACCGCTAGAAGAAGATACACCAGAAGAAAGAACAGAATCTGCTACCTTCA

GGAAATCTTCTCTAACGAGATGGCTAAGGTTGATGATTCTTTCTTCCACA

GACTTGAGGAGTCTTTCCTTGTTGAGGAGGATAAGAAGCACGAGAGACAC

CCAATCTTCGGAAACATCGTTGATGAGGTTGCTTACCACGAGAAGTACCC

AACCATCTACCACCTTAGAAAGAAGTTGGTTGATTCTACCGATAAGGCTG

ATCTTAGACTTATCTACCTTGCTCTTGCTCACATGATCAAGTTCAGAGGA

CACTTCCTTATCGAGGGAGACCTTAACCCAGATAACTCTGATGTTGATAA

GTTGTTCATCCAGCTTGTTCAGACCTACAACGAGCTTTTCGAGGAGAACC

CAATCAACGCTTCTGGAGTTGATGCTAAGGCTATCCTTTCTGCTAGACTT

TCTATCTCGTAGACTTGAGAACCTTATCGCTCAGCTTCCAGGAGAGAAGA

AGAACGGACTTTTCGGAAACCTTATCGCTCTTTCTCTTGGACTTACCCCA

AACTTCAAGTCTAACTTGGATCTTGCTGAGGATGCTAAGTTGCAGCTTTC

TAAGGATACCTACGATGATGATCTTGATAACCTTCTTGCTCAGATCGGAG

ATCAGTACGCTGATCTTTTCCTTGCTGCTAAGAACCTTTCTGATGCTATC

CTTCTTTCTGACATCCTTAGAGTTAACACCGAGATCACCAAGGCTCCACT

TTCTGCTTCTATGATCAAGAGATACGATGAGCACCACCAGGATCTTACCC

TTTTGAAGGCTCTTGTTAGACAGCAGCTTCCAGAGAAGTACAAGGAAATC

TTCTTCGATCAGTCTAAGAACGGATACGCTGGATACATCGATGGAGGAGC

TTCTCAGGAGGAGTTCTACAAGTTCATCAAGCCAATCCTTGAGAAGATGG

ATGGAACCGAGGAGCTTCTTGTTAAGTTGAACAGAGAGGATCTTCTTAGA

AAGCAGAGAACCTTCGATAACGGATCTATCCCACACCAGATCCACCTTGG

AGAGCTTCACGCTATCCTTGGTAGACAGGAGGATTTCTACCCATTCTTGA

AGGATAACAGAGAGAAGATCGAGAAGATCCTTACCTTCAGAATCCCATAC

TACGTTGGACCACTTGCTAGAGGAAACTCTCGTTTCGCTTGGATGACCAG

AAAGTCTGAGGAGACCATCACCCCTTGGAACTTCGAGGAGGTAAGTTTCT

GCTTCTACCTTTGATATATATATAATAATTATCATTAATTAGTAGTAATA

TAATATTTCAAATATTTTTTTCAAAATAAAAGAATGTAGTATATAGCAAT

TGCTTTTCTGTAGTTTATAAGTGTGTATATTTTAATTTATAACTTTTCTA

ATATATGACCAAAATTTGTTGATGTGCAGGTTGTTGATAAGGGAGCTTCT

GCTCAGTCTTTCATCGAGAGAATGACCAACTTCGATAAGAACCTTCCAAA

CGAGAAGGTTCTTCCAAAGCACTCTCTTCTTTACGAGTACTTCACCGTTT

ACAACGAGCTTACCAAGGTTAAGTACGTTACCGAGGGAATGAGAAAGCCA

GCTTTCCTTTCTGGAGAGCAGAAGAAGGCTATCGTTGATCTTCTTTTCAA

GACCAACAGAAAGGTTACCGTTAAGCAGTTGAAGGAGGATTACTTCAAGA

AGATCGAGTGCTTCGATTCTGTTGAAATCTCTGGAGTTGAGGATAGATTC

AACGCTTCTCTTGGAACCTACCACGATCTTTTGAAGATCATCAAGGATAA

GGATTTCCTTGATAACGAGGAGAACGAGGACATCCTTGAGGACATCGTTC

-continued

```
TTACCCTTACCCTTTTCGAGGATAGAGAGATGATCGAGGAGAGACTCAAG

ACCTACGCTCACCTTTTCGATGATAAGGTTATGAAGCAGTTGAAGAGAAG

AAGATACACCGGATGGGGTAGACTTTCTCGTAAGTTGATCAACGGAATCA

GAGATAAGCAGTCTGGAAAGACCATCCTTGATTTCTTGAAGTCTGATGGA

TTCGCTAACAGAAACTTCATGCAGCTTATCCACGATGATTCTCTTACCTT

CAAGGAGGACATCCAGAAGGCTCAGGTTTCTGGACAGGGAGATTCTCTTC

ACGAGCACATCGCTAACCTTGCTGGATCTCCAGCTATCAAGAAGGGAATC

CTTCAGACCGTTAAGGTTGTTGATGAGCTTGTTAAGGTT
```

The sequence continues to the next page.

[Chem. 3]

Continuation of Cas9 sequence

```
ATGGGTAGACACAAGCCAGAGAACATCGTTATCGAGATGGCTAGAGAGAA

CCAGACCACCCAGAAGGGACAGAAGAACTGTCGTGAGAGAATGAAGAGAA

TCGAGGAGGGAATCAAGGAGCTTGGATCTCAAATCTTGAAGGAGCACCCA

GTTGAGAACACCCAGCTTCAGAACGAGAAGTTGTACCTTTACTACCTTCA

GAACGGAAGAGATATGTACGTTGATCAGGAGCTTGACATCAACAGACTTT

CTGATTACGATGTTGATCACATCGTTCCACAGTCTTTCTTGAAGGATGAT

TCTATCGATAACAAGGTTCTTACCCGTTCTGATAAGAACAGAGGAAAGTC

TGATAACGTTCCATCTGAGGAGGTTGTTAAGAAGATGAAGAACTACTGGA

GACAGCTTCTTAACGCTAAGTTGATCACCCAGAGAAAGTTCGATAACCTT

ACCAAGGCTGAGAGAGGAGGACTTTCTGAGCTTGATAAGGCTGGATTCAT

CAAGAGACAGCTTGTTGAGACCAGACAGATCACCAAGCACGTTGCTCAGA

TCCTTGATTCTCGTATGAACACCAAGTACGATGAGAACGATAAGTTGATC

AGAGAGGTTAAGGTTATCACCTTGAAGTCTAAGTTGGTTTCTGATTTCAG

AAAGGATTTCCAGTTCTACAAGGTTAGAGAGATCAACAACTACCACCACG

CTCACGATGCTTACCTTAACGCTGTTGTTGGAACCGCTCTTATCAAGAAG

TACCCAAAGTTGGAGTCTGAGTTCGTTTACGGAGATTACAAGGTTTACGA

TGTTAGAAAGATGATCGCTAAGTCTGAGCAGGAGATCGGAAAGGCTACCG

CTAAGTACTTCTTCTACTCTAACATCATGAACTTCTTCAAGACCGAGATC

ACCCTTGCTAACGGAGAGATCAGAAAGAGACCACTTATCGAGACCAACGG

AGAGACCGGAGAGATCGTTTGGGATAAGGGAAGAGATTTCGCTACCGTTA

GAAAGGTTCTTTCTATGCCACAGGTTAACATCGTTAAGAAAACCGAGGTT

CAGACCGGAGGATTCTCTAAGGAGTCTATCCTTCCAAAGAGAAACTCTGA

TAAGTTGATCGCTAGAAAGAAGGATTGGGACCCAAAGAAGTACGGAGGAT

TCGATTCTCCAACCGTTGCTTACTCTGTTCTTGTTGTTGCTAAGGTTGAG

AAGGGAAAGTCTAAGAAGTTGAAGTCTGTTAAGGAGCTTCTTGGAATCAC

CATCATGGAGCGTTCTTCTTTCGAGAAGAACCCAATCGATTTCCTTGAGG

CTAAGGGATACAAGGAGGTTAAGAAGGATCTTATCATCAAGTTGCCAAAG

TACTGTCTTTTCGAGCTTGAGAACGGAAGAAAGAGAATGCTTGCTTCTGC

TGGAGAGCTTCAGAAGGGAAACGAGCTTGCTCTTCCATCTAAGTACGTTA
```

-continued

```
ACTTCCTTTACCTTGCTTCTCACTACGAGAAGTTGAAGGGATCTCCAGAG

GATAACGAGCAGAAGCAGCTTTTCGTTGAGCAGCACAAGCACTACCTTGA

TGAGATCATCGAGCAAATCTCTGAGTTCTCTAAGAGAGTTATCCTTGCTG

ATGCTAACCTTGATAAGGTTCTTTCTGCTTACAACAAGCACAGAGATAAG

CCAATCAGAGAGCAGGCTGAGAACATCATCCACCTTTTCACCCTTACCAA

CCTTGGTGCTCCAGCTGCTTTCAAGTACTTCGATACCACCATCGATAGAA

AAAGATACACCTCTACCAAGGAGGTTCTTGATGCTACCCTTATCCACCAG

TCTATCACCGGACTTTACGAGACCAGAATCGATCTTTCTCAGCTTGGAGG

AGATAAGAGACCAGCTGCTACCAAGAAGGCTGGACAGGCTAAGAAGAAGA

AGTGAgtcgac
```

In the above Cas9 sequence over 2 pages, the underlined portions indicate the NdeI sequence and the SalI sequence.

With use of pRI201-AN in which the Cas9 and the sgRNA expression cassette were introduced, *Agrobacterium* LBA4404 was transformed by electroporation. The *Agrobacterium* was grown on an AB plate containing kanamycin at 25 μg/ml. Then, *Agrobacterium* of a single colony was isolated.

(b) Transformation of Tobacco and Cultivation of Transformant

Segments of a cotyledon collected from tobacco (variety: SR-1) 10 days after sowing were co-cultured for 3 days with the transformed *Agrobacterium* obtained as described above. Then, the *Agrobacterium* was then removed from the segments of the cotyledon by washing the segments with use of distilled water containing an antibacterial agent (cefotaxime). Then, the *Agrobacterium* was completely removed by culturing, for 4 days, the washed segments of the cotyledon in Linsmaier and Skoog medium containing an antibacterial agent. Then, the segments of the cotyledon were transferred to and cultured in Linsmaier and Skoog medium containing antibiotics (kanamycin), so that redifferentiated individuals (shoots) having kanamycin resistance were obtained. The shoots were transferred to Linsmaier and Skoog rooting medium and then rooted. From the rooted shoots, individuals having high-level expression of Cas9 mRNA (having an expression level twice as much or higher in comparison with eukaryotic elfa which is the reference) were selected, and then transplanted into and grown in a 9-cm pot containing soil for transplantation (Compost: 40 L, wild soil: 30 L, Akadama soil (small): 10 L, Akadama soil (medium): 10 L, vermiculite: 10 L, fertilizer (S625): 1000 g).

(c) Confirmation of Presence/Absence of Mutation and Mutant Sequence

PCR was performed by use of Tks Gflex (trademark) DNA polymerase (Takara-Bio Inc.) with genomic DNA as a template, which genomic DNA was extracted from a leaf of a transformant of tobacco. The reaction conditions and primers of the PCR are as follows.

(Reaction Conditions)

30 seconds at 94° C.

40 cycles while each cycle includes 10 seconds at 98° C., 15 seconds at 55° C., and 60 seconds at 68° C.

60 seconds at 68° C.

(Primers)

```
T genome
Combination of NtBl1-1_2A_F1:
                                  (SEQ ID NO: 103)
AAGTATTACTACTACAAAATTCCAACG,
and
```

-continued

```
Nb_B11_2A_R1:
                                   (SEQ ID NO: 104)
CCATCTGATGAAGAACAACTTGC

S genome
Combination of NtB11-2_1A_F1:
                                   (SEQ ID NO: 105)
TTAAACACTAGAGAGTGAGAGAGTGC,
and

NtB11-2_2A_F1:
                                   (SEQ ID NO: 106)
CAGATGTTTAATTATTAAGACAAAGTTCC.
```

After the PCR reactions, denaturation and annealing were performed under the following conditions. Denaturation: 5 minutes at 95° C., annealing: 1 second at 85° C./1 second at 85° C., 1 second at 60° C., constant at 30° C. The Ramp Rate at 85° C. to 60° C. was 5% (drop rate of 0.1° C./second), and the Ramp Rate at 60° C. to 30° C. was 10% (drop rate of 0.1° C./second). The PCR products of 5 μl after the denaturation and annealing were treated in a reaction system of 10 μl with use of T7 endonuclease I (New England Biolabs) of 1 U, and then were separated by electrophoresis. Then, it was checked whether or not the PCR products were cleaved by the enzyme. Separately, the PCR products were cloned with use of Zero Blunt TOPO PCR Cloning Kit (Life Technologies Corporation), and the nucleotide sequence of the clone was determined.

(d) Selection of Recombinant

Individuals of T0 generation having mutations (deletion or insertion of 1 or more bases) in a T genome and an S genome were selfed and collected, so that a T1 line was obtained. The presence/absence of the mutations in the individuals of the T1 line was confirmed as in (c) above. Based on the results of the confirmation, individuals of a T1 line (T+S+) having homozygous mutations in a T genome and an S genome were selfed so that individuals of a T2 line (T+S+) were obtained.

Mutant polypeptide in individuals of T2 line obtained 2A-1_121, 2A-1_126, 2A-133_1, 2A-161_17 (B11-1: 1b deletion)

While WT consists of 336 amino acids, a polypeptide is produced such that unrelated 12 amino acids (TGILNSRKSLWD (SEQ ID NO: 107)) are added in addition to up to 107 amino acids identical to those of WT.

2A-1_121, 2A-1_126 (B11-2: 5b deletion)

While WT consists of 338 amino acids, a polypeptide is produced such that unrelated 3 amino acids (LEY) are added in addition to up to 106 amino acids identical to those of WT.

2A-133_1 (B11-2: 3b deletion)

337 amino acids in which 107th N (asparagine) is deleted from 338 amino acids constituting WT 2A-161_8, 2A-161_122 (B11-1: 22b deletion)

While WT consists of 336 amino acids, a polypeptide is produced such that unrelated 11 amino acids (EILNSRKSLWD (SEQ ID NO: 108)) are added in addition to up to 101 amino acids identical to those of WT.

2A-161_8, 2A-161_17, 2A-161_122 (B11-2: 2b deletion)

While WT consists of 338 amino acids, a polypeptide is produced such that unrelated 4 amino acids (KLEY (SEQ ID NO: 166)) are added in addition to up to 106 amino acids identical to those of WT.

Of the recombinants thus selected, 2A-1_121 (in which 1 base is deleted in NtB11 of T genome, and 5 bases are deleted in NtB11 of S genome) was used for preparation of double mutants.

(2. Mutant Produced by EMS Treatment)

(a) Screening of Mutant

Seeds were subjected to ethylmethane sulfonate (EMS) treatment so that mutant panel (TUM) of tobacco (variety: Tsukuba No. 1) was prepared (Literature: The 2011 Annual Meeting of the Phytopathological Society of Japan, P234, "Construction of mutant panel in *Nicotiana tabacum* L."). This mutant panel consists of (i) a set of seeds (M2 bulk seeds) of selfed mutant progeny obtained from each individual (M1 generation) bred from several thousands of seeds which were subjected to the EMS treatment as a mutagen treatment and (ii) a set of bulk DNA extracted from seedlings of 8 individuals of each line grown from the sown M2 seeds. Mutants having mutations in NtREV or NUS were selected based on the results of performing, with this DNA samples as a template, Single-strand conformation polymorphism (SSCP) analysis of genomes of a mutant library or direct sequencing of PCR amplification fragments. In the SSCP, the target site was amplified by PCR using PCR primers to which fluorescent dye was binding. Then, the amplified fragments were detected with use of a capillary electrophoresis apparatus (ABI 3130×1DNA analyzer). With use of QIAGEN Multiplex PCR Kit (QIAGEN), PCR was performed according to the manual included in the kit. The sequences of the PCR primers are as follows.

```
(NtLS, S genome)
Combination of LS_F2_seq:
                                   (SEQ ID NO: 54)
ATTTCCCCTCCTCCATCATTG,
and

LS1-R1:
                                   (SEQ ID NO: 89)
CAACAACATTAGATGGTGTCAAG

Combination of LS1-F2:
                                   (SEQ ID NO: 55)
CTTGACACCATCTAATGTTGTTG,
and

NtLS_QPCR_RV1:
                                   (SEQ ID NO: 51)
ATCTAAGGCCTAAAGAGTGAGCAAAT

Combination of LS1,2-F3:
                                  (SEQ ID NO: 109)
TTCGTAGAACCGGAGATCGT,
and

LS1,2_R3:
                                  (SEQ ID NO: 110)
GCAAAGTTGCTTCCAATGAAT

Combination of LS1,2_F4:
                                   (SEQ ID NO: 86)
GTGGAGGCTTTGGATTATTATG,
and

N.t_LS_TRV_R2:
                                   (SEQ ID NO: 70)
GAAGACCTCTTTGTCCTTCACCATGCAG

(NtLS, T genome)
Combination of LS_F2_seq:
                                   (SEQ ID NO: 54)
ATTTCCCCTCCTCCATCATTG,
and

LS2-R1:
                                   (SEQ ID NO: 85)
AACATTAGATGATGCATTAGGTGT

Combination of LS2-F2:
                                   (SEQ ID NO: 52)
ACACCTAATGCATCATCTAATGTT,
```

-continued and

NtLS_QPCR_RV1:

(SEQ ID NO: 51)

ATCTAAGGCCTAAAGAGTGAGCAAAT

Combination of LS1,2-F3:

(SEQ ID NO: 109)

TTCGTAGAACCGGAGATCGT,
and

LS1,2_R3:

(SEQ ID NO: 110)

GCAAAGTTGCTTCCAATGAAT

Combination of LS1,2_F4:

(SEQ ID NO: 86)

GTGGAGGCTTTGGATTATTATG,
and

N.t_LS_TRV_R2:

(SEQ ID NO: 70)

GAAGACCTCTTTGTCCTTCACCATGCAG
(NtREV, S genome)

Combination of Nt_in0_F1:

(SEQ ID NO: 111)

TTGGTTTGGGATTTTGAGGTTTGAGG,
and

Nt_ex1_R1:

(SEQ ID NO 82)

TCCATCACTGATCTAACTAATCCAAG:

Combination of Ns_in1_F1:

(SEQ ID NO: 112)

TTTGGAATTGAGGGTGAACATTGTGC,
and

Ns_in2_R1:

(SEQ ID NO: 113)

ACGTTACCATTCGTCTACAGTAAGC

Combination of Ns_in2_F1:

(SEQ ID NO: 114)

CCAATAAACAAGAAACAGATGATGG,
and

Ns_in3_R1:

(SEQ ID NO: 115)

GAATGGACACCATAGACGGAAAGGA

Combination of Ns_in3_F1:

(SEQ ID NO: 116)

TTTCCGTCTATGGTGTCCATTCTCC,
and

Ns_in4_R1:

(SEQ ID NO: 117)

GAGACATGGCAATACTGAATTTTCA

Combination of Ns_in4_F1:

(SEQ ID NO: 64)

GAAAATTCAGTATTGCCATGTC,
and

Ns_in6_R1:

(SEQ ID NO: 118)

AGCCTACGTGAAGATTGATGAGAAG
(NtREV, T genome)

Combination of Nt_in0_F1:

(SEQ ID NO: 111)

TTGGTTTGGGATTTTGAGGTTTGAGG,
and

Nt_ex1_R1:

(SEQ ID NO: 82)

TCCATCACTGATCTAACTAATCCAAG

-continued

Combination of Nt_in1_F1:

(SEQ ID NO: 119)

TCGATTGGGTTGTATGAGTTAACCGT,
and

Nt_in2_R1:

(SEQ ID NO: 120)

GTTACCATAAGCTGTGGAATATCAGG

Combination of Nt_in2_F1:

(SEQ ID NO: 121)

AACCAATGGACAAGAAACGGATGGCA,
and

Nt_in4_R1:

(SEQ ID NO: 122)

TTTAGCTATCCAGTCAAAGAGGCACG

Combination of Nt_in4_F1:

(SEQ ID NO: 67)

AAAAAAATTCAGTATTGCCACGTGC,
and

Nt_in6_R1:

(SEQ ID NO: 123)

AGCCTACGTGAAGATTGATGAGAAA

The sequence of the genes into which the mutation was introduced was identified by (i) cloning PCR amplification fragments obtained from the genomes of mutants of M2 generation and (ii) determining the nucleotide sequence of fragments of the clones. The differences between polypeptide (MT), which were expressed by the genes into which mutations was introduced and wild-type polypeptide (WT), are as follows.

The polypeptide (Ns1630, SEQ ID NO: 29) expressed by NtREV into which a mutation at an S genome was introduced had the following difference from the wild-type polypeptide.

Mt: 111aa, Wt: 838aa

The full length was shortened to 111aa due to the fact that 112th glutamine (Q) was changed to a stop codon.

The polypeptide (Nt1605, SEQ ID NO: 30) expressed by NtREV into which a mutation at a T genome was introduced had the following difference from the wild-type polypeptide.

MT: 116aa, WT: 838aa

The full length was shortened to 116aa due to the fact that 117th glutamine (Q) was changed to a stop codon.

The polypeptide (Nt5850, SEQ ID NO: 31) expressed by NtREV into which a mutation at a T genome was introduced had the following difference from the wild-type polypeptide.

MT: 68aa, WT: 838aa

The full length was shortened to 68aa due to the fact that 69th glutamine (Q) was changed to a stop codon.

The polypeptide (Nt1145, SEQ ID NO: 32) expressed by NtLS into which a mutation at a T genome was introduced had the following difference from the wild-type polypeptide.

Mt: 398aa, Wt: 410aa

The full length was shortened to 398aa due to the fact that 399th glutamine (Q) was changed to a stop codon.

The polypeptide (Nt1025, SEQ ID NO: 33) expressed by NtLS into which a mutation at a T genome was introduced had the following difference from the wild-type polypeptide.

Mt: 145aa, Wt: 410aa

The full length was shortened to 145aa due to the fact that 146th glutamine (Q) was changed to a stop codon.

The polypeptide (Ns369, SEQ ID NO: 34) expressed by NtLS into which a mutation at an S genome was introduced had the following difference from the wild-type polypeptide.

Mt: 163aa, Wt: 407aa

The full length was shortened to 163aa due to the fact that 164th glutamine (Q) was changed to a stop codon.

(b) Selection of Desired Mutant from M2 Mutant Population

From the M2 mutant population predicted to have mutations in the target genes, mutants ($T^+S^+$) homozygously having a mutation in each target gene in both a T genome and an S genome and mutants ($T^-S^-$) having no mutation in each target gene in both a T genome and an S genome were prepared according to the following procedure.

First, the following 4 groups were selected from the M2 mutant population:

M2 mutants ($T^+$) homozygously having mutations in target gene in T genome

M2 mutants ($S^+$) homozygously having mutations in target gene in S genome

M2 mutants ($T^-$) having no mutation in target gene in T genome

M2 mutants ($S^-$) having no mutation in target gene in S genome

Then, F1 line prepared by crossing $T^+$ and $S^+$ was selfed, so that target F2 mutants ($T^+S^+$) were prepared. $T^-S^-$ was likewise prepared.

In the procedure above, Cycleave PCR method was carried out as described in the next paragraph in order to determine the presence/absence of a mutation on a genome. Genomic DNA which was extracted by use of a simple extraction method was used as a template in the Cycleave PCR for checking a mutation of NtREV gene. Fragments, which had been obtained by selectively subjecting only S genome or T genome to PCR amplification from genomic DNA, were 300-fold to 500-fold diluted and then used as templates in the Cycleave PCR for examining a mutation of NtLS gene. The PCR was performed with use of Tks Gflex (trademark) DNA polymerase (Takara-Bio Inc.). The reaction conditions and primers of the PCR are as follows.

(Reaction conditions)

30 seconds at 94° C.

35 cycles while each cycle includes 10 seconds at 98° C., 15 seconds at 55° C., and 90 seconds at 68° C.

90 seconds at 68° C.

(Primers)

```
T genome
Combination of NtLS_prePCR_Ntom_F1:
                                    (SEQ ID NO: 124)
CCCAGACCCCCTTTTCCTCT,
and

NtLS_prePCR_Ntom_R1:
                                    (SEQ ID NO: 125)
AATTTCCCTTATAATTTAACGCC

S genome
Combination of NtLS_prePCR_Nsyl_F1:
                                    (SEQ ID NO: 126)
CCCTAGAGAGACCCCTTTTTC,
and

NtLS_prePCR_Nsyl_R1:
                                    (SEQ ID NO: 127)
GGGTTTTAAATTTAACGCCAA
```

The primers and probes for the Cycleave PCR method (Table 1) were designed with use of Cycleave (registered trademark) PCR Assay Designer (SNPs) which is available on a web page of Takara-Bio Inc. Along with the primers and probes, Cycleave PCR Reaction Mix (Takara-Bio Inc.) was used according to the manual provided by Takara-Bio Inc. to carry out the Cycleave PCR method. PCR reaction was made with use of Applied Biosystems (registered trademark) StepOnePlus (trademark) real-time PCR system (Thermo Fisher Scientific Inc.).

TABLE 1

| Gene | Primer/probe name | Sequence | Genome type |
|---|---|---|---|
| REV | Nt_5850_P2-1Primer F | GTGAATGCCCTATTCTGTC (SEQ ID NO: 128) | T genome |
| | Nt_5850_P2-1Primer R | ATCACTGATCTAACTAATCCAAG (SEQ ID NO: 129) | |
| | Nt_5850_P2-1Probe T-FAM | ctttgatct(A)ct 5'-Eclipse/3'-FAM (SEQ ID NO: 130) | |
| | Nt_5850_P2-1Probe C-HEX | tgatct(G)ctt 5'-Eclipse/3'-HEX (SEQ ID NO: 131) | |
| | Nt_1605_P4-2Primer F | ATTGATGGAGGAGAATGAT (SEQ ID NO: 132) | T genome |
| | Nt_1605_P4-2Primer R | GACAAGATACGTTAAGTGAAA (SEQ ID NO: 133) | |
| | Nt_1605_P4-2Probe T-FAM | acaagct(A)cg 5'-Eclipse/3'-FAM (SEQ ID NO: 134) | |
| | Nt_1605_P4-2Probe C-HEX | caagct(G)cg 5'-Eclipse/3'-HEX | |
| | Ns_1630_P3-1Primer F | CCATTTCAGGTGTCGAG (SEQ ID NO: 135) | S genome |
| | Ns_1630_P3-1Primer R | ACGTTACCATTCGTCTACAG (SEQ ID NO: 136) | |
| | Ns_1630_P3-1Probe T-FAM | tt(A)caagcga 5'-Eclipse/3'-FAM (SEQ ID NO: 137) | |
| | Ns_1630_P3-1ProbeC-HEX | gC(a)aaaacag 5'-Eclipse/3'-HEX (SEQ ID NO: 138) | |
| LS | 369_Ns-1Primer F | TCCCTAAACCAAGTGACTCC (SEQ ID NO: 139) | S genome |
| | 369_Ns-1Primer R | GGTATCAAGGTCATTTCCAG (SEQ ID NO: 140) | |
| | 369_Ns-1ProbeT-FAM | tgT(a)agcacta 5'-Eclipse/3'-FAM (SEQ ID NO: 141) | |
| | 369_Ns-1ProbeC-HEX | gC(a)agcact 5'-Eclipse/3'-HEX | |
| | L6_1145-3Primer F | AGAGGATGACAGTGGAGCAA (SEQ ID NO: 142) | T genome |
| | L6_1145-3Primer R | TAACGCCAAGAAGATATGGAA (SEQ ID NO: 143) | |
| | L6_1145-3ProbeT-FAM | ggT(a)aaatcaac 5'-Eclipse/3'-FAM (SEQ ID NO: 144) | |
| | L6_1145-3ProbeC-HEX | ggC(a)aaatca 5'-Eclipse/3'-HEX (SEQ ID NO: 145) | |
| | 1025_T547-3Primer F | GTTGAAAGTTCAAATGATTCAG (SEQ ID NO: 146) | T genome |
| | 1025_T547-3Primer R | GAGGAGGGTAACGATCAG (SEQ ID NO: 147) | |
| | 1025_T547-3Probe T-FAM | gcttgttA(g)tt 5'-Eclipse/3'-FAM (SEQ ID NO: 148) | |
| | 1025_T547-3Probe C-HEX | cttgttG(g)tta 5'-Eclipse/3'-HEX (SEQ ID NO: 149) | |

Of the mutants thus obtained, NtLS single mutants of 1 line (encoding Nt1145 in T genome and encoding Ns369 in S genome) were used for preparation of double mutants.

(3. Preparation of Double Mutants)

(a) Double Mutants of NtB11 and NtLS

Double mutants of the NtB11 gene and the NtLS gene were prepared by crossing (i) single mutants (T2 individuals) of the NtB11 gene obtained in the item 1. above and (ii) single mutants (F3 individuals) of the NtLS genes obtained in the item 2.

The individuals of the F1 line obtained by crossing the two single mutants were selfed, so that individuals of the F2 line were obtained. The mutations of two genes in each individual of the F2 line were analyzed according to the descriptions in the items 1. and 2. Furthermore, the F2 individuals selected according to the mutation were selfed, so that individuals of the F3 line were obtained. 2 lines (11_llbb and 45_llbb) having mutations in all of the alleles (8 alleles) in the two genes were obtained. In addition, 1 line (456_LLBB) having no mutation in any of the alleles was obtained. The individuals of these 3 lines were further selfed, so that individuals of the F4 line were obtained.

The polypeptides expressed by the mutations of the NtB11 gene and the NtLS gene in the double mutants are as follows.

The polypeptide (Nt1145 derived, SEQ ID NO: 32) expressed by NtLS into which a mutation at a T genome was introduced had the following difference from the wild-type polypeptide.

Mt: 398aa, Wt: 410aa

The full length was shortened to 398aa due to the fact that 399th glutamine (Q) was changed to a stop codon.

The polypeptide (Ns369 derived, SEQ ID NO: 34) expressed by NtLS into which a mutation at an S genome was introduced had the following difference from the wild-type polypeptide.

Mt: 163aa, Wt: 407aa

The full length was shortened to 163aa due to the fact that 164th glutamine (Q) was changed to a stop codon.

The polypeptide (2A-1_121 derived, SEQ ID NO: 35) expressed by NtB11 into which a mutation at an S genome was introduced had the following difference from the wild-type polypeptide.

While WT consists of 338 amino acids, the polypeptides is produced such that unrelated 3 amino acids (LEY) are added in addition to up to 106 amino acids identical to those of WT.

The polypeptide (2A-1_121 derived, SEQ ID NO: 36) expressed by NtB11 into which a mutation at a T genome was introduced had the following difference from the wild-type polypeptide.

While WT consists of 336 amino acids, the polypeptides is produced such that unrelated 12 amino acids (TGILNSRKSLWD (SEQ ID NO: 107)) are added in addition to up to 107 amino acids identical to those of WT.

(b) Double Mutants of NtB11 and NtREV

By use of CRISPR/Cas9 system, mutations were further introduced into the individuals of T3 line obtained by selfing the individuals of the single mutants (T2 line) of the NtB11 gene. The procedures of the introduction are as described in the item 1. Life Technologies Corporation was entrusted with synthesis of sgRNA expression cassette through GeneArt (registered trademark) Strings (trademark) DNA Fragments. The nucleotide sequences of the sgRNA expression cassette, with which Life Technologies Corporation was entrusted, are as follows (G2: Chem. 4 and G5: Chem. 5).

[Chem. 4]

```
                                       (SEQ ID NO: 150)
aattggtaccAAGCTTCGTTGAACAACGGAAACTCGACTTGCCTTCCGCA
CAATACATCATTTCTTCTTAGCTTTTTTTCTTCTTCTTCGTTCATACAGT
TTTTTTTTGTTTATCAGCTTACATTTTCTTGAACCGTAGCTTTCGTTTTC
TTCTTTTTAACTTTCCATTCGGAGTTTTTGTATCTTGTTTCATAGTTTGT
CCCAGGATTAGAATGATTAGGCATCGAACCTTCAAGAATTTGATTGAATA
AAACATCTTCATTCTTAAGATATGAAGATAATCTTCAAAAGGCCCCTGGG
AATCTGAAAGAAGAGAAGCAGGCCCATTTATATGGGAAAGAACAATAGTA
TTTCTTATATAGGCCCATTTAAGTTGAAAACAATCTTCAAAAGTCCCACA
TCGCTTAGATAAGAAAACGAAGCTGAGTTTATATACAGCTAGAGTCGAAG
TAGTGATTgagttcctttccaaggctacGTTTTAGAGCTAGAAATAGCAA
GTTAAAATAAGGCTAGTCCGTTATCAACTTGAAAAAGTGGCACCGAGTCG
GTGCTTTTTTTggatccaatt
```

The underlined portion indicates the guide sequence. The portion upstream to the underlined portion indicates the AtU6-26 promoter sequence. The portion downstream to the underlined portion indicates the scaffold-polyT sequence. The lower case letters at the terminus indicate restriction enzyme sequences of KpnI and BamHI.

[Chem. 5]

```
                                       (SEQ ID NO: 151)
aattggtaccAAGCTTCGTTGAACAACGGAAACTCGACTTGCCTTCCGCA
CAATACATCATTTCTTCTTAGCTTTTTTTCTTCTTCTTCGTTCATACAGT
TTTTTTTTGTTTATCAGCTTACATTTTCTTGAACCGTAGCTTTCGTTTTC
TTCTTTTTAACTTTCCATTCGGAGTTTTTGTATCTTGTTTCATAGTTTGT
CCCAGGATTAGAATGATTAGGCATCGAACCTTCAAGAATTTGATTGAATA
AAACATGTTCATTCTTAAGATATGAAGATAATCTTCAAAAGGCCCCTGGG
AATCTGAAAGAAGAGAAGCAGGCCCATTTATATGGGAAAGAACAATAGTA
TTTCTTATATAGGCCCATTTAAGTTGAAAACAATCTTCAAAAGTCCCACA
TCGCTTAGATAAGAAAACGAAGCTGAGTTTATATACAGCTAGAGTCGAAG
TAGTGATTggagtggcagcccgagcatgGTTTTAGAGCTAGAAATAGCAA
GTTAAAATAAGGCTAGTCCGTTATCAACTTGAAAAAGTGGCACCGAGTCG
GTGCTTTTTTTggatccaatt
```

The underlined portion indicates the guide sequence. The portion upstream to the underlined portion indicates the AtU6-26 promoter sequence. The portion downstream to the underlined portion indicates the scaffold-polyT sequence. The lower case letters at the terminus indicate restriction enzyme sequences of KpnI and BamHI.

The presence/absence of the mutation and mutant sequence were examined by PCR using Tks Gflex (trademark) DNA polymerase (Takara-Bio Inc.) with genomic DNA as a template, which genomic DNA was extracted from a leaf of a transformant of tobacco. The reaction conditions and primers of the PCR are as follows.

(Reaction Conditions)

REVG2

60 seconds at 94° C.

45 cycles while each cycle includes 10 seconds at 98° C., 15 seconds at 60° C., and 50 seconds at 68° C.

REVG5

60 seconds at 94° C.

45 cycles while each cycle includes 10 seconds at 98° C., 15 seconds at 62° C., and 50 seconds at 68° C.

(Primers)

```
REVG2_T genome
Combination of REV_Nt_in2_F1:
                                 (SEQ ID NO: 121)
AACCAATGGACAAGAAACGGATGGCA,
and

REV_Nt_in4_R1:
                                 (SEQ ID NO: 122)
TTTAGCTATCCAGTCAAAGAGGCACG

REVG2_S genome
Combination of REV_Ns_in2_F1:
                                 (SEQ ID NO: 114)
CCAATAAACAAGAAACAGATGATGG,
and

REV_Ns_in4_R1:
                                 (SEQ ID NO: 116)
GAGACATGGCAATACTGAATTTTCA

REVG5_T genome
Combination of REV_Nt_in4_F1:
                                  (SEQ ID NO: 67)
AAAAAAATTCAGTATTGCCACGTGC,
and

REV_Nt_in6_R1
                                 (SEQ ID NO: 123)
AGCCTACGTGAAGATTGATGAGAAA

REVG5_S genome
Combination of REV_Ns_in4_F1:
                                  (SEQ ID NO: 64)
GAAAATTCAGTATTGCCATGTC,
and

REV_Ns_in6_R1:
                                 (SEQ ID NO: 118)
AGCCTACGTGAAGATTGATGAGAAG
```

The PCR products were treated with use of ExoSAP-IT (Affymetrix) according to the enclosed manual, and the treated PCR products were used as a template in a sequence reaction. For the sequence reaction, 3730×1 DNA Analyzer (ABI) was used. After X terminator purification (ABI), the sequence reaction was analyzed with use of Big Dye Terminator v.3.1 cycle sequencing kit (ABI).

The polypeptides, which are expressed by the mutations of the NtB11 and the NtREV in the B11/REV double mutants, are as follows.

The polypeptide (2A-1_121 derived, SEQ ID NO: 35) expressed by NtB11 into which a mutation at an S genome was introduced had the following difference from the wild-type polypeptide.

While WT consists of 338 amino acids, the polypeptides is produced such that unrelated 3 amino acids (LEY) are added in addition to up to 106 amino acids identical to those of WT.

The polypeptide (2A-1_121 derived, SEQ ID NO: 36) expressed by NtB11 into which a mutation at a T genome was introduced had the following difference from the wild-type polypeptide.

While WT consists of 336 amino acids, the polypeptides is produced such that unrelated 12 amino acids (TGILNSRKSLWD (108th to 119th amino acids in SEQ ID NO: 36)) are added in addition to up to 107 amino acids identical to those of WT.

The polypeptide (bbrrG2-44, SEQ ID NO: 37) expressed by NtREV into which a mutation at an S genome was introduced had the following difference from the wild-type polypeptide.

While WT consists of 838 amino acids, the polypeptides is produced such that unrelated 5 amino acids (YRNCC (177th to 181st amino acids in SEQ ID NO: 37)) are added in addition to up to 176 amino acids identical to those of WT.

The polypeptide (bbrrG2-44, SEQ ID NO: 38) expressed by NtREV into which a mutation at a T genome was introduced had the following difference from the wild-type polypeptide.

While WT consists of 839 amino acids, the polypeptides is produced such that unrelated 9 amino acids (KTDGRYLLL (177th to 185th amino acids in SEQ ID NO: 38)) are added in addition to up to 176 amino acids identical to those of WT.

The polypeptide (bbrrG5-63, SEQ ID NO: 39) expressed by NtREV into which a mutation at an S genome was introduced had the following difference from the wild-type polypeptide.

While WT consists of 838 amino acids, the polypeptides is produced such that unrelated 51 amino acids (VRSSKIDHLGSETAGTLKFSRCFLQEMEQLSFCTRRYMLLPPWL LHVIFGL (210th to 260th amino acids in SEQ ID NO: 39)) are added in addition to up to 209 amino acids identical to those of WT.

The polypeptide (bbrrG5-63, SEQ ID NO: 40) expressed by NtREV into which a mutation at a T genome was introduced had the following difference from the wild-type polypeptide.

While WT consists of 839 amino acids, the polypeptides is produced such that unrelated 4 amino acids (MWSC (213rd to 216th amino acids in SEQ ID NO: 40)) are added in addition to up to 212 amino acids identical to those of WT.

The polypeptide (bbrrG5-7, SEQ ID NO: 41) expressed by NtREV into which a mutation at an S genome was introduced had the following difference from the wild-type polypeptide.

While WT consists of 838 amino acids, the polypeptide is produced such that 11 amino acid (SGVAARACGLV) (206th to 216th amino acids in SEQ ID NO: 41) are deleted so as to constitute 827 amino acids.

The polypeptide (bbrrG5-7, SEQ ID NO: 42) expressed by NtREV into which a mutation at a T genome was introduced had the following difference from the wild-type polypeptide.

While WT consists of 839 amino acids, the polypeptides is produced such that unrelated 6 amino acids (IAMWSC (206th to 215th amino acids in SEQ ID NO: 42)) are added in addition to up to 205 amino acids identical to those of WT.

The polypeptide (bbrrG5-9, SEQ ID NO: 43) expressed by NtREV into which a mutation at an S genome was introduced had the following difference from the wild-type polypeptide.

While WT consists of 838 amino acids, the polypeptides is produced such that unrelated 4 amino acids (MWSC (211st to 214th amino acids in SEQ ID NO: 43)) are added in addition to up to 210 amino acids identical to those of WT.

The polypeptide (bbrrG5-9, SEQ ID NO: 44) expressed by NtREV into which a mutation at a T genome was introduced had the following difference from the wild-type polypeptide.

While WT consists of 839 amino acids, the polypeptides is produced such that unrelated 14 amino acids (VTLINLNVVLLLYY (212nd to 225th amino acids in SEQ ID NO: 44)) are added in addition to up to 211 amino acids identical to those of WT.

The polypeptide (bbrrG2-46-23a, SEQ ID NO: 45) expressed by NtREV into which a mutation at an S genome was introduced had the following difference from the wild-type polypeptide.

While WT consists of 838 amino acids, the polypeptides is produced such that unrelated 5 amino acids (YRNCC (177th to 181st amino acids in SEQ ID NO: 45)) are added in addition to up to 176 amino acids identical to those of WT.

The polypeptide (bbrrG2-46-23a, SEQ ID NO: 46) expressed by NtREV into which a mutation at a T genome was introduced had the following difference from the wild-type polypeptide.

While WT consists of 839 amino acids, the polypeptides is produced such that unrelated 5 amino acids (YRNCC (177th to 181st amino acids in SEQ ID NO: 46)) are added in addition to up to 176 amino acids identical to those of WT.

The polypeptide (bbrrG2-46-23b, SEQ ID NO: 45) expressed by NtREV into which a mutation at an S genome was introduced had the following difference from the wild-type polypeptide.

While WT consists of 838 amino acids, the polypeptides is produced such that unrelated 5 amino acids (YRNCC (177th to 181st amino acids in SEQ ID NO: 45)) are added in addition to up to 176 amino acids identical to those of WT.

The polypeptide (bbrrG2-46-23b, SEQ ID NO: 46) expressed by NtREV into which a mutation at a T genome was introduced had the following difference from the wild-type polypeptide.

While WT consists of 839 amino acids, the polypeptides is produced such that unrelated 5 amino acids (YRNCC (177th to 181st amino acids in SEQ ID NO: 46)) are added in addition to up to 176 amino acids identical to those of WT.

The polypeptide (bbrrG5-9-5a, SEQ ID NO: 47) expressed by NtREV into which a mutation at an S genome was introduced had the following difference from the wild-type polypeptide.

While WT consists of 838 amino acids, the polypeptides is produced such that unrelated 4 amino acids (MWSC (211st to 214th amino acids in SEQ ID NO: 47)) are added in addition to up to 210 amino acids identical to those of WT.

The polypeptide (bbrrG5-9-5a, SEQ ID NO: 48) expressed by NtREV into which a mutation at a T genome was introduced had the following difference from the wild-type polypeptide.

While WT consists of 839 amino acids, the polypeptides is produced such that unrelated 14 amino acids (VTLINLNVVLLLYY (212nd to 225th amino acids in SEQ ID NO: 48)) are added in addition to up to 211 amino acids identical to those of WT.

The polypeptide (bbrrG5-9-5b, SEQ ID NO: 49) expressed by NtREV into which a mutation at an S genome was introduced had the following difference from the wild-type polypeptide.

While WT consists of 838 amino acids, the polypeptide is produced such that 212nd alanine is substituted with glutamic acid so as to constitute 838 amino acids.

The polypeptide (bbrrG5-9-5b, SEQ ID NO: 48) expressed by NtREV into which a mutation at a T genome was introduced had the following difference from the wild-type polypeptide.

While WT consists of 839 amino acids, the polypeptides is produced such that unrelated 14 amino acids (VTLINLNVVLLLYY (212nd th 225th amino acids in SEQ ID NO: 48)) are added in addition to up to 211 amino acids identical to those of WT.

The polypeptides (bbrrG5-9-5c, SEQ ID NOs: 47 and 49) expressed by NtREV into which a mutation at an S genome was introduced had the following differences from the wild-type polypeptide.

While WT consists of 838 amino acids, (i) the polypeptide is produced such that unrelated 4 amino acids (MWSC (211st to 214th amino acids in SEQ ID NOs: 47 and 49)) are added in addition to up to 210 amino acids identical to those of WT and (ii) the polypeptide is produced such that 212nd alanine is substituted with glutamic acid, so as to constitute 838 amino acids.

The polypeptide (bbrrG5-9-5c, SEQ ID NO: 48) expressed by NtREV into which a mutation at a T genome was introduced had the following difference from the wild-type polypeptide.

While WT consists of 839 amino acids, the polypeptides is produced such that unrelated 14 amino acids (VTLINLNVVLLLYY (212nd to 225th amino acids in SEQ ID NO: 48)) are added in addition to up to 211 amino acids identical to those of WT.

Although the NtREV genes on T genomes in bbrrG2-46-23a and in bbrrG2-46-23b are encoding polypeptides of an identical sequence (SEQ ID NO: 46), the NtREV genes have differing nucleotide sequences. Although the NtREV genes have mutations of the same kind (insertion of 1 base in comparison with WT), NtREV genes are different in terms of which base is inserted (former: A, latter: T).

(4. Evaluation of Development of Axillary Buds in Double Mutants Obtained)

Figure 2:
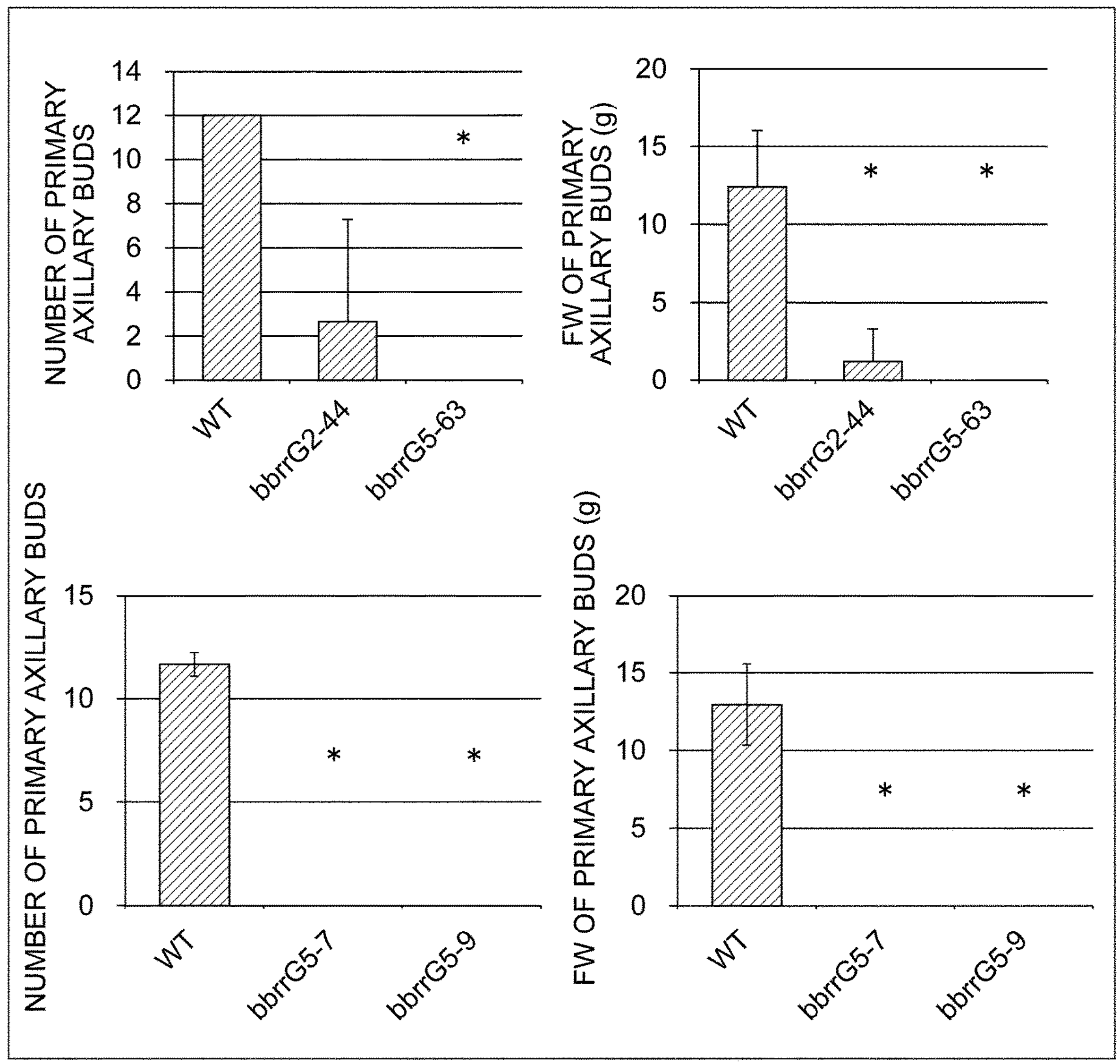
FIG. 2 is a view showing the results of evaluation of effects of suppressing primary axillary buds in a tobacco plant in accordance with another example of the present invention.

The axillary buds were evaluated according to the description in the item "(d) Evaluation of axillary buds in greenhouse" described later. Note that the T1 line and the T2 line were subjected to the evaluation. FIGS. 1 and 2 show the results of examining the effects, on the development of axillary buds, of the mutations simultaneously introduced into two genes. As shown in FIG. 1, the tobacco plant, in which the mutations were introduced into the NtB11 gene and the NtLS gene, revealed that the development of primary axillary buds was suppressed (the number or fresh weight of the primary axillary buds was ½ or less) in comparison with the wild-type (456_LLBB). In particular, 11_llbb exhibited a statistically significant decrease in the number and fresh weight of the primary axillary buds in comparison with the wild-type.

As shown in FIG. 2, the tobacco plant, in which the mutations were introduced into the NtB11 gene and the NtREV gene, revealed that the development of primary axillary buds was suppressed (the number or fresh weight of the primary axillary buds was ½ or less) in comparison with the wild-type (WT). In particular, bbrrG5-63, bbrrG5-7, and bbrrG5-9 produced no primary axillary buds.

Figure 6:
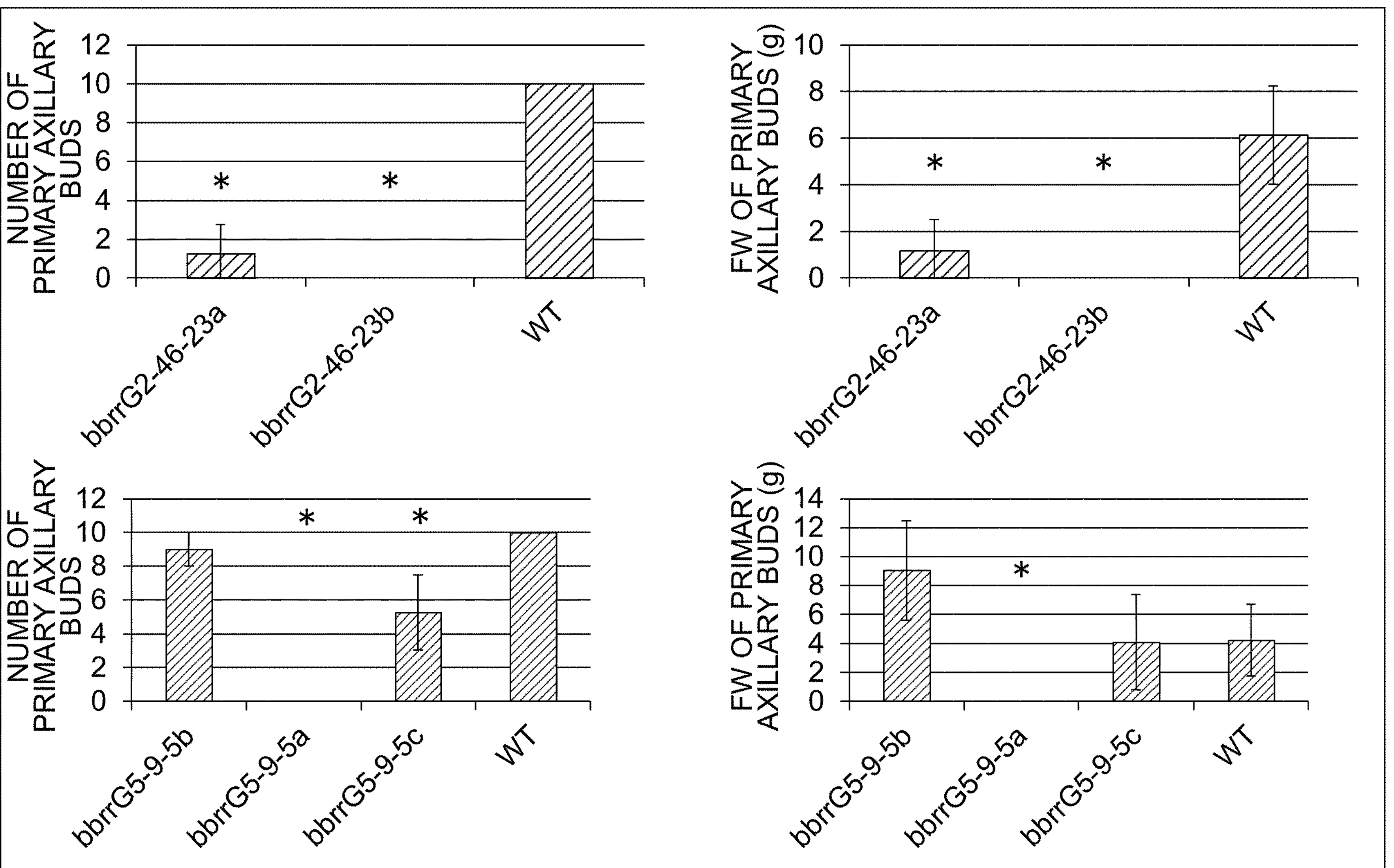
FIG. 6 is a view showing the results of evaluation of effects of suppressing primary axillary buds in a tobacco plant in accordance with yet another example of the present invention.

FIG. 6 shows the results of examining the effects, on the development of axillary buds, of the mutations simultaneously introduced into the NtB11 gene and the NtREV gene. The upper row of FIG. 6 shows the results comparison between (i) the tobacco plants of 2 lines (bbrrG2-46-23a, bbrrG2-46-23b) and (ii) the wild-type (WT). In each of the tobacco plants of the 2 lines, mutations, which cause frame shifting, were introduced into all of the NtB11 genes and the NtREV genes in each of the S genome and the T genome. As shown in the upper row of FIG. 6, the tobacco plants of the 2 lines each exhibited that the development of primary axillary buds was remarkably suppressed, so that the primary axillary buds were hardly produced.

The lower row of FIG. 6 shows the results of comparison between (i) tobacco plants in which only the NtREV gene on the S genome has a mutation (substitution of 1 amino acid) not causing frame shifting and (ii) the wild-type (WT). The overview of the mutations in the tobacco plants shown in the lower row of FIG. 6 will be described below.

bbrrG5-9-5a: Sr++Tr++Sb++Tb++ bbrrG5-9-5b: Sr−−Tr++Sb++Tb++ bbrrG5-9-5c: Sr+−Tr++Sb++Tb++

(Note that (i) the capital letters "S" and "T" indicate S genome and T genome, respectively, (ii) the lower-case letters "r" and "b" indicate the NtREV gene and the NtB11 gene, respectively, and (iii) the symbols "+" and "−" indicate frame-shift mutation and non-frame-shift mutation, respectively.)

As shown in the lower row of FIG. 6, bbrrG5-9-5a did not result in primary axillary buds. This is similar to the results shown in the upper row. In addition, bbrrG5-9-5b did not exhibit statistically significant reduction in primary axillary buds in comparison with the wild-type (WT). However, bbrrG5-9-5c exhibited statistically significant reduction in the number of primary axillary buds. It is therefore evident that the reduction in primary axillary buds does not require functional suppression of all (the total of four genes) of the NtB11 gene and the NtREV gene on each of S genome and T genome, but one of the four genes can be functional.

Comparative Examples: Effects of Functional Suppression of One Gene on Development of Axillary Buds Comparative Examples below reveal that the development of primary axillary buds is not suppressed in a tobacco plant in which only one gene functionally suppressed. Comparative Examples below also reveal that in addition to the methods in Examples described above, various methods can be employed for preparing a tobacco plant in which desired two genes are functionally suppressed simultaneously. Those skilled in the art who refer to Comparative Examples will understand that, by use of various publicly-known methods in the technical field concerned, it is possible to prepare (i) the mutants of tobacco plants in Examples described above and (ii) recombinants (in which two genes are functionally suppressed simultaneously) of tobacco plants, which have phenotypes similar to those of the mutants.

(1. Recombinant in which Expression of Each Gene is Suppressed)

(a) Preparation for Transformation

In order to prepare a recombinant in which expression of each gene is suppressed (hereinafter such a recombinant will be simply referred to as "recombinant"), vectors for transformation were first prepared as described below.

RNAi trigger sequences for suppressing the expression of NtB11, NtLS, and NtREV (hereinafter also collectively referred to as "target genes") were amplified by PCR in which PrimeSTAR Max DNA Polymerase (Takara-Bio Inc.) was used, while cDNA derived from SR-1 produced based on the results of Example 1 was used as a template. The conditions and primers of the PCR are as follows.

(Conditions of PCR)

30 seconds at 94° C.

30 cycles to 40 cycles while each cycle includes 10 seconds at 98° C., 5 seconds at 55° C., and 10 seconds at 72° C.

10 seconds at 72° C.

(Primer for NtB11)

```
Combination of N.t_BL(hit1)_TRV_F1:
                                   (SEQ ID NO: 152)
CACCTCAAGAAAAAGCTTATGGG,
and

N.t_BL(hit1)_TRV_R1:
                                   (SEQ ID NO: 153)
GCAGCAGCTAACAAGTTGTA
```

(Primer for NtLs)

```
Combination of LS_TRV_F3:
                                   (SEQ ID NO: 69)
CACCGAAGAAACTGATGATCAACGG,
and

LS_TRV_R3:
                                   (SEQ ID NO: 68)
TCGCTTGATTAGCAGTCAGC
```

(Primer for NtREV)

```
Combination of NtREV_TrFW2:
                                   (SEQ ID NO: 66)
CACCGCCTATGTAGCTTCGTCAATG,
and

NtREV_TrRV2:
                                   (SEQ ID NO: 154)
CACTGTAGCCAGAGACCACA.
```

For the expression suppression of NtREV, a sequence of a translated region downstream (3' end) of an HD-Zip domain was selected as an RNAi trigger sequence. For the expression suppression of NtB11, a sequence of a translated region downstream (3' end) of a Myb domain was selected as an RNAi trigger sequence. For the expression suppression of NtLS, a 5' end side of a translated region was selected as an RNAi trigger sequence. In addition, each RNAi trigger sequence amplified by the PCR was added with CCAC at the 5' end, and was designed so that the RNAi trigger sequence has a length of 400 bp to 500 bp.

The PCR products were cloned to pENTR (trademark)/D-TOPO vectors (Life Technologies Corporation). Then, the nucleotide sequence of each RNAi trigger sequence was checked. Then, with use of Gateway LR Clonase II Enzyme Mix (Life Technologies Corporation), each RNAi trigger sequence was introduced into a pSP231 vector. In order to check the introduced sequence, each RNAi trigger sequence introduced into the pSP231 vector was amplified by PCR in which TakaRa Ex Taq and PrimeSTAR Max DNA Polymerase (Takara-Bio Inc.) were used, such that a sense strand and an antisense strand were individually amplified (the vector pSP231 is a vector in which a GFP (Green-fluorescent protein gene) expression cassette was inserted into a SacI site of pHellsgate 12 (see the literature: Wesley et al., 2001, Plant J., 27, 581-590) and is a binary vector that can express, with a cauliflower mosaic virus 35S RNA gene promoter, an RNAi sequence formed with a pdk/cat intron located between inverted repeat sequences of the RNAi trigger sequence). The PCR products were purified with use of MiniElute (QIAGEN), and then subjected to sequencing. The nucleotide sequences of the RNAi trigger sequences introduced into the pSP231 vector are as represented below. Note that in the nucleotide sequences shown here, CACC at the 5' end is omitted.

(NtB11)

(SEQ ID NO: 155)

```
ctcaagaaaa agcttatggg attaatgcaa tcaacaaacc
aaagaaaatc accatatttt ccagctacta attctcttca
agcccaaccc cagataaatt caagtctttt tagagactta
tattacaacc caaataatag gcctattatt acaggcctaa
atcagtccat ttcttctgcc caccagccaa attttctcta
cactaatagt aacatgaatt ttcctaattt gggtgctaca
aatagtcaat atccttataa tattcaaagt cataatttac
ttatgtttgg agaagcaagt tgttcttcat cagatggaag
ttgtagccaa atgagttttg gcaaagaaat caagagagag
gaaattatga gtaattgttt acaacaaggt caaatttcaa
gtgttaatgc ttttgaagaa aatcagaatt tcactcttga
ttatggtaac agtagtagta attgggtgga tcaaaaacca
aatgtgtatt ttggaaatac tactactactactcaagtac
ttcagtatga tgttgaagaa gttaagcagc agctaacaag
ttgta
```

(NtLS)

(SEQ ID NO: 156)

```
gaagaaactg atgatcaacg gcggagattc agttccactt
cccctgcaat ccaaatccgg caactactca ttagctgcgc
ggagttaatc tcgcggtccg atttctcggc cgcaaacaga
ctcctcacca ttttatcaac taactcttcc ccttttggtg
attcaactga aagattagtc catcagttca ctcgcgcact
ttctcttcgc ctcaaccgtt atatctcttc agccactaat
ttcttgacac catctaatgt tgttgaaagt tcaaatgatt
cagctctact tcagtcatcc tatctttccc taaaccaagt
gactcctttc attagattta gtcagctgac tgctaatcaa
gcga
```

(NtREV)

(SEQ ID NO: 157)

```
gcctatgtagcttcgtcaat gaaatcttgt tcatatgcat
atcctgggat gaggcctacc agatttaccg gaagtcagat
aataatgcca cttggccata caattgaaca tgaagagatg
cttgaggtta ttagattgga aggacactct attggccagg
aagatacttt tatgccaaga gatgttcacc ttctccagat
gtgtagtgga actgatgagaatgctgtcgg agcttgttct
gaactagttt ttgctgcaat tgatgagatg tttccagatg
atgcacccct gttgccctcc gggtttcgta tcattcctct
cgagtcaaaa tcaagcgatc cccaggatac atcgaatgct
catagaacac tggatctggc atcaagtctt gaagttggcc
cagcaacaaa ccctgctact ggagatgtgg tctctggcta
cagtg
```

With use of the pSP231 vector containing each RNAi trigger sequence, *Agrobacterium* (*Agrobacterium tumefaciens*) LBA4404 was transformed by electroporation. After it was confirmed by PCR that each RNAi trigger sequence was amplified in LBA4404, the *Agrobacterium* was used for the transformation of tobacco.

(b) Transformation of Tobacco and Collection of Transformed Seeds

With use of the variety MC1 (transformation of NtB11) or SR-1 (transformation of each of NtL and NtREV), tobacco was transformed by a common method as described below. A section of a tobacco leaf was infected with the *Agrobacterium* thus transformed, and was cultured in Linsmaier and Skoog medium containing kanamycin, so that calluses were obtained. From the calluses thus obtained, redifferentiated individuals, which are kanamycin-resistant, were obtained. From these redifferentiated individuals, the following individuals were selected: the individual in which (i) intense fluorescence based on GFP in the entire leaf was confirmed and (ii) high-level expression at a spacer portion (PPDK intron) was confirmed. The individuals thus selected (T0 individuals) were transplanted to 9-cm pots, and were cultivated under fixed conditions in a containment greenhouse at 23° C. to 25° C. The T0 individuals were selfed, so that T1 seeds were collected.

(c) Selection of T1 Recombinants

The T1 seeds were aseptically sowed in Linsmaier and Skoog medium, and fluorescence based on GFP of seedling was observed. From a segregation ratio of genotypes (homozygous (homo)/hemizygous (hetero) and null segregant (null)) of transgenes, lines in which the number of loci of the transgenes was predicted to be 1 to 2 were selected.

By qPCR in which total RNA isolated from a leaf or root of T1 line was used, the expression level of target genes was determined. The expression level was evaluated as a ratio of the expression level in homo lines to the expression level in null lines. From the homo lines and null lines, lines in which the ratio above is small (i.e., the degree to which the expressions of the target genes are suppressed is large) were selected. The details of the qPCR are as follows.

The primers and probes of the qPCR were designed with use of dedicated software (PrimerExpress, ABI) or Sigma-Aldrich Japan was requested to perform such designing. As described in (b) of 1-1., cDNA was synthesized from total RNA isolated from the leaf or root. The qPCR was performed with use of (i) cDNA which was 2 to 5-fold diluted, (ii) the primers obtained as described above, and (iii) Taq Man Fast Advanced Master Mix (ABI). As a quantification reference, eukaryotic elongation factor-la gene (accession No. AF120093, efla) was amplified. As a quantification probe, a combination of reporter dye and quencher (FAM-TAMURA (gene to be analyzed) and VIC-TAMURA (reference)) was used. The sequences of the primers and probes for the qPCR are shown below. In the sequence targeting each gene below, the first is a forward primer, the second is a reverse primer, and the third is a probe.

(NtB11)

NtB11_qFW1:

(SEQ ID NO: 158)

GAGAAAACAAATGTAAGTACACCATTAGG

NtB11_qRV1:

(SEQ ID NO: 159)

GAAAAAGTTTGAATCTTCTTGCCAA

NtB11_P1:

(SEQ ID NO: 160)

GATTTGAAAGGGCGTTTGGGTATGGG

-continued

```
(NtLS)
NtLS_qFW1:
                                    (SEQ ID NO: 161)
CCGGTACTGGAAATGACCTTGA

NtLS_qRV1:
                                     (SEQ ID NO: 51)
ATCTAAGGCCTAAAGAGTGAGCAAAT

NtLS_P1:
                                    (SEQ ID NO: 162)
CCCTTCGTAGAACCGGAGATCGTTTAGCT

(NtREV)
NtREV1_qFW1:
                                    (SEQ ID NO: 163)
TCTCCAGGCTCCCCTGAAG

NtREV1_qRV1:
                                    (SEQ ID NO: 164)
TGTCCCCATGTGATAACTGTAGCT

NtREV1_P1:
                                    (SEQ ID NO: 165)
AACGTTGTCGCACTGGATCTGCCA
```

As a result of the selection above, the individuals to be subjected to test for evaluation of axillary bud were selected per target gene whose expression is suppressed. The individuals are as follows.

NtB11: 3 individuals of T1 line, selected from 15 individuals of T1 line whose expression level was evaluated, which has one locus and exhibits remarkable expression suppression (line number: 6, 9, and 12)

NtLS: 3 individuals of T1 line, selected from 24 individuals of T1 line whose expression level was evaluated, which has one locus and exhibits remarkable expression suppression (line number: 10, 15, and 19)

NtREV: 3 individuals of T1 line, selected from 10 individuals of T1 line whose expression level was evaluated, which has one locus and exhibits remarkable expression suppression (line number: 3, 8, and 14)

The ratios of expression levels of the target genes in the T1 family of each recombinant (where the expression level in null lines is set to 1) are as follows.

NtB11—line 6: 0.33, line 9: 0.35, line 12: 0.25

NtLS—line 10: 0.50, line 15: 0.58, line 19: 0.43

NtREV—line 3: 0.56, line 8: 0.57, line 14: 0.74

(d) Evaluation of Axillary Buds in Greenhouse

The seeds of T1 line of each recombinant obtained as described above were sowed and cultivated in a containment greenhouse or an artificial light growth cabinet, Koitotron (Koito Manufacturing Co., Ltd.). The conditions of the containment greenhouse were set so that the temperature was maintained at room temperature of 23° C. to 25° C., and the day length was that of a natural day. The conditions of Koitotron were set so that the day length was 12 hours, and the temperature was 25° C. (light period) and 18° C. (dark period). The individuals were cultivated in 15-cm pots which were filled with rich soil having a volume of 500 mL/pot to 800 mL/pot. The composition of the rich soil was as follows. Compost: 40 L, wild soil: 30 L, Akadama soil (small): 10 L, Akadama soil (medium): 10 L, vermiculite: 10 L, fertilizer (S625): 1000 g.

Topping was performed when 12 to 13 true leaves were produced during a period starting at budding and ending before flowering. The target selected to be evaluated was an axillary bud which was produced in a fourth true leaf from the bottom of an aerial part or a higher leaf. Each week since the topping, the number of axillary buds with a stem having a length of approximately 5 mm or longer was recorded. The axillary buds thus recorded were picked by hand from the base thereof, and the fresh weight (FW) of the axillary buds thus picked was measured. Until the development of new axillary buds was no longer found, the number and weight of axillary buds were measured over substantially 5 times.

Figure 3:
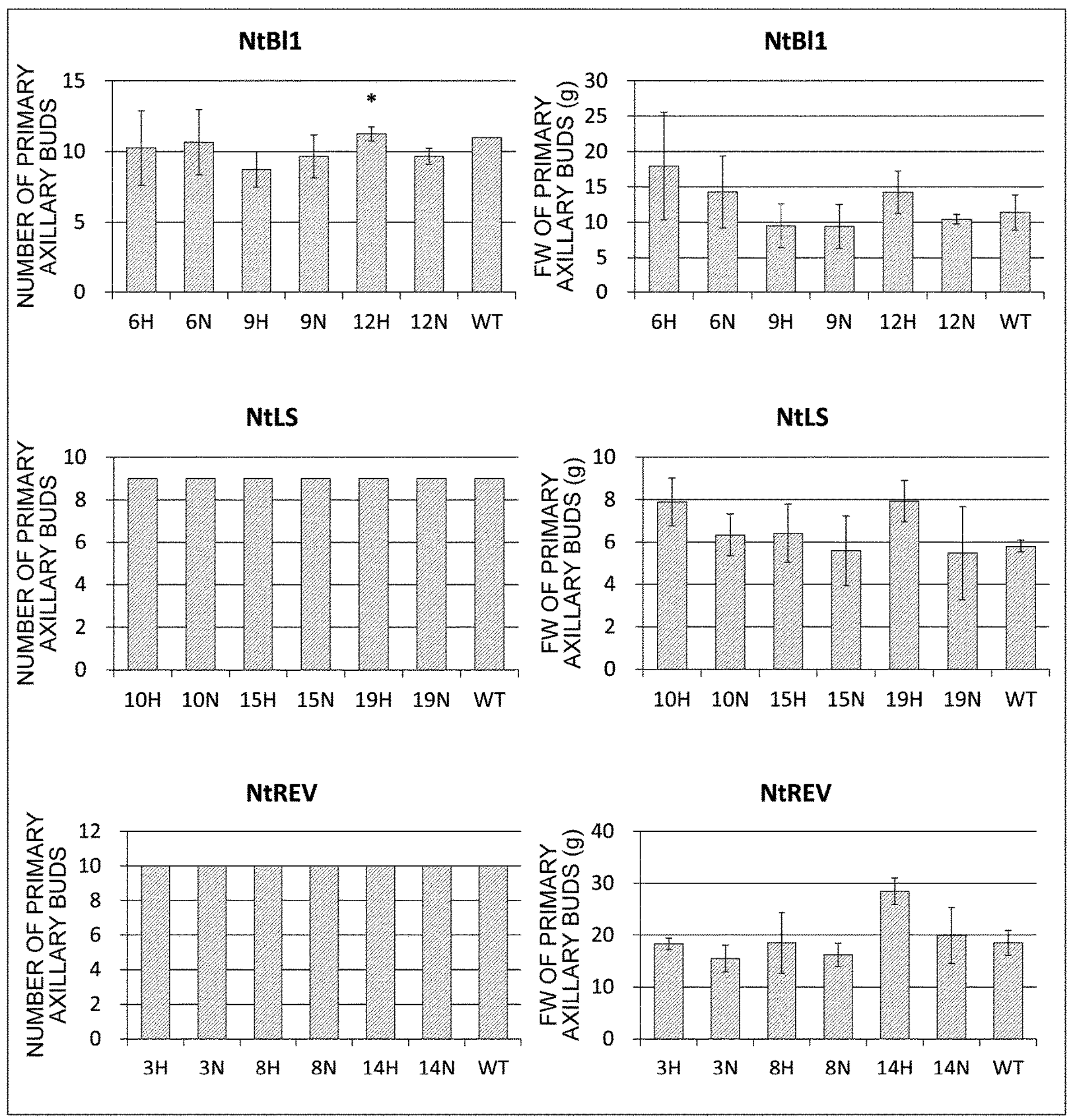
FIG. 3 is a view showing the results of evaluation of suppression of primary axillary buds in a tobacco plant in accordance with a comparative example.

FIG. 3 shows the results of the evaluation of axillary bud development in (i) the recombinants in which NtB11 expression was suppressed (cultivated in Koitotron), (ii) the recombinants in which NtLS expression was suppressed (cultivated in Koitotron), and (iii) the recombinants in which NtREV expression was suppressed (cultivated in a containment greenhouse). As shown in FIG. 3, although the recombinants in which the expression of any of NtB11, NtLS, and NtREV was suppressed exhibited some variance between lines, these recombinants also exhibited the development of primary axillary buds to approximately the same extent as the wild-type.

(2. Mutant in which Mutation was Introduced into Each Gene)

The individuals of T2 line ($T^+S^+$) of the NtB11 single mutant obtained in the item 2. in Examples were cultivated in a greenhouse, and axillary buds were evaluated. The details of the evaluation are as described in "(d) Evaluation of axillary buds in greenhouse" described above.

Figure 4:
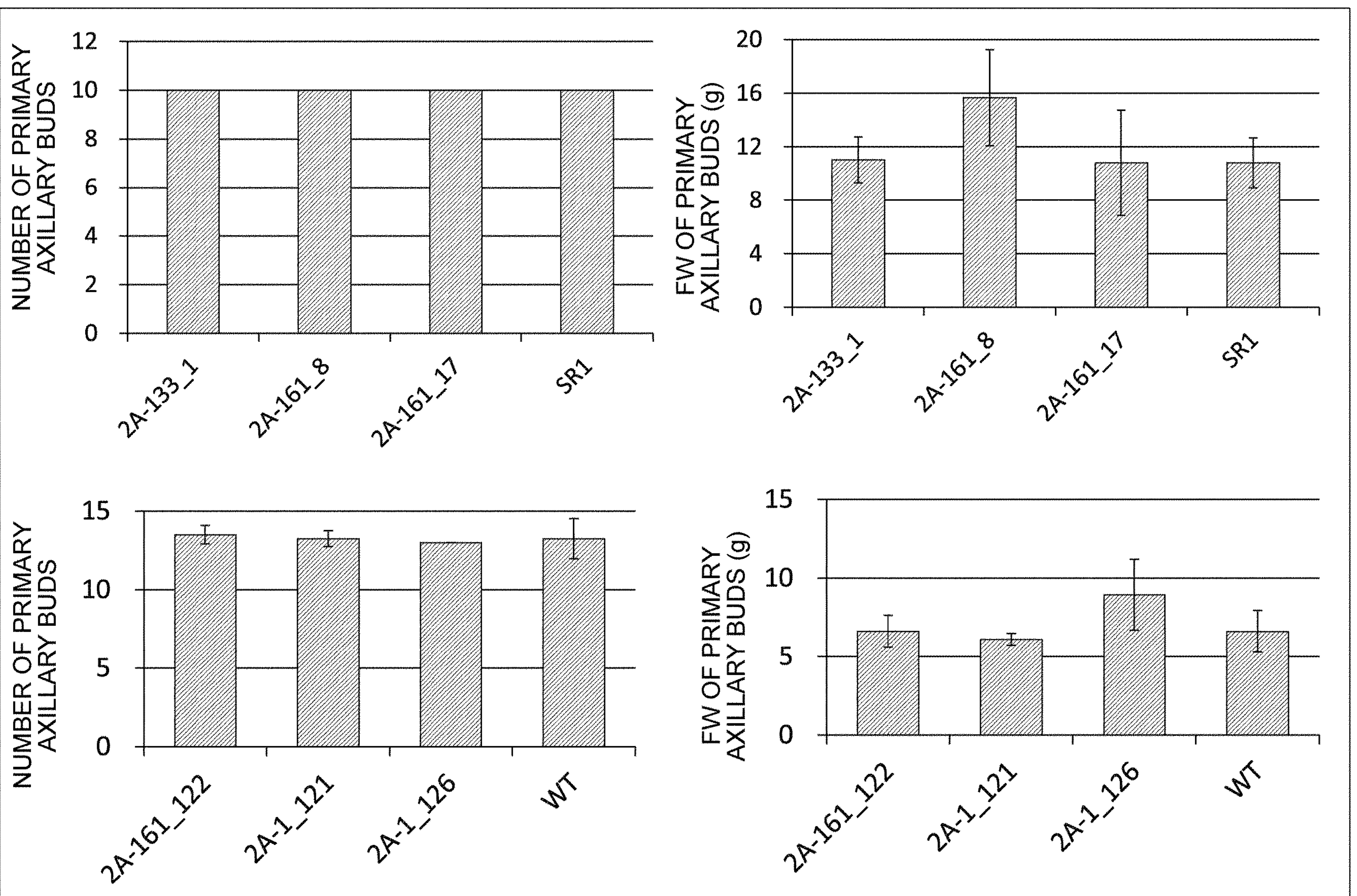
FIG. 4 is a view showing the results of evaluation of suppression of primary axillary buds in a tobacco plant in accordance with another comparative example.

FIG. 4 shows the results of the evaluation of the development of axillary buds of mutants in which mutations were introduced into the NtB11 gene. As shown in FIG. 4, any individual in which the mutation was introduced into the NtB11 gene exhibited the development of the primary axillary buds to approximately the same extent as the wild-type.

The NtREV single mutants and NtLS mutants obtained in the item 3. in Examples were cultivated in a field, and axillary buds were evaluated. The details of the process from the cultivation through the evaluation were as follows.

Cultivation in Field

In the field of Leaf Tobacco Research Center, during an ordinary cultivation period (sowing in March and planting in April), each line of the mutants was cultivated by a high-ridge, mulch-cultivation method under the following conditions, ridge length: 16 m, ridge intervals: 120 cm, planting distance: 43 cm, and the number of plan per ridge: 37. 1 ridge was assigned for cultivation of 1 line, and, one month after transplant, 10 to 15 individuals showing approximately identical growth were determined by appearance and were preliminarily selected. Then, 10 individuals from those were subjected to a subsequent examination. During the examination, no agrochemicals for suppressing axillary buds (such as Contact) was used at all.

Determination of Flowering Time

During flowering time, the number of above-ground leaves was determined. Immediately before topping, predicted flowering time was determined. By performing topping through cutting off 1 to 4 leaves below the first flower branch, the numbers of above-ground leaves were made the same among lines to be compared and evaluated.

Evaluation of Development of Axillary Buds

Over the total of 7 times on the day of topping and each week since the topping, the number of axillary buds with a stem having a length of approximately 5 mm was recorded. The axillary buds thus recorded were picked by hand from the base thereof, and the fresh weight (FW) of the axillary buds thus picked was measured. The primary axillary buds were individually measured and recorded. The measurement records are then put together.

Figure 5:
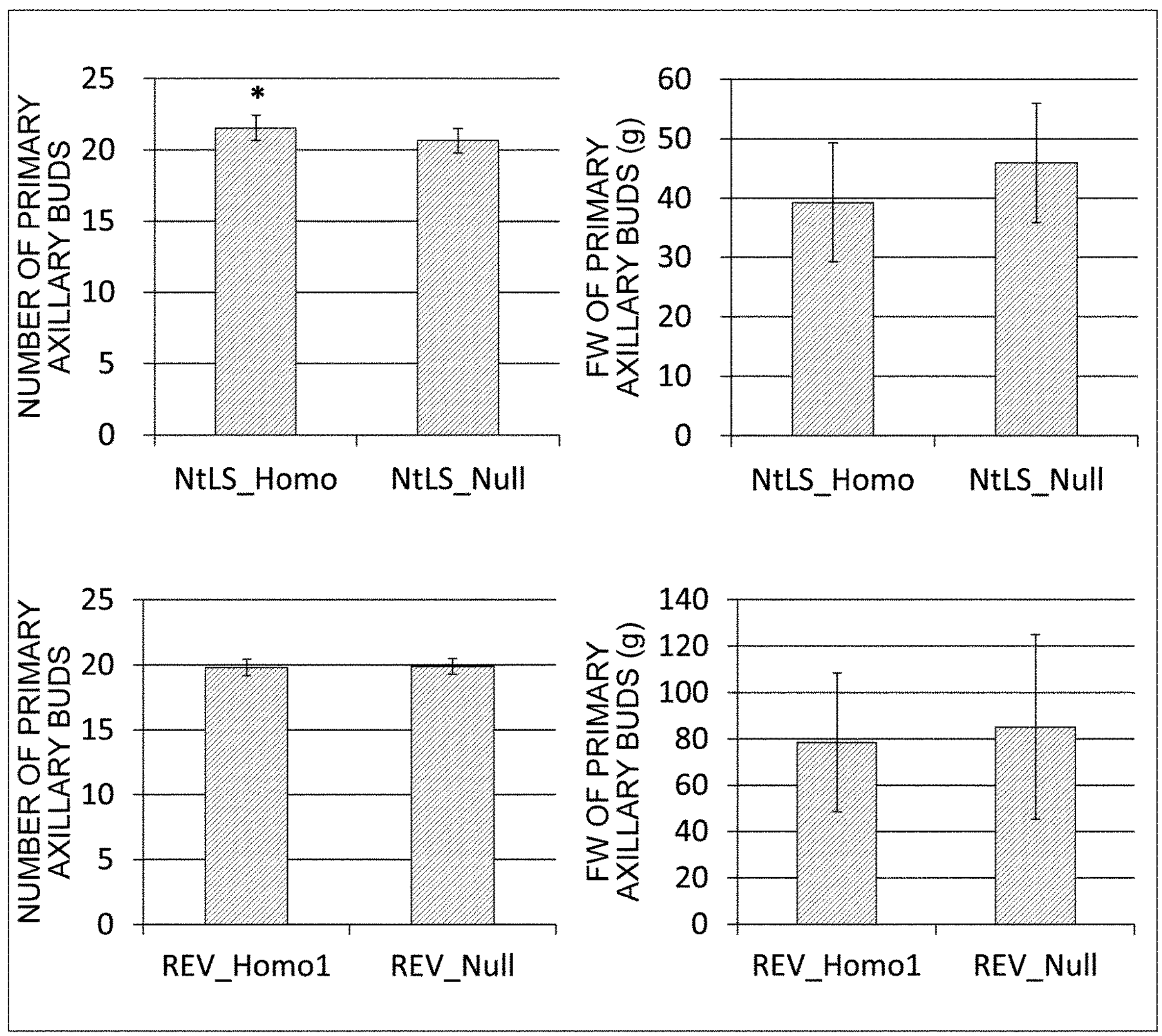
FIG. 5 is a view showing the results of evaluation of suppression of primary axillary buds in a tobacco plant in accordance with another comparative example.

FIG. 5 shows the results of the evaluation of the development of axillary buds in (i) mutants in which the mutation was introduced into NtLS (upper row) and (ii) mutants in which the mutation was introduced into NtREV (lower row). As shown in the upper row of FIG. 5, there was no statistically significant difference in the number and fresh weight of primary axillary buds between NtLS_Homo line ($T^+S^+$) and NtLS_Null line ($T^-S^-$). As shown in the lower row of FIG. 5, there was no statistically significant difference in the number and fresh weight of primary axillary buds between NtREV_Homo line ($T^+S^+$) and NtREV_Null line ($T^-S^-$). It was therefore found that the development of primary axillary buds was not suppressed in the NtREV mutant or NtLS mutant.

REFERENCES

1. Li J F, Norville J E, Aach J, McCormack M, Zhang D, Bush J, Church G M, Sheen J. (2013) Multiplex and homologous recombination-mediated genome editing in *Arabidopsis* and *Nicotiana benthamiana* using guide RNA and Cas9. Nat Biotechnol. 31(8), 688-91.
2. Waibel F, Filipowicz W. (1990) U6 snRNA genes of *Arabidopsis* are transcribed by RNA polymerase III but contain the same two upstream promoter elements as RNApolymerase II-transcribed U-snRNA genes. Nucleic Acids Res. 25; 18(12), 3451-8.
3. Marshallsay C1, Kiss T, Filipowicz W. (1990) Amplification of plant U3 and U6 snRNA gene sequences using primers specific for an upstream promoter element and conserved intragenic regions. Nucleic Acids Res. 25; 18(12), 3459-66

INDUSTRIAL APPLICABILITY

With an embodiment of the present invention, it is possible to suppress the development of unnecessary axillary buds during cultivation of tobacco plant. This allows for a reduction in labor and cost during cultivation, and leads to an increase in quality of leaves to be harvested.

The invention claimed is:

1. A mutated tobacco plant comprising at least six mutations in the genome of said plant, wherein said at least six mutations cause functional suppression of each of at least two of the following nucleotide products (1) through (3):

(1) a gene comprising, as a coding region, a polynucleotide (a) and a gene comprising, as a coding region, a polynucleotide (c);

(2) a gene comprising, as a coding region, a polynucleotide (e); and a gene comprising, as a coding region, a polynucleotide (g); and (3) a gene comprising, as a coding region, a polynucleotide (i) and a gene comprising, as a coding region, a polynucleotide (k), the polynucleotide (a) being a polynucleotide encoding a polypeptide having a sequence identity of 98% or higher with an amino acid sequence represented by SEQ ID NO: 1, the polynucleotide (c) being a polynucleotide encoding a polypeptide having a sequence identity of 98% or higher with an amino acid sequence represented by SEQ ID NO: 2, the polynucleotide (e) being a polynucleotide encoding a polypeptide having a sequence identity of 98% or higher with an amino acid sequence represented by SEQ ID NO: 3, the polynucleotide (g) being a polynucleotide encoding a polypeptide having a sequence identity of 98% or higher with an amino acid sequence represented by SEQ ID NO: 4, the polynucleotide (i) being a polynucleotide encoding a polypeptide having a sequence identity of 98% or higher with an amino acid sequence represented by SEQ ID NO: 5, and the polynucleotide (k) being a polynucleotide encoding a polypeptide having a sequence identity of 98% or higher with an amino acid sequence represented by SEQ ID NO: 6;

wherein the functional suppression causes the number or weight of primary axillary buds to decrease to not more than ½ of that of a wild-type plant which is a wild type of a variety identical to that of said mutated tobacco plant that comprises at least two of said nucleotide products (1)-(3) and not having said at least six mutations;

wherein the tobacco plant is *Nicotiana tabacum;* wherein all of four genes constituting the nucleotide products (1) and (2); or (1) and (3); are functionally suppressed, and among eight alleles constituting the four genes, (i) six or seven alleles have a mutation that causes the functional suppression, and one or two alleles do not have the mutation, or (ii) eight alleles have a mutation that causes the functional suppression; and the mutation that causes the functional suppression is selected from the group consisting of a frame-shift mutation; a nonsense mutation; or deletion in a part or all of a coding region.

2. The tobacco plant according to claim 1, wherein the functional suppression is a decrease, as compared with a wild-type plant, in abundance of polypeptides which are expression products of the at least two nucleotide products.

3. The tobacco plant according to claim 2, wherein the functional suppression is a decrease, as compared with a wild-type plant, in an amount of translation of the polypeptides which are expression products of the at least two nucleotide products.

4. The tobacco plant according to claim 2, wherein the functional suppression is a decrease, as compared with a wild-type plant, in an amount of transcription from the at least two nucleotide products to mRNA.

5. The tobacco plant according to claim 1, wherein the mutation is introduced into each of the at least two nucleotide products.

6. The tobacco plant according to claim 5, wherein the mutation is introduced by spontaneous mutation, mutagen treatment, gene recombination, genome editing, or gene knockout.

7. A method of producing a mutated tobacco plant, comprising the step of:

(A) introducing, into the genome of a tobacco plant, at least six mutations causing functional suppression of each of at least two of the following nucleotide products (1) through (3):

(1) a gene comprising, as a coding region, a polynucleotide (a); and a gene comprising, as a coding region, a polynucleotide (c);

(2) a gene comprising, as a coding region, a polynucleotide (e); and a gene comprising, as a coding region, a polynucleotide (g); and (3) a gene comprising, as a coding region, a polynucleotide (i); and a gene comprising, as a coding region, a polynucleotide (k), the polynucleotide (a) being a polynucleotide encoding a polypeptide having a sequence identity of 98% or higher with an amino acid sequence represented by SEQ ID NO: 1, the polynucleotide (c) being a polynucleotide encoding a polypeptide having a sequence identity of 98% or higher with an amino acid sequence represented by SEQ ID NO: 2, the polynucleotide (e) being a polynucleotide encoding a polypeptide having a sequence identity of 98% or higher with an amino acid sequence represented by SEQ ID NO: 3, the polynucleotide (g) being a polynucleotide encoding a polypeptide having a sequence identity of 98% or higher with an amino acid sequence represented by SEQ ID NO: 4, the polynucleotide (i) being a polynucleotide encoding a polypeptide having a sequence identity of 98% or higher with an amino acid sequence represented by SEQ ID NO: 5, the polynucleotide (k) being a polynucleotide encoding a polypeptide having a sequence identity of 98% or higher with an amino acid sequence represented by SEQ ID NO: 6;

wherein the functional suppression causes the number or weight of the primary axillary buds to decrease to not more than ½ of that of a wild-type plant which is a wild type of a variety identical to that of said mutated tobacco plant that comprises at least two of said nucleotide products (1)-(3) and not having said at least six mutations;

wherein the tobacco plant is *Nicotiana tabacum;* wherein all of four genes constituting the nucleotide products (1) and (2); or (1) and (3);

are functionally suppressed, and among eight alleles constituting the four genes, (i) six or seven alleles have a mutation that causes the functional suppression, and one or two alleles do not have the mutation, or (ii) eight alleles have a mutation that causes the functional suppression; and the mutation that causes the functional suppression is selected from the group consisting of a frame-shift mutation; a nonsense mutation; or deletion in a part or all of a coding region.

8. The method according to claim 7, further comprising the step of:

(B) selecting, from individuals produced by the step (A), an individual in which development of the primary axillary buds is suppressed.

9. The method according to claim 8, wherein in the step (B), an individual, in which the number or weight of the primary axillary buds is decreased in comparison with that of a wild-type plant, is selected.

10. The method according to claim 7, wherein the step (A) includes introducing the mutation into each of the at least two nucleotide products.

11. A method of determining a mutated tobacco plant in which development of primary axillary buds is suppressed, so that said primary axillary buds are decreased in number or weight as compared with a wild-type plant, the method comprising the steps of:

(A) obtaining a sample by collecting a part of a tobacco plant, said tobacco plant being obtained by the method according to claim 7;

(B) detecting, from the genome in the tobacco plant included in the sample, at least six mutations causing functional suppression of each of at least two of the following nucleotide products (1) through (3) on the genome:

(1) a gene comprising, as a coding region, a polynucleotide (a); and a gene comprising, as a coding region, a polynucleotide (c);

(2) a gene comprising, as a coding region, a polynucleotide (e); and a gene comprising, as a coding region, a polynucleotide (g); and (3) a gene comprising, as a coding region, a polynucleotide (i); and a gene comprising, as a coding region, a polynucleotide (k); and (C) determining that a tobacco plant, in which the mutation has been detected, is a tobacco plant in which the development of the primary axillary buds is suppressed, so that said primary axillary buds are decreased in number or weight as compared with a wild-type plant, the polynucleotide (a) being a polynucleotide encoding a polypeptide having a sequence identity of 98% or higher with an amino acid sequence represented by SEQ ID NO: 1, the polynucleotide (c) being a polynucleotide encoding a polypeptide having a sequence identity of 98% or higher with an amino acid sequence represented by SEQ ID NO: 2, the polynucleotide (e) being a polynucleotide encoding a polypeptide having a sequence identity of 98% or higher with an amino acid sequence represented by SEQ ID NO: 3, the polynucleotide (g) being a polynucleotide encoding a polypeptide having a sequence identity of 98% or higher with an amino acid sequence represented by SEQ ID NO: 4, the polynucleotide (i) being a polynucleotide encoding a polypeptide having a sequence identity of 98% or higher with an amino acid sequence represented by SEQ ID NO: 5, the polynucleotide (k) being a polynucleotide encoding a polypeptide having a sequence identity of 98% or higher with an amino acid sequence represented by SEQ ID NO: 6;

wherein the functional suppression causes the number or weight of the primary axillary buds to decrease to not more than ½ of that of a wild-type plant which is a wild type of a variety identical to that of said mutated tobacco plant that comprises at least two of said nucleotide products (1)-(3) and not having said at least six mutations;

wherein the tobacco plant is *Nicotiana tabacum;* wherein all of four genes constituting the nucleotide products (1) and (2); or (1) and (3); are functionally suppressed, and among eight alleles constituting the four genes, (i) six or seven alleles have a mutation that causes the functional suppression, and one or two alleles do not have the mutation, or (ii) eight alleles have a mutation that causes the functional suppression; and the mutation that causes the functional suppression is selected from the group consisting of: a frame-shift mutation; a nonsense mutation; or deletion in a part or all of a coding region.

12. An offspring or a bred progeny, wherein:

the offspring is of the tobacco plant according to claim 1, and the bred progeny is obtained by crossing the tobacco plant according to claim 1.

13. A leaf tobacco harvested from the tobacco plant according to claim 1.

14. A leaf tobacco harvested from the offspring or the bred progeny according to claim 12.

15. A cured tobacco obtained from the leaf tobacco according to claim 13.

16. A cured tobacco obtained from the leaf tobacco according to claim 14.

17. A tobacco product obtained from the cured tobacco according to claim 15.

18. A tobacco product obtained from the cured tobacco according to claim 16.

19. The tobacco plant according to claim 1, wherein six alleles have a mutation that causes the functional suppression, and two alleles do not have the mutation.

20. The tobacco plant according to claim 1, wherein seven alleles have a mutation that causes the functional suppression, and one allele does not have the mutation.

21. The tobacco plant according to claim 1, wherein eight alleles have a mutation that causes the functional suppression.

* * * * *

SEQUENCE LISTING

```
<160> NUMBER OF SEQ ID NOS: 166

<210> SEQ ID NO 1
<211> LENGTH: 337
<212> TYPE: PRT
<213> ORGANISM: Nicotiana tabacum

<400> SEQUENCE: 1

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
```

```
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Asn Gly
    290                 295                 300

Asn Asn Gly Ser Thr Ile Gly Cys Asn Asn Asn Asn Ser Met Phe Val
305                 310                 315                 320

Phe Asn Asp Glu Asn Tyr Asn Lys Ser Asn Glu Ile Glu Met Phe Tyr
                325                 330                 335

Tyr


<210> SEQ ID NO 2
<211> LENGTH: 336
<212> TYPE: PRT
<213> ORGANISM: Nicotiana tabacum

<400> SEQUENCE: 2

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
        115                 120                 125

Ser Pro Tyr Phe Pro Ala Thr Asn Ser Leu Gln Ala Gln Pro Gln Ile
    130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Cys Leu Gln
225                 230                 235                 240

Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
```

```
            260                 265                 270

Asn Val Tyr Phe Gly Asn Thr Thr Thr Thr Thr Gln Val Leu Gln Tyr
        275                 280                 285

Asp Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Gly Met Phe Tyr Tyr
                325                 330                 335


<210> SEQ ID NO 3
<211> LENGTH: 407
<212> TYPE: PRT
<213> ORGANISM: Nicotiana tabacum

<400> SEQUENCE: 3

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300
```

```
Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Phe Leu Gly Trp Gln Asn Gln Pro Leu
385                 390                 395                 400

Phe Ser Ile Ser Ser Trp Arg
                405


<210> SEQ ID NO 4
<211> LENGTH: 410
<212> TYPE: PRT
<213> ORGANISM: Nicotiana tabacum

<400> SEQUENCE: 4

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270
```

```
Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Trp Gln Asn
385                 390                 395                 400

Gln Pro Leu Phe Ser Ile Ser Ser Trp Arg
                405                 410


<210> SEQ ID NO 5
<211> LENGTH: 838
<212> TYPE: PRT
<213> ORGANISM: Nicotiana tabacum

<400> SEQUENCE: 5

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Pro Ser Trp Phe Arg Asp Cys Arg Asn Val
```

```
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Val Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Met Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Thr Phe Met Pro Arg Asp Val
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655
```

Gln Tyr Val Arg Ser Val Val Ser Ser Val Gln Arg Val Ala Met Ala
660 665 670

Ile Ser Pro Ala Gly Val Asn Ser Thr Phe Gly Ser Lys Leu Ser Pro
675 680 685

Gly Ser Pro Glu Ala Val Thr Leu Ser His Trp Ile Cys Gln Ser Tyr
690 695 700

Ser Tyr His Met Gly Thr Glu Leu Leu Gln Thr Asp Ser Arg Gly Asp
705 710 715 720

Glu Ser Val Leu Lys Asn Leu Trp Gln His Gln Asp Ala Ile Leu Cys
725 730 735

Cys Ser Leu Lys Ser Leu Pro Val Phe Ile Phe Ala Asn Lys Ala Gly
740 745 750

Leu Asp Met Leu Glu Thr Thr Leu Val Ala Leu Gln Asp Ile Thr Leu
755 760 765

Asp Lys Ile Phe Asp Glu Ser Gly Arg Lys Val Leu Phe Ala Glu Phe
770 775 780

Pro Lys Ile Met Glu Gln Gly Phe Ala Tyr Leu Pro Gly Gly Ile Cys
785 790 795 800

Met Ser Ala Met Gly Arg His Ile Ser Tyr Glu Gln Ala Ile Ala Trp
805 810 815

Lys Val Phe Ala Ser Glu Glu Thr Val His Cys Leu Ala Phe Ser Phe
820 825 830

Ile Asn Trp Ser Phe Val
835

<210> SEQ ID NO 6
<211> LENGTH: 839
<212> TYPE: PRT
<213> ORGANISM: Nicotiana tabacum

<400> SEQUENCE: 6

Met Ala Met Val Ala Gln Gln His Arg Glu Ser Ser Ser Gly Ser Ile
1 5 10 15

Thr Lys His Leu Asp Ser Ser Gly Lys Tyr Val Arg Tyr Thr Ala Glu
20 25 30

Gln Val Glu Ala Leu Glu Arg Val Tyr Ala Glu Cys Pro Lys Pro Ser
35 40 45

Ser Leu Arg Arg Gln Gln Leu Ile Arg Glu Cys Pro Ile Leu Ser Asn
50 55 60

Ile Glu Pro Lys Gln Ile Lys Val Trp Phe Gln Asn Arg Arg Cys Arg
65 70 75 80

Glu Lys Gln Arg Lys Glu Ser Ser Arg Leu Gln Thr Val Asn Arg Lys
85 90 95

Leu Ser Ala Met Asn Lys Leu Leu Met Glu Glu Asn Asp Arg Leu Gln
100 105 110

Lys Gln Val Ser Gln Leu Val Cys Glu Asn Gly Phe Met Arg Gln Gln
115 120 125

Leu His Thr Ala Ser Ala Ala Thr Thr Asp Val Ser Cys Glu Ser Val
130 135 140

Val Thr Thr Pro Gln His Ser Leu Arg Asp Ala Asn Asn Pro Ala Gly
145 150 155 160

Leu Leu Ser Ile Ala Glu Glu Thr Leu Ala Glu Phe Leu Ser Lys Ala
165 170 175

Thr Gly Thr Ala Val Asp Trp Val Pro Met Pro Gly Met Lys Pro Gly

```
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Ser Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Ala Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Val Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Ala Phe Met Pro Arg Asp Ile
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605
```

```
Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Ala Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Arg Ile Phe Asp Glu Ser Gly Arg Lys Val Leu Phe Ala Glu Phe
    770                 775                 780

Pro Lys Ile Met Asp Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Ser Val His Cys Leu Ala Phe Ser
            820                 825                 830

Phe Ile Asn Trp Ser Phe Val
        835
```

<210> SEQ ID NO 7
<211> LENGTH: 1239
<212> TYPE: DNA
<213> ORGANISM: Nicotiana tabacum

<400> SEQUENCE: 7

```
gtccatctgt ctatataggt agaatgagag taaaggagaa aacatatcct cctctccatt      60

tctgtagaca aagattctca aagagaaaca aattaaacac tagagagtga gagagtgcta     120

taagaaaaag aatatgggga gagctccatg ttgtgataaa gcaaatgtga agagagggcc     180

atggtctcct gaagaagatg ctaaactcaa agatttcatt cacaaatatg gaactggtgg     240

aaattggatt gctcttcctc aaaaagctgg actaaagaga tgtgggaaga gttgtagatt     300

gagatggcta aattatttaa ggcctaacat taaacatggt gatttttctg aggaagaaga     360

tagagttatt tgcaccttgt attccaccat tggaagcagg tggtcaataa tagcagctca     420

attaccggga agaactgaca atgatatcaa gaattactgg aatactaagc tcaagaaaaa     480

acctatggga ttaatgcaat caactaacca aagaaaatca ccatattttc cagctactaa     540

ttctcttcaa acccaacccc agataaattc aagtcttttt agagacttat attacacccc     600

aaataatagg cctaatatta caggcctaaa tcatcagtcc atttcttctg cccaccagac     660

aaattttctc tacactaata ataacatgaa ctttcctaat ttgggtgcta caaataatca     720

atatccttat aatatccaaa gtcataattt acttatgttt ggagaagcaa gttgttcttc     780
```

```
atcagatgga agttgcagcc aaatgagttt tggtaaagaa atcaagagag aagaaattat    840

gagtaatagt ttacaacaag gtcaaatttc aagtgttaat gcttttgaag aaaaccacca    900

gaattttact cttgattatg gcaatagtag tagtaattgg gtggatcaaa aaccaaatgt    960

gtattttggt actactacta ctcaagtact tcagtatgat aatgttgaag aagttaagca   1020

gcagctaaca agttgtacca atggcaacaa tggtagtact attggatgta acaacaacaa   1080

cagtatgttc gtgttcaatg atgagaatta taacaagtca aatgagatag agatgttcta   1140

ttactaaaga agaaatgact gttgaaaaga aaacaaatgc aagtaccatt aggaagattt   1200

gaaagggcgt ttgggtatgg gggttgccaa gaagattca                         1239
```

```
<210> SEQ ID NO 8
<211> LENGTH: 1362
<212> TYPE: DNA
<213> ORGANISM: Nicotiana tabacum

<400> SEQUENCE: 8

gtccacttgt ctatatagca agaaagagag taaaggagaa aacatattct cctctccatt     60

tctgtagaca agattctcaa aaagaaacaa attaaacact agagagtgag agagaactat    120

aagaaaaaga atatggggag agctccatgt tgtgataaag caaatgtgaa gagagggcca    180

tggtctcctg aagaagatgc taaactcaaa gatttcattc acaaatatgg aactggtgga    240

aattggattg ctcttcccca aaaagcagga ctaaagagat gtgggaagag ttgtagattg    300

agatggctaa attatctaag gcctaatatc aaacatggtg atttttcgga ggaagaagat    360

agagttattt gcagcttgta ttccaccatt ggaagcaggt ggtcaataat agcagctcaa    420

ttaccaggaa ggactgacaa tgatatcaag aattactgga atactaaact caagaaaaag    480

cttatgggat taatgcaatc aacaaaccaa agaaaatcac catattttcc agctactaat    540

tctcttcaag cccaacccca gataaattca agtcttttta gagacttata ttacaaccca    600

aataataggc ctattattac aggcctaaat cagtccattt cttctgccca ccagccaaat    660

tttctctaca ctaatagtaa catgaatttt cctaatttgg gtgctacaaa tagtcaatat    720

ccttataata ttcaaagtca taatttactt atgtttggag aagcaagttg ttcttcatca    780

gatggaagtt gtagccaaat gagttttggc aaagaaatca agagagagga aattatgagt    840

aattgtttac aacaaggtca aatttcaagt gttaatgctt ttgaagaaaa tcagaatttc    900

actcttgatt atggtaacag tagtagtaat tgggtggatc aaaaaccaaa tgtgtatttt    960

ggaaatacta ctactactac tcaagtactt cagtatgatg ttgaagaagt taagcagcag   1020

ctaacaagtt gtaccaatgg caacaatggc agtactattg gatgtaacaa caacaacagt   1080

atgttcgtgt tcaatgatga gaattataac aagtcaaatg agatagggat gttctattac   1140

tgaagaagaa atgactagct gttgaaaaga gaaaacaaat gtaagtacac cattaggaag   1200

atttgaaagg gcgtttgggt atgggggttg gcaagaagat tcaaactttt tctggggttt   1260

tgtgtaattg tggtggaatt attattattg aaacttcttt acttcaattt aaatcgtcgg   1320

tacatattac gtagttgtag tacaaaaaaa aaaaaaaaat ag                      1362
```

```
<210> SEQ ID NO 9
<211> LENGTH: 1619
<212> TYPE: DNA
<213> ORGANISM: Nicotiana tabacum

<400> SEQUENCE: 9
```

```
atttcccctc ctccatcatt gaaaacccccc tctgtccttt cccctagaga gacccctttt     60
tcctctctct ctcctttctc tttttattag acgcatatat tctctcttct ttctctttct    120
agggttttca cctgaaatag ttttatttcg gtgatatgtt aggatccttt ggttcatcat    180
ctcaatctca tgatgaagaa actgatgatc aacggcggag attcagttcc acttcccctg    240
caatccaaat ccggcaacta ctcattagct gcgcggagtt aatctcgcgg tccgatttct    300
cggccgcaaa cagactcctc accattttat caactaactc ttccccctttt ggtgattcaa    360
ctgaaagatt agtccatcag ttcactcgcg cactttctct tcgcctcaac cgttatatct    420
cttcagccac taatttcttg acaccatcta atgttgttga aagttcaaat gattcagctc    480
tacttcagtc atcctatctt tccctaaacc aagtgactcc tttcattaga tttagtcagc    540
taactgctaa tcaagcgatt ttggaagcta ttaacgataa ccaacaagcg atccacatcg    600
ttgattttga tattaatcac ggtgttcaat ggccaccgtt aatgcaagca ctagctgatc    660
gttaccctcc tccaactctt cggattaccg gtactggaaa tgaccttgat acccttcgta    720
gaaccggaga tcgtttagct aaatttgctc actctttagg ccttagattt cagtttcacc    780
ctcttttgat taccaataat aatgacaatg atcatgaccc ttcaataatt tcttctattg    840
ttcttctccc tgatgagaca ttagctatca actgtgtatt ttatcttcac aggctcttga    900
aagaccgcga aaagttaagg atttttttgc ataggattaa atccatgaac cctaaagttg    960
taacgctggc cgagagagaa gcaaatcata atcacccact ttttttgcaa agatttgtgg   1020
aggctttgga ttattatgca gctgtgtttg attcattgga agcaactttg ccaccgagca   1080
gtagagagag gatgacagtg gaacaagttt ggttcgggag agaaataatt gatatagtag   1140
cagcagaagg agataagaga agagaaagac acgagagatt cagatcatgg gaagtaatgt   1200
tgaggagctg tggatttagc aatgttgctt taagcccttt tgcactctca caagctaaac   1260
ttctcttgag acttcattac ccatctgaag gataccagct tagtgtttcg agtacgagta   1320
attctttctt cttgggttgg caaaatcaac cccttttttc catatcttct tggcgttaaa   1380
tttaaaaccc taaaaaacaa gatttttatc tatctgcatg gtgaaggaca aagaggtctt   1440
caatctcagg ttcttttttt ttttttttat atatatatct tgtttgggtt taaggttatt   1500
gggctgatga atgttttaat tttaacatag gtctacttac gtagtagtta taggttgata   1560
atgagatata attaactaag tctttgtata atgcagatcc tgaacttaat ctttatttg    1619
```

<210> SEQ ID NO 10
<211> LENGTH: 1827
<212> TYPE: DNA
<213> ORGANISM: Nicotiana tabacum

<400> SEQUENCE: 10

```
aggttcttct tccttaatat tgagtcaaga ttagtactac tactatagcc aagaaaatgt     60
gaaatcatat agtactaact ttcccttctc cctagctact gataactcta attaatttca    120
gatgccaaaa ccataaattt cccctcctcc atcattgaaa acccctttgt cctttccccc    180
cagacccccct tttcctctct ctctctctcc tttctctttt tattagacgc atattctctc    240
ttctttctct ttctagggtt ttcacctgaa atagttttat ttcgttgata tgttaggatc    300
ctttggttca tcatctcaat ctcatgatga agaagctgat gatcaacggc ggagatgcag    360
ttccacttcc cctgcaatcc aaatccggca actactcatt agctgcgcgg agttaatctc    420
acggtccgat ttctcggcgg caaacagact cctcaccatt ttatcaacta actcttcccc    480
ttttggtgat tcaactgaaa gattagtcca tcagttcact cgcgcacttt ccattcgcct    540
```

caaccgctat atctcttcag ccactaattt cttgacacct aatgcatcat ctaatgttgt 600
tgaaagttca aatgattcag ctctacttca gtcatcctat ctttccctaa accaagtgac 660
cccttttatt agatttagtc agctaactgc taatcaagcg attttagaag ctattaacga 720
taaccaacaa gcgatccaca tcgttgattt tgatattaat cacggtgttc aatggccacc 780
gttaatgcaa gcactagctg atcgttaccc tcctccaact cttcggatta ccggtactgg 840
aaatgacctc gataccccttc gtagaaccgg agatcgttta gctaaatttg ctcactcttt 900
aggccttaga tttcagtttc accctctttt gatcaccaat aataatgaca atgatcatga 960
cccttcaatc atttcttcta ttgttcttct ccctgatgag acattagcaa tcaactgtgt 1020
attttatctt cacaggctct taaaagaccg cgaaatgtta aggatttttt tgcataggat 1080
taaatccatg aaccctaaag ttgtaacact ggccgagaga gaagcaaatc ataatcaccc 1140
actttttttg caaagatttg tggaggcttt ggattattat gcagctgtct ttgattcatt 1200
ggaagcaact ttgccgccga gcagtagaga gaggatgaca gtggagcaag tttggttcgg 1260
aagagaaatt atagatatag tagcagcaga aggagataag agaagagaaa gacacgagag 1320
attcagatca tgggaagtaa tgttgaggag ctgtggattt agcaatgttg ctttaagtcc 1380
ttttgcactt tcacaagcta aacttctctt gagacttcat taccccttctg aaggatacca 1440 gcttagtgtt tcgagtacga gtaattcttt cttcttgggt tggcaaaatc aacccctttt 1500
ttccatatct tcttggcgtt aaattataag ggaaattaaa accctaaaaa caagatttta 1560
tctatctgca tggtgaagga caaagaggtc ttcaatctca ggttcttttt gtttttttaa 1620
cttgtttgga tatgaggtta ttgagctgat gaatgtttta attttaacat aggcctactt 1680
acgtagtagt tataggttga taatgatata tatttaacta agtctttgta taatgcagat 1740
cctgaactta atttttattt ttattatttt gttgttaatg aaagattctg ttaccaaatt 1800
ttatcagtct atttaattag aggccaa 1827

<210> SEQ ID NO 11
<211> LENGTH: 3900
<212> TYPE: DNA
<213> ORGANISM: Nicotiana tabacum

<400> SEQUENCE: 11
gaaagcttta actcaagcaa attctctctc tctctctctc tctctctctc tctctctctc 60
tcttcatttt ctttttctct tttctcaccc accactctca cacacctctt cacctcacct 120
tacacactaa aaaaacatca ctcctctctc taaaaaattc aatctttttg ctgttccaac 180
atgtctttta gagtttgttt cagtttcaga tcttaagggc gggagtgtta tgcttcttct 240
aatattttga agctcaagaa aacagagcaa atttttgctt tcttttctcc tactttttgt 300
ggggggtaat tcttgttttt gtaatctcaa agctggctgt tttatgtata tactgaaggg 360
gttgtggtga tttgtttgtc tactttaaga aggtgccatc tttttcagta atatttgggt 420
aaaagttctc tctttttttgg ccttaaacgc gaagattcag gcctctctca acgtgtcatc 480
tgttctctgt attaaacaca gctggagaat taattacata gaggtaaaaa aaggggttaa 540
agtcgccaaa gaattgaaaa aaaacagagg gctgaggtaa aaagttgatg gtttttaaaa 600
aaaaataaaa gcttaaatga tgataaagtt tggagcttta tgtgaatgga aatggtgttg 660
tgtttgtatc aaacacgagt agtttacagc ttatgtgaat ttgaaagaga gagaattttt 720
gtctgtattt atatcctttt cagccatatc tttcgttaga gcagttttgg ctgtacctta 780

```
atttgtaagg gtttaagcgt gaagtgtgtg tttgagcctt ctgttataag gggcacaaag    840

tatagaaaca acaaaagggg cacctaggaa tcttctggct caatcaagat cgttcattta    900

atcttgtctg agatcactag aaaaagaaaa aggaaagata aagataaagt ctttgtttca    960

gagaatctta gttctctgtg ttgatatata taataaaagc tgtttgcagg gaatatatct   1020

acttgggggt gtttttattt cttttaaggg tgtttgaaaa tttggaaatc ttgattattt   1080

ttttgtttgg gattttgggg tttgacggca aatggctatg gtggtacagc agcataggga   1140

gagtagtagt ggtagtatta caaaacatct tgacagtagt ggaaagtatg tccggtatac   1200

agctgagcaa gtggaggcat tagagagggt ttatgcagag tgccctaaac ctagctcgtt   1260

gcgccgccag caattgatcc gcgaatgccc tattctgtcg aatatcgagc ctaagcagat   1320

caaagtttgg tttcaaaaca gaaggtgtcg agagaagcaa aggaaagagt cttctagact   1380

acagactgta aatagaaagc tgtctgcaat gaataaacta ttaatggagg agaatgatcg   1440

cttgcaaaaa caggtttcac agcttgtgtg tgaaaatggc tttatgcggc aacaattgca   1500

tactgcatca gcggccacta ctgatgtaag ttgtgagtca gtggttacca cccctcagca   1560

ttccctcaga gatgctaaca accctgctgg actgctgtcg attgcagagg aaaccttagc   1620

agagttcctt tccaaggcta caggaactgc tgttgattgg gtcccgatgc ctgggatgaa   1680

gcctggtccg gattcagttg ggatttttgc catctcacac agttgtagtg gagtggcagc   1740

ccgagcatgt ggtcttgtta gtttagagcc gacaaagatt gctgagatcc tcaaagatcg   1800

accatcttgg ttccgagact gccggaacgt tgaagttttc acgatgtttt ctgcaggaaa   1860

tggaacaatt gagcttttgt acacgcagat atatgctcct accaccttgg ctcctgcacg   1920

tgatttttgg actctgagat acacaaccac cctggagaat ggtagttttg tggtttgtga   1980

aagatccctc tctggtactg gagctgggcc gaatgctgct tctgcttccc agtttgtaag   2040

agctcaaatg cttccgtccg gatatctaat ccgaccgtgt gacggtggag gatccattat   2100

acatattgtt gaccatctga atcttgaggc atggagtgcc cctgagattt tgcgtccact   2160

ttatgaatcg tcaaaagttg tggcacagaa aatgactatt gcggcactgc gatatgcaag   2220

gcaaatagct caggagacta gtggggaggt tgtatatggt ctgggaaggc aacctgcagt   2280

tcttcgaaca tttagccaga gattaagcag aggcttcaat gacgccatca atggattcag   2340

tgatgatggc tggtcattgt taagttctga tggtggtgaa gatgttatag ttgctgtcaa   2400

ttcaaggaag aacattgcca ccacttccgt tcctctttca ccgctgggag gcatcctttg   2460

tgccaaagca tcaatgctac tccagaatgt tcctcctgtg gtactggttc gatttctcag   2520

ggagcaccgt tcagagtggg cggactttaa tgttgatgcc tatgtagctt cgtcaatgaa   2580

atcttgttca tatgcatatc ctgggatgag gcctaccaga tttaccggaa gtcagataat   2640

aatgccactt ggccatacaa ttgaacatga agagatgctt gaggttatta gattggaagg   2700

acactctatt ggccaggaag atacttttat gccaagagat gttcaccttc tccagatgtg   2760

tagtggaact gatgagaatg ctgtcggagc ttgttctgaa ctagtttttg ctgcaattga   2820

tgagatgttt ccagatgatg cacccctgtt gccctccggg tttcgtatca ttcctctcga   2880

gtcaaaatca agcgatcccc aggatacatc gaatgctcat agaacactgg atctggcatc   2940

aagtcttgaa gttggcccag caacaaaccc tgctactgga gatgtggtct ctggctacag   3000

tgcacgatct gtgttgacaa ttgcttttca atttccattc gaggacaatc ttcaggacaa   3060

tgtagctacc atggcgcgcc agtatgttcg cagtgtggtt tcatctgtcc aacgggttgc   3120

catggcaata tctcccgcag gagtgaattc aacattcggg tccaagcttt ctccaggctc   3180
```

```
ccctgaagct gtaacgttgt cgcactggat ctgccagagc tacagttatc acatggggac   3240

agagttgctt caaactgatt cgaggggcga tgaatcagtg ctaaaaaatc tttggcaaca   3300

tcaggatgct attttgtgct gctcattgaa gtccctgccg gttttcattt ttgctaataa   3360

ggctgggctt gatatgctgg agacaacctt agttgcttta caggacatta ctctagataa   3420

gatatttgat gaatctggcc ggaaagtgtt gttcgctgaa tttcccaaga tcatggaaca   3480

gggttttgcg tacttgccgg gtggtatttg catgtcagca atgggacgac atatttcata   3540

tgaacaagct attgcatgga aagtctttgc ttctgaagaa actgtccact gcttagcctt   3600

ctcatttatt aactggtcat ttgtttaatg ttgctgtcaa atctcctttc tttttttcc   3660

tttttgtttt ttgacatctt cctcacagag gacactgaca gccaggaaca cagttgaacg   3720

gaatgatctt tgggacggat gaaaattttg taacttgggg ggctcccgtc tgttttacct   3780

ttaatttaat tagactaaat ttgtattttg cttcctgaat tcttcatact cttatgtaaa   3840

ttttctagtg cagctttttt gagtgcagat gtttgtttcc gcaaaaaaaa aaaaaaaatag   3900
```

<210> SEQ ID NO 12
<211> LENGTH: 2884
<212> TYPE: DNA
<213> ORGANISM: Nicotiana tabacum

<400> SEQUENCE: 12

```
aagctgtttg cagggaatat atctacttgg gggtgttttt atttcttaaa agggtgtttg     60

aaaatttgga aatcttgatt tttttttttgg tttgggattt tgaggtttga gggcaatggc    120

tatggttgca cagcagcaca gggagagtag tagtggtagt attacaaaac atcttgacag    180

tagtggaaag tatgtccggt atacagctga gcaagttgag gcattggaga gggtttatgc    240

tgagtgccct aagcctagct ccttgcgccg ccaacaattg atccgtgaat gccctattct    300

gtcgaatatc gagcctaagc agatcaaagt ttggtttcaa aacagaaggt gtcgagagaa    360

gcaaaggaaa gagtcttctc gactacagac tgtaaataga aagctgtctg caatgaataa    420

actattgatg gaggagaatg atcgcttgca aaaacaggtt tcgcagcttg tgtgtgaaaa    480

tggctttatg cggcaacagt tgcatactgc atcagcggcc actactgatg taagttgtga    540

gtctgtggta actacccctc agcattccct cagagatgct aacaaccctg ctggactgct    600

gtcgattgca gaggaaacct tagcagagtt cctttccaag gctacaggaa ctgctgttga    660

ttgggtcccg atgcctggga tgaagcctgg tccggattca gttgggattt ttgccatctc    720

acacagttgt agtggagtgg cagcccgagc atgtggtctt gttagtttag agccgacaaa    780

gattgctgag atcctcaaag atcgatcttc ttggttccga gattgccgga acgttgaagt    840

tttcacaatg ttttctgcag gaaatggaac aattgaactt ttgtacacgc agatatatgc    900

tcctaccacc ttggctcctg cacgtgattt ttggactctg agatacacaa ccaccctgga    960

gaatggtagc tttgtggttt gtgaaagatc cctctctggt actggagctg ggccgaatgc   1020

tgcttctgct tcccagtttg taagagctca aatgcttccg tctggatatc taatccgacc   1080

gtgtgacggt ggaggatcca ttatacatat tgttgaccac ctgaatcttg aggcatggag   1140

tgcccctgag attttgcgtc cactttatga atcgtcaaaa gttgtggcac agaaaatgac   1200

tattgcggca ctgcgatatg caaggcaaat agctcaggag actagtgggg aggttgtata   1260

tggtctggga aggcaacctg cagttcttcg aacatttagc cagagattaa gcagaggctt   1320

caatgatgcc atcaatggat tcagtgatga tggctggtca ttgttaagtt ctgatggtgg   1380
```

```
tgaagatgtt atagttgctg tcaattcaag gaagaacatt gccaccactt ccgttcctct   1440

ttcaccactt ggaggcatcc tttgtgccaa agcatcaatg ctactccaga atgttcctcc   1500

tgcggtactg gttcgatttc tcagggagca ccgttcagag tgggcggact ttaatgttga   1560

tgcctatgta gcttcctcaa tgaaatcttg ttcatatgca tatcctgggg tgaggcctac   1620

cagatttacc ggaagccaga taataatgcc actgggccac acaatagaac atgaagagat   1680

gcttgaagtt attagattgg aagggcactc tattggccag gaagatgctt ttatgccgag   1740

agatattcac cttctccaga tgtgtagtgg aaccgatgag aatgctgtcg gagcttgttc   1800

tgaactagtt tttgctgcaa ttgatgagat gtttccagat gatgcacccc tgttgccctc   1860

cgggtttcgt atcattcctc tcgagtcaaa atcaagcgat ccccaggata catcgaatgc   1920

tcatagaaca ctggatctgg catcaagtct tgaagttggc ccagcaacaa accctgctac   1980

tggagatgtg gtctctggct acagtgcacg atctgtattg acaattgctt ttcaatttcc   2040

attcgaggac aatcttcagg ataatgtagc taccatggcg cgccagtatg ttcgcagtgt   2100

ggtttcatct gtccaacggg ttgccatggc aatatctccc gcaggagtga attcaacatt   2160

cgggtccaag ctttctccag gctcccctga agctgtaact ttgtcgcact ggatctgcca   2220

gagctacagt tatcacatgg ggacagagtt gcttcaagct gattcgaggg gcgatgaatc   2280

agtgctaaag aatctttggc aacatcagga tgctattttg tgctgctcat tgaagtcgct   2340

gccggttttc atttttgcta ataaggctgg gcttgatatg ctggagacaa cattagttgc   2400

tttgcaagac attactctag ataggatatt tgacgaatct ggccggaaag tgttgttcgc   2460

tgaatttccc aagatcatgg atcagggttt cgcgtacctg ccgggtggta tttgcatgtc   2520

tgcaatggga cgacatattt catatgaaca agctattgca tggaaagtct ttgcttctga   2580

agaaactagt gtccactgct tagccttctc atttattaac tggtcatttg tttaatgttg   2640

ctgtcaaatc tcctcttttt tttccttttt gtttttttgac atcttcctca cagaggacac   2700

tgacagacag gaacacagtt gaacggaaag atcttgggac cgatgaaaat ttttgtaact   2760

tgtggggctc ctgtctgttt tgccttaatt taattagact aaatttgtat tttgcttccc   2820

ggattcttca tactcttgtg taaatttact agtgcagctt ttttgagtgc agatgtttgt   2880

ttcc                                                                2884
```

```
<210> SEQ ID NO 13
<211> LENGTH: 9770
<212> TYPE: DNA
<213> ORGANISM: Nicotiana tabacum

<400> SEQUENCE: 13

gtctacaaga aaatatgcat ccggatattc aaaaatccaa aagaaaagaa aagttgaaaa     60

tttaataaaa tctcaaaaag gagttctcga gaattttttg acaaataata aaaaaactaa    120

atcgcaaaat gtaggagaat attctgtaga tgaacaagtc actaactttg agtcagatga    180

taacaaaatt caaattgaag aagatgttta tgagaaatct gacgaagaaa caaactttag    240

ccttaggccc tatattaaac tttggcccta ggcctcatat gagcttgagt cgcccctaat    300

tctaatacaa gtattagtgg ctactttcac ggcttgtgac ttatggatta caaacaactt    360

tacagttacg tcaaggctcc acgtagttct caatttatgg agcatatatt agatgattaa    420

cgcagggaaa gattctgctc tcctctgata catggctatt attcctcgtt tagttcaaaa    480

aggaaaaaga gggtagtctt gttatattat tggggaatga attatggttt caaacttttc    540

aaacttaaag gattttgtac atggtaaaac ctaaattgac acgtaacttg gtactttcaa    600
```

```
agacacgatc ttttacgcga tattttaaat aaagaaaaga tcaagtcaaa acatgggcca    660
aaaagaaaaa ccccatgatt ttttctgata aaaagctgct aacttttagt ttgttttatc    720
caataaaaca tctttaacgg tctgcctgct ttagtttaat cctcttttta agatgtaatt    780
aagcataaaa tagaaaaggg aaaaaaaagg tccattggat tttggaagaa attttaagaa    840
agtacaagaa ctagtaaagt cattttgtat agagtatgtt aaaaaggtga gtgacaattc    900
gaaaaagaaa gcattgataa gtcaatcact aaataaaaaa gcacacctaa taatcattca    960
ttcaaaaaaa caaatttcta tgaaagataa tcattatcat aagtcactgc agaaatccca   1020
tatacagtag agtaccagga ttttacgata aggtgttagc aaactatcta ttcatttttt   1080
gacaagcatt ttatgtttgg tcatttgttg ggaaaaatta gggagaaatt taaaaatagt   1140
tagatttaca actggtcatt aaaaatagcc caatttcaaa agtaatcgaa atttagccac   1200
ttttcatgta aagataaatc tgagcgaaaa tattgttcaa aacccggaaa atacgcccgt   1260
atattatact ggagttccag cataagtatg cttgaactcc agcatattat acgggagttc   1320
taggataact atgttggaac tccagcataa tatgttggag ttccagcata agtacactag   1380
aactccagca tattatacgg gagttccaac aagtataact gtcccgtata atatattgga   1440
gtttggagca ccggtgctcc agtctcccgt atattataca ggagtcagca aagtataccg   1500
gtccagcata atatgctgga gttcgtacac agatgcaccg aactcacgta tattatgcgg   1560
aaccggtctc tgttgcagca aaatagtggc tatttttcat tgacttcgta aacggtggct   1620
atttttgaat gaccagtccg aaaactggct ataccgtgct attttgacga aaaattatcc   1680
ccccacccac ccacccaccc aaacgcacct tacacacatt agtgcacatc ttttaactag   1740
tttttggtta ttttttatt tgatgcccga tattcgtata tggatttcga ttaattagaa   1800
ttcacaccga aacattcttt cttaggattt tgtacatact taatatgcga atacaaaacc   1860
tatgcggaaa ggtaagggaa cctattcatc cctctacagt acttgtgata atgttatact   1920
tttttgaatt taatttggga gacatgtcaa tctttatttt gaaaaaaaaa tagaataaaa   1980
ccatagggaa atgaacaatt tatctttcac tcctatctca ttttatttgt cttgaatttt   2040
tcaaaatttt gaattatatt ttgaaacttc ttcaatttat tttcttggaa tcttcagaat   2100
tcaatttaaa attccaaaat tccaaggatt tagctcccgt ttggccacag attttggctt   2160
catttttta aaaaaaattt tgaaaacatt ctttgtttat gcaatatgat catgttttag   2220
gggaaaaaaa ttaaaaaaaa taaaaaaaaa tcaaattccc aaaaactggt taggcaattt   2280
ttggatgata ttttttcttc cactcacaaa actttaacat gtccaaacac aacttcaact   2340
tcaaaaatta ttttcaacac aattttaaaa actctttttt caagtttcaa tcaaatctat   2400
atccaaatgt tagcttagta tcaaataagt gattgaaatc aaattaaaat cgagtggtaa   2460
ataaaataga ggagagctcg gtaaattaca agagtgcggt aaatcttttc tcctttactc   2520
tcactgtagc ctattctatc tgttgtaact aataagtaac tgagctacgg aaaaagtgcc   2580
tagactttta acttcacaag tataataaat agaagtcaat tctttcataa tattgtttcc   2640
atcctatcaa acagactttg tctcactgac cttccttctg agtgtgtctt ttatatgtca   2700
tttttagtga atccatatga tttagagact ctaatattcc acatgcgggt cttaatttgg   2760
tgtatatgta tatggtaata atttttgtta ggtagctgta gtattctatt attgttatgt   2820
attgactcat catgtaaata aagccggtta gataaggcta gaaaaatatg agtataccta   2880
gaaattatta gcatattgtt tggaacatgt caaaaatttc aatgacctag ctagagctgt   2940
```

```
caattagtca aataacttta ttaatattta cttatgaaaa cactttgaaa ttcttggagt   3000
ttaagggaaa gactactgac taaaaaacaa agcaaaagtc tatgcattac tatactatac   3060
acagcacagc attttccaat agtatttgag atgaatctcc aatcagctac tgttgttctt   3120
ttcttttctt tatttagttt aagttttatg tgttgatggt atacaaatta tttgcacaat   3180
caaatggctt atctggataa tataggtaaa cctcttgtaa tcactaattg gtaatctggt   3240
aaaaataaca ctatttctat tccaatttat gtgatcaatt tcactagaca aaaatttaag   3300
aaagaaataa attttttaga acttgtagtc ataaacaagt tgtaacattt gtatggctat   3360
aatttttta acttgtgatg ttaaacatgt cagattgttt gtgtagctat aaaagttttt   3420
cattaggcgt aaaattaaaa atttagatta aattattatt aaatttagaa agaggtcatt   3480
ttttttagcg aagtaaaaaa gaaatcggtt cacataaacc gaaacataga gtaagtaatc   3540
tgttatgaca aattaaaaat tacttgtagt gtaaaaaaat ctttacaaca ttcgtgtata   3600
tacttaaatc tttttatttt tttggcaaga gatagttgtt cagcaaaagt aagttagaaa   3660
taggtctgtc cttctgactt tgtaactctg aaatgaaaat ttcaaaatcc cttctatttt   3720
tactgttacc cccccccccc cctcacaaac cccaactcac tcttatttaa taaaaagctc   3780
tacttagaaa agacaccctt gtccatctgt ctatataggt agaatgagag taaaggagaa   3840
aacatatcct cctctccatt tctgtagaca aagattctca aagagaaaca aattaaacac   3900
tagagagtga gagagtgcta taagaaaaag aatatgggga gagctccatg ttgtgataaa   3960
gcaaatgtga agagagggcc atggtctcct gaagaagatg ctaaactcaa agatttcatt   4020
cacaaatatg gaactggtgg aaattggatt gctcttcctc aaaaagctgg taacaacaac   4080
ttctactcca ctagtcctct atgtgtatgt attttattat tattattatt attattatta   4140
ttattattat tattattatt attcatgaat cgaagggaca aaggtctaaa tctcagtggg   4200
tcgtggtagc aaggccattc cgccatttat aatatcttct tgcaaattcc accagtttca   4260
tatgtgtatg ttttttttctt attagtcata aatcaaagcg acgaagggtt aaatttcagt   4320
tgattgtgat agcaaggtca cactctaccg cttataatat ctcgtggcgt atttaacatt   4380
gtttgtatgt atatgtttga gtataaaggg aggaaagctt atatttatat ttgagtggat   4440
tgagtttttt tccttgttgc tgcattattt atgatttgat gagatttatg ttgggaactg   4500
caggactaaa gagatgtggg aagagttgta gattgagatg gctaaattat ttaaggccta   4560
acattaaaca tggtgatttt tctgaggaag aagatagagt tatttgcacc ttgtattcca   4620
ccattggaag caggtaatat atatatacct ttttttggtc gtaatttttt tttcattttt   4680
tatcatcttt ctgatgaatt tgagactgaa acaaaaactg ttcccactaa aaatggaaaa   4740
gtaaaacctc aataagtaag aaaagggaaa aaacaatgag ggctcagaaa gaaatgcaaa   4800
tagtcagttg gatttttaat taaagattct gccatttatg gacatatttt tctgcatgca   4860
tgccaggttt agatctaaga tcaagtcttt atttactcac ttacagatgt ttaattatta   4920
agacaaagtt ccaatttttc ttctttcttc tctttctttt tgtggaaatt ttttctctag   4980
taaaccaatt aatttttgtt ataacatgtg caatataata tgttaacagg tggtcaataa   5040
tagcagctca attaccggga agaactgaca atgatatcaa gaattactgg aatactaagc   5100
tcaagaaaaa acctatggga ttaatgcaat caactaacca aagaaaatca ccatattttc   5160
cagctactaa ttctcttcaa acccaacccc agataaattc aagtcttttt agagacttat   5220
attacacccc aaataatagg cctaatatta caggcctaaa tcatcagtcc atttcttctg   5280
cccaccagac aaattttctc tacactaata ataacatgaa ctttcctaat ttgggtgcta   5340
```

```
caaataatca atatccttat aatatccaaa gtcataattt acttatgttt ggagaagcaa   5400
gttgttcttc atcagatgga agttgcagcc aaatgagttt tggtaaagaa atcaagagag   5460
aagaaattat gagtaatagt ttacaacaag gtcaaatttc aagtgttaat gcttttgaag   5520
aaaaccacca gaattttact cttgattatg gcaatagtag tagtaattgg gtggatcaaa   5580
aaccaaatgt gtattttggt actactacta ctcaagtact tcagtatgat aatgttgaag   5640
aagttaagca gcagctaaca agttgtacca atggcaacaa tggtagtact attggatgta   5700
acaacaacaa cagtatgttc gtgttcaatg atgagaatta taacaagtca aatgagatag   5760
agatgttcta ttactaaaga agaaatgact gttgaaaaga aaacaaatgc aagtaccatt   5820
aggaagattt gaaagggcgt ttgggtatgg gggttgccaa gaagattcag actttttttg   5880
gggttttgtg tagttgtggt agaattatta ttgaatgaaa aaaaaaaact tcctgtactt   5940
taattcgtca gtacatacta catactacta caaagtagtt aaaagcctat tctatttgtg   6000
cttttttttt cactcgatgt tcaataatta tattggtttt tgattaaatt tgaatttgag   6060
caaggaagat caacattgga gggataaatt gtttcctaac gaaggcgatt acatacttag   6120
aacttgaact caatatctct aattaaaaat gaagtaatac ttataataac tccaccacaa   6180
ttcttattgt tgtgcatttc tttataaaat atgtaaataa tgggtcatat atattgttta   6240
ccttttctat tcatatacat agattttaaa ttaattatac acatatatat aatacattaa   6300
ttattcatat attatatttt tgctagctat ttttagttta agcgatttgg taggcgacta   6360
cttgggttaa ttcttttttt ttaatatata tatcaaaata atgaagctgt ataatacact   6420
taaaaatcat atttgaaagg tattaaatac gacttaggag agttcttaaa ccattttgga   6480
accttgtcta cgtactttta tgcaatagct gtttttgttt gtctctgcta aaacctatgc   6540
tccccaaccg tgcaccaatc aacttagaag ttagaactca gaaataaatg taactatact   6600
ccacagaaag ttaaaaagtt ttactgttac cattcactca aggatcagaa actgaaagac   6660
aaatgaatca gtgcttcact gttcttcact aaaagaaata ctgtttacat tagtttcaaa   6720
agagtttaat cataaaaaca aatgtaccat aaaaagggga gattatcaac ctgaaaatga   6780
aacagaacat acgttatata tcaatctata tacggtcgag atcggactcg tctattacac   6840
gacagatcgg gattgaaacg taacagtttt gaagatcaac cccgggttcc gtcggaccga   6900
ggtacaaggt cagaatgccc gttctcgaga acatcgagtc catgacccca gaatcaaccc   6960
tgaccccaaa tgagctcgag gaaacatccg gataacggaa ggcgaaatat ccgtaaccgg   7020
tcgggtatca cggcatgaat ttcggcacgt aacaatgaga aaccggctaa ttagcaaatc   7080
atggaatttt ttacctttta tagaattgta actaaagtgg gattccccta ctatgtaaag   7140
ggggtctgac tatttgtacg ggacattcat taaacgcatc ccaaagtaat ataatattat   7200
tttctttttg taagctattg ttctcctgta tctgatacta tttgaattgc atcaagttca   7260
agtgagactc atttttcaa ggctataatt gttcaagtcg cacggtttga atttattcga   7320
tcattgttcg ctttaattac aattcaattc atcgctttat gtcaaattaa tccacatatc   7380
cttaaaacca cttacaaatt taattgttat caaattttaa gggtaaacag tttggcgctc   7440
accgtggagc taaggataat agtggttgtt tgatatagat tttcataaca cacactattt   7500
tacaattgtt cttcgaagtg tctctcattt caggtttaag ctcaaaatgt caaactcaca   7560
attggcaccc ctacctgcac acaatgagtc tggtcaccat ggtgaaaata acaacatagc   7620
acctggtaac gaggtaccgc ccgctgatcc catcagaatt tcaatcgcgg acccgttgga   7680
```

-continued

```
cgctaactcg catgtggcta tcgacatgtt acagtctcaa caggcgacga tagctcagtt   7740
acaaaaccaa agccgcacac cgagcagagt tgaactcgat ccgtcccgga aaatcacctg   7800
cagggaagaa ccgtccgcgg agaggtcaaa tggagatgag tcggggacta accccgagat   7860
cataaaaatg cttgaggaac cgatgatacg gattgaatca ggggaaaaga aaatcgaggc   7920
aaatgacaag aaggtaaaaa cttacaattt cacggtcaac caaatcccgg gagcaccgcc   7980
ggtactgaaa agcttggatt ccaagaagtt cgtgcaaaaa catttccctc cgagtgtggc   8040
cccgaaatcg atcccaaaaa catttatatg cccgagattc ttaagtataa tgggacaacc   8100
gacccaaacg agtatgtcac ttcttacaca tgccctatca aagggaacaa cttagaggtt   8160
gatgagatcg agtctgtttt gttgaagaaa ttcggagaga ccctgtcaaa tggagctatg   8220
atatggtatc acttacctcc taattctatt gactcatttg caatgcttgc aaactctttc   8280
gtgaaagcac acgccagggc tatcaaggtc gagacccaga agtcggacct cttcaaagta   8340
agacagaagg ataatgagat gctcaaagag tccgtgtcct agtttcaaat gaaacagaag   8400
gacctaccac cggtcgctga tgattgggcc gttcaagctt tcacccaagg actcaatgtt   8460
cgaagctcgg tggcttcaca gcagttgaag caaaatctga taaagtaccc aactgttatt   8520
tgggccaatg tgcataaccg ctatcaatca aaaatcaaag tcgaagatga tcaacttgag   8580
gctctttccg ggtcggttta ccctgtcaga ctcgtcgaca gaatcaagag agatatcgac   8640
cgtgaaccaa ggtcaaacgt agatcattac tagccatatg atggagattg gaaaagcaat   8700
aggtctgggt gaagttctac acagaatgaa aagagaaatg atccaggtca gagcactcga   8760
ggactcgcaa gcaagaacga cttcgacagg cctatcaggc ctaaagaagc accaaggtta   8820
tcgaaatata actttaatat tgatgcggct gccatcgtat cagctatcag acgcatcaaa   8880
gataccaaat ggcctcgacc tttacaatcc gatccagccc aaagggatcc taaccaaatg   8940
tgcaaatatc atggcacttc tggccacaga ataaaggatt gtcgacggtt aagagaggaa   9000
gtagcccggt tgttcaataa cgggcacctt caagaatttc tgagcgaccg agccaagaat   9060
cattttagaa atagggattc taacaaatag accgaaccag aagaacctca acacgtcatt   9120
aacatgatca tcggtggagt cgatgcccct caagtgctga tgttgaagcg caccaaagtg   9180
tccattacaa gggaaaaacg gactcgagat tacatattag aaggaacctt gtctttcaac   9240
gacgaggatg cagaagggat cgtgcagcct cacaatgatg cattggtaat atctgtactc   9300
ataaataaat ctcgagttaa gcgtgtgtta attgatccag gtagctcaac caacatcatc   9360
cgattgaggg tcctagaatg gcttggccta caagatcaaa tcatgcctgc agtccgagtt   9420
ctaaatggat tcaacatagc atgcaaaacc actaagggag aaataacatt gccggtgaat   9480
accaccagaa ccatccagga aaccaagttt tatgtgatcg aaggagacat gaggtacaac   9540
gctctgttcg ggaggctaag gatctacagc atgagggcag caccctcgac tcttcaccaa   9600
gtgttaaagt tcccaacgtc gggagggatc aaaacaatct acggggagca accggccgca   9660
aaagaaatat ttgcagtcga agaagagatc ccggtataga cactagcaac atcaaaggaa   9720
ccgagttcgg ataagaaata ataggctaaa tagcaattat cgacaccagc              9770
```

<210> SEQ ID NO 14
<211> LENGTH: 9150
<212> TYPE: DNA
<213> ORGANISM: Nicotiana tabacum

<400> SEQUENCE: 14

```
tttaagactg tttttattt gatttatact ctttaattgt attttcgcac gaaaataacc      60
```

```
gatcaaagtt agtcgatttt attaaaaaat aaaattaccg accaaagttg gtcggttttt    120
taaaatgacc ggccgaatta accgaccaat tttggtcggt tttttaatat taatttttat    180
ttattttaat tgaaaaactg accaaaattg gtcggtttct tgaaaaataa atttcacggg    240
actcgaaaat agtttttcgc atttttgctc caaagaaaac cgaccaaagt tggtcgattt    300
cgtaaaaaaa aattaaaaat aaaatatttt aaaaaaaccga ccaacttttg tcggtttttt   360
ggtcggtgtt ttgaccgacc aaagttggtc ggtcgacctt ggtcggtttt tgccgaattt    420
ctagtagtga tataccctta gagttacaca attggcacat atatgccctt ctcaaaacga    480
aattcaccca aaaattatgg tttaaacttt aaaataataa aaacatctca aactttaaca    540
atactcaaaa gaccaaaata tttaaattat ttctaaaaag ataatttaat gattaaaagc    600
ctagagttca agttgtagtg ttataaattt gagttgttag tctttttcat ctttttttcag   660
ctggacattt tctatttttt ttattaacta tgtaaattag gggtgtacat ggaacgggtt    720
ggatcgattt ttatcaaaac taaaccaaac cgattatatc ggtttgaatt gttcggtttt    780
attggttttt tcagattttt tgttacataa atattatttc aatcttgctt tgttaaattt    840
tttagaacta aatatatgtt cagtaaaact taaaaaattg acaaacatat gatctatctt    900
gattacctta tgggagaatt ttcttagtaa ttggaattca tgagttttgt caagtgaaat    960
tggtgacgaa aatagagaag acatcagtaa ttgaggaaat cggataaggg agaaagaaaa   1020
agaaaaaaag aaaaaaagaa gaaagaaaag agaaaggtaa agaaaaaagc actaataaaa   1080
aggaaatagt atttgtaata tactttaata caattaacgt aagagctaat tagtttgagt   1140
ggattccgtt ttgaaaaggg catacatgtg ccaattatat aactctaagg gcatatatgg   1200
accaactatc tgacggtaag ggcatatttg agttaatata ttaacgaatg acaaatgtgc   1260
tcaatttcgt ataatacaag gacatattac attttcccta ttatgaaatg gttcaaactt   1320
aaggattttg tacatggtaa aacctaaatt gacatgtaac ttggtacttt ccattgggca   1380
aagacacgat cttttacgtg atattttaaa tcaagtaaag atcaagtcgg gccaaaaaga   1440
aaaaaaccca tgattttttta agataaaaag ctgctaactt ttagtttgtt tcatccaata   1500
aaacatcttt aacgatctgt ctgctttagt ttaatcctct ttttaagatg taactaagca   1560
tgaaatagaa aaggggaaaa aaaaggacca ttggattttg gaagaagttt taagaaagta   1620
caagaactag taaagtcatt ttgtatagag tatgttaaaa aggtgagtga caattcgaaa   1680
aagagagagc attgataagt caatcaataa aataaaagca cacctgataa tcattcattc   1740
agaaaacaaa tttctatgaa tgataatcat tatcataagt cactgcagaa atcccatata   1800
cagtagagta ccaggatttt acgataaggt gttagcagac tatctattca tttttttgaca   1860
accattttac gtttggtcat tttttgggaa acgaactctc ccaacattct tccaaattac   1920
cccacgcacc ttactgtgca catcttttaa ccaacttctg gttatttttt cttttgatgt   1980
ccgatattcg tatatgaatt cccattaatt ctaagttgca ccgaaatggt ttttatcaag   2040
attttgtata tatttaatat tcgaattcaa aactaatggt cgaaggtgga agatcgtatc   2100
catcccatca taatatttgg ttggtaatat cacacctttt tgaatttggg agacttgtca   2160
atttttattt tgaaaaaaga aaaaaaaaag aaatagaaac taaaaccata gggaaatgaa   2220
caattttatt ttcactccta cctcatttta tttgtcttga atttttcaat tttgttttga   2280
aacttcttca gtttattttc ttggaatctt cagaatttaa tttgaaattc caaaattcca   2340
aggatttagt gtcaaatcag tgcttgaaat taaatttaaa acgagtggta aataaaatag   2400
```

```
aggagaactc ggtaaattac aggagtgcgg taaatctttt ctccttttct ctctttggag   2460
cctactctat tctattgtaa ctaagtaact taactacgaa aaacgtgcct agacttttaa   2520
cttcacaagt ataataaata gaagtcaaat tctttcataa tattgtttcc atcctatcaa   2580
acagactttg cctcactgac tctccttctg agtgtgtctt ttttatgtca tttttagtga   2640
atccaattga tttagagact caaatattcc acatgcgtgt cttaatttgg tgtatatatg   2700
gtaataattt ttgttaggta gctgtagtat tctattattg ttatgtatta actcatgtaa   2760
ataaaagccg gttagataag actagaaaaa atagagtcta cttagaaatt attagcctat   2820
tgtttggaac atgtcaaaaa ttcagtgact cagctagagc tgtcaattag tcaaataact   2880
ttattaatat taacttatga aaacacttgg ggattcttgt agtttaaggg aaagactact   2940
gactgaaaaa caaagcaaaa gtctatgcat tactatatta tacacaatac agcattttcc   3000
aatagtattt tagataaatc tccaatcagc tactgttgtt cttttctttt ctttttagt   3060
ttaagttgta tgtgttgacg gtatacaaat tatttgcaca attagatggc ttatctagat   3120
aatacgtgta aatctattga taatcattaa ttagtaatct ggtaaaaata atattgcttt   3180
tgttctaata taatgtgata tatttgactg ggtacgaaat ttaaaaaaaa ataagacata   3240
tagaacttgt tgtcttaaac aattcataac atttgtgtgg ctataattct tttgaaactt   3300
atggtgttaa acatgtctaa ttgtttgtgt atgtataaaa gattctcatt aagcgtagga   3360
aaatttgaat taaattattt ttttaattta aaaagagatc actcctttta gagctgactt   3420
aaaaagaaat tgattcacat aaactcgcac ggagggaata agtaatatac tatcaaaaat   3480
taaaaatcac ttgtagtgta aaaaaatctt tacaccaatc gtgtatattc tcaatttttt   3540
ttttttttt ggcgagaggt agttgttcag caaaagtaag ttagaaatag gtctgtactt   3600
ttgactttgt aactctgaaa tgaaaaattc aaaatctctt ctttttact gttttaaaaa   3660
ctccaactca ctcttattaa tataaagctc tagttagcaa agacaccctt gtccacttgt   3720
ctatatagca agaaagagag taaaggagaa aacatattct cctctccatt tctgtagaca   3780
agattctcaa aaagaaacaa attaaacact agagagtgag agagaactat aagaaaaaga   3840
atatggggag agctccatgt tgtgataaag caaatgtgaa gagagggcca tggtctcctg   3900
aagaagatgc taaactcaaa gatttcattc acaaatatgg aactggtgga aattggattg   3960
ctcttcccca aaaagcaggt aacaacaact tctactccct tattcccaga atcgaagcga   4020
caaagggtta aatctcagtg gattgtggta gcaagatcat attctatcgc ttacaatatc   4080
tcgtcgcgta tttaacactt tcgtatgtat atgtttgaat ataggggag ggaagcttac   4140
attaatattt atactttgag tggattaagt tttttttgg ttgcttcatt atttatgatt   4200
ttgatgagat atatgtttgg aactgcagga ctaaagagat gtgggaagag ttgtagattg   4260
agatggctaa attatctaag gcctaatatc aaacatggtg atttttcgga ggaagaagat   4320
agagttattt gcagcttgta ttccaccatt ggaagcaggt acaatatacc tttttttagt   4380
cttaaattgt tttccatttt ttatcatctt tctgatgaat ttgagactga aacaaaaact   4440
gttcccacta aaaatggaaa agaagaacct taataaataa gaaaagggaa aaaacaatga   4500
gggctcagaa agaaatgcaa atagtctgtt ggatttttaa ttaaagattc tgccatttat   4560
ggacattttt ttctgcatgc atgccaggtt tagatctaag atcaagtctt tatttactca   4620
cttacagctg tttaagtatt actactacaa aattccaacg tttcttcttt tctctctttt   4680
ttttttttt tttggaaaac ttttcctttt gtaaaccaat taaattttgt tataacatat   4740
gcaatatatt atgttaacag gtggtcaata atagcagctc aattaccagg aaggactgac   4800
```

```
aatgatatca agaattactg gaatactaaa ctcaagaaaa agcttatggg attaatgcaa   4860
tcaacaaacc aaagaaaatc accatatttt ccagctacta attctcttca agcccaaccc   4920
cagataaatt caagtctttt tagagactta tattacaacc caaataatag gcctattatt   4980
acaggcctaa atcagtccat ttcttctgcc caccagccaa attttctcta cactaatagt   5040
aacatgaatt ttcctaattt gggtgctaca aatagtcaat atccttataa tattcaaagt   5100
cataatttac ttatgtttgg agaagcaagt tgttcttcat cagatggaag ttgtagccaa   5160
atgagttttg gcaaagaaat caagagagag gaaattatga gtaattgttt acaacaaggt   5220
caaatttcaa gtgttaatgc ttttgaagaa aatcagaatt tcactcttga ttatggtaac   5280
agtagtagta attgggtgga tcaaaaacca aatgtgtatt ttggaaatac tactactact   5340
actcaagtac ttcagtatga tgttgaagaa gttaagcagc agctaacaag ttgtaccaat   5400
ggcaacaatg gcagtactat tggatgtaac aacaacaaca gtatgttcgt gttcaatgat   5460
gagaattata acaagtcaaa tgagataggg atgttctatt actgaagaag aaatgactag   5520
ctgttgaaaa gagaaaacaa atgtaagtac accattagga agatttgaaa gggcgtttgg   5580
gtatgggggt tggcaagaag attcaaactt tttctggggt tttgtgtaat tgtggtggaa   5640
ttattattat tgaaacttct ttacttcaat ttaaatcgtc ggtacatatt acgtagttgt   5700
agtaaaagcc ttttcctttt tgtgcttttt tttttttttc gtgttcgtat taagacttca   5760
ttaaatccaa atttgcatag ggacggtcaa cattagagga ataaattgct tcctaacaaa   5820
gacgatttta tactcaagag ttcgagcccg aaaaacgacc tctggttaag ggtaaaaata   5880
gtaattacaa taactccacc acaatcctta ttggtgtgca tttcttcatt aaatactccc   5940
tccaatccac tttaattgat ttgtttttgg ctatttttat atatattaag gaattatctt   6000
ttagcattaa tcaataatga aattgaccat attaaccttt tagttcattg gaaatataac   6060
aaatactcct aggcttttta attcaagagc aacttttaaa tccgaatttg ggctaagaat   6120
acaagcttgt tctttttttat ctgtttttca ctcggtgtac gaggactcaa ttaaatccga   6180
atttgagcta agaatacaga cattagaggt aatatgcttt ctaacaaatg tgactcaatg   6240
ttcagactca gaactcgata tctctggtaa ggatgacata gtacttacaa taactccatc   6300
ataatcttta taggtatgta tttctttata aaatatgtaa atagtgttat gattttttgt   6360
atcaaaaatg atgaagtata atactcttaa aaatcatact ccatccgttt caatttatgt   6420
gaacgtattt tctttttagt ctgtgccaaa aagaatgacc tatttcctta tttggaaata   6480
atttaccttt atgcaatgat ttatagtcac acaaaatata tgtgtctcat ttttaaccac   6540
aagttcaaaa gtcttctatc ttttttttaaa ctctgtgccc agtcaaatga gttcacataa   6600
attaaaacgg agggaataat aaaaatgtat taaagactac ttaggagagt tcttaaaaaa   6660
ccattttgga accttgtcta cgtactttta tgcaataact gcttaagttt gtctctgcta   6720
aaacctatgc tccccaaccg tgcaccaatc agcttagaaa tttgaactca ggaataaatg   6780
taactacact ccacagaaac ttaaaaagtt ttactgttac cattcactca aggatcagaa   6840
ctgaaaaaca aaagaatcag tgcttcacta aaagaaatac tgtttacatt attttcaaaa   6900
gagtttaatc attaaaatag atgtaccatc agattagcta aaagataaat aatcgttaaa   6960
aaaaggagat tatcaacttg aaaatgaaac aaattatatg ttataatatg tcaaaatata   7020
ctgacagtat aaaaactcgt taaatgtgtt aaatcctatg aaaaaactgc ccaaataaat   7080
atttgagctt aggtgtcaaa tgttgtactc aacaacaata acaacaacgc attaggatcc   7140
```

```
tactagtggg gtgtccaatg ttgtactatt gaacattatt caactaactt ttgttaggtg   7200
ttcctgtagt ttagtgaaat taaagtccac tgttccccta tatattaatc ccaaattaat   7260
taatcaagtg cagataaaaa tttctcattt tctattaatt tattaagtgt aacaaactaa   7320
agaaattcaa gaatcttgaa tgatgagaaa gagtcatgca tgtagaaaaa tagataataa   7380
tacatggaaa tatatatgta tttggggatt tgcatggtag ctcaaagatt attggaaagt   7440
gacaggaaga taaatcaaaa tctcagtgtt atttcaaaaa taaaaggcac agattattta   7500
aataattgac agccagtttt ataatactat gtgggagggg acagagatca atccatgtac   7560
gtgcatggct aatattaaag taagggagaa aaaaatatta agttaattga tgattaaaaa   7620
tagtaaaatt tcagacgtat atcacggcaa tgaagagttt gatctttaat atctgtataa   7680
tggtcccata atatgatgga taggcgttgt ttatgatatg attgattgat cattgatcat   7740
tgactattgt ttcttgaata attaatcagt atgggaaagg ggtcccatta aagttgacca   7800
tttgcttagc aatattatct taggtaagct ccatattagt ttaatccact tgcgaatata   7860
ttccgtcctc gcaaatcaat atttacaatt cttttttca gttttctatc cggtatctga    7920
tacttgcatt ggtgttcgac aaaatctgta ttcgcgtcaa aaaatttcat attatggggc   7980
aaaatgctcc ataataaaag cgactcaata ttagggctcg aaccaatggc ggaaacaaga   8040
tttttactaa gggaattcaa aaaataaaaa cgataaacac atgaagaacc tcagggaatt   8100
caacatctaa tataaatata tgaaataaaa atttgattct attgtaattt gatatacagt   8160
gtaatttaca ccgtagggga tttggctaaa cctccttccg cgtacctagc tccgtccctg   8220
actcgaatcc gaggtatttg gttaaaaatg aaagagtact tctcataacc tcgtcggttt   8280
ttgtttctaa tcaatcttta tattgttaaa acataaaacg tttacttcct ttcttcttct   8340
tttaagtttt gaaaatgata actacttttg tttgactaat attttgtagt ttttgatgct   8400
aatcaatttt gtaaaaatta ctgtacttca actagcgttt actaccccac ctcactttaa   8460
aaaattccct aaagagataa ctttttgatt aattcataaa ctaaattgaa gaacttttca   8520
aatgagagta agttgaaaat gcatattata ttgtagtata taattgcaat tttgcataac   8580
ttaccgtaaa atgttcttcc ttttaatgat ttgttaatat gggaaatttg aacttttctt   8640
tctttgaaat tgtattcttg tcccatggtt tctatgcaat ctcaatcatc aaattgcaat   8700
tattttttt tgttttttgt tggcaaattc aggagagctt aggtcagtga tatatgaaaa    8760
actatttttt actcttattt attttaccct ttacttatta aagaataaag tccaagacga   8820
atagacgatg tacaacgcaa atgtaaaaat acagaaaaaa tgtttacgac ttcttctcta   8880
tttattttct acttaattta cttattaaac aagtacttac ttgttaaact agctaatctg   8940
accaacaatg tgaaaatgtt tgacattata catcttgact ttttatttct ctattatttt   9000
ctcgatggtt acttcaaatc atagatttgc taatctgacc aatatcgttt aacttcaagt   9060
agaacgaaat gaacatttca aggttttaga aaacagttga aattggaccc taaaataaat   9120
aaaatgaagt tattaatagg tttacacccc                                    9150
```

<210> SEQ ID NO 15
<211> LENGTH: 9830
<212> TYPE: DNA
<213> ORGANISM: Nicotiana tabacum

<400> SEQUENCE: 15

```
acaagtgttt attgcccaga caggagagaa gtcacattgc caattacatg gatctagttc     60
ttatagagtg cctggagaga ggaaagcaaa tcaattgtct gccttcatta tcaagctgct    120
```

```
cgacagggtt ataaatggct ccaaggctca tgctactctt tatggcttta ttctaaccac    180
agttctggat agtctcaatg tgcctctaaa gaaatgggaa atgatctcga gaaaggatca    240
ctttggcatc aatactcttc ttgcttgtga ctatgcagtc aatgacatcc caaatgaacc    300
tggtacatcc tagaagacac ccatcaacag caaagtcagg actctggttc aggaatatgt    360
agccaaggat gctgaaatag ctaggctttt ggctcgtgtg attgaagtga aatttgagag    420
ggatggtctc agaactgagc ttgacaaaga aaaggagaaa aatgatggaa ttcttcataa    480
catgctgaac cttctccaag cccaaaccca accatatagt tcttccaagc cttaggactc    540
ctagcttttg tctcctgaac ttgtttagta cctcagtgac ccagattagg gatttttcta    600
tcttttattt ttgctcatga tttggatgtt tttctttctt tttgtggatt gttggtggca    660
acatatctct gtcaatgata actactattt tgctcttgtt taatgttaat ttgtccttga    720
tattttaaat atattttctt gattactgat gattactcca tgattacatt tgcagttgcc    780
gcagtggcca tgggtactta ttaaaatctg ggaatcacac tttgtatgta acatttcgat    840
gatgccaaaa gggagaagag agttgtgctt tacacacatt ctgaaataag taatatttat    900
aacctaatta acctggtcct tgatgttaag tgaattttct aagtttagta ttgatggtta    960
agctgagttc ttacaggtcc caaataagta aaaagcacag agtttgtcat catcaaaaag   1020
ggatatttgt tggcccaaga acaggtgaag ttttgaagat tgacaaaaga actcagacat   1080
ggaccaggtc catcttgtga agcacagtca tgatcaacct atacatgtga gatgcacgtg   1140
aaagagataa gtcttactga ttaagcaaca atatctcttg atctgatcga aaaggatgaa   1200
gatagtgtta gagtttgaga tcatcatgaa ctcttccacg atagaagagc agcaattgag   1260
tcacaatcaa actctgatta ctaacctatt aaatgtcagt ttgttctctt ttacaggaaa   1320
tacacatacg caaaagttaa actaaattga gagcaaaaga gcaaggcgat tttgcaagca   1380
atttatgtgt gatttgagtg tgcactcctg aagctacttg aacgagatag aagaaccagt   1440
tccatcgtgt ctatctttta ttctagttca attgtagtag gtggtttaaa attatacctt   1500
tcagctttca tagaagcaat tgtattagat acctagagtg ttcaagttat agctaacttg   1560
aagttgtcgc aacagttgag gttgtgtgcc acaacgggat tagagttaat ccttaggttt   1620
ataaagagtt tttgtaaaag ctattttggc tcagtgattt tagtggaagt ttgggaaaat   1680
cctactgagt tgtaggtcat ggttttttca ccttttgagc caggtgtttt ccacgtaaaa   1740
atctccgtgt tctttatttt ctgtatttat tattccgcaa ttagtagtag ttggaacacc   1800
tagaaaacca agttcttcta tagagtagtt aagcgaaaat tgggtgccac acaaatcacc   1860
cctctagtgt ggtattgacg cttaaaacat caattagtta atttctggag caactagcta   1920
ctagttgtta ttaaaatagt tagtttcttt gttagctaat atgttgtttt ggttgtaaat   1980
tagttccggt gtgtagtttg gactttggaa gaagacttgt accagattgt agtttgttat   2040
tttctttggt cttatgaatg ctcacactaa acatcaagtt ggtactttga ttttgcattt   2100
gaattagaag tagtagttga gacgtgttgt tgctatgcat aagtagtaaa agattggttt   2160
gagcttagtt ggtttcgtga taagattgga aataaaagaa atgtgtcaaa gttatgtaaa   2220
aatcagtaaa ataggctgct accttttaat attaccacaa gtccacattt attttagttt   2280
taaacaatat aaatttgtta aggtaatctt cttacaatag tctcatcttt taatttagta   2340
acagataatt gcaaagtcaa tccaactaat catacactac ccatatgtaa aaaaaaaaaa   2400
aaaaaaaaaa aaaaaaaaaa aaaaaaagtg aacaatcaat gcacaaaaag aaaaaaaaat   2460
```

```
atttttcttc tttaattaat tccataacat agtccttaaa attagttaat tctttgtttt   2520

agaaaaattg taacagtcta gttaattctc caaaatgaag caaaagattt tttttcttaa   2580

gtattacgtc actttttta ttaatccacc aaataaatta aattagattt agttcactaa   2640

ataaactcaa taagatcaga tgttttattt atttataaaa ataactcaat tacttaatca   2700

caaatgatca tgactaactc aaaagtaatt tgttttaaca aaaataatta atttcgtctt   2760

aaccgatgtc gggacgactc attttggaat aaatacataa ataaaatggc caggtcgcga   2820

ggacacgtca tattccaatt ctttcaaata agcttgttat ttattaactt tgagtaggct   2880

ccaattttag gtgcggcgca cgaactaagg tcggagatat tcatcttggt tagcgtaagc   2940

tagggttggg gatattcgtc ctagtttgag attaattaag tcatcaacag taaaagtgga   3000

cataggcaaa acatgaaaac cgaataaagc acaatttatc cataattaat tcatgccaaa   3060

tttaagttaa taaagcaact gtgctagaac cacggactcg gagaatgctt tacaccttct   3120

ccccgatcaa caaaaatctt tattcggact ttatttttgc agaccgataa taatagagtc   3180

aaatcttcct ttgactaggg attcaaataa aaagtgactt ggaacatgca aaaatcaatt   3240

ccaagcgggc gaatctgtaa acaaaataat ccttattcaa atttgtcact ttaattgaaa   3300

aactctttaa cccactattc ataacatata tatttttggg gtagaaaagg ggtgtgacag   3360

ttatgaccta ctttatgcat cagtgttcga atttattttg atcaacaccc ttttggaaga   3420

gcgtttgata gaaatggttg gcttaataaa caatcatatt atcatcacct gcggaatcat   3480

atcattaact tttgaaaatt aaaatggttt tcaaagacgt tttgataaaa gaattcctat   3540

tgtcgcagtt ggaatctaca agaccaagat gttgatctag tgctatattt ggagaaagtg   3600

ccttaattaa aaaaaaattg ttcattagtt gtcttaagat tttttattat ttaaaaaaaa   3660

attaagacac aaagaaacac atttacgagt atatgtcggc cgactaatgt gaagttcccc   3720

acggacaacc cacacatatt gtggtcaaga tggattctat cataatcaaa agtcatcatc   3780

aattcaattc tcatatttgg catctcaagt acatgcacaa aagcaactta ggatgtaagt   3840

ttatatgcac attcttgaaa tagaacctat ttagtacgta gtacttaatt agttacagta   3900

gtattattta ttctctgcta cagagctatg gtttatcaaa tatatcagat tatcatttgt   3960

tgtgtaggcc atttccttat ttgtacttgg tattaattct ggcaaaagca caaaactggg   4020

aaatgaggtt cttcttcctt aatattgagt cacagattag taccactact atagccaaga   4080

aaatgtgaaa tcatatagta ctaaatatta atttcagatg ccaaaaccat aaatttcccc   4140

tcctccatca ttgaaaaccc cctctgtcct ttcccctaga gagacccctt tttcctctct   4200

ctctcctttc tctttttatt agacgcatat attctctctt ctttctcttt ctagggtttt   4260

cacctgaaat agttttattt cggtgatatg ttaggatcct ttggttcatc atctcaatct   4320

catgatgaag aaactgatga tcaacggcgg agattcagtt ccacttcccc tgcaatccaa   4380

atccggcaac tactcattag ctgcgcggag ttaatctcgc ggtccgattt ctcggccgca   4440

aacagactcc tcaccatttt atcaactaac tcttcccctt ttggtgattc aactgaaaga   4500

ttagtccatc agttcactcg cgcactttct cttcgcctca accgttatat ctcttcagcc   4560

actaatttct tgacaccatc taatgttgtt gaaagttcaa atgattcagc tctacttcag   4620

tcatcctatc tttccctaaa ccaagtgact cctttcatta gatttagtca gctaactgct   4680

aatcaagcga ttttggaagc tattaacgat aaccaacaag cgatccacat cgttgatttt   4740

gatattaatc acggtgttca atggccaccg ttaatgcaag cactagctga tcgttaccct   4800

cctccaactc ttcggattac cggtactgga aatgaccttg atacccttcg tagaaccgga   4860
```

```
gatcgtttag ctaaatttgc tcactcttta ggccttagat ttcagtttca ccctcttttg   4920
attaccaata ataatgacaa tgatcatgac ccttcaataa tttcttctat tgttcttctc   4980
cctgatgaga cattagctat caactgtgta ttttatcttc acaggctctt gaaagaccgc   5040
gaaaagttaa ggattttttt gcataggatt aaatccatga accctaaagt tgtaacgctg   5100
gccgagagag aagcaaatca taatcaccca cttttttgc aaagatttgt ggaggctttg   5160
gattattatg cagctgtgtt tgattcattg gaagcaactt tgccaccgag cagtagagag   5220
aggatgacag tggaacaagt ttggttcggg agagaaataa ttgatatagt agcagcagaa   5280
ggagataaga gaagagaaag acacgagaga ttcagatcat gggaagtaat gttgaggagc   5340
tgtggattta gcaatgttgc tttaagccct tttgcactct cacaagctaa acttctcttg   5400
agacttcatt acccatctga aggataccag cttagtgttt cgagtacgag taattctttc   5460
ttcttgggtt ggcaaaatca acccctttt tccatatctt cttggcgtta aatttaaaac   5520
cctaaaaaac aagattttta tctatctgca tggtgaagga caaagaggtc ttcaatctca   5580
ggttcttttt ttttttttt tttatatata tatcttgttt gggtttaagg ttattgggct   5640
gatgaatgtt ttaattttaa cataggtcta cttacgtagt agttataggt tgataatgag   5700
atataattaa ctaagtcttt gtataatgca gatcctgaac ttaatcttta tttgtattat   5760
ttttttttgt tactgaaaga ttctgttacc aaattttatc agtctattta attagaggcc   5820
aacgattgtt aggtatgtgg cacttcgagt gggaaatgat atattcccat taaaggtgtt   5880
aattaaccac caaattgttc tttaggtctg tttgtcattt tgtattaagg tggatggttt   5940
attatatata tcttctcttt aatgctaatc atgcttaact ttttcattta gtaccagcaa   6000
gcatatttgt ttactttatt ggttattcct tatcaaagtc ttcatcttgt tgcttttttt   6060
tattgtactt tacaaaagat ttctagtatt aatggaaagt gctcatattt ggaaaaagac   6120
atggccaaca agaaatgtct atatacccca tttcttcttc ttcttctttt tttccgaaaa   6180
tttcttattt ttgtttttat ttctgtttct tgttgagtgc tttcatggta gaagaagaag   6240
taggagattc ttggacatgg ctgcatgaga attgttaaat aaccccgtat acatacacaa   6300
gtagtgttgg ctgtctttga tatcaaacca tttattgccc taatttctgc cttttgtccc   6360
ctcaacaaaa ccatcaaagt tctcaaagag ggtttattct tgtttcccac tttgcccccc   6420
acctattagg gccaccccac caaagggatc tctctcgtgt ctagtgtttt ttcccaagga   6480
ccaccactcc ttttttttc tctaccataa cttcgtccac accatcttat tgtgatattt   6540
tcgtttaatg aatttgcagc catgccttca ttcatcatca gaactcagtc ataagcacag   6600
attctgagag agtaattaat gaatgaatca gtggtgattt gacgtaaagt atacatgatt   6660
atggttttta gctgaataag cagagggaga aaatatatac atatataaac aagtagagta   6720
aaagaatgac gcaagattag taccaaaaga gtgaaggaag agatttaata ttatagggaa   6780
aagggaagta gtaggtgata cttgacaggt tgataagatg gttattacta caagttgatg   6840
tattgacgct aactcacgca agagagacct actcactgta caatattttt acaagaataa   6900
gcgattcttt ctctctttac ttgcaagaat tgtgtgttgt gtgagttgta tggcgcattt   6960
tctaggagcc tgtggtagtg atggatgtat tcatataata caatacaata catatggaat   7020
agatagatag ataagatggt gcacgcatga gaggcaatta tgcaacttac gtcaactact   7080
tccatccatc catcttttct tccttctgtt tctgtctgat atagtgagta tatgcttgtg   7140
ctggtgttgt gtgcttttct ggcctgggat tttcctaaca ctttagataa tttaggttcc   7200
```

```
catcaataat aatgtctttt tagaggagca tcatcgatag atattcaaat attaaacctg   7260
gcctagctac tatctagggc gtctgctagg tttttccatt accctttgta tatctcttat   7320
gtgggacctt ttgtttatgg aagaatatgg agtactttta ttcatctcgt agggtcttga   7380
atacaagatt ttatatatat cactctttaa aaatgaccat cctaaaattc ttcctctttc   7440
atttgcattt accagaattg atattagtac ctaaactagt actcttcact gaggcctttt   7500
gtatttagtc ctattatatt tgaatttggc actatttaaa ttaaaaaaat aatctacaat   7560
aaaaaattct tccctaaaca ttacccatca aatactcacc acctaaggta actctaccat   7620
gtattaattt tttggatcaa atctagtgag gattaattct ccacttatgt tctttcggaa   7680
ctggctaagt aatcttcaaa agctagggca tctccgcagt catatcgtgc cctcccaagt   7740
atagcgaccg cttctatatt ttccctgaat ttcatctgtg ctagggcttg ttttcacgtt   7800
gatttcaaac aaaggctaac aatttcattg agtaactttt tctcatttca ggactcgaac   7860
cttaaacctc tgttcaaata acttctaaga agtatatatg tatacaatgt ttgtattcat   7920
tgtgacaaag tattatgagt tgtacaactt tcttgtgaag atagagcata atgttaaaca   7980
aggatctata tagagcataa tgtcaacaaa acaacaacat caacccagta atcatcctac   8040
taataggatt tggggagggt agagtgtacg taaaccttac ccatacaggg gagggggtaa   8100
agaggttatt ttcgggagac cctcggctca gagacaaaaa aatctataat aacaacagaa   8160
accagacaaa taatatcagc atcataagag acaacaaata agtggaatga caataattat   8220
gccaataata acattgaaaa aaataaaatt aaaaattaaa aataaaaata gtgtgatgaa   8280
caaaaatcgc tagcagtctt agacaaaaca ctatcagact agctggaaca acgaggaaaa   8340
acgctgaagt accccctaac ctacaaccct aatgctcgac atccacacct ccctatccag   8400
ggtcatgtcc tcggaaatct caaatcgcgt catgtcctgc ctgatcacct cgccccatta   8460
cttcttaggt cgccctctac ctcttctcat acctgtcaaa gccaaccgtc acacctccta   8520
actggggcat ctaggcttct cggggccggc cagcccgtag atctaaaagg atccatccat   8580
agcgcccgaa ccatccacgc ctcgctttcc gcatcttgtc gtccatggga gccacgccca   8640
ccttatccag ccttatccag cctagtgtgc ccccacatca tctcaacatc ctcatttcga   8700
ctactttcat cttctggata caagaattct tgactggcca acattcagct ccatacaaca   8760
tggtcgatct aaccaccact ctataaaact tgcctttaaa tttcagtggc atgttagtat   8820
gtttacttta gatacaatgt tttttagagt cttatagtct tgttagaata ctatatatta   8880
taaaatatgg agacttctgg gcacttttgt tttattttat ataagatagg attggaatga   8940
attcaattgg agggacatgc atgataaatg aatattcatg tagccgatat atgtttggga   9000
ctgaaacgac attattattg tgaaatattt tacaattgca tttcacactc actgaagtga   9060
aactttgatt ccacgtcggt caatacttag gtgttacggt ttggctgcga ggggaatcga   9120
agagagcaaa ttaattaaag tatttaatga ggaatcatga gttagttggt ggaattataa   9180
tagtcaaatg aatgagttat tcgcctgata atatagttga tagtagtata tactatatat   9240
gttgatacta gttattggtg gtgacctaat taagtaaaga gaagagaaga gtggttatgt   9300
aaaggaatct aggtatagtg ggggatgggg ggaggcaagg ttaaaagaaa ggtggaaaat   9360
ccaagaatcc tgcttcctct agtaacatag catatcctgc aattcgtgct tttgtttcct   9420
ctcacaagat aactactttt ttgattaatt attacatttg acacatacat acaaacctat   9480
aaaattagac atccttatgg aatcttacga ctccgaactt gtcatatatc ctttaattat   9540
gcttagcttt ttgctaaaaa caaaaaggat atccttattc caaaatgcaa ctaggagcat   9600
```

cttcccacat ttctttttta tgcctctgca tcatcaaatc ccataatgcc gcacaacaat 9660
ttctttttac ttgagtatat tctagcttag ctatttcata cgaataatgg gtatacaaat 9720
ttgcttattt taggttttaa ataccgattt aaatatattg gatgggttca acttttaaaa 9780
ttcttacact gatatacatg catagaatat gtggaaaact ttaatattaa 9830

<210> SEQ ID NO 16
<211> LENGTH: 10589
<212> TYPE: DNA
<213> ORGANISM: Nicotiana tabacum

<400> SEQUENCE: 16
gacgtcttac ccggttcaat gcctattgca cctcgttgaa gaggctctac gtgcctactt 60
cattcatctt tgcctaatcc ttatcggtca ccaggcaacg aaggtagctg gctatgccga 120
ccggagcgga cagggctcgg gcgtccatcg ggatagtaag aatgaccatt ctcttacggt 180
cggggtcaac acccgggggg agggaacttc ttcactagtt tcgggctcaa gctcgagctc 240
ggcttgctcg ctcccgatga cacatccttt tttgggacct ccaggtgacc aagcctggag 300
aagtcctcca atgcgaccat gtccatgcca tcaaagaacg tgttgagggc attatctgga 360
cccgacgcta tctcatttaa tttctcttta ttagcttgaa cctcttcgag catggactca 420
gtataggacg gcgtctctgc gatgtcaatg atactagcta catccttcgg gacaggagcg 480
gcttctcgat aggccatgga ctccgtctct ccctctggtt ctcgagctag agggggatcg 540
acctcttggt cacctttcct ggttgccacc ttctccctct cgttgagggt cgactcatga 600
gcaatgaact caaggtcgtc atcctcagga taatccctaa gccggtagag ggaatcagat 660
ttcggtaccc tcgacttggt gctctttttg tttttctgga cctggacgac caccctcttc 720
ttcttcacct cgacatccgg ggagcctgtg gatttccttt tattcttctt tttctcttcc 780
cttacggcgg cctcgggctg tcccgaagcg gagggttcag cgagcgagga cggatcctcg 840
tcctcatcca atggcttgag ctcggtggtc atgggtgaac ctgtgagaag aaagaagact 900
tagcgatata ttcatcaagt atatgaatgt aatcattcgg gagagagact cactatggga 960
acgagcctcc catttgccct tcgagagctt gcgccatacg ctcgaagtag gacatctatt 1020
tgcacatccc ctcgattcac tccttgaagc aggggaatgt attaggaacc tgggcaactg 1080
ctacataatg gcaaatacag gcaattagaa aaaagaataa aaggaaatgc cagatactcg 1140
agagggaaaa gacttacggg atgcgtttca ctttttgagg aatggtagaa attcggagag 1200
gatgaggtct tcggttttca cccgaacgaa cctcccctac caacctcgat ctcggtcctc 1260
gtcgatgctc gagaacggag ccttgcttgc tcggcgaacg atcttaatca acccctctcg 1320
gaagattcga ggactgtata gatgaagtag atgttcgagg gtgaactgag gtgcttcagt 1380
tttgtttaca aagtgttgga ggaggattac gatcctccaa aaggacaggt gaaggcagac 1440
cttgcacctt ttatagatgt cgaggactat ggggtccacc gggacgagcg tgaaggagta 1500
agtgtaaaca cttaggtacc cctccacgtg agtggtgatg tctttgttgg gcccggggac 1560
gaccacctcc tttccctccc agttacactc tacccgaact atgggtagtg tctcctcagt 1620
aacagagcat atgtacctcc atgctccctc gtctcggtcc tgttgactgg aggctttctc 1680
gacgttgaag tcattctcga tagagcagcc cccgagtacg aagctcttca agggaggctc 1740
atgggctacc tcaggaatgg ccacctcggc atttatggcc agattggaaa ataaaggagc 1800
ggtttgttga ggaacgaatt tgaaagtttt tgctatcggg ttctgaaaaa tatgaaggtt 1860

```
tgaagaaaaa atatgaagat ttgaagatag aatggaaata tgaaggtctg ggttgaagat   1920
tgaaagagaa tgtatgaaga ttgaggatga aggtatgaaa atctaaggag caatctatga   1980
agatttgaag gagttaaagg tatgtaaaga attcaagggt aaatcaagga gctctagaat   2040
cgaaaagtgg agaagtgaaa aaggggtcgg agcttttata gaggaaggac aatcaatgca   2100
tgacgtttca cattcgagga cagtcaatca acggccgata cgtgtccgat gttagaacga   2160
tgcgactaat gggacgtttc attgatccgt catctcggtt gtaacgtacg aagaaaggaa   2220
tcggggttca tttatcgctt cccgtcgttt cgataaatct atcctccgaa aaacaagggg   2280
actatctgta tacgggtaaa atcaggcaat gtctaccctg attctcctat aagagaataa   2340
agggggagcg cggatccgcg agattgtaat cgaggacaga gacccatcgt atcaagatcc   2400
aagaagagtg aacgatatat ctaacatcag acacggcaaa gcgatgtacc ccggaccgaa   2460
tataactcct agacctcggg agaagcgggg gacggttatg catgacagat aggagactgt   2520
atactcgccc tcaatcggat attacgacgc gaatctcgtc agtaacaatt atggatcaat   2580
aattactgga aaaagaagat ttttaccttt tttagactta tactaggact gaaattctcg   2640
tactatataa aggtaaagtt tttctttgat ctgacacatt gtaacacgca attcaaagaa   2700
ataaaaattt gtttttgcct tctaactaat gttaaaaatt ttgctcactt gttctgttct   2760
tcattcacga ctggactcga accgagggtc caatcgagta cgaggtcact gttcaatcta   2820
agatcatgct tggtcataac attgcgattg gtttgatcat ttatttcgtc tttaattcat   2880
ttatctgtta tttttaatta ttcgtgttga attaaatcac gtatcattta aaccgcgtac   2940
aaatttaatt gttacccatt tttaaggtaa acaactatag acgaaaaaaa aaatataaat   3000
attaaatatt atgtttcgaa agatacacaa tagacaagaa aagaaaagaa aaatccctta   3060
taaaatttgg atttagccca ccagttttat tgagacgtct ttgtgtgtta gttacccggc   3120
aaaggttatg aacctacttt atgcgtcaat gtccgaattt atttttatca acatcctttt   3180
ggaagagctt ttgatagaaa tggttggctt aattagcaat catattatca tcacctgcgc   3240
tttggtgtta tatcattcgg aatcatatca ttaccttttg aaatttaaaa tggttttcaa   3300
agacgtttcg ataaaaaaat tcctattgtc gcagttggaa tctacaagac gaagatgttg   3360
atctagtgct atatttggag aaagtgcctt aattaaaaat aaaaaattgt tgatcagttg   3420
tcttaagatt ttttattatt aaaaaaaaaa aattaagata caaagaaaca catttacgag   3480
tatatgtcgg ccgactaatt aatgtgaagt tccacacggt caacccacac atattgtggt   3540
caagatagat tctatcataa tcaaaagtca ttatcgactc aattttcata tttggcatct   3600
taagtacatg cacaaaagct acttaggatg taagtttata atcattcatt cttgaaatag   3660
aacctattta atagtactta attagttaca gtagtataat ttattctctg ctaaagagct   3720
attgttcatc aaatatatca gattatcctt tgtggtgtag accatttcct tatttgtact   3780
tagtattaat tctggcaaaa gcacaaaact gggaaatgag gttcttcttc attaatgttg   3840
agtcaagatt agtactacta ctatagccaa gaaaatgtga aatcatatag tactaacttt   3900
cccttctccc tagctactga taactctaat taatttcaga tgccaaaacc ataaatttcc   3960
cctcctccat cattgaaaac ccctttgtcc tttcccccca gaccccccttt tcctctctct   4020
ctctctcctt tctcttttta ttagacgcat attctctctt ctttctcttt ctagggtttt   4080
cacctgaaat agttttattt cgttgatatg ttaggatcct ttggttcatc atctcaatct   4140
catgatgaag aagctgatga tcaacggcgg agatgcagtt ccacttcccc tgcaatccaa   4200
atccggcaac tactcattag ctgcgcggag ttaatctcac ggtccgattt ctcggcggca   4260
```

```
aacagactcc tcaccatttt atcaactaac tcttcccctt ttggtgattc aactgaaaga   4320
ttagtccatc agttcactcg cgcactttcc attcgcctca accgctatat ctcttcagcc   4380
actaatttct tgacacctaa tgcatcatct aatgttgttg aaagttcaaa tgattcagct   4440
ctacttcagt catcctatct ttccctaaac caagtgaccc cttttattag atttagtcag   4500
ctaactgcta atcaagcgat tttagaagct attaacgata accaacaagc gatccacatc   4560
gttgattttg atattaatca cggtgttcaa tggccaccgt taatgcaagc actagctgat   4620
cgttaccctc ctccaactct tcggattacc ggtactggaa atgacctcga tacccttcgt   4680
agaaccggag atcgtttagc taaatttgct cactctttag gccttagatt tcagtttcac   4740
cctcttttga tcaccaataa taatgacaat gatcatgacc cttcaatcat ttcttctatt   4800
gttcttctcc ctgatgagac attagcaatc aactgtgtat tttatcttca caggctctta   4860
aaagaccgcg aaatgttaag gatttttttg cataggatta aatccatgaa ccctaaagtt   4920
gtaacactgg ccgagagaga agcaaatcat aatcacccac tttttttgca aagatttgtg   4980
gaggctttgg attattatgc agctgtcttt gattcattgg aagcaacttt gccgccgagc   5040
agtagagaga ggatgacagt ggagcaagtt tggttcggaa gagaaattat agatatagta   5100
gcagcagaag gagataagag aagagaaaga cacgagagat tcagatcatg ggaagtaatg   5160
ttgaggagct gtggatttag caatgttgct ttaagtcctt ttgcactttc acaagctaaa   5220
cttctcttga gacttcatta cccttctgaa ggataccagc ttagtgtttc gagtacgagt   5280
aattctttct tcttgggttg gcaaaatcaa ccccttttttt ccatatcttc ttggcgttaa   5340
attataaggg aaattaaaac cctaaaaaca agattttatc tatctgcatg gtgaaggaca   5400
aagaggtctt caatctcagg ttctttttgt ttttttaact tgtttggata tgaggttatt   5460
gagctgatga atgttttaat tttaacatag gcctacttac gtagtagtta taggttgata   5520
atgatatata tttaactaag tctttgtata atgcagatcc tgaacttaat ttttattttt   5580
attattttgt tgttaatgaa agattctgtt accaaatttt atcagtctat ttaattagag   5640
gccaaagatt gttaggtatg tggcacttgg agtgggaaat gatatattcc cattaaaggt   5700
gttaattaac caccaaattg ttctttaggt ctgtttgtca ttttgtatta aggtggatgg   5760
ttcattatct tctctttaat gctaatcatg cttcaccttt tcatttagta ctagcaagca   5820
tatttgttta ctttattggt tattccttat caaagtcttt atcttgttgc tttttttttt   5880
tattgtactt tacaaaagat ttctggtatt aatggaaagt gctcatattt ggaaaaagac   5940
atggccaaca agaaaggtgt ataccccatt tctttttctt tttctccaaa tttttttttt   6000
tttttttctg tttcttgttg agttctttca tggaagaaga agaagagtag gagattcttg   6060
gacatggctg catgagaatt gttattgttt tgtgcactta aataaccccg tatacataca   6120
caagtagtgt tggctgtctt tgatattgca ccatttattg ccctaatttc tgccttttgt   6180
cccctcaaca aaaccatcaa agttctcaaa tagggtttat tcttgtttcc cactttgccc   6240
cccacccatt agggccaccc caccaaaggg atctctctcg tgtctagtgt tttttcccaa   6300
ggaccaccac tacttttttt tttttctcta ccataacttc cacaccatct tgtgatcttt   6360
cgtttaataa tgattttgca gccatgcctt cgttcatcag aactcggtca taagcacaga   6420
ttctgagaga gtaattaatg aatgaatcag tggtgatttg acttatacat gattatggtt   6480
tttagctcaa taagcagagg gagaaaatat atataaacaa gtaaatctag tagaagaagt   6540
agaagtttta tagctagagt agtgggaaag aatgacgcaa gattagtacc aaaagagtga   6600
```

```
aggaagagct ttaatatagg gaaaagggaa gtagtaggtg atacttgaca ggttgataag   6660
atggttacta ctacaagttg atgtattgac gctaactcac gcaagagacc tactcactgt   6720
gcaatattta caagaagcga ttctttctct ctttacttgc aagagttgtg tgttccgagt   6780
tgtatggcgc atatgaacct tttttcatac aatacaatac atatggaata gatagataag   6840
acggtgcacg catgaggcaa ttatgcaact taacatcaac tacttccatc atcttttctt   6900
ccctctgttt ctgtttctgt ttctgtttct gtctgatata ctatatgctt ctctggcctg   6960
gattttccta actcttttga taatttaggt tcccatcaat aatgtctttt tagaggagca   7020
tcatatcgat agatattcaa atattaaacc tggcctaggg ctagggcgtc tgctaggttt   7080
ttgcattact ctttgtatat ctcatctgtg ggaccttttg tttatggaag aatatacttt   7140
tattcatctt gttgggtctt aaattcaaga tttaatatta ctctttaaaa attaatgact   7200
atcctaaaat tcttcctctt ttatttgcat ttacaagaat tgatattagt acctaaaact   7260
cttctctggg gccttttgta tttagtcctt ttatgtttga aattgacact atttaaataa   7320
aacataatct acaataagat gttcttcacc cttcgggttg cccggttggt ttggatggga   7380
tcgattcccc cgatatcttc tgggttgagc atatcgcaca gggcttgtct agtgcggttt   7440
gcattcccta tgtggtttgc attccctatg tggtttgcat gctattatac atgggtttac   7500
ccagtggaca caaagtattc aatacagagt gttcacccga agaacagagg ctgtggcaaa   7560
gattgtaacg gccgcgggtt tcccctctta caaaaaaaaa aaatgttctt ccttaaacat   7620
tacccatcaa agactcacca aagatagctc taccaagtat tatttttgga tcaaatggca   7680
tttccacggt catatctcct cccccccccc cctccccccc ccccccaaag ctagtgatca   7740
cttccatatt ttttcctgat ttcatcggtg ctcaaatact tgttcattca tcttcattcc   7800
aaacaaaggc gaaaaacttc actattgagt gctttttttcc tattccaagt gtcaaaccct   7860
aaacttctag tcaaataata tctaagatgt atactcttat actatgtttg tattcattat   7920
gacaaagtat gatgagttgt acaattttct tgcggactta gtgaaaatag agcataatgt   7980
taaaaaaata tttacatgat attaattagc cggattaagt ttataacgtt agtatatatg   8040
tctactttag gtacaataca agtcttatac tcttgtcaga atttatatgt cacaaaatat   8100
agaaacttct agctactttt ttttaatttt atataatata atattggaat gaatttaagt   8160
ggagcaaaag tgaatattca tgtagtcgat atattctaat ctgtttgggg ctgagatgac   8220
atgattgtag tgaaatattg taccattgca tttcacactc actgaactga aactttggtt   8280
ccacgtcggt gatcatttgc atgtttcatt agtcaatact gtggctgtta tgatttggct   8340
gcgagggggga tcgaagagag cacattaaag tatttaatca ggatttatga gttgaatgct   8400
gttagttggc ggaattaata gtcaaataat gaatgagtta ctcgctgata tagttaatag   8460
tactccgtat atatgttgat tctagttatt ggtggtgacc taagtaaaga gaatagatga   8520
gaggagtggt ggtatgtaaa ggaatctagg taaaggggtg ggggtggggg gaggcaaagt   8580
tgaaaagaaa ggtggaaaat ccaagaatcc tgcttcctct agtaacatag catatcctgc   8640
tattcgtgct tttgtttcct ctcacaagat aactactttt tgattaatta ttacatttga   8700
cgcatacaaa cctataaaat taaactaatc aacgacatcc ttatggaatc ttacgagtcc   8760
gaacttgtca tatatataac tttaaagtac tttgtcactt cttaatatgc tcctttaatt   8820
gtgcttagct ttttgctaaa aaacaaaaag gatatcctta ttccaaaatg caactgggag   8880
catcttctca cttttctttt ttatgcctct gcatcatcaa atcccacaat gccgcacaac   8940
aaactcttgt tacttaagta tatattctac ttcataagaa taatgggtat aaaaatttgc   9000
```

```
ttattttatg ttttaaatac caccgaaaat tcataagcaa attcaggatt taaatatatt   9060
aaatgaattc aacttttaaa attgttgcac ttatatatat atatatatat atatatgcat   9120
atccaagttg agggatacgg gttcacatga actcatatta ctttctctaa accatgtata   9180
acaatgttat attttttcaa aattatttaa atatatgtgt gtgaacccat tctcaaaatc   9240
tcttatggtg caattattat tgggtgcaca tctacaagtg aaatttgcag ctcaaaacct   9300
catctgggcg gtcttgtttt ccgcatggag tataactata tatgtgaaaa ttactagaat   9360
ttcaaaatga atataatttt gaaatgttgt gggttcctgg taagagacta aagttaaact   9420
cgtcaaatat aaattctaga tccacctctt cacaatagtg cacccattct tttgaaattc   9480
tggatctgcc tctgttaata atatatatat atatatatat atatatatat atatatgaac   9540
acaaaataat atgtggaaaa ctttactatt aataccactg ctaaacattt gaatggattc   9600
ttcatgccgt gtgctccttt gttgaagaac acgtacttgg gagggcgaga tttcgaataa   9660
aaaagttata ctaataacaa acagcaacaa ttataagaaa atgaaaataa aagggaaaga   9720
gcactcacat aaactagaaa ctgtagagtt ggcaagtacc aggtatatat gtccttgaat   9780
gttttttacg aggaattgag taaaacgcta gctatttcaa cacatatata aaaagcatca   9840
ataccaattt tatggtttct cttaggtgtt gatagattct cttttgtcag caaagttctt   9900
gcattaacta tatgaaattt ataataaaaa tgctgctctt ttaattgagt atacatgcag   9960
tctcctaaca tatacattct ccgtcccgat atatacttga tttgatgcat ttcaaaaatt  10020
aaatgtttga gtgttttggt gaattgtgct tgatatagaa gtatttaaaa taagaaagaa  10080
atgtaacggc agaatcttaa gtcgaaagtc aaattaaatt tgaaaaataa aaaataatac  10140
tcttgatact tactagtact agtcaatggg cagctctttc gggactaacc aaaagcatta  10200
ttcttattgt ttccggcata gtattaaaat gtaacaatgc ttaattatgt tacaaaatta  10260
atgtttttgt ggacttcgga ataatttatt tctgaattcg ccggtgttat cgaaaacatg  10320
gggacagtcc ccccaaaatc cacgggttat tgtgcaaaga cgaacataca agtttatttt  10380
tgataattta atcccaagca tcaactttct catacttctc taatcccttt gcatccaaaa  10440
ttatcaaaaa tagagaatat taaatgatag ggggaaaatg atcattaaat gcttcccttc  10500
cgggacatcc ggtttaaggg gggaaaagga gatattagat gcatgcaaaa taataaattc  10560
ttggaagtaa ttaatccgaa gttctgacg                                    10589
```

<210> SEQ ID NO 17
<211> LENGTH: 15103
<212> TYPE: DNA
<213> ORGANISM: Nicotiana tabacum

<400> SEQUENCE: 17

```
ttctagggat tacggaaatt catttacgta catttagttt gaataacttc ttaacaaaat     60
ggtaattgtt tttaaattct aaaaataaag gatagagaag gaaaatgtca cgacccgaaa    120
ttctcacctt cgggatcgtg acggtatcta acattttact tgctaggcaa gtcaacgttt    180
gagtaaatta tatgttattt caacaactca agtaattaaa ctcatttaaa ctgaaatgaa    240
actaaaaaga agtgtgaggt gacataataa cccaaaatat ttaagtacaa tccggacctg    300
gagttacaag tacatgagct actagaaatt ctacaaacag agtctgcaat aaatgtaatc    360
gtctcgaata aaatgaacag taactaagga aagaggaagc ggacttcaag gtctgcggac    420
gccatcagat ctaccccgag tctccgagta tgtcaatccg agccgataca gctcacgtag    480
```

```
tgctgggact agttctaaaa tctgcacaag aagtttagag tagtatgagt acaaccgacc    540
caatgtccat aagtgtcgag cctaacctca acgaggtagt gacgaggcta taacaggaca    600
ctcacgtaat tcaacatgta cgaactaaga catatacaca atatagtaac aataaagaat    660
taatctatga aattgggagg ggacatgcaa acggggaaca agatacgata attacaacat    720
aaataacaac ataagacagt caaataaatc atcaaccaag aaaagggata aacatgatga    780
ataaagatgg cacaacattg cccatcgtgc ttttactctc aaccttgcca tgaaataata    840
ataatagcac gacatcaccc ttcgtgtttt tactctcaat ctctccatga acaataaata    900
cggcacgaca tcactcttcg tgctttaact ctctttctca ccatgtatta atcagtaatt    960
gaaacaaata ataacacgac atcacccttc gtgctttaac actctccctt accatgtagt   1020
aatgaatata aaaataaaca agaataaacc ttacgtcaat aatgatttcg aaacacaaat   1080
cctcaatttc aaagaaatac tcaactatca caacttaatt cataaatgca gggagaacaa   1140
tcaaataaga aataaactaa tctaagcatg gacatcatga gtaaagaagg caataaatta   1200
caagcagcaa gtatcactcg catgttttaa cccaataata acacataagt actcgtcacc   1260
tcacttatat gttataccca aacatttaaa catatagcaa ataggcaaac aagtcctaat   1320
cactcaagtc aaggttagcg acgacactta cccacttcat agtccactca gagctctatc   1380
gaggcatttc ctctagaatc cgcctccaac ccactcgtat ctaaccacaa tcgactcgat   1440
aacgtcaaat aatgttaaga aaatcaatta cattacataa agaaaggatt tttacacctt   1500
ttcccaaaag taaaaaaaag tcaacctcga gctcgcttag tcaaaatccg agagtccgac   1560
caaaactcat ttatccattc accccgagtc cgattatgta attaattttg aaattcgaac   1620
tcaaattaag gtctaaatcc cgtatttgca aaaatccaaa attcttccta aatccctagt   1680
tttctactat ggaagaacaa agtttagggc tagaaattaa tgggcgatgt tacaaattga   1740
agaaaatgag ttaaagtgta caaacctatg aattggtatt gggttttcca ttcaaaattg   1800
catctaggcc gagctctaat ggagagtttt atgaaaaagg gtgaaatcct gtttttgaaa   1860
catttaaatc actgggcgtc aggtgttcat cacgatcgcg tgaaacttga cgcgttcgcg   1920
gagagcattg cctaactggc ttatacgatc gcgagtatct ccacacgttc gtgaaggttt   1980
agcctgcctc tcctccgcat tcgcgagcct aggttcgctt tcgcatagag taacctcaac   2040
tcctagccca gcctatctaa cactacgcgt tcgcgaagag cagacccccc agtgctccgc   2100
gttggcaacc aaggtctcgc gttcgggtag aataaaatcc tccccaatcc cagattccct   2160
ttcgcgaccg cgagaaaggc ttcgctgtct cgaagcacaa tacactagat gacagctgaa   2220
cctcgaaacc catatttttc taagttcaaa tggtccgtag gctatccaaa attcacccaa   2280
gccctagggg ctccaaacca aatatgcacg caagtacaaa aatattatac gaactcgctc   2340
gcacgatcaa agctccaaat aatacttaga actacgaatc aaacaccaaa tcgaatgaaa   2400
ttttcaataa agcttaagaa cattcaattt ttcaatcgga cgtccgaatc acgtcaaatc   2460
atttccgttt tgcaccaaat tttacagaca agtcataaat atagtaatga acatatacca   2520
agtttcggaa ctaagatccg gacccggtat caacaaagtc aaacatcggt caaatttata   2580
aagtctttaa acctttaaat ttcaaattct cgacaaattg cgataactcg agctagggat   2640
atccgaattc aattccgggc atacgctcaa gtcccaaatc acgatacaaa ctatcgggat   2700
cgtcaaaata cgaatccggt tctgtttcct taaaatattg gccgaaatca attcaaatga   2760
attttaaagc acgaattcac attttaatta atttttcaca tataagcctt cgggaagtat   2820
gaacttaaca cgcaaatcga cctgtcgggt tatcacagaa aaaaccatga gtaccaccag   2880
```

```
tagagttctc ttttaacttc tttttcctta gagtttagct ctgagttaaa aaaaatcttc   2940
ttgataatag taaccatata tagaataaaa atgtcctata atttcaaggg cagatatagg   3000
atacatgaat tatgaattca atcaaataca ataatatgtt caaatatcca attatcattg   3060
aattcagcgt tattactatc cacaaaattc gaactttaaa tatacttttg cataatttag   3120
attcaactaa acaaagatca tataagaaca aagatgtcct gtgatttcag ggcagatatg   3180
cgacataagg tatgaattca gtcaaattca atatttttag tatcagatgt acaaatatta   3240
aattctaatc tagtaactca aatggtcatt aaaatttagt ggtagtccaa ccacaaaatt   3300
gaaattctaa atctcctttt atataatgta gatcaagtta agaaatttca tctagacaat   3360
attgaccata tttggacaaa gatgtccttt gaacttttcc ttttatgttt atagctagaa   3420
aaaataatcc aaacagcggt gatcacatat tttattaaaa agaaaaagaa aaagaagttg   3480
tattattata ctctatcgga ttactgaata ttttatattc gtacattata atttcaatta   3540
aatagttgaa gagaaaggac ataaaagaaa acagaaaaac acaaaggcaa gagcaacaac   3600
agcagcataa aaacactggc attttcgatt tgcgagctca taaagcttta actcaagcaa   3660
attctctctc tctctctctc tctctctctc tctctctctc tctctccatt ttctttttct   3720
cttttctcac ccaccactct cacacacctc ttcacctcac cttacacact aaaaaaacat   3780
cactcctctc tctaaaaaat tcaatctttt tgctgttcca acatgtcttt tagagtttgt   3840
ttcagtttca gatcttaagg gcgggagtgt tatgcttctt ctaatatttt gaagctcaag   3900
aaaacagagc aaatttttgc tttcttttct cctacttttt gtggggggta attcttgttt   3960
ttgtaatctc aaagctggct gttttatgta tatactgaag ggttgtggt gatttgtttg   4020
tctactttaa gaaggtgcca tctttttcag taatatttgg gtaaaagttc tctctttttt   4080
ggccttaaac gcgaagattc aggcctctct caacgtgtca tttgttctct gtattaaaca   4140
cagctggaga attaattaca tagaggtaaa aaaagggggtt aaagattcca aagaattgaa   4200
aaaaaacaga gggctgaggt aaaaagttga tggtttttaa aaaaaaataa aagcttaaat   4260
gatgataaag tttggagctt tatgtgaatg gaaatggtgt tgtgtttgta tcaaacacga   4320
gtagtttaca gcttatgtga atttgaaaga gagagaattt ttgtctgtat ttatatcctt   4380
ttcagccata tctttcgtta gagcagtttt ggctgtacct taatttgtaa gggtttaagc   4440
gtgaagtgtg tgtttgagcc ttctgttata aggggcacaa agtatagaaa caacaaaagg   4500
ggcacctagg aatcttctgg ctcaatcaag atcgttcatt taatcttgtc tgagatcact   4560
agaaaaagaa aaaggaaaga taaagataaa gtctttgttt cagagaatct tagttctctg   4620
tgttgatata tataataaaa gctgtttgca gggaatatat ctacttgggg gtgtttttat   4680
ttcttttaag ggtgtttgaa aatttggaaa tcttgattat ttttttgttt gggattttgg   4740
ggtttgaggg caaatggcta tggtggtaca gcagcatagg gagagtagta gtggtagtat   4800
tacaaaacat cttgacagta gtggaaagta tgtccggtat acagctgagc aagtggaggc   4860
attagagagg gtttatgcag agtgccctaa acctagctcg ttgcgccgcc agcaattgat   4920
ccgcgaatgc cctattctgt cgaatatcga gcctaagcag atcaaagttt ggtttcaaaa   4980
cagaaggtac actgcccgct gttcaatttt gattgctcca atttggtttc ttttttgttc   5040
ttaaatgcat atatttaggt gtcgtgcact tgtgatcttg gactgaaata tgggataagt   5100
tagatgagtg atggttaaat tggaatatat cactgtgctt ctagtttcct aggcttgtcg   5160
attgggttgt atggattaat cggggggggg gggcattaag tgaatcgtga attggatgtg   5220
```

-continued

```
tagtttgatt tctgtctgtc gggtagttga gcttagattt tggaattgag ggtgaacatt   5280
gtgccatttc aggtgtcgag agaagcaaag gaaagagtct tctagactac agactgtaaa   5340
tagaaagctg tctgcaatga ataaactatt aatggaggag aatgatcgct tgcaaaaaca   5400
ggtttcacag cttgtgtgtg aaaatggctt tatgcggcaa caattgcata ctgtaagtta   5460
acataatttt tcctttatac ttgtggtaaa aagctttatt ttttgcttac tgtagacgaa   5520
tggtaacgta tatcttgtct tttgtttctg atgaaatggc taagcactat gaattttaag   5580
atttctgata ttccacagct tatggtaaca tattttaaac agtgtaaata aactttattc   5640
tgatgacact gttttaggac attcttatag ttatggaatg catggcttta gatatgggac   5700
taaattttat gttcatcgtg tttttgcatt ctatattctt ctactcgccc ttgttttgct   5760
gtgaagttga accaataaac aagaaacaga tgatggatat ctccggtgat cttttgttcc   5820
ataggattaa ttagactgta tttgtgtttt ctgcaggcat cagcggccac tactgatgta   5880
agttgtgagt cagtggttac cacccctcag cattccctca gagatgctaa caaccctgct   5940
gggtaattaa tttcaaacac ctatttctcc catcctttcc gtctatggtg tccattctcc   6000
aacatattta tgttatttat tcaatggcat atacaacatt ttgaggggct aatttgttta   6060
tctctaagtc aagtttgttc tctatgcaga ctgctgtcga ttgcagagga aaccttagca   6120
gagttccttt ccaaggctac aggaactgct gttgattggg tcccgatgcc tgggatgaag   6180
gtttgaactt tagtcaatcc tctttatttt ttgaaaattc agtattgcca tgtctctttg   6240
actggatagc taaaaaacta aattttcatt ctattgccag cctggtccgg attcagttgg   6300
gatttttgcc atctcacaca gttgtagtgg agtggcagcc cgagcatgtg gtcttgttag   6360
tttagagccg acaaaggtaa gcagtcatgt ggaaaattaa tttaaatgta gtgctgttgc   6420
tctattacta gttttggtcc tttgacgggt gtactagatg ttgccagttt cttcttagta   6480
aatatatttt tgtcaaatat ttacagattg ctgagatcct caaagatcga ccatcttggt   6540
tccgagactg ccggaacgtt gaagttttca cgatgttttc tgcaggaaat ggaacaattg   6600
agcttttgta cacgcaggta attaattacc ttctcatcaa tcttcacgta ggcttctgat   6660
tggagaagct acagcattga ggggattttt gaaatcattt cttttcagat atatgctcct   6720
accaccttgg ctcctgcacg tgatttttgg actctgagat acacaaccac cctggagaat   6780
ggtagttttg tggtatgcac atcctccgca ttagcgtgtc ttaggataag caatctggcc   6840
acttttgtac ttagttatga atattttgct gatagtttgt tgtatgtgcc atcaattcct   6900
cctcccctca aggtttgtga aagatccctc tctggtactg gagctgggcc gaatgctgct   6960
tctgcttccc agtttgtaag agctcaaatg cttccgtccg gatatctaat ccgaccgtgt   7020
gacggtggag gatccattat acatattgtt gaccatctga atcttgaggt cagattgcac   7080
actgtactac cacttccctt tctttttaac ttgttctgtc ttgcagctgg acttcacggc   7140
ataatgtttt tcttcaggca tggagtgccc ctgagatttt gcgtccactt tatgaatcgt   7200
caaaagttgt ggcacagaaa atgactattg cggtgagttg aaccgttgat tgtcattaaa   7260
tactggatgt gtaacaacct ttttagtctt cacaactaga tctcaatttt tgttgagctc   7320
tgaagtcgaa agggttgtaa tttctggacg agcagttaga tatagcctga tatttttgtt   7380
tattcagtta gaagttccca gctttaaaaa tatagaacac ctgacaaatc cttagtctct   7440
taatgcacgt tattgaggat ttctttgttt tttcgagttt tctaaggttc attattgttt   7500
tcctcatggg gttgccataa aagtctgcat gtgaaacata tagtattgaa gaactgtagg   7560
ctgtgaagcg caccatactc ttaactgcat tagttgttgc tttaattcca tatgttgctc   7620
```

```
tgagaatact tgcagcattt tttatgtttc aagtacttga gcaattaccg tagcttacca   7680
tcacaacaaa agaaatacta attatagtat gtttttgctg taaaggcact gcgatatgca   7740
aggcaaatag ctcaggagac tagtggggag gttgtatatg gtctgggaag gcaacctgca   7800
gttcttcgaa catttagcca gagattaagc aggtgctgtt tattgctctg attgttctgt   7860
gctatgagat atgatatgcc ataaaagtag acatacgaat tctgaagcac aagtatcata   7920
attaagctat tttctatatt gcagaggctt caatgacgcc atcaatggat tcagtgatga   7980
tggctggtca ttgttaagtt ctgatggtgg tgaagatgtt atagttgctg tcaattcaag   8040
gaagaacatt gccaccactt ccgttcctct ttcaccgctg ggaggcatcc tttgtgccaa   8100
agcatcaatg ctactccagg tgaatagatt accttttaac tgactagaaa ttttcattgg   8160
ccaactacct ttgccttgtt agataaaatt gttccagact gttgcagatt ttgatgatgc   8220
tttcaatttc taaactcttg gaatgaatcg ggattcctgg aatataagag aatattactc   8280
agtgttctat aaagctattt gtttaatgca ccatgtgggg catcttgttg ctattaaatg   8340
gaagaatgag aattgacttt taactcttct gtatggtggc agaatgttcc tcctgtggta   8400
ctggttcgat ttctcaggga gcaccgttca gagtgggcgg actttaatgt tgatgcctat   8460
gtagcttcgt caatgaaatc ttgttcatat gcatatcctg ggatgaggcc taccagattt   8520
accggaagtc agataataat gccacttggc catacaattg aacatgaaga ggtaagcact   8580
ttgcacttgc cccagttcca tccatcccat gtgttggagt gtgcttatac agcaccagta   8640
ttttttataa tcagaaagtt agcactcttt gaattgctag gcttgttacc taatattgct   8700
aatattatac tttagacttc ctctcatttt ttttttattt tgttttgctt tgcagatgct   8760
tgaggttatt agattggaag gacactctat tggccaggaa gatactttta tgccaagaga   8820
tgttcacctt ctccaggtac cttttgccta tgcattgatg tttcggtgtg ttatctacgt   8880
acagacattg ttgaagcaat agctaacaaa cggttatttc tagatgtgta gtggaactga   8940
tgagaatgct gtcggagctt gttctgaact agtttttgct gcaattgatg agatgtttcc   9000
agatgatgca cccctgttgc cctccgggtt tcgtatcatt cctctcgagt caaaatcagt   9060
tgagtaaaaa tatttcattt tcaactttaa gcattgaatt tggccaatct attgtttaca   9120
tggattattt ttcattttgc ttgattttgg agcataaccg gtgattctat tttcagagcg   9180
atccccagga tacatcgaat gctcatagaa cactggatct ggcatcaagt cttgaagttg   9240
gcccagcaac aaaccctgct actggagatg tggtctctgg ctacagtgca cgatctgtgt   9300
tgacaattgc ttttcaattt ccattcgagg acaatcttca ggacaatgta gctaccatgg   9360
cgcgccagta tgttcgcagt gtggtttcat ctgtccaacg ggttgccatg gcaatatctc   9420
ccgcaggagt gaattcaaca ttcgggtcca agctttctcc aggctcccct gaagctgtaa   9480
cgttgtcgca ctggatctgc cagagctaca ggtaaaatga tttctcaact atggtgaaac   9540
cttgttctct tcgtttcagc tcaatatggg gtttattgct ttacatgttc atactgtcgt   9600
gcttacaagt cactcgttgc aaatctcatt taccaccaag agccaaagta gtgtcaagtg   9660
tgcatgttga gatcttcaat tattttatga gaatttttcc tttctcaaca tattgagaaa   9720
aagcagacgg tcttagaagt acttttctga ttgttaacat accgttttct tcttttgcat   9780
ttaatatcca gttatcacat ggggacagag ttgcttcaaa ctgattcgag gggcgatgaa   9840
tcagtgctaa aaaatctttg gcaacatcag gatgctattt tgtgctgctc attgaaggta   9900
tgaattctct tatcatgtaa acagcatgtt acggttagta aaaaaatatt gtatgttgtg   9960
```

```
ttgcggtgaa acatgaacat atacgtaaag aaaaaatgta ttaacctagt aaatccacga  10020
tgaaggcaga tttgttcaaa agttaatctc atgaccctaa ttaatattag aatacgaaag  10080
agctggacaa ggatattaga aataagtccg acttaaatta tacttgtgat ggtgatattt  10140
tatggtgaaa atgccatatc atgggtgtat atttgaacta cttgtgattg gcattttgat  10200
tgtcctcatt ttggtcccta gcatgctttt gacatgtcaa catggaaatg agttgctaag  10260
aaattggaag gactgaccta ttcgttcacg ttccttttat cttgttaaaa gaatgtgttt  10320
agtaagttaa atttctttct ctgctgttgc agtccctgcc ggttttcatt tttgctaata  10380
aggctgggct tgatatgctg gagacaacct tagttgcttt acaggacatt actctagata  10440
agatatttga tgaatctggc cggaaagtgt tgttcgctga atttcccaag atcatggaac  10500
aggtatttac agctgactct ggtcttttgc agaacctaga aaacaaaagt tgaggtctta  10560
actgttactt ttttccgcga tgttgattct tgatcatagg gttttgcgta cttgccgggt  10620
ggtatttgca tgtcagcaat gggacgacat atttcatatg aacaagctat tgcatggaaa  10680
gtctttgctt ctgaagaaac tgtccactgc ttagccttct catttattaa ctggtcattt  10740
gtttaatgtt gctgtcaaat ctcctttctt ttttttcctt tttgtttttt gacatcttcc  10800
tcacagagga cactgacagc caggaacaca gttgaacgga atgatctttg ggacggatga  10860
aaattttgta acttgggggg ctcccgtctg ttttaccttt aatttaatta gactaaattt  10920
gtattttgct tcctgaattc ttcatactct tatgtaaatt ttctagtgca gctttttttga  10980
gtgcagatgt ttgtttccgc atattctacc actgattcat tttatattta gctttagtat  11040
ttgcagtgat attcaagatg ctgcaatgtt gctaagctta tgtgatattt ttttcttata  11100
acaactgaga aaacttattt cgacaactta acttgaacgg aaatcctaca ttattaaaca  11160
aagagtagat aaaggttagt cgtgaatgga agataaatta ttataatata tacaacaaag  11220
ataagtacaa aataatgatg gtctcgattg ttattttaaa ataaatttta ggtttaatgt  11280
gtgcttttgg acttgaataa caagctcaag atgtgctagg gagattgcct ccaatgaata  11340
agacctgtct tatcatccat tatatgctat gtaatgtcaa agattcaagg gtgcccacta  11400
tacttttgca caatcctgca catatagcaa cagccaacaa gcatagcaca actcaagttt  11460
gcgcattgac ctgctttaca caatttgtat ttacacactg cagcggcaat tgtatgtttt  11520
ttggacatgg atcatccaga caaacatctg caatatcaga acaaaaatca gttctttaca  11580
aaaatgtttg gatattgttt gagtatttcc tgagaaccat tcttcctctt caccgagatg  11640
caagtgacca aaagtttaag agaaatgatg gcatagcaca gaaccagcta agaaaggcca  11700
tggcagtagc agtctcaaac tctgtgcagt gattctgaga gcagacacca aggtcattgc  11760
caatcagtac agtaatgcca gcagaagcac aggctgcagc aaacgtgagg gtagaagtga  11820
cctgcaagaa agatagtatt tataaggaga tgaatggaaa ggagtcatgt agctactcag  11880
atgcttcagg atgagcttat atacaacttg tgttaaatgc tcaaagcgga atgtggtgca  11940
cgcatagccc gaaaagttta taataatgga gtaaaaggaa gagaccaatt caagaagtgc  12000
aaaatggaga taggtacggg ggatttgctg ttataataaa ttacaaatct ggttatcaag  12060
aaacaataaa ctattaactc cagactatga gatatttaaa agataataga gcttttctac  12120
ctacaaggta atttctacat catattagaa gggttgagga accaggttaa aaaaaccaat  12180
tttatgtctg acctcacaga ccttgaggga tcagcgatgg atcagaaatg cccaagaata  12240
catcaaaaag tagcaaaatc tcctacaaaa tgaacagact gaggaagaag ttcccaccag  12300
acgggtaact gggctaagag ggctcaaaat ctgtttcagt tattgcacgg aagttgtcca  12360
```

```
actgtgacta agtcttacat aaactgtgtc actctcttcc atcattaggg acgaatgatc  12420
tggatcccca gccattcata tcataactct ttcatgcaag agtttatcac tctattcata  12480
attaattttg cagtcaattt tattccgaaa agaaacatag caagactata ttaatattaa  12540
ccaatttaaa gtcccaaatg agccatgaca tatatcaata ggcatattaa acttggagag  12600
aacgaaagag ggcatgctgc caaagtttat atcaataggc atattaaact tggagcgaaa  12660
acgaaaaaag ggaatgttgc caaagtttac ttgcaaagag gaaattttag gggaaaagtc  12720
atatttacta attctctaat accatttcaa ttcactttta aacaattact atgagtagcc  12780
caaatcattg attatgttta actgcgcatc tttcatatct ttctgagctc cttaaataaa  12840
tggctattgc ctattgcaaa attcatatac cacaagtata cgaccaactt tactggtgca  12900
gtaaaatact gcttatccgg ctcttaaatg taaaaaaggc atgttgctta taaggcaacc  12960
aagagaatgt gaccatctta aacgtaaagg gtacctaatt ttaatatttc attgctgagt  13020
atacaataaa aaaattaggc aactcaactt ctctattttt tttttctgta taaactctat  13080
ggatacacca tcttactccc ttcttccact atccttttta gtgcaccccc aaaagattga  13140
aacatttcta tttatgaaaa ctacctccca acactatcct tttcactaaa aaagaaaatt  13200
ttaatgctca tttctaccaa gagcgagcca tcagcattca tgatgaagta tatcatgata  13260
gaaaggccat tttcgcaact tgtgtttgtt ttacttatgt gtgtatacat ttctaaaatt  13320
cactttccaa taaaaccacc tcataaatatg gaacggacgg agtactaaaa gtcataagtt  13380
tataggaatt ccaagttcat gaaacaccct taacagctag ccaagttatc aaaggctatg  13440
ccctacttct tgagttgtca cccgcgtttt atgagtttct catagttgca tcatcgcggt  13500
gcctagaggg gatatgtacc aacttaatct taccaattag tctaaagaaa ataatttgat  13560
atgtatttgt gcaagacgtt gaagcaagct ggtagaggtt gtattcaacg gcacaaaaac  13620
caatgaagcc ccttaatttt ttgaatccaa tataatactt ttagaatcct tataaaaaaa  13680
atgtttagaa tgccattact agaatttagt aagcatacca tgaggtctct aagaaattaa  13740
tcatctctct catggcatta tatattacac aaccttccct taaattttgg tacctatacg  13800
agaccctctg gatgggtcaa aaactgaata actaaagaaa caacaaagaa ataggcatta  13860
ctttttctta ttttacctta taaaatagaa ataattaatt ttcaaacttt atgccataga  13920
ggatgcccta tccatcactg gtaactactc gtgagaccaa gcaagtggaa taatccgaag  13980
aaagaggggt gagggagact cctaattgtt tcccccattt agatcctgta aatgcaattt  14040
aattccctca tcctatttgt ttgctccatt aagatattat taataaacac attttaataa  14100
aattagtaga gatgcatatt tccaagtgat tgttttgtat taaccaaacg taataaataa  14160
ggatatttac aaaaactcta gtacatattg caagatccat tcaatgggat ggaagaagca  14220
tgcagatcac ttcacaaact attgacatag tttttttatta tctggattga tcatatttgc  14280
aaatagttta caaagtttta agattaaatg cattaaattg gtataatata taggatctaa  14340
agtcattcaa ttcactagaa aactcgtgaa attgtgacct tggaccttaa atagcaacag  14400
aagaatgaaa ggccagcgga aattctgtta aatacatggt cattatggac aagagaaaat  14460
gggtatggtc attgcacaga attactccat gagtagatgt gaatattgac aatattgaat  14520
tgtgtttaat ccagcacaag ctgcccccact cttgagctag tcaattttcc ggcacttctt  14580
ccacatacat aagagttgaa aaccaaaaat tggccctgga taacttatat ccaagcttca  14640
tatttcaaag actactaggt aggcaattag ggcataatat ctctggaaac ctagccaatt  14700
```

```
tctttgttaa aaagaaaaat gggtaaataa aaataatcaa acattctaaa caactgaaga  14760
gtagttaaac aaaggtcatt ttgcataaac aggaagttag tgcatgcata atatacaagc  14820
tatctcaatt aaaactggat aagacataaa gaaaaatcat atcgatccaa gtatatatgt  14880
attaaaattt tcagtgcaat tgcaaggtgg aactaaacca gaaacacata agcaaaagtc  14940
atatctttcc atgccaatcg caagctggaa agttttttaa ttccatatta tacttatcaa  15000
acgaaagaaa gtcacgacac tcatctattt gatcaattgc aatagctatc ttttgtatca  15060
agtccttgca cgtctgattg tatcagtctc tattcaaaag cta                    15103
```

```
<210> SEQ ID NO 18
<211> LENGTH: 14465
<212> TYPE: DNA
<213> ORGANISM: Nicotiana tabacum

<400> SEQUENCE: 18

agattttggc tattcttttt tgaaaatatt gtttgttcat gaaatatgat cacttttgat     60
tcaatttcaa gttgcagttt ttgggtgaaa attttctttc actcacaaaa atttaactct    120
ttttcaaatt aaatgcatat caaacacaac ttcaacttcc aaaagttatt ttcaccataa    180
cttcaaaaac tattttatca agttttgaca aaatctatat ccaaacgcta gcgaattgtt    240
tttacccaag aactgtccta cataagtttt tgaaaactcg aaatttctct tcaatttttt    300
tttaaaattg atcatattcc atgaatatac aatattttta attttttttt taaatagcca    360
aaagtatatg accaaccggg agctaaagtt taggttaaac aatcaaatgg ttaaaagact    420
agcataacaa tttagtcatg taggtgattt gctagtcatt ttcaaaatgt tacatttcct    480
agactggagc aggagcaaag attcaagaaa ttaatcctaa tactgacaca aatattagat    540
gactagtgtg aattgatctc ataggggat catccattca cttgctacct tactagccat    600
cagttaaaac aacgaaaaga ttgatacaga ttctcacaaa tgaagaaaaa aagaagtaaa    660
ctacaaggac aaaaaacaaa gatttaaagc ccatttggat ggtcttaaag atttgactgt    720
tatttttggt tcgttttaag taattttcaa cttatttcaa actctttata attttgagcc    780
cgttaggatt aactgattta aactagctga taagcattta gtgctgaaaa atatttttaa    840
gtgttgaaac tgatttaata aataagcagt tacatgtttg attacaagtg ctgaaattga    900
taataagttg ctgcaatatt tgataaaaaa aatgccgata aattcctttt ttgttaaaat    960
gacttaaata accttagaag tgtttacact tataaggacg taatttcttc aaaattttaa   1020
attccaaatc gatccaaata caaaatattc tatttgtcat ttttttaaaa tacaactgtg   1080
cttagataag ataactttta tgataaatat aatttatttt atgctaagta tataatcata   1140
agttataata attaataaat tgataaaaaa ttttcaataa aaaataaacc taaataggac   1200
aaaatatttg aagagaaaca aacactgtgt ttatcaccac aacacttaga aagcaacaca   1260
cgtcctcatt tattacatac aattcaaaga ttaatacaca atcaatagat ataaatatgc   1320
aaaggaataa ataatttgct tatcttaaat agtcaatgag cattgtaggc ttgaagaggc   1380
gggggagggg ggtttaggtt gaaatagtac ttgagtcagt gagtatccat gtaagagttt   1440
tgttctaaaa aaaaatattt taaggataaa atagtaaaat ttttgatcaa atttaaagtg   1500
cttataagct aaaaatttat aagctgaggg tgaccgactt atgatttatt tttgacttat   1560
aagcacttga cttataaaca cttttaactt taccaaacgc gtaaatatac cgataaatgc   1620
ttataagcta gtttgacgag cttataaact taaccgaaca ccctcttact tatataaaaa   1680
taaaagaaaa tattaaaagt aataaatctt tttgcagaga gtagagtaga ggggtgaaac   1740
```

```
cctaatagtc agagagacag agtatagacc acaaaggggc acagtagcca taggtattgg   1800
cagaagaaaa gattatgatt tgaccaaagc atttatatcc acagtacatg gcgtgggtct   1860
tatatgtcat ttcatatact gtacattgga ctagcttgta aatgcgccga atgggtaata   1920
ttaaattttt tgtttttata ataataatgg ctaaatcaat ttattattta tcaactaatt   1980
tcacggtata tatatgttat cacaaaataa ataactttat attgacactt catagttttt   2040
gataattatt aatttttaat tatcaactag aaatattact gagaaaagaa tccagacagt   2100
agagatcata aatattaaca aagttctatt agtatcttat aaatgaggct taaatctaag   2160
tcaaaacaca agagacgttt gcaaatgtgc caacttatca aattatgaat cacatttcac   2220
aatctgcctg ataatccctt tgaatttaca ttaatacatg ctccaaaaaa tttaacttta   2280
ctcactttaa cttaagaaca ttggctttat tcctctaatt tgtgaatata caagcagctt   2340
gttctagaca ttactgaaat tcatttacgt acatttagtt tgaataacta tttaacaaat   2400
ggtaattgtt tttaaattct aaaaataaag gatagagaag gaaaaaacca tgagtaccac   2460
ccgtagagtt ctcttttaac ttctttttcc ttagagttta gctctgagtt aaaaaaattc   2520
atcttgataa tagtaaccat atatggaata aaaatgtcct ataatttcaa gggcagatat   2580
acgatatata taaattatga attcaatcaa atccaattgt atgttcaaat attcaattat   2640
cattgaattt agcattattg ctatccacaa aattcaaact ctagatatgc tttgatataa   2700
tttagattca tctagacaat agagaccata tagaaaaaaa aaatcctgta atttgaggga   2760
cagatatgcc atgtaagtta cgaattcagt caaattcaat aatttagtat cagatgtaca   2820
tatattaaat tctaatttag taactcaaat gatcattaaa tttagtggta ttccaaccac   2880
aaaatttaaa ttctaaatct ccttttatat ataatgtaga tcaagttaaa acattcatca   2940
agacaatatt gaccatatat ggacaaaaat gtcctttgaa cttttccctt ttatgtttat   3000
agctagaatt catgtttata gctagaaaaa atcatccaaa cagtggtgat cacatatttt   3060
attttattaa aaggaaaaag aaaaagaaaa agaagttgta ttattatact ctagcagata   3120
actgaatatt tatattcgta cgtaccatat tgcaatttta attaaattat tagtgaagaa   3180
aaaggacata aaataaaaga aaacagaaaa acacaaaggc aagagcaaca gcagcagcat   3240
aaaaacactg gcattttcga tttgcgagct cataaagctt taagtcaagc aaattcccac   3300
atcacagtct ctctctctct ctccattttc ttttgccctt ttctcaccca ccactctcac   3360
acacctcttc acctcacctt acacacacta aaaaaacatc acttctctct gtctctctct   3420
ctaaaaaaaa ttctatcttt ttgctgttcc aacatgtctt ttagagtttg tttcagtttc   3480
agatcttaag tgggaggtgt tatgcttctt cttatatatt gaagctcaag aaaactaaga   3540
aaacagagca aatttttgct ttcttttctc ctacttttttg tgggggtaat tcttgttttt   3600
gtaatctcaa agctggctat tttatgtata tactgaaggg gttgtggtga tttgtttgtc   3660
tactttaaga aggtgccatc tttttcagta atatttgggt aaaggttctc tttttttggc   3720
cttacacgcg aagattcagg cctctctgaa cgtgtcattt gttctctgta ttaaacacag   3780
ctggagaagt aattacatca aggtagaaaa aggggttaaa gattccaaag aattgagtgt   3840
ttgaaaaaaa aaacagaggg ctgaggtaaa aagttgatgg ttttaaaaaa aataaattaa   3900
atgatgatag agtttggagc tttatgtgaa tggaaatggt gttgtgtttt tatcaaacac   3960
gagtagttta cagcttatgt gaatttgaaa gagagagaga atttttgtct gtatttatat   4020
ccttttcagc catatctttc gttagagcag ttttggctgt accttaattt gtaagttttt   4080
```

```
aagcgtgaag tgtgtgtttg agccttctgt tataaggggc acaaagtata gaaacaacaa   4140
aagggggcac ctaggaatct tctggctcaa tcaagatcgt tcatttaatc ttgtctgaga   4200
tcactagaaa aagaaaaaaa aaagagataa agataaagtc tttgtttcag agaatcttag   4260
ttctctgtgt tgatatatat aataaaagct gtttgcaggg aatatatcta cttgggggtg   4320
tttttatttc ttaaaagggt gtttgaaaat ttggaaatct tgattttttt tttggtttgg   4380
gattttgagg tttgagggca atggctatgg ttgcacagca gcacagggag agtagtagtg   4440
gtagtattac aaaacatctt gacagtagtg gaaagtatgt ccggtataca gctgagcaag   4500
ttgaggcatt ggagagggtt tatgctgagt gccctaagcc tagctccttg cgccgccaac   4560
aattgatccg tgaatgccct attctgtcga atatcgagcc taagcagatc aaagtttggt   4620
ttcaaaacag aaggtacact gcccattgtt caatttggat tactccaatt tggtttcttt   4680
tttgttctta aatgcatata tttaggtgtg tactgcactt gtgatcttgg gctctagttt   4740
gtttggtact gctcaaatct tggattagtt agatcagtga tggatgaagt ggaatatatc   4800
actgtccttc tagtttccta ggcttgtcga ttgggttgta tgagttaacc gtggggcatt   4860
aagtgaatca tgaattgcat atgtagtttg atttctgtct gttgggtagt tgagcttaga   4920
ttttggaata gagggtgaat attgtatcat ttcaggtgtc gagagaagca aaggaaagag   4980
tcttctcgac tacagactgt aaatagaaag ctgtctgcaa tgaataaact attgatggag   5040
gagaatgatc gcttgcaaaa acaggtttcg cagcttgtgt gtgaaaatgg ctttatgcgg   5100
caacagttgc atactgtaag ttaacataat ttttccttta ttatttatgg taaaaaacct   5160
tttttttcac ttaacgtatc ttgtcttttg tttctgataa gcactatgga ttttaagatt   5220
cctgatattc cacagcttat ggtaacatat tttaaacagt gtaaattgtc tttattttga   5280
tgacaggttt taggtcattc ttatagttac gaaatgcatg actaaatttt gaattcatcg   5340
tgtttttgct ttctatattc ttctacccgc ccttcttgtt ttgctgtgat attgaaccaa   5400
tggacaagaa acggatggca gatatctccg gtgatctttt gttctgtagg aattaattag   5460
actgtatttg tgttttctgc aggcatcagc ggccactact gatgtaagtt gtgagtctgt   5520
ggtaactacc cctcagcatt ccctcagaga tgctaacaac cctgctgggt aattaatttc   5580
aaactcctat ttctcccacc ccttctgtct atggtgttta tacatattta tgttatttat   5640
taaatggcat agaccacatt ttgaggggct aatttgttta tctctaagtc aagtttgttc   5700
tctccgcaga ctgctgtcga ttgcagagga aaccttagca gagttccttt ccaaggctac   5760
aggaactgct gttgattggg tcccgatgcc tgggatgaag gtttgaactt tagtcaatcc   5820
tttttgttt taaaaaaaaa ttcagtattg ccacgtgcct ctttgactgg atagctaaaa   5880
aactaaattt tcattctatt gtcagcctgg tccggattca gttgggattt ttgccatctc   5940
acacagttgt agtggagtgg cagcccgagc atgtggtctt gttagtttag agccgacaaa   6000
ggtaagcagt cttgtggaaa attaatttaa atgtagtgct gctgctctat tactagtttt   6060
ggtcccttga tgagtgtact agattatgcc agtttcttct aagtacatat atttttgtct   6120
aatatttaca gattgctgag atcctcaaag atcgatcttc ttggttccga gattgccgga   6180
acgttgaagt tttcacaatg ttttctgcag gaaatggaac aattgaactt ttgtacacgc   6240
aggtaattaa ttactttctc atcaatcttc acgtaggctt ctgattggag aagctacagc   6300
attgagggga ttgttgaaat catttttttt ccagatatat gctcctacca ccttggctcc   6360
tgcacgtgat ttttggactc tgagatacac aaccaccctg gagaatggta gctttgtggt   6420
aagcacatcc ttcacattag tgtgtcttag gattagcaat ctggccactt ttgtacttag   6480
```

```
ttatgaatat tttgctgata gtttgttgta tgtgcccatc aattcctcct ccccgtaagg   6540
tttgtgaaag atccctctct ggtactggag ctgggccgaa tgctgcttct gcttcccagt   6600
ttgtaagagc tcaaatgctt ccgtctggat atctaatccg accgtgtgac ggtggaggat   6660
ccattataca tattgttgac cacctgaatc ttgaggtcag attacacgct gtactaccac   6720
ttctctttct tattagcttg ttctgtcttg cagctggact tcactgcata atattgtttt   6780
tcaggcatgg agtgcccctg agattttgcg tccactttat gaatcgtcaa aagttgtggc   6840
acagaaaatg actattgcgg tgagttgaac ccttggtttt tattaactac tggatgttta   6900
acaacctttt tggtcttcac aactagatct caatttttgt tcagctctga agtagatagg   6960
attgtacttt ctggacgagc agttagatat agcctgatat ttttgtttat tctgttagaa   7020
gttcccagct ttaaaaatat agaacacctg acaaatcctt agtctcttaa tgcacgttat   7080
cgaggatttc ttcgttattc gagttttcaa aggttcatta ttgttttcct cattgtgttg   7140
ccataaaagt ctgcatgtga aacatataag taatgaagaa ccttatgctg tgaagcacag   7200
catactgtta actgcattcg atgttgctta attccagaag ttgctctgag aatacttaca   7260
gccttttttt atattttaag tacttgagca attaccgtta cttaccacaa cagcaaaaga   7320
aatactaatt atggttagtt tttgctgtaa aggcactgcg atatgcaagg caaatagctc   7380
aggagactag tggggaggtt gtatatggtc tgggaaggca acctgcagtt cttcgaacat   7440
ttagccagag attaagcagg tgctggttat tgctctgatt gttctgtgct tcgagatatg   7500
atatgccata aaagtagaca tacgaatcct gaagcgcaag tatcataatt aggctatttt   7560
ctatattgca gaggcttcaa tgatgccatc aatggattca gtgatgatgg ctggtcattg   7620
ttaagttctg atggtggtga agatgttata gttgctgtca attcaaggaa gaacattgcc   7680
accacttccg ttcctctttc accacttgga ggcatccttt gtgccaaagc atcaatgcta   7740
ctccaggtca acagattaag ctttcttgaa ctaactacag attttcattg gccaactacc   7800
tttgccttgt taattcactg aataggtcaa gtaattctaa agacaagttt tgcagtgctc   7860
ttgttgcctt gttagttcat agcaaacaga gttgcagctg ttcaaagtag gatcatatat   7920
tgtgatacct attcagtatc tgtattagat ctagtatcac aagacaagtt ttctttactg   7980
ctcttgtttc ttagaaattg gctctatact cttactaaaa aagagcgata atggtagatt   8040
ttgaagtcga ggaaaaatta aaatcgttcc ggattgttgc agatttttat tatgctttca   8100
atttctaatt ctaggaaaga atcaggattc ctggaatatt agagaatatt actcagtgtt   8160
ttataaagct atttgtttaa tgctctgagt agggcatctt gctattaatt ggaagaatga   8220
gaattgactt ttaactcttt tgttcggtgg cagaatgttc ctcctgcggt actggttcga   8280
tttctcaggg agcaccgttc agagtgggcg gactttaatg ttgatgccta tgtagcttcc   8340
tcaatgaaat cttgttcata tgcatatcct ggggtgaggc ctaccagatt taccggaagc   8400
cagataataa tgccactggg ccacacaata gaacatgaag aggtaagcgg tttgcaattg   8460
ccccagttct cacttatgtg ttatggggaa tgcctcgaca tacatgagca agaatttgag   8520
acttgagact tcctctcact ttattttggt ttgcagatgc ttgaagttat tagattggaa   8580
gggcactcta ttggccagga agatgctttt atgccgagag atattcacct tctccaggta   8640
cttttgctta tacattgatg tttcggtgtg ttgtatgtac atacattgtt gaaggataat   8700
gctaacaaac agttatttct agatgtgtag tggaaccgat gagaatgctg tcggagcttg   8760
ttctgaacta gtttttgctg caattgatga gatgtttcca gatgatgcac ccctgttgcc   8820
```

```
ctccgggttt cgtatcattc ctctcgagtc aaaatcagtt gagtaaaata ttttgatttt   8880
caacttcaag cattgaattt ggcaaatcta ttgtttacat ggattttttt ttttcttttc   8940
attttgctcg attttggagc ataaccggtg attctatttt cagagcgatc cccaggatac   9000
atcgaatgct catagaacac tggatctggc atcaagtctt gaagttggcc cagcaacaaa   9060
ccctgctact ggagatgtgg tctctggcta cagtgcacga tctgtattga caattgcttt   9120
tcaatttcca ttcgaggaca atcttcagga taatgtagct accatggcgc gccagtatgt   9180
tcgcagtgtg gtttcatctg tccaacgggt tgccatggca atatctcccg caggagtgaa   9240
ttcaacattc gggtccaagc tttctccagg ctcccctgaa gctgtaactt tgtcgcactg   9300
gatctgccag agctacaggt aaaatgattt ctcaactatg gtgaaacctt attctctgca   9360
tttcagctca atatggggtt tattgcttta catgttcata ctgtcgtgct tacaagtcga   9420
ttcattgcaa atctcattta ccaccaagag cggaagcagt gtcgagtgtg catgttgatc   9480
ttcaattatt ttttgagaat ttttcctttc tcaacatatt gagaaaaatc agatggtctt   9540
agaagtactt ttctgattgt taacataccg ttttcttctt ttgcatataa tatccagtta   9600
tcacatgggg acagagttgc ttcaagctga ttcgaggggc gatgaatcag tgctaaagaa   9660
tctttggcaa catcaggatg ctattttgtg ctgctcattg aaggtatgaa ttctcttatg   9720
aactcatgta aacagcatat tacggtttgt tagtaaaaaa attgtaggtt gtgttgcggt   9780
gaaacatgaa catatgcata aagaaaaatg tattaaccta gtagtgtcat gaccctaatt   9840
aatattagaa tatgaaggag ctggacaatg atattaagaa ataagctcga cttaaattat   9900
atttgtgatg gtgatttttt atggtgaaaa tgtcatatca tgggtgcata tttgaactac   9960
ttgtgattgg cattttgatt gtcctcattt tggtccctag catgcttttg acatgtcaac  10020
atgcattgct tttgacctat tcatccgcct tctagtcttt tatcttgtta aatgaatggc  10080
gttagtaagt tgaatttctt tctctgctgt tgcagtcgct gccggttttc atttttgcta  10140
ataaggctgg gcttgatatg ctggagacaa cattagttgc tttgcaagac attactctag  10200
ataggatatt tgacgaatct ggccggaaag tgttgttcgc tgaatttccc aagatcatgg  10260
atcaggtatt tacagccgac tcttagtctt tgcagaaccg agaaaccaaa gttgaggtct  10320
taactcttac tttcttcgat tctgtttatt cttgatcata gggtttcgcg tacctgccgg  10380
gtggtatttg catgtctgca atgggacgac atatttcata tgaacaagct attgcatgga  10440
aagtctttgc ttctgaagaa actagtgtcc actgcttagc cttctcattt attaactggt  10500
catttgttta atgttgctgt caaatctcct cttttttttcc tttttgtttt ttgacatctt  10560
cctcacagag gacactgaca gacaggaaca cagttgaacg gaaagatctt gggaccgatg  10620
aaaatttttg taacttgtgg ggctcctgtc tgttttgcct taatttaatt agactaaatt  10680
tgtattttgc ttcccggatt cttcatactc ttgtgtaaat ttactagtgc agctttttttg  10740
agtgcagatg tttgtttcca aatattcgtt cactgaatca tttcaattta gctctagtat  10800
ttgcagtgag aatcaaaagt ttgtgatact tttttggtat atcagcagag aaaacttctt  10860
tcagcaactt atcaatttga ttggcaatcc tatacgacta aatagactcg ataaaggctg  10920
gttgtgtgaa tgtaagataa taaattatat atactacagc aagagttaag gatgaagtac  10980
aaaataatga cagcctcttc gattgttatt ttgaaacaag ttttaggtga aatatgtgtg  11040
cttttggact tgaatctaaa tgttacgttt gaataacgtc ggaacaaact ccaaatgtgc  11100
taggaagagt gcccacgtga tgtcaaagat tcaagagtgc ctactatagt ttttgcacaa  11160
tcctgcacat ataatagcag caagcatatc acaacacaag tttgcgcatt gacctgcttt  11220
```

```
acacaatttg tatttacaca ctgcagcagc aattgtatgt ttcttggaca ttgatcatct  11280
agacaaacat ttgcaatatc agaacaaaaa gcagttcttt ccaaaaatgt tcggacattg  11340
tttgagtatt tccttgagaa ccattcttct tcctcttcac cgggatgcaa gtgaccaaaa  11400
atttatgaga aatgatggca tagcacagaa ccagctaaga aaagccatgg cagtagctgt  11460
ctcaaactct atgcagtgat tctgagagca gacaccaagg tcattgccaa tcagtacagt  11520
aatgccagca gaagcacagg ctgcagcaaa cgtgagggta gaagtgacct gcaagaaagc  11580
tgatattttt acaaggagat gaatggaaag gagtcgtgaa gctattcaga tgcttcagga  11640
tgagcttata tacaccttgc gttaaatgca caaagttgaa tgtggcgcac acatattccg  11700
aaaaagttta taataatgga gtaaaaggaa gagacaaaat caagaagtgc aaaatggaga  11760
taggtacatg ggatttgctg ttataataaa caccaactct ggttatcaag aaataataaa  11820
ctcttaactc cagattatga gatatttaaa agatgataga gctttttttaa ctttgctaca  11880
aggtaatttc cacatcaaat tataagggtt gtggagacca ggttaaaaac accaatttca  11940
tgtctgacct cacagacctt gagggatcag cgatggatca gaaatgccca agaatacatc  12000
aaaaagtagc aaaatctcct acaaaatgaa cagaatgagg atgaaagttc ccgggtaacc  12060
gagctaaaag ggctcaaaaa actgtttcag ttattgcact gaagttgtcc aagctgtgat  12120
taagtcttac ataagctgtg tcactctctt tagggacaag tgatttactt ctggatccct  12180
agccatttct atcataactc tttcatgcaa gagtttatca ctctattcat aaataatttt  12240
gcagtcaatt ttattccgaa tagaaacata gcgagactat atttacatta gccaatttaa  12300
agtcccaaat gagccatgac atatatcaat aagcatatta aacttggaga gagaacgaaa  12360
gagggcctgc tgccaaagtt tacttgcaaa gaggaaattt tagaggaaaa gtcatattta  12420
ctaattctct aataccattt aaattcactt ttaaacaatt accatgagta gcccaaatca  12480
ttgattacgt ttaactgcgc atcttccata tctttttgag ctccttaatt ggctattgcc  12540
tattgaaaaa ttcatatacc acaagtatac gaccaacttt actgttgcag ttaaatactt  12600
gcttatgcag ctctccagga tatgcatcct agattctaat ttatctatat ctcccaaatg  12660
gaaaggcaac caagagaatg tgaccatctt aaacgtaaag ggtaactaat tttaatattt  12720
ccttgctgag tttacagtaa aaaagttagg caactgaact tctctatttt ttttttctgt  12780
aaatactcta tggatagacc atcttactcc cttcttccac tatccttttt agtgcacccc  12840
caaaagattg aaacatttct atttacaaaa actacctccc aacactatcc ttttccttaa  12900
ttaatgctca tttctgccaa gagtgagcca tcagcattca tgatgaagta tatcatgata  12960
gaaagacaat gctggcaact tgcatttgtt ttacttatgc gtctatacac aggggcggat  13020
gtagttcatt accgacgggt tcaattgaac ccataacttt tgacgcagag taaaaatcat  13080
aactttaaaa atataatagg ttcaatgcta aaaactttaa aagttgaacc cataggattt  13140
aaatcctgga tccgcctctg tctatacatt tcaaaaattc actttccaat aaaactacct  13200
cataatatgg aagtgaccga gtactaaagg tcataagttt atatgaattc aagttcatga  13260
aatactctta acagctagcc aagttagcaa aggctatgcc ctacttcttg agttgtcacc  13320
cacgttttat gagtttctca tagttgcatc atcacagtgc ctagagggga tatgtaccaa  13380
cttaatctta ccaattagtc taaagaaaat aatttgacat gtatttgtgc aagacgttga  13440
agcaagctga tagaggttgt ataatggcac aaaaaccaat gaaggccatt aatttttttaa  13500
tccaatatat atttttagaa tccctaaaaa aaatgcttgg aatggcattt cttaaagtat  13560
```

```
ttagtaagca tacaatgagg tttctaagaa attaatcatc tctctcatgg cattatatat  13620

tacacaacct tccctaaaat tttgatacct atacgagacc ctctgaatgg gtcaaaaact  13680

gaataactcg agaaacaaca aagaaatagg tagtactttt tcttatcgta ccttataaaa  13740

aagaaataat taattttcaa actttatgcc ataaaggatg ccctatccat cactggttta  13800

ctcatgagac caagcaagtg gaataatcca aagaaagagg ggtgagggag actcctaatt  13860

ttttgctcca tttagatttg taaatgcatt ttaattccct catcctaatt gtttgcttca  13920

ttacgatata gttaataaac gcattttaat aaaattagta gaaatgcata tttccaggtg  13980

attgttttgt attaaccaaa cataataaat aaggatatta acaaaatctc tagtacatat  14040

tgcaagatcc attaaattgg atggaggaag tatgccgatc acttcacaaa ctattgacag  14100

tcttttacta tttggaagga ccaaatttgc acatagtgta caaagttttg tgattaaatg  14160

cattaaattg gtataatata tttggatctt aagtcattca attcactgca aaactcgtga  14220

aattgtgacc ttggacctta aataggaaca gaaggacgaa aggccagcgg aaattctgtt  14280

aaatacatgg tcattatgga caagagaaaa taggtatggt cattgcacag aattactcca  14340

tgagtagatg tgaatattga cagttaatat gcaaggaatt gtgttaaatc cagcacaagc  14400

ttccccactt ttgagctagt caattttccg gcacttcttc catactagtg gaggtaacgc  14460

ccgtg                                                              14465
```

<210> SEQ ID NO 19
<211> LENGTH: 337
<212> TYPE: PRT
<213> ORGANISM: Nicotiana tabacum

<400> SEQUENCE: 19

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205
```

```
Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Asn Gly
    290                 295                 300

Asn Asn Gly Ser Thr Ile Gly Cys Asn Asn Asn Asn Ser Met Phe Val
305                 310                 315                 320

Phe Asn Asp Glu Asn Tyr Asn Lys Ser Asn Glu Ile Glu Met Phe Tyr
                325                 330                 335

Tyr


<210> SEQ ID NO 20
<211> LENGTH: 336
<212> TYPE: PRT
<213> ORGANISM: Nicotiana tabacum

<400> SEQUENCE: 20

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Cys Leu Gln
225                 230                 235                 240
```

```
Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
            260                 265                 270

Asn Val Tyr Phe Gly Asn Thr Thr Thr Thr Thr Gln Val Leu Gln Tyr
        275                 280                 285

Asp Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Gly Met Phe Tyr Tyr
                325                 330                 335


<210> SEQ ID NO 21
<211> LENGTH: 1209
<212> TYPE: DNA
<213> ORGANISM: Nicotiana tabacum

<400> SEQUENCE: 21

gtccatctgt ctatataggt agaatgagag taaaggagaa aacatatcct cctctccatt      60

tctgtagaca aagattctca aagagaaaca aattaaacac tagagagtga gagagtgcta     120

taagaaaaag aatatgggga gagctccatg ttgtgataaa gcaaatgtga agagagggcc     180

atggtctcct gaagaagatg ctaaactcaa agatttcatt cacaaatatg gaactggtgg     240

aaattggatt gctcttcctc aaaaagctgg actaaagaga tgtgggaaga gttgtagatt     300

gagatggcta aattatttaa ggcctaacat taaacatggt gatttttctg aggaagaaga     360

tagagttatt tgcaccttgt attccaccat tggaagcagg tggtcaataa tagcagctca     420

attaccggga agaactgaca atgatatcaa gaattactgg aatactaagc tcaagaaaaa     480

acctatggga ttaatgcaat caactaacca aagaaaatca ccatattttc cagctactaa     540

ttctcttcaa acccaacccc agataaattc aagtcttttt agagacttat attacacccc     600

aaataatagg cctaatatta caggcctaaa tcatcagtcc atttcttctg cccaccagac     660

aaattttctc tacactaata ataacatgaa ctttcctaat ttgggtgcta caaataatca     720

atatccttat aatatccaaa gtcataattt acttatgttt ggagaagcaa gttgttcttc     780

atcagatgga agttgcagcc aaatgagttt tggtaaagaa atcaagagag aagaaattat     840

gagtaatagt ttacaacaag gtcaaatttc aagtgttaat gcttttgaag aaaaccacca     900

gaattttact cttgattatg gcaatagtag tagtaattgg gtggatcaaa aaccaaatgt     960

gtattttggt actactacta ctcaagtact tcagtatgat aatgttgaag aagttaagca    1020

gcagctaaca agttgtacca atggcaacaa tggtagtact attggatgta acaacaacaa    1080

cagtatgttc gtgttcaatg atgagaatta taacaagtca aatgagatag agatgttcta    1140

ttactaaaga agaaatgact gttgaaaaga aaacaaatgc aagtaccatt aggaagattt    1200

gaaagggcg                                                             1209


<210> SEQ ID NO 22
<211> LENGTH: 1211
<212> TYPE: DNA
<213> ORGANISM: Nicotiana tabacum

<400> SEQUENCE: 22

ccacttgtct atatagcaag aaagagagta aaggagaaaa catattctcc tctccatttc      60

tgtagacaag attctcaaaa agaaacaaat taaacactag agagtgagag agaactataa     120
```

```
gaaaaagaat atggggagag ctccatgttg tgataaagca aatgtgaaga gagggccatg    180
gtctcctgaa gaagatgcta aactcaaaga tttcattcac aaatatggaa ctggtggaaa    240
ttggattgct cttccccaaa aagcaggact aaagagatgt gggaagagtt gtagattgag    300
atggctaaat tatctaaggc ctaatatcaa acatggtgat ttttcggagg aagaagatag    360
agttatttgc agcttgtatt ccaccattgg aagcaggtgg tcaataatag cagctcaatt    420
accaggaagg actgacaatg atatcaagaa ttactggaat actaaactca agaaaaagct    480
tatgggatta atgcaatcaa caaaccaaag aaaatcacca tattttccag ctactaattc    540
tcttcaaacc caaccccaga taaattcaag tctttttaga gacttatatt acaacccaaa    600
taataggcct attattacag gcctaaatca gtccatttct tctgcccacc agccaaattt    660
tctctacact aatagtaaca tgaattttcc taatttgggt gctacaaata gtcaatatcc    720
ttataatatt caaagtcata atttacttat gtttggagaa gcaagttgtt cttcatcaga    780
tggaagttgt agccaaatga gttttggcaa agaaatcaag agagaggaaa ttatgagtaa    840
ttgtttacaa caaggtcaaa tttcaagtgt taatgctttt gaagaaaatc agaatttcac    900
tcttgattat ggtaacagta gtagtaattg ggtggatcaa aaaccaaatg tgtattttgg    960
aaatactact actactactc aagtacttca gtatgatgtt gaagaagtta agcagcagct   1020
aacaagttgt accaatggca acaatggcag tactattgga tgtaacaaca acaacagtat   1080
gttcgtgttc aatgatgaga attataacaa gtcaaatgag atagggatgt tctattactg   1140
aagaagaaat gactagctgt tgaaaagaga aaacaaatgt aagtacacca ttaggaagat   1200
ttgaaagggc g                                                          1211
```

<210> SEQ ID NO 23
<211> LENGTH: 9227
<212> TYPE: DNA
<213> ORGANISM: Nicotiana tabacum

<400> SEQUENCE: 23

```
gagggtagtc ttgttatatt attggggaat gaattatggt ttcaaacttt tcaaacttaa     60
aggattttgt acatggtaaa acctaaattg acacgtaact tggtactttc aaagacacga    120
tcttttacgc gatattttaa ataaagaaaa gatcaagtca aaacatgggc caaaaagaaa    180
aaccccatga ttttttctga taaaaagctg ctaactttta gtttgtttta tccaataaaa    240
catctttaac ggtctgcctg ctttagttta atcctctttt taagatgtaa ttaagcataa    300
aatagaaaag ggaaaaaaaa ggtccattgg attttggaag aaattttaag aaagtacaag    360
aactagtaaa gtcattttgt atagagtatg ttaaaaaggt gagtgacaat tcgaaaaaga    420
aagcattgat aagtcaatca ctaaataaaa aagcacacct aataatcatt cattcaaaaa    480
aacaaatttc tatgaaagat aatcattatc ataagtcact gcagaaatcc catatacagt    540
agagtaccag gattttacga taaggtgtta gcaaactatc tattcatttt ttgacaagca    600
ttttatgttt ggtcatttgt tgggaaaaat tagggagaaa tttaaaaata gttagattta    660
caactggtca ttaaaaatag cccaatttca aaagtaatcg aaatttagcc acttttcatg    720
taaagataaa tctgagcgaa aatattgttc aaaacccgga aaatacgccc gtatattata    780
ctggagttcc agcataagta tgcttgaact ccagcatatt atacgggagt tctaggataa    840
ctatgttgga actccagcat aatatgttgg agttccagca taagtacact agaactccag    900
catattatac gggagttcca acaagtataa ctgtcccgta taatatattg gagtttggag    960
```

-continued caccggtgct ccagtctccc gtatattata caggagtcag caaagtatac cggtccagca 1020
taatatgctg gagttcgtac acagatgcac cgaactcacg tatattatgc ggaaccggtc 1080
tctgttgcag caaaatagtg gctatttttc attgacttcg taaacggtgg ctatttttga 1140
atgaccagtc cgaaaactgg ctataccgtg ctattttgac gaaaaattat ccccccaccc 1200
acccacccac ccaaacgcac cttacacaca ttagtgcaca tcttttaact agtttttggt 1260
tattttttta tttgatgccc gatattcgta tatggatttc gattaattag aattcacacc 1320
gaaacattct ttcttaggat tttgtacata cttaatatgc gaatacaaaa cctatgcgga 1380
aaggtaaggg aacctattca tccctctaca gtacttgtga taatgttata ctttttttgaa 1440 tttaatttgg gagacatgtc aatctttatt ttgaaaaaaa aaatagaata aaaccatagg 1500
gaaatgaaca atttatcttt cactcctatc tcattttatt tgtcttgaat ttttcaaaat 1560
tttgaattat attttgaaac ttcttcaatt tattttcttg gaatcttcag aattcaattt 1620
aaaattccaa aattccaagg atttagctcc cgtttggcca cagattttgg cttcattttt 1680
ttaaaaaaaa ttttgaaaac attctttgtt tatgcaatat gatcatgttt taggggaaaa 1740
aaattaaaaa aaataaaaaa aaatcaaatt cccaaaaact ggttaggcaa tttttggatg 1800 atatttttttc ttccactcac aaaactttaa catgtccaaa cacaacttca acttcaaaaa 1860
ttattttcaa cacaatttta aaaactcttt tttcaagttt caatcaaatc tatatccaaa 1920
tgttagctta gtatcaaata agtgattgaa atcaaattaa aatcgagtgg taaataaaat 1980
agaggagagc tcggtaaatt acaagagtgc ggtaaatctt ttctccttta ctctcactgt 2040
agcctattct atctgttgta actaataagt aactgagcta cggaaaaagt gcctagactt 2100
ttaacttcac aagtataata aatagaagtc aattctttca taatattgtt tccatcctat 2160
caaacagact ttgtctcact gaccttcctt ctgagtgtgt cttttatatg tcatttttag 2220
tgaatccata tgatttagag actctaatat tccacatgcg ggtcttaatt tggtgtatat 2280
gtatatggta ataattttttg ttaggtagct gtagtattct attattgtta tgtattgact 2340
catcatgtaa ataaagccgg ttagataagg ctagaaaaat atgagtatac ctagaaatta 2400
ttagcatatt gtttggaaca tgtcaaaaat ttcaatgacc tagctagagc tgtcaattag 2460
tcaaataact ttattaatat ttacttatga aaacactttg aaattcttgg agtttaaggg 2520
aaagactact gactaaaaaa caaagcaaaa gtctatgcat tactatacta tacacagcac 2580
agcattttcc aatagtattt gagatgaatc tccaatcagc tactgttgtt cttttctttt 2640
ctttatttag tttaagtttt atgtgttgat ggtatacaaa ttatttgcac aatcaaatgg 2700
cttatctgga taatataggt aaacctcttg taatcactaa ttggtaatct ggtaaaaata 2760
acactatttc tattccaatt tatgtgatca atttcactag acaaaaattt aagaaagaaa 2820
taaatttttt agaacttgta gtcataaaca agttgtaaca tttgtatggc tataattttt 2880
ttaacttgtg atgttaaaca tgtcagattg tttgtgtagc tataaaagtt tttcattagg 2940
cgtaaaatta aaaatttaga ttaaattatt attaaattta gaaagaggtc atttttttta 3000
gcgaagtaaa aaagaaatcg gttcacataa accgaaacat agagtaagta atctgttatg 3060
acaaattaaa aattacttgt agtgtaaaaa aatctttaca acattcgtgt atatacttaa 3120 atcttttttta tttttggca agagatagtt gttcagcaaa agtaagttag aaataggtct 3180
gtccttctga ctttgtaact ctgaaatgaa aatttcaaaa tcccttctat ttttactgtt 3240
accccccccc cccctcacaa accccaactc actcttattt aataaaaagc tctacttaga 3300
aaagacaccc ttgtccatct gtctatatag gtagaatgag agtaaaggag aaaacatatc 3360

```
ctcctctcca tttctgtaga caaagattct caaagagaaa caaattaaac actagagagt   3420
gagagagtgc tataagaaaa agaatatggg gagagctcca tgttgtgata aagcaaatgt   3480
gaagagaggg ccatggtctc ctgaagaaga tgctaaactc aaagatttca ttcacaaata   3540
tggaactggt ggaaattgga ttgctcttcc tcaaaaagct ggtaacaaca acttctactc   3600
cactagtcct ctatgtgtat gtaattttat tattattatt attattatta ttattattat   3660
tattattatt attcatgaat cgaagggaca aaggtctaaa tctcagtggg tcgtggtagc   3720
aaggccattc cgccatttat aatatcttct tgcaaattcc accagtttca tatgtgtatg   3780
tttttttctt attagtcata aatcaaagcg acgaagggtt aaatttcagt tgattgtgat   3840
agcaaggtca cactctaccg cttataatat ctcgtggcgt atttaacatt gtttgtatgt   3900
atatgtttga gtataaaggg aggaaagctt atatttatat ttgagtggat tgagtttttt   3960
tccttgttgc tgcattattt atgatttgat gagatttatg ttgggaactg caggactaaa   4020
gagatgtggg aagagttgta gattgagatg gctaaattat ttaaggccta acattaaaca   4080
tggtgatttt tctgaggaag aagatagagt tatttgcacc ttgtattcca ccattggaag   4140
caggtaatat atatatacct ttttttggtc gtaatttttt tttcattttt tatcatcttt   4200
ctgatgaatt tgagactgaa acaaaaactg ttcccactaa aaatggaaaa gaaaaacctc   4260
aataagtaag aaaagggaaa aaacaatgag ggctcagaaa gaaatgcaaa tagtcagttg   4320
gatttttaat taaagattct gccatttatg gacatatttt tctgcatgca tgccaggttt   4380
agatctaaga tcaagtcttt atttactcac ttacagatgt ttaattatta agacaaagtt   4440
ccaatttttc ttctttcttc tctttctttt tgtggaaatt ttttctctag taaaccaatt   4500
aatttttgtt ataacatgtg caatataata tgttaacagg tggtcaataa tagcagctca   4560
attaccggga agaactgaca atgatatcaa gaattactgg aatactaagc tcaagaaaaa   4620
acctatggga ttaatgcaat caactaacca aagaaaatca ccatattttc cagctactaa   4680
ttctcttcaa acccaacccc agataaattc aagtcttttt agagacttat attacacccc   4740
aaataatagg cctaatatta caggcctaaa tcatcagtcc atttcttctg cccaccagac   4800
aaattttctc tacactaata ataacatgaa ctttcctaat ttgggtgcta caaataatca   4860
atatccttat aatatccaaa gtcataattt acttatgttt ggagaagcaa gttgttcttc   4920
atcagatgga agttgcagcc aaatgagttt tggtaaagaa atcaagagag aagaaattat   4980
gagtaatagt ttacaacaag gtcaaatttc aagtgttaat gcttttgaag aaaaccacca   5040
gaattttact cttgattatg gcaatagtag tagtaattgg gtggatcaaa aaccaaatgt   5100
gtattttggt actactacta ctcaagtact tcagtatgat aatgttgaag aagttaagca   5160
gcagctaaca agttgtacca atggcaacaa tggtagtact attggatgta acaacaacaa   5220
cagtatgttc gtgttcaatg atgagaatta taacaagtca aatgagatag agatgttcta   5280
ttactaaaga agaaatgact gttgaaaaga aaacaaatgc aagtaccatt aggaagattt   5340
gaaagggcgt ttgggtatgg gggttgccaa gaagattcag actttttttg gggttttgtg   5400
tagttgtggt agaattatta ttgaatgaaa aaaaaaaact tcctgtactt taattcgtca   5460
gtacatacta catactacta caaagtagtt aaaagcctat tctatttgtg cttttttttt   5520
cactcgatgt ccaataatta tattggtttt tgattaaatt tgaatttgag caaggaagat   5580
caacattgga gggataaatt gtttcctaac gaaggcgatt acatacttag aacttgaact   5640
caatatctct aattaaaaat gaagtaatac ttataataac tccaccacaa ttcttattgt   5700
```

```
tgtgcatttc tttataaaat atgtaaataa tgggtcatat atattgttta ccttttctat   5760
tcatatacat agattttaaa ttaattatac acatatatat aatacattaa ttattcatat   5820
attatatttt tgctagctat ttttagttta agcgatttgg taggcgacta cttgggttaa   5880
ttcttttttt ttaatatata tatcaaaata atgaagctgt ataatacact taaaaatcat   5940
atttgaaagg tattaaatac gacttaggag agttcttaaa ccattttgga accttgtcta   6000
cgtactttta tgcaatagct gtttttgttt gtctctgcta aaacctatgc tccccaaccg   6060
tgcaccaatc aacttagaag ttagaactca gaaataaatg taactatact ccacagaaag   6120
ttaaaaagtt ttactgttac cattcactca aggatcagaa actgaaagac aaatgaatca   6180
gtgcttcact gttcttcact aaaagaaata ctgtttacat tagtttcaaa agagtttaat   6240
cataaaaaca aatgtaccat aaaaagggga gattatcaac ctgaaaatga aacagaacat   6300
acgttatata tcaatctata tacggtcgag atcggactcg tctattacac gacagatcgg   6360
gattgaaacg taacagtttt gaagatcaac cccgggttcc gtcggaccga ggtacaaggt   6420
cagaatgccc gttctcgaga acatcgagtc catgacccca gaatcaaccc tgaccccaaa   6480
tgagctcgag gaaacatccg gataacggaa ggcgaaatat ccgtaaccgg tcgggtatca   6540
cggcatgaat ttcggcacgt aacaatgaga aaccggctaa ttagcaaatc atggaatttt   6600
ttacctttta tagaattgta actaaagtgg gattccccta ctatgtaaag gggtctgac   6660
tatttgtacg ggacattcat taaacgcatc ccaaagtaat ataatattat tttctttttg   6720
taagctattg ttctcctgta tctgatacta tttgaattgc atcaagttca agtgagactc   6780
atttttcaa ggctataatt gttcaagtcg cacggtttga atttattcga tcattgttcg   6840
ctttaattac aattcaattc atcgctttat gtcaaattaa tccacatatc cttaaaacca   6900
cttacaaatt taattgttat caaattttaa gggtaaacag tttggcgctc accgtggagc   6960
taaggataat agtggttgtt tgatatagat tttcataaca cacactattt tacaattgtt   7020
cttcgaagtg tctctcattt caggtttaag ctcaaaatgt caaactcaca attggcaccc   7080
ctacctgcac acaatgagtc tggtcaccat ggtgaaaata acaacatagc acctggtaac   7140
gaggtaccgc ccgctgatcc catcagaatt tcaatcgcgg acccgttgga cgctaactcg   7200
catgtggcta tcgacatgtt acagtctcaa caggcgacga tagctcagtt acaaaaccaa   7260
agccgcacac cgagcagagt tgaactcgat ccgtcccgga aaatcacctg cagggaagaa   7320
ccgtccgcgg agaggtcaaa tggagatgag tcggggacta accccgagat cataaaaatg   7380
cttgaggaac cgatgatacg gattgaatca ggggaaaaga aaatcgaggc aaatgacaag   7440
aaggtaaaaa cttacaattt cacggtcaac caaatcccgg gagcaccgcc ggtactgaaa   7500
agcttggatt ccaagaagtt cgtgcaaaaa catttccctc cgagtgtggc cccgaaatcg   7560
atcccaaaaa catttatatg cccgagattc ttaagtataa tgggacaacc gacccaaacg   7620
agtatgtcac ttcttacaca tgccctatca aagggaacaa cttagaggtt gatgagatcg   7680
agtctgtttt gttgaagaaa ttcggagaga ccctgtcaaa tggagctatg atatggtatc   7740
acttacctcc taattctatt gactcatttg caatgcttgc aaactctttc gtgaaagcac   7800
acgccagggc tatcaaggtc gagacccaga agtcggacct cttcaaagta agacagaagg   7860
ataatgagat gctcaaagag tccgtgtcct agtttcaaat gaaacagaag gacctaccac   7920
cggtcgctga tgattgggcc gttcaagctt tcacccaagg actcaatgtt cgaagctcgg   7980
tggcttcaca gcagttgaag caaaatctga taaagtaccc aactgttatt tgggccaatg   8040
tgcataaccg ctatcaatca aaaatcaaag tcgaagatga tcaacttgag gctctttccg   8100
```

```
ggtcggttta ccctgtcaga ctcgtcgaca gaatcaagag agatatcgac cgtgaaccaa   8160
ggtcaaacgt agatcattac tagccatatg atggagattg gaaaagcaat aggtctgggt   8220
gaagttctac acagaatgaa aagagaaatg atccaggtca gagcactcga ggactcgcaa   8280
gcaagaacga cttcgacagg cctatcaggc ctaaagaagc accaaggtta tcgaaatata   8340
actttaatat tgatgcggct gccatcgtat cagctatcag acgcatcaaa gataccaaat   8400
ggcctcgacc tttacaatcc gatccagccc aaagggatcc taaccaaatg tgcaaatatc   8460
atggcacttc tggccacaga ataaaggatt gtcgacggtt aagagaggaa gtagcccggt   8520
tgttcaataa cgggcacctt caagaatttc tgagcgaccg agccaagaat catttttagaa   8580
atagggattc taacaaatag accgaaccag aagaacctca acacgtcatt aacatgatca   8640
tcggtggagt cgatgcccct caagtgctga tgttgaagcg caccaaagtg tccattacaa   8700
gggaaaaacg gactcgagat tacatattag aaggaacctt gtctttcaac gacgaggatg   8760
cagaagggat cgtgcagcct cacaatgatg cattggtaat atctgtactc ataaataaat   8820
ctcgagttaa gcgtgtgtta attgatccag gtagctcaac caacatcatc cgattgaggg   8880
tcctagaatg gcttggccta caagatcaaa tcatgcctgc agtccgagtt ctaaatggat   8940
tcaacatagc atgcaaaacc actaagggag aaataacatt gccggtgaat accaccagaa   9000
ccatccagga aaccaagttt tatgtgatcg aaggagacat gaggtacaac gctctgttcg   9060
ggaggctaag gatctacagc atgagggcag caccctcgac tcttcaccaa gtgttaaagt   9120
tcccaacgtc gggagggatc aaaacaatct acggggagca accggccgca aaagaaatat   9180
ttgcagtcga agaagagatc ccggtataga cactagcaac atcaaag                 9227
```

<210> SEQ ID NO 24
<211> LENGTH: 9159
<212> TYPE: DNA
<213> ORGANISM: Nicotiana tabacum

<400> SEQUENCE: 24

```
agactgtttt ttatttgatt tatactcttt aattgtattt tcgcacgaaa ataaccgatc     60
aaagttagtc gattttatta aaaaataaaa ttaccgacca aagttggtcg gttttttaaa    120
atgaccggcc gaattaaccg accaattttg gtcggttttt taatattaat ttttatttat    180
tttaattgaa aaactgacca aaattggtcg gtttcttgaa aaataaattt cacgggactc    240
gaaaatagtt tttcgcattt ttgctccaaa gaaaaccgac caaagttggt cgatttcgta    300
aaaaaaaatt aaaaataaaa tattttaaaa aaccgaccaa cttttgtcgg ttttttggtc    360
ggtgttttga ccgaccaaag ttggtcggtc gaccttggtc ggtttttgcc gaatttctag    420
tagtgatata cccttagagt tacacaattg gcacatatat gcccttctca aaacgaaatt    480
cacccaaaaa ttatggttta aactttaaaa taataaaaac atctcaaact ttaacaatac    540
tcaaaagacc aaaatattta aattatttct aaaaagataa tttaatgatt aaaagcctag    600
agttcaagtt gtagtgttat aaatttgagt tgttagtctt tttcatcttt tttcagctgg    660
acattttcta ttttttttat taactatgta aattaggggt gtacatggaa cgggttggat    720
cgatttttat caaaactaaa ccaaaccgat tatatcggtt tgaattgttc ggttttattg    780
gtttttttcag atttttttgtt acataaatat tatttcaatc ttgctttgtt aaatttttta    840
gaactaaata tatgttcagt aaaacttaaa aaattgacaa acatatgatc tatcttgatt    900
accttatggg agaattttct tagtaattgg aattcatgag ttttgtcaag tgaaattggt    960
```

-continued

```
gacgaaaata gagaagacat cagtaattga ggaaatcgga taagggagaa agaaaaagaa   1020
aaaaagaaaa aaagaagaaa gaaaagagaa aggtaaagaa aaaagcacta ataaaaagga   1080
aatagtattt gtaatatact ttaatacaat taacgtaaga gctaattagt ttgagtggat   1140
tccgttttga aaagggcata catgtgccaa ttatataact ctaagggcat atatggacca   1200
actatctgac ggtaagggca tatttgagtt aatatattaa cgaatgacaa atgtgctcaa   1260
tttcgtataa tacaaggaca tattacattt tccctattat gaaatggttc aaacttaagg   1320
attttgtaca tggtaaaacc taaattgaca tgtaacttgg tactttccat tgggcaaaga   1380
cacgatcttt tacgtgatat tttaaatcaa gtaaagatca agtcgggcca aaaagaaaaa   1440
aacccatgat tttttaagat aaaaagctgc taacttttag tttgtttcat ccaataaaac   1500
atctttaacg atctgtctgc tttagtttaa tcctcttttt aagatgtaac taagcatgaa   1560
atagaaaagg ggaaaaaaaa ggaccattgg attttggaag aagttttaag aaagtacaag   1620
aactagtaaa gtcattttgt atagagtatg ttaaaaaggt gagtgacaat tcgaaaaaga   1680
gagagcattg ataagtcaat caataaaata aaagcacacc tgataatcat tcattcagaa   1740
aacaaatttc tatgaatgat aatcattatc ataagtcact gcagaaatcc catatacagt   1800
agagtaccag gattttacga taaggtgtta gcagactatc tattcatttt ttgacaacca   1860
ttttacgttt ggtcattttt tgggaaacga actctcccaa cattcttcca aattacccca   1920
cgcaccttac tgtgcacatc ttttaaccaa cttctggtta ttttttcttt tgatgtccga   1980
tattcgtata tgaattccca ttaattctaa gttgcaccga aatggttttt atcaagattt   2040
tgtatatatt taatattcga attcaaaact aatggtcgaa ggtggaagat cgtatccatc   2100
ccatcataat atttggttgg taatatcaca cctttttgaa tttgggagac ttgtcaattt   2160
ttattttgaa aaaagaaaaa aaaaagaaat agaaactaaa accataggga aatgaacaat   2220
tttattttca ctcctacctc attttatttg tcttgaattt ttcaattttg ttttgaaact   2280
tcttcagttt attttcttgg aatcttcaga atttaatttg aaattccaaa attccaagga   2340
tttagtgtca aatcagtgct tgaaattaaa tttaaaacga gtggtaaata aaatagagga   2400
gaactcggta aattacagga gtgcggtaaa tcttttctcc ttttctctct ttggagccta   2460
ctctattcta ttgtaactaa gtaacttaac tacgaaaaac gtgcctagac ttttaacttc   2520
acaagtataa taaatagaag tcaaattctt tcataatatt gtttccatcc tatcaaacag   2580
actttgcctc actgactctc cttctgagtg tgtctttttt atgtcatttt tagtgaatcc   2640
aattgattta gagactcaaa tattccacat gcgtgtctta atttggtgta tatatggtaa   2700
taatttttgt taggtagctg tagtattcta ttattgttat gtattaactc atgtaaataa   2760
aagccggtta gataagacta gaaaaaatag agtctactta gaaattatta gcctattgtt   2820
tggaacatgt caaaaattca gtgactcagc tagagctgtc aattagtcaa ataactttat   2880
taatattaac ttatgaaaac acttggggat tcttgtagtt taagggaaag actactgact   2940
gaaaaacaaa gcaaaagtct atgcattact atattataca caatacagca ttttccaata   3000
gtattttaga taaatctcca atcagctact gttgttcttt tcttttcttt tttagtttaa   3060
gttgtatgtg ttgacggtat acaaattatt tgcacaatta gatggcttat ctagataata   3120
cgtgtaaatc tattgataat cattaattag taatctggta aaaataatat tgcttttgtt   3180
ctaatataat gtgatatatt tgactgggta cgaaatttaa aaaaaaataa gacatataga   3240
acttgttgtc ttaaacaatt cataacattt gtgtggctat aattcttttg aaacttatgg   3300
tgttaaacat gtctaattgt ttgtgtatgt ataaaagatt ctcattaagc gtaggaaaat   3360
```

```
ttgaattaaa ttatttttt aatttaaaaa gagatcactc cttttagagc tgacttaaaa   3420
agaaattgat tcacataaac tcgcacggag ggaataagta atatactatc aaaaattaaa   3480
aatcacttgt agtgtaaaaa aatctttaca ccaatcgtgt atattctcaa ttttttttt   3540
ttttttggcg agaggtagtt gttcagcaaa agtaagttag aaataggtct gtacttttga   3600
ctttgtaact ctgaaatgaa aaattcaaaa tctcttcttt tttactgttt taaaaactcc   3660
aactcactct tattaatata aagctctagt tagcaaagac acccttgtcc acttgtctat   3720
atagcaagaa agagagtaaa ggagaaaaca tattctcctc tccatttctg tagacaagat   3780
tctcaaaaag aaacaaatta aacactagag agtgagagag aactataaga aaaagaatat   3840
ggggagagct ccatgttgtg ataaagcaaa tgtgaagaga gggccatggt ctcctgaaga   3900
agatgctaaa ctcaaagatt tcattcacaa atatggaact ggtggaaatt ggattgctct   3960
tccccaaaaa gcaggtaaca acaacttcta ctcccttatt cccagaatcg aagcgacaaa   4020
gggttaaatc tcagtggatt gtggtagcaa gatcatattc tatcgcttac aatatctcgt   4080
cgcgtattta acactttcgt atgtatatgt ttgaatatag ggggagggaa gcttacatta   4140
atatttatac tttgagtgga ttaagttttt ttttggttgc ttcattattt atgattttga   4200
tgagatatat gtttggaact gcaggactaa agagatgtgg gaagagttgt agattgagat   4260
ggctaaatta tctaaggcct aatatcaaac atggtgattt ttcggaggaa gaagatagag   4320
ttatttgcag cttgtattcc accattggaa gcaggtacaa tataccttttt tttagtctta   4380
aattgttttc catttttat catctttctg atgaatttga gactgaaaca aaaactgttc   4440
ccactaaaaa tggaaaagaa gaaccttaat aaataagaaa agggaaaaaa caatgagggc   4500
tcagaaagaa atgcaaatag tctgttggat ttttaattaa agattctgcc atttatggac   4560
atttttttct gcatgcatgc caggtttaga tctaagatca agtctttatt tactcactta   4620
cagctgttta agtattacta ctacaaaatt ccaacgtttc ttcttttctc tcttttttt   4680
ttttttgga aaacttttcc ttttgtaaac caattaaatt ttgttataac atatgcaata   4740
tattatgtta acaggtggtc aataatagca gctcaattac caggaaggac tgacaatgat   4800
atcaagaatt actggaatac taaactcaag aaaaagctta tgggattaat gcaatcaaca   4860
aaccaaagaa aatcaccata ttttccagct actaattctc ttcaaaccca accccagata   4920
aattcaagtc tttttagaga cttatattac aacccaaata ataggcctat tattacaggc   4980
ctaaatcagt ccatttcttc tgcccaccag ccaaattttc tctacactaa tagtaacatg   5040
aattttccta atttgggtgc tacaaatagt caatatcctt ataatattca aagtcataat   5100
ttacttatgt ttggagaagc aagttgttct tcatcagatg gaagttgtag ccaaatgagt   5160
tttggcaaag aaatcaagag agaggaaatt atgagtaatt gtttacaaca aggtcaaatt   5220
tcaagtgtta atgcttttga agaaaatcag aatttcactc ttgattatgg taacagtagt   5280
agtaattggg tggatcaaaa accaaatgtg tattttggaa atactactac tactactcaa   5340
gtacttcagt atgatgttga agaagttaag cagcagctaa caagttgtac caatggcaac   5400
aatggcagta ctattggatg taacaacaac aacagtatgt tcgtgttcaa tgatgagaat   5460
tataacaagt caaatgagat agggatgttc tattactgaa gaagaaatga ctagctgttg   5520
aaaagagaaa acaaatgtaa gtacaccatt aggaagattt gaaagggcgt ttgggtatgg   5580
gggttggcaa gaagattcaa actttttctg ggttttgtg taattgtggt ggaattatta   5640
ttattgaaac ttctttactt caatttaaat cgtcggtaca tattacgtag ttgtagtaaa   5700
```

```
agccttttcc tttttgtgct tttttttttt ttcgtgttcg tattaagact tcattaaatc   5760
caaatttgca tagggacggt caacattaga ggaataaatt gcttcctaac aaagacgatt   5820
ttatactcaa gagttcgagc ccgaaaaacg acctctggtt aagggtaaaa atagtaatta   5880
caataactcc accacaatcc ttattggtgt gcatttcttc attaaatact ccctccaatc   5940
cactttaatt gatttgtttt tggctatttt tatatatatt aaggaattat cttttagcat   6000
taatcaataa tgaaattgac catattaacc ttttagttca ttggaaatat aacaaatact   6060
cctaggcttt ttaattcaag agcaactttt aaatccgaat ttgggctaag aatacaagct   6120
tgttcttttt tatctgtttt tcactcggtg tacgaggact caattaaatc cgaatttgag   6180
ctaagaatac agacattaga ggtaatatgc tttctaacaa atgtgactca atgttcagac   6240
tcagaactcg atatctctgg taaggatgac atagtactta caataactcc atcataatct   6300
ttataggtat gtatttcttt ataaaatatg taaatagtgt tatgattttt tgtatcaaaa   6360
atgatgaagt ataatactct taaaaatcat actccatccg tttcaattta tgtgaacgta   6420
ttttcttttt agtctgtgcc aaaaagaatg acctatttcc ttatttggaa ataatttacc   6480
tttatgcaat gatttatagt cacacaaaat atatgtgtct catttttaac cacaagttca   6540
aaagtcttct atcttttttt aaactctgtg cccagtcaaa tgagttcaca taaattaaaa   6600
cggagggaat aataaaaatg tattaaagac tacttaggag agttcttaaa aaaccatttt   6660
ggaaccttgt ctacgtactt ttatgcaata actgcttaag tttgtctctg ctaaaaccta   6720
tgctccccaa ccgtgcacca atcagcttag aaatttgaac tcaggaataa atgtaactac   6780
actccacaga aacttaaaaa gttttactgt taccattcac tcaaggatca gaactgaaaa   6840
acaaaagaat cagtgcttca ctaaaagaaa tactgtttac attattttca aaagagttta   6900
atcattaaaa tagatgtacc atcagattag ctaaaagata aataatcgtt aaaaaaagga   6960
gattatcaac ttgaaaatga aacaaattat atgttataat atgtcaaaat atactgacag   7020
tataaaaact cgttaaatgt gttaaatcct atgaaaaaac tgcccaaata aatatttgag   7080
cttaggtgtc aaatgttgta ctcaacaaca ataacaacaa cgcattagga tcctactagt   7140
ggggtgtcca atgttgtact attgaacatt attcaactaa cttttgttag gtgttcctgt   7200
agtttagtga aattaaagtc cactgttccc ctatatatta atcccaaatt aattaatcaa   7260
gtgcagataa aaatttctca ttttctatta atttattaag tgtaacaaac taaagaaatt   7320
caagaatctt gaatgatgag aaagagtcat gcatgtagaa aaatagataa taatacatgg   7380
aaatatatat gtatttgggg atttgcatgg tagctcaaag attattggaa agtgacagga   7440
agataaatca aaatctcagt gttatttcaa aaataaaagg cacagattat ttaaataatt   7500
gacagccagt tttataatac tatgtgggag gggacagaga tcaatccatg tacgtgcatg   7560
gctaatatta aagtaaggga gaaaaaaata ttaagttaat tgatgattaa aaatagtaaa   7620
atttcagacg tatatcacgg caatgaagag tttgatcttt aatatctgta taatggtccc   7680
ataatatgat ggataggcgt tgtttatgat atgattgatt gatcattgat cattgactat   7740
tgtttcttga ataattaatc agtatgggaa aggggtccca ttaaagttga ccatttgctt   7800
agcaatatta tcttaggtaa gctccatatt agtttaatcc acttgcgaat atattccgtc   7860
ctcgcaaatc aatatttaca attctttttt tcagttttct atccggtatc tgatacttgc   7920
attggtgttc gacaaaatct gtattcgcgt caaaaaaattt catattatgg ggcaaaatgc   7980
tccataataa aagcgactca atattagggc tcgaaccaat ggcggaaaca agatttttac   8040
taagggaatt caaaaaataa aaacgataaa cacatgaaga acctcaggga attcaacatc   8100
```

```
taatataaat atatgaaata aaaatttgat tctattgtaa tttgatatac agtgtaattt   8160

acaccgtagg ggatttggct aaacctcctt ccgcgtacct agctccgtcc ctgactcgaa   8220

tccgaggtat ttggttaaaa atgaaagagt acttctcata acctcgtcgg tttttgtttc   8280

taatcaatct ttatattgtt aaaacataaa acgtttactt cctttcttct tcttttaagt   8340

tttgaaaatg ataactactt ttgtttgact aatattttgt agtttttgat gctaatcaat   8400

tttgtaaaaa ttactgtact tcaactagcg tttactaccc cacctcactt taaaaaattc   8460

cctaaagaga taacttttttg attaattcat aaactaaatt gaagaacttt tcaaatgaga   8520

gtaagttgaa aatgcatatt atattgtagt atataattgc aattttgcat aacttaccgt   8580

aaaatgttct tccttttaat gatttgttaa tatgggaaat ttgaactttt ctttctttga   8640

aattgtattc ttgtcccatg gtttctatgc aatctcaatc atcaaattgc aattattttt   8700

ttttgttttt tgttggcaaa ttcaggagag cttaggtcag tgatatatga aaaactattt   8760

tttactctta tttattttac cctttactta ttaaagaata aagtccaaga cgaatagacg   8820

atgtacaacg caaatgtaaa aatacagaaa aaatgtttac gacttcttct ctatttattt   8880

tctacttaat ttacttatta aacaagtact tacttgttaa actagctaat ctgaccaaca   8940

atgtgaaaat gtttgacatt atacatcttg actttttatt tctctattat tttctcgatg   9000

gttacttcaa atcatagatt tgctaatctg accaatatcg tttaacttca agtagaacga   9060

aatgaacatt tcaaggtttt agaaaacagt tgaaattgga ccctaaaata aataaaatga   9120

agttattaat aggtttacac cccaatctta tctaatgct                          9159
```

```
<210> SEQ ID NO 25
<211> LENGTH: 838
<212> TYPE: PRT
<213> ORGANISM: Nicotiana tabacum

<400> SEQUENCE: 25

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
```

```
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Pro Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Val Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Met Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Thr Phe Met Pro Arg Asp Val
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605
```

```
Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Thr Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Lys Ile Phe Asp Glu Ser Gly Arg Lys Val Leu Phe Ala Glu Phe
    770                 775                 780

Pro Lys Ile Met Glu Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Val His Cys Leu Ala Phe Ser Phe
            820                 825                 830

Ile Asn Trp Ser Phe Val
        835


<210> SEQ ID NO 26
<211> LENGTH: 839
<212> TYPE: PRT
<213> ORGANISM: Nicotiana tabacum

<400> SEQUENCE: 26

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
```

```
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Ser Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Ala Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Val Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Ala Phe Met Pro Arg Asp Ile
    530                 535                 540

His Leu Leu Gln Met Cys Ser Gly Thr Asp Glu Asn Ala Val Gly Ala
545                 550                 555                 560
```

```
Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Ala Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Arg Ile Phe Asp Glu Ser Gly Arg Lys Val Leu Phe Ala Glu Phe
    770                 775                 780

Pro Lys Ile Met Asp Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Ser Val His Cys Leu Ala Phe Ser
            820                 825                 830

Phe Ile Asn Trp Ser Phe Val
        835
```

<210> SEQ ID NO 27
<211> LENGTH: 2640
<212> TYPE: DNA
<213> ORGANISM: Nicotiana tabacum

<400> SEQUENCE: 27

```
ttgtttggga ttttggggtt tgagggcaaa tggctatggt ggtacagcag catagggaga      60

gtagtagtgg tagtattaca aaacatcttg acagtagtgg aaagtatgtc cggtatacag     120

ctgagcaagt ggaggcatta gagagggttt atgcagagtg ccctaaacct agctcgttgc     180

gccgccagca attgatccgc gaatgcccta ttctgtcgaa tatcgagcct aagcagatca     240

aagtttggtt tcaaaacaga aggtgtcgag agaagcaaag gaaagagtct tctagactac     300

agactgtaaa tagaaagctg tctgcaatga ataaactatt aatggaggag aatgatcgct     360

tgcaaaaaca ggtttcacag cttgtgtgtg aaaatggctt tatgcggcaa caattgcata     420

ctgcatcagc ggccactact gatgtaagtt gtgagtcagt ggttaccacc cctcagcatt     480
```

```
ccctcagaga tgctaacaac cctgctggac tgctgtcgat tgcagaggaa accttagcag    540
agttcctttc caaggctaca ggaactgctg ttgattgggt cccgatgcct gggatgaagc    600
ctggtccgga ttcagttggg atttttgcca tctcacacag ttgtagtgga gtggcagccc    660
gagcatgtgg tcttgttagt ttagagccga caaagattgc tgagatcctc aaagatcgac    720
catcttggtt ccgagactgc cggaacgttg aagttttcac gatgttttct gcaggaaatg    780
gaacaattga gcttttgtac acgcagatat atgctcctac caccttggct cctgcacgtg    840
atttttggac tctgagatac acaaccaccc tggagaatgg tagttttgtg gtttgtgaaa    900
gatccctctc tggtactgga gctgggccga atgctgcttc tgcttcccag tttgtaagag    960
ctcaaatgct tccgtccgga tatctaatcc gaccgtgtga cggtggagga tccattatac   1020
atattgttga ccatctgaat cttgaggcat ggagtgcccc tgagattttg cgtccacttt   1080
atgaatcgtc aaaagttgtg gcacagaaaa tgactattgc ggcactgcga tatgcaaggc   1140
aaatagctca ggagactagt ggggaggttg tatatggtct gggaaggcaa cctgcagttc   1200
ttcgaacatt tagccagaga ttaagcagag gcttcaatga cgccatcaat ggattcagtg   1260
atgatggctg gtcattgtta agttctgatg gtggtgaaga tgttatagtt gctgtcaatt   1320
caaggaagaa cattgccacc acttccgttc ctctttcacc gctgggaggc atcctttgtg   1380
ccaaagcatc aatgctactc cagaatgttc ctcctgtggt actggttcga tttctcaggg   1440
agcaccgttc agagtgggcg gactttaatg ttgatgccta tgtagcttcg tcaatgaaat   1500
cttgttcata tgcatatcct gggatgaggc ctaccagatt taccggaagt cagataataa   1560
tgccacttgg ccatacaatt gaacatgaag agatgcttga ggttattaga ttggaaggac   1620
actctattgg ccaggaagat acttttatgc caagagatgt tcaccttctc cagatgtgta   1680
gtggaactga tgagaatgct gtcggagctt gttctgaact agtttttgct gcaattgatg   1740
agatgtttcc agatgatgca cccctgttgc cctccgggtt tcgtatcatt cctctcgagt   1800
caaaatcaag cgatccccag gatacatcga atgctcatag aacactggat ctggcatcaa   1860
gtcttgaagt tggcccagca acaaaccctg ctactggaga tgtggtctct ggctacagtg   1920
cacgatctgt gttgacaatt gcttttcaat ttccattcga ggacaatctt caggacaatg   1980
tagctaccat ggcgcgccag tatgttcgca gtgtggtttc atctgtccaa cgggttgcca   2040
tggcaatatc tcccgcagga gtgaattcaa cattcgggtc caagctttct ccaggctccc   2100
ctgaagctgt aacgttgtcg cactggatct gccagagcta cagttatcac atggggacag   2160
agttgcttca aactgattcg aggggcgatg aatcagtgct aaaaaatctt tggcaacatc   2220
aggatgctat tttgtgctgc tcattgaagt ccctgccggt tttcattttt gctaataagg   2280
ctgggcttga tatgctggag acaaccttag ttgctttaca ggacattact ctagataaga   2340
tatttgatga atctggccgg aaagtgttgt tcgctgaatt tcccaagatc atggaacagg   2400
gttttgcgta cttgccgggt ggtatttgca tgtcagcaat gggacgacat atttcatatg   2460
aacaagctat tgcatggaaa gtctttgctt ctgaagaaac tgtccactgc ttagccttct   2520
catttattaa ctggtcattt gtttaatgtt gctgtcaaat ctcctttctt ttttttcctt   2580
tttgtttttt gacatcttcc tcacagagga cactgacagc caggaacaca gttgaacgga   2640
```

<210> SEQ ID NO 28
<211> LENGTH: 2726
<212> TYPE: DNA
<213> ORGANISM: Nicotiana tabacum

<400> SEQUENCE: 28

```
aagctgtttg cagggaatat atctacttgg gggtgttttt atttcttaaa agggtgtttg     60
aaaatttgga aatcttgatt tttttttgg tttgggattt tgaggtttga gggcaatggc    120
tatggttgca cagcagcaca gggagagtag tagtggtagt attacaaaac atcttgacag    180
tagtggaaag tatgtccggt atacagctga gcaagttgag gcattggaga gggtttatgc    240
tgagtgccct aagcctagct ccttgcgccg ccaacaattg atccgtgaat gccctattct    300
gtcgaatatc gagcctaagc agatcaaagt ttggtttcaa aacagaaggt gtcgagagaa    360
gcaaaggaaa gagtcttctc gactacagac tgtaaataga aagctgtctg caatgaataa    420
actattgatg gaggagaatg atcgcttgca aaaacaggtt tcgcagcttg tgtgtgaaaa    480
tggctttatg cggcaacagt tgcatactgc atcagcggcc actactgatg taagttgtga    540
gtctgtggta actacccctc agcattccct cagagatgct aacaaccctg ctggactgct    600
gtcgattgca gaggaaacct tagcagagtt cctttccaag gctacaggaa ctgctgttga    660
ttgggtcccg atgcctggga tgaagcctgg tccggattca gttgggattt ttgccatctc    720
acacagttgt agtggagtgg cagcccgagc atgtggtctt gttagtttag agccgacaaa    780
gattgctgag atcctcaaag atcgatcttc ttggttccga gattgccgga acgttgaagt    840
tttcacaatg ttttctgcag gaaatggaac aattgaactt ttgtacacgc agatatatgc    900
tcctaccacc ttggctcctg cacgtgattt ttggactctg agatacacaa ccaccctgga    960
gaatggtagc tttgtggttt gtgaaagatc cctctctggt actggagctg ggccgaatgc   1020
tgcttctgct tcccagtttg taagagctca aatgcttccg tctggatatc taatccgacc   1080
gtgtgacggt ggaggatcca ttatacatat tgttgaccac ctgaatcttg aggcatggag   1140
tgcccctgag attttgcgtc cactttatga atcgtcaaaa gttgtggcac agaaaatgac   1200
tattgcggca ctgcgatatg caaggcaaat agctcaggag actagtgggg aggttgtata   1260
tggtctggga aggcaacctg cagttcttcg aacatttagc cagagattaa gcagaggctt   1320
caatgatgcc atcaatggat tcagtgatga tggctggtca ttgttaagtt ctgatggtgg   1380
tgaagatgtt atagttgctg tcaattcaag gaagaacatt gccaccactt ccgttcctct   1440
ttcaccactt ggaggcatcc tttgtgccaa agcatcaatg ctactccaga atgttcctcc   1500
tgcggtactg gttcgatttc tcagggagca ccgttcagag tgggcggact ttaatgttga   1560
tgcctatgta gcttcctcaa tgaaatcttg ttcatatgca tatcctgggg tgaggcctac   1620
cagatttacc ggaagccaga taataatgcc actgggccac acaatagaac atgaagagat   1680
gcttgaagtt attagattgg aagggcactc tattggccag gaagatgctt ttatgccgag   1740
agatattcac cttctccaga tgtgtagtgg aaccgatgag aatgctgtcg gagcttgttc   1800
tgaactagtt tttgctgcaa ttgatgagat gtttccagat gatgcacccc tgttgccctc   1860
cgggtttcgt atcattcctc tcgagtcaaa atcaagcgat ccccaggata catcgaatgc   1920
tcatagaaca ctggatctgg catcaagtct tgaagttggc ccagcaacaa accctgctac   1980
tggagatgtg gtctctggct acagtgcacg atctgtattg acaattgctt ttcaatttcc   2040
attcgaggac aatcttcagg ataatgtagc taccatggcg cgccagtatg ttcgcagtgt   2100
ggtttcatct gtccaacggg ttgccatggc aatatctccc gcaggagtga attcaacatt   2160
cgggtccaag ctttctccag gctcccctga agctgtaact ttgtcgcact ggatctgcca   2220
gagctacagt tatcacatgg ggacagagtt gcttcaagct gattcgaggg gcgatgaatc   2280
agtgctaaag aatctttggc aacatcagga tgctattttg tgctgctcat tgaagtcgct   2340
```

```
gccggttttc atttttgcta ataaggctgg gcttgatatg ctggagacaa cattagttgc   2400

tttgcaagac attactctag ataggatatt tgacgaatct ggccggaaag tgttgttcgc   2460

tgaatttccc aagatcatgg atcagggttt cgcgtacctg ccgggtggta tttgcatgtc   2520

tgcaatggga cgacatattt catatgaaca agctattgca tggaaagtct ttgcttctga   2580

agaaactagt gtccactgct tagccttctc atttattaac tggtcatttg tttaatgttg   2640

ctgtcaaatc tcctcttttt ttccttttttg ttttttgaca tcttcctcac agaggacact   2700

gacagacagg aacacagttg aacgga                                         2726


<210> SEQ ID NO 29
<211> LENGTH: 111
<212> TYPE: PRT
<213> ORGANISM: Nicotiana tabacum

<400> SEQUENCE: 29

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu
            100                 105                 110


<210> SEQ ID NO 30
<211> LENGTH: 116
<212> TYPE: PRT
<213> ORGANISM: Nicotiana tabacum

<400> SEQUENCE: 30

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser
        115


<210> SEQ ID NO 31
<211> LENGTH: 68
<212> TYPE: PRT
```

<213> ORGANISM: Nicotiana tabacum

<400> SEQUENCE: 31

```
Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys
65
```

<210> SEQ ID NO 32
<211> LENGTH: 398
<212> TYPE: PRT
<213> ORGANISM: Nicotiana tabacum

<400> SEQUENCE: 32

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
```

```
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Trp
385                 390                 395


<210> SEQ ID NO 33
<211> LENGTH: 145
<212> TYPE: PRT
<213> ORGANISM: Nicotiana tabacum

<400> SEQUENCE: 33

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn
145


<210> SEQ ID NO 34
<211> LENGTH: 163
<212> TYPE: PRT
<213> ORGANISM: Nicotiana tabacum

<400> SEQUENCE: 34

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
```

```
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met


<210> SEQ ID NO 35
<211> LENGTH: 109
<212> TYPE: PRT
<213> ORGANISM: Nicotiana tabacum

<400> SEQUENCE: 35

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Leu Glu Tyr
            100                 105


<210> SEQ ID NO 36
<211> LENGTH: 119
<212> TYPE: PRT
<213> ORGANISM: Nicotiana tabacum

<400> SEQUENCE: 36

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110
```

```
Ser Arg Lys Ser Leu Trp Asp
        115


<210> SEQ ID NO 37
<211> LENGTH: 181
<212> TYPE: PRT
<213> ORGANISM: Nicotiana tabacum

<400> SEQUENCE: 37

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys
            180


<210> SEQ ID NO 38
<211> LENGTH: 185
<212> TYPE: PRT
<213> ORGANISM: Nicotiana tabacum

<400> SEQUENCE: 38

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125
```

```
Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Lys Thr Asp Gly Arg Tyr Leu Leu Leu
            180                 185


<210> SEQ ID NO 39
<211> LENGTH: 260
<212> TYPE: PRT
<213> ORGANISM: Nicotiana tabacum

<400> SEQUENCE: 39

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Val Arg Ser Ser Lys Ile Asp His Leu Gly Ser Glu Thr Ala Gly
    210                 215                 220

Thr Leu Lys Phe Ser Arg Cys Phe Leu Gln Glu Met Glu Gln Leu Ser
225                 230                 235                 240

Phe Cys Thr Arg Arg Tyr Met Leu Leu Pro Pro Trp Leu Leu His Val
                245                 250                 255

Ile Phe Gly Leu
            260


<210> SEQ ID NO 40
<211> LENGTH: 216
<212> TYPE: PRT
<213> ORGANISM: Nicotiana tabacum

<400> SEQUENCE: 40
```

```
Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Met Trp Ser Cys
    210                 215


<210> SEQ ID NO 41
<211> LENGTH: 827
<212> TYPE: PRT
<213> ORGANISM: Nicotiana tabacum

<400> SEQUENCE: 41

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
```

```
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Leu Glu
        195                 200                 205

Pro Thr Lys Ile Ala Glu Ile Leu Lys Asp Arg Pro Ser Trp Phe Arg
    210                 215                 220

Asp Cys Arg Asn Val Glu Val Phe Thr Met Phe Ser Ala Gly Asn Gly
225                 230                 235                 240

Thr Ile Glu Leu Leu Tyr Thr Gln Ile Tyr Ala Pro Thr Thr Leu Ala
                245                 250                 255

Pro Ala Arg Asp Phe Trp Thr Leu Arg Tyr Thr Thr Thr Leu Glu Asn
            260                 265                 270

Gly Ser Phe Val Val Cys Glu Arg Ser Leu Ser Gly Thr Gly Ala Gly
        275                 280                 285

Pro Asn Ala Ala Ser Ala Ser Gln Phe Val Arg Ala Gln Met Leu Pro
    290                 295                 300

Ser Gly Tyr Leu Ile Arg Pro Cys Asp Gly Gly Gly Ser Ile Ile His
305                 310                 315                 320

Ile Val Asp His Leu Asn Leu Glu Ala Trp Ser Ala Pro Glu Ile Leu
                325                 330                 335

Arg Pro Leu Tyr Glu Ser Ser Lys Val Val Ala Gln Lys Met Thr Ile
            340                 345                 350

Ala Ala Leu Arg Tyr Ala Arg Gln Ile Ala Gln Glu Thr Ser Gly Glu
        355                 360                 365

Val Val Tyr Gly Leu Gly Arg Gln Pro Ala Val Leu Arg Thr Phe Ser
    370                 375                 380

Gln Arg Leu Ser Arg Gly Phe Asn Asp Ala Ile Asn Gly Phe Ser Asp
385                 390                 395                 400

Asp Gly Trp Ser Leu Leu Ser Ser Asp Gly Gly Glu Asp Val Ile Val
                405                 410                 415

Ala Val Asn Ser Arg Lys Asn Ile Ala Thr Thr Ser Val Pro Leu Ser
            420                 425                 430

Pro Leu Gly Gly Ile Leu Cys Ala Lys Ala Ser Met Leu Leu Gln Asn
        435                 440                 445

Val Pro Pro Val Val Leu Val Arg Phe Leu Arg Glu His Arg Ser Glu
    450                 455                 460

Trp Ala Asp Phe Asn Val Asp Ala Tyr Val Ala Ser Ser Met Lys Ser
465                 470                 475                 480

Cys Ser Tyr Ala Tyr Pro Gly Met Arg Pro Thr Arg Phe Thr Gly Ser
                485                 490                 495

Gln Ile Ile Met Pro Leu Gly His Thr Ile Glu His Glu Glu Met Leu
            500                 505                 510

Glu Val Ile Arg Leu Glu Gly His Ser Ile Gly Gln Glu Asp Thr Phe
        515                 520                 525

Met Pro Arg Asp Val His Leu Leu Gln Met Cys Ser Gly Thr Asp Glu
    530                 535                 540

Asn Ala Val Gly Ala Cys Ser Glu Leu Val Phe Ala Ala Ile Asp Glu
545                 550                 555                 560

Met Phe Pro Asp Asp Ala Pro Leu Leu Pro Ser Gly Phe Arg Ile Ile
                565                 570                 575
```

```
Pro Leu Glu Ser Lys Ser Ser Asp Pro Gln Asp Thr Ser Asn Ala His
            580                 585                 590

Arg Thr Leu Asp Leu Ala Ser Ser Leu Glu Val Gly Pro Ala Thr Asn
        595                 600                 605

Pro Ala Thr Gly Asp Val Val Ser Gly Tyr Ser Ala Arg Ser Val Leu
    610                 615                 620

Thr Ile Ala Phe Gln Phe Pro Phe Glu Asp Asn Leu Gln Asp Asn Val
625                 630                 635                 640

Ala Thr Met Ala Arg Gln Tyr Val Arg Ser Val Val Ser Ser Val Gln
                645                 650                 655

Arg Val Ala Met Ala Ile Ser Pro Ala Gly Val Asn Ser Thr Phe Gly
            660                 665                 670

Ser Lys Leu Ser Pro Gly Ser Pro Glu Ala Val Thr Leu Ser His Trp
        675                 680                 685

Ile Cys Gln Ser Tyr Ser Tyr His Met Gly Thr Glu Leu Leu Gln Thr
    690                 695                 700

Asp Ser Arg Gly Asp Glu Ser Val Leu Lys Asn Leu Trp Gln His Gln
705                 710                 715                 720

Asp Ala Ile Leu Cys Cys Ser Leu Lys Ser Leu Pro Val Phe Ile Phe
                725                 730                 735

Ala Asn Lys Ala Gly Leu Asp Met Leu Glu Thr Thr Leu Val Ala Leu
            740                 745                 750

Gln Asp Ile Thr Leu Asp Lys Ile Phe Asp Glu Ser Gly Arg Lys Val
        755                 760                 765

Leu Phe Ala Glu Phe Pro Lys Ile Met Glu Gln Gly Phe Ala Tyr Leu
    770                 775                 780

Pro Gly Gly Ile Cys Met Ser Ala Met Gly Arg His Ile Ser Tyr Glu
785                 790                 795                 800

Gln Ala Ile Ala Trp Lys Val Phe Ala Ser Glu Glu Thr Val His Cys
                805                 810                 815

Leu Ala Phe Ser Phe Ile Asn Trp Ser Phe Val
            820                 825


<210> SEQ ID NO 42
<211> LENGTH: 211
<212> TYPE: PRT
<213> ORGANISM: Nicotiana tabacum

<400> SEQUENCE: 42

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
```

```
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ile Ala Met
        195                 200                 205

Trp Ser Cys
    210


<210> SEQ ID NO 43
<211> LENGTH: 214
<212> TYPE: PRT
<213> ORGANISM: Nicotiana tabacum

<400> SEQUENCE: 43

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Met Trp Ser Cys
    210


<210> SEQ ID NO 44
<211> LENGTH: 225
<212> TYPE: PRT
<213> ORGANISM: Nicotiana tabacum

<400> SEQUENCE: 44

Met Ala Met Val Ala Gln Gln His Arg Glu Ser Ser Ser Gly Ser Ile
```

```
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Val Thr Leu Ile Asn Leu Asn Val Val Leu Leu Leu Tyr
    210                 215                 220

Tyr
225


<210> SEQ ID NO 45
<211> LENGTH: 181
<212> TYPE: PRT
<213> ORGANISM: Nicotiana tabacum

<400> SEQUENCE: 45

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140
```

```
Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys
            180


<210> SEQ ID NO 46
<211> LENGTH: 181
<212> TYPE: PRT
<213> ORGANISM: Nicotiana tabacum

<400> SEQUENCE: 46

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys
            180


<210> SEQ ID NO 47
<211> LENGTH: 214
<212> TYPE: PRT
<213> ORGANISM: Nicotiana tabacum

<400> SEQUENCE: 47

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95
```

```
Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Met Trp Ser Cys
    210


<210> SEQ ID NO 48
<211> LENGTH: 225
<212> TYPE: PRT
<213> ORGANISM: Nicotiana tabacum

<400> SEQUENCE: 48

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Val Thr Leu Ile Asn Leu Asn Val Val Leu Leu Leu Tyr
    210                 215                 220

Tyr
225


<210> SEQ ID NO 49
```

```
<211> LENGTH: 838
<212> TYPE: PRT
<213> ORGANISM: Nicotiana tabacum

<400> SEQUENCE: 49

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Glu Cys Gly Leu Val Ser Leu Glu Pro Thr Lys Ile Ala
    210                 215                 220

Glu Ile Leu Lys Asp Arg Pro Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
```

```
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Val Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Met Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Thr Phe Met Pro Arg Asp Val
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Thr Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Lys Ile Phe Asp Glu Ser Gly Arg Lys Val Leu Phe Ala Glu Phe
    770                 775                 780

Pro Lys Ile Met Glu Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815
```

```
Lys Val Phe Ala Ser Glu Glu Thr Val His Cys Leu Ala Phe Ser Phe
            820                 825                 830

Ile Asn Trp Ser Phe Val
        835


<210> SEQ ID NO 50
<211> LENGTH: 26
<212> TYPE: DNA
<213> ORGANISM: Artificial Sequence
<220> FEATURE:
<223> OTHER INFORMATION: synthetic primer

<400> SEQUENCE: 50

aggttcttct tccttaatat tgagtc                                          26


<210> SEQ ID NO 51
<211> LENGTH: 26
<212> TYPE: DNA
<213> ORGANISM: Artificial Sequence
<220> FEATURE:
<223> OTHER INFORMATION: synthetic primer

<400> SEQUENCE: 51

atctaaggcc taaagagtga gcaaat                                          26


<210> SEQ ID NO 52
<211> LENGTH: 24
<212> TYPE: DNA
<213> ORGANISM: Artificial Sequence
<220> FEATURE:
<223> OTHER INFORMATION: synthetic primer

<400> SEQUENCE: 52

acacctaatg catcatctaa tgtt                                            24


<210> SEQ ID NO 53
<211> LENGTH: 26
<212> TYPE: DNA
<213> ORGANISM: Artificial Sequence
<220> FEATURE:
<223> OTHER INFORMATION: synthetic primer

<400> SEQUENCE: 53

caaataaaga ttaagttcag gatctg                                          26


<210> SEQ ID NO 54
<211> LENGTH: 21
<212> TYPE: DNA
<213> ORGANISM: Artificial Sequence
<220> FEATURE:
<223> OTHER INFORMATION: synthetic primer

<400> SEQUENCE: 54

atttcccctc ctccatcatt g                                               21


<210> SEQ ID NO 55
<211> LENGTH: 23
<212> TYPE: DNA
<213> ORGANISM: Artificial Sequence
<220> FEATURE:
<223> OTHER INFORMATION: synthetic primer

<400> SEQUENCE: 55

cttgacacca tctaatgttg ttg                                             23
```

<210> SEQ ID NO 56
<211> LENGTH: 23
<212> TYPE: DNA
<213> ORGANISM: Artificial Sequence
<220> FEATURE:
<223> OTHER INFORMATION: synthetic primer

<400> SEQUENCE: 56
aagctgtttg cagggaatat atc 23

<210> SEQ ID NO 57
<211> LENGTH: 21
<212> TYPE: DNA
<213> ORGANISM: Artificial Sequence
<220> FEATURE:
<223> OTHER INFORMATION: synthetic primer

<400> SEQUENCE: 57
tctctggcta aatgttcgaa g 21

<210> SEQ ID NO 58
<211> LENGTH: 26
<212> TYPE: DNA
<213> ORGANISM: Artificial Sequence
<220> FEATURE:
<223> OTHER INFORMATION: synthetic primer

<400> SEQUENCE: 58
gtaagttgtg agtctgtggt aactac 26

<210> SEQ ID NO 59
<211> LENGTH: 22
<212> TYPE: DNA
<213> ORGANISM: Artificial Sequence
<220> FEATURE:
<223> OTHER INFORMATION: primer

<400> SEQUENCE: 59
ggaaacaaac atctgcactc aa 22

<210> SEQ ID NO 60
<211> LENGTH: 26
<212> TYPE: DNA
<213> ORGANISM: Artificial Sequence
<220> FEATURE:
<223> OTHER INFORMATION: synthetic primer

<400> SEQUENCE: 60
gtccatctgt ctatataggt agaatg 26

<210> SEQ ID NO 61
<211> LENGTH: 21
<212> TYPE: DNA
<213> ORGANISM: Artificial Sequence
<220> FEATURE:
<223> OTHER INFORMATION: synthetic primer

<400> SEQUENCE: 61
tgaatcttct tggcaacccc c 21

<210> SEQ ID NO 62
<211> LENGTH: 25
<212> TYPE: DNA
<213> ORGANISM: Artificial Sequence
<220> FEATURE:
<223> OTHER INFORMATION: synthetic primer

<400> SEQUENCE: 62
tctcaaagct ggctgtttta tgtat 25

<210> SEQ ID NO 63
<211> LENGTH: 26
<212> TYPE: DNA
<213> ORGANISM: Artificial Sequence
<220> FEATURE:
<223> OTHER INFORMATION: synthetic primer

<400> SEQUENCE: 63
taccattctc cagggtggtt gtgtat 26

<210> SEQ ID NO 64
<211> LENGTH: 22
<212> TYPE: DNA
<213> ORGANISM: Artificial Sequence
<220> FEATURE:
<223> OTHER INFORMATION: synthetic primer

<400> SEQUENCE: 64
gaaaattcag tattgccatg tc 22

<210> SEQ ID NO 65
<211> LENGTH: 20
<212> TYPE: DNA
<213> ORGANISM: Artificial Sequence
<220> FEATURE:
<223> OTHER INFORMATION: synthetic primer

<400> SEQUENCE: 65
gcaaaaacta gttcagaaca 20

<210> SEQ ID NO 66
<211> LENGTH: 25
<212> TYPE: DNA
<213> ORGANISM: Artificial Sequence
<220> FEATURE:
<223> OTHER INFORMATION: synthetic primer

<400> SEQUENCE: 66
caccgcctat gtagcttcgt caatg 25

<210> SEQ ID NO 67
<211> LENGTH: 25
<212> TYPE: DNA
<213> ORGANISM: Artificial Sequence
<220> FEATURE:
<223> OTHER INFORMATION: synthetic primer

<400> SEQUENCE: 67
aaaaaaattc agtattgcca cgtgc 25

<210> SEQ ID NO 68
<211> LENGTH: 20
<212> TYPE: DNA
<213> ORGANISM: Artificial Sequence
<220> FEATURE:
<223> OTHER INFORMATION: synthetic primer

<400> SEQUENCE: 68
tcgcttgatt agcagtcagc 20

<210> SEQ ID NO 69

<211> LENGTH: 25
<212> TYPE: DNA
<213> ORGANISM: Artificial Sequence
<220> FEATURE:
<223> OTHER INFORMATION: synthetic primer

<400> SEQUENCE: 69
caccgaagaa actgatgatc aacgg 25

<210> SEQ ID NO 70
<211> LENGTH: 28
<212> TYPE: DNA
<213> ORGANISM: Artificial Sequence
<220> FEATURE:
<223> OTHER INFORMATION: synthetic primer

<400> SEQUENCE: 70
gaagacctct ttgtccttca ccatgcag 28

<210> SEQ ID NO 71
<211> LENGTH: 24
<212> TYPE: DNA
<213> ORGANISM: Artificial Sequence
<220> FEATURE:
<223> OTHER INFORMATION: synthetic primer

<400> SEQUENCE: 71
caccatgttt gatattaggc ctta 24

<210> SEQ ID NO 72
<211> LENGTH: 24
<212> TYPE: DNA
<213> ORGANISM: Artificial Sequence
<220> FEATURE:
<223> OTHER INFORMATION: synthetic primer

<400> SEQUENCE: 72
tgatgagatt tatgttggga actg 24

<210> SEQ ID NO 73
<211> LENGTH: 25
<212> TYPE: DNA
<213> ORGANISM: Artificial Sequence
<220> FEATURE:
<223> OTHER INFORMATION: synthetic primer

<400> SEQUENCE: 73
tctcatcatt gaacacgaac atact 25

<210> SEQ ID NO 74
<211> LENGTH: 25
<212> TYPE: DNA
<213> ORGANISM: Artificial Sequence
<220> FEATURE:
<223> OTHER INFORMATION: synthetic primer

<400> SEQUENCE: 74
ccacttgtct atatagcaag aaaga 25

<210> SEQ ID NO 75
<211> LENGTH: 24
<212> TYPE: DNA
<213> ORGANISM: Artificial Sequence
<220> FEATURE:
<223> OTHER INFORMATION: synthetic primer

<400> SEQUENCE: 75
ctaaggccta atatcaaaca tggt 24

<210> SEQ ID NO 76
<211> LENGTH: 25
<212> TYPE: DNA
<213> ORGANISM: Artificial Sequence
<220> FEATURE:
<223> OTHER INFORMATION: synthetic primer

<400> SEQUENCE: 76
aagaacattg gctttagtcc tctaa 25

<210> SEQ ID NO 77
<211> LENGTH: 26
<212> TYPE: DNA
<213> ORGANISM: Artificial Sequence
<220> FEATURE:
<223> OTHER INFORMATION: synthetic primer

<400> SEQUENCE: 77
accatcactc atctaactta tcccat 26

<210> SEQ ID NO 78
<211> LENGTH: 23
<212> TYPE: DNA
<213> ORGANISM: Artificial Sequence
<220> FEATURE:
<223> OTHER INFORMATION: synthetic primer

<400> SEQUENCE: 78
agacaggaac acagttgaac gga 23

<210> SEQ ID NO 79
<211> LENGTH: 25
<212> TYPE: DNA
<213> ORGANISM: Artificial Sequence
<220> FEATURE:
<223> OTHER INFORMATION: synthetic primer

<400> SEQUENCE: 79
cttgacaaac actctgattc tacac 25

<210> SEQ ID NO 80
<211> LENGTH: 27
<212> TYPE: DNA
<213> ORGANISM: Artificial Sequence
<220> FEATURE:
<223> OTHER INFORMATION: synthetic primer

<400> SEQUENCE: 80
ttgagatagc ttgtatatta tgcatgc 27

<210> SEQ ID NO 81
<211> LENGTH: 25
<212> TYPE: DNA
<213> ORGANISM: Artificial Sequence
<220> FEATURE:
<223> OTHER INFORMATION: synthetic primer

<400> SEQUENCE: 81
ttgtacccat tgaaggatga ctact 25

<210> SEQ ID NO 82
<211> LENGTH: 26
<212> TYPE: DNA

<213> ORGANISM: Artificial Sequence
<220> FEATURE:
<223> OTHER INFORMATION: synthetic primer

<400> SEQUENCE: 82
tccatcactg atctaactaa tccaag 26

<210> SEQ ID NO 83
<211> LENGTH: 24
<212> TYPE: DNA
<213> ORGANISM: Artificial Sequence
<220> FEATURE:
<223> OTHER INFORMATION: synthetic primer

<400> SEQUENCE: 83
cacgggcgtt acctccacta gtat 24

<210> SEQ ID NO 84
<211> LENGTH: 23
<212> TYPE: DNA
<213> ORGANISM: Artificial Sequence
<220> FEATURE:
<223> OTHER INFORMATION: synthetic primer

<400> SEQUENCE: 84
aaggtcatta gaatatgcgg agc 23

<210> SEQ ID NO 85
<211> LENGTH: 24
<212> TYPE: DNA
<213> ORGANISM: Artificial Sequence
<220> FEATURE:
<223> OTHER INFORMATION: synthetic primer

<400> SEQUENCE: 85
aacattagat gatgcattag gtgt 24

<210> SEQ ID NO 86
<211> LENGTH: 22
<212> TYPE: DNA
<213> ORGANISM: Artificial Sequence
<220> FEATURE:
<223> OTHER INFORMATION: synthetic primer

<400> SEQUENCE: 86
gtggaggctt tggattatta tg 22

<210> SEQ ID NO 87
<211> LENGTH: 26
<212> TYPE: DNA
<213> ORGANISM: Artificial Sequence
<220> FEATURE:
<223> OTHER INFORMATION: synthetic primer

<400> SEQUENCE: 87
cgtcagaact tcggattaat tacttc 26

<210> SEQ ID NO 88
<211> LENGTH: 20
<212> TYPE: DNA
<213> ORGANISM: Artificial Sequence
<220> FEATURE:
<223> OTHER INFORMATION: synthetic primer

<400> SEQUENCE: 88
aaatgaggcc tgagcacaag 20

<210> SEQ ID NO 89
<211> LENGTH: 23
<212> TYPE: DNA
<213> ORGANISM: Artificial Sequence
<220> FEATURE:
<223> OTHER INFORMATION: synthetic primer

<400> SEQUENCE: 89
caacaacatt agatggtgtc aag 23

<210> SEQ ID NO 90
<211> LENGTH: 23
<212> TYPE: DNA
<213> ORGANISM: Artificial Sequence
<220> FEATURE:
<223> OTHER INFORMATION: synthetic primer

<400> SEQUENCE: 90
ttatgggatt tgatgatgca gag 23

<210> SEQ ID NO 91
<211> LENGTH: 30
<212> TYPE: DNA
<213> ORGANISM: Artificial Sequence
<220> FEATURE:
<223> OTHER INFORMATION: synthetic primer

<400> SEQUENCE: 91
atatagaagg atgagacata gtaacatacc 30

<210> SEQ ID NO 92
<211> LENGTH: 21
<212> TYPE: DNA
<213> ORGANISM: Artificial Sequence
<220> FEATURE:
<223> OTHER INFORMATION: synthetic primer

<400> SEQUENCE: 92
ctttgtccct tcgattcatg a 21

<210> SEQ ID NO 93
<211> LENGTH: 20
<212> TYPE: DNA
<213> ORGANISM: Artificial Sequence
<220> FEATURE:
<223> OTHER INFORMATION: synthetic primer

<400> SEQUENCE: 93
aggcctaaat catcagtcca 20

<210> SEQ ID NO 94
<211> LENGTH: 25
<212> TYPE: DNA
<213> ORGANISM: Artificial Sequence
<220> FEATURE:
<223> OTHER INFORMATION: synthetic primer

<400> SEQUENCE: 94
gctggtgtcg ataattgcta tttag 25

<210> SEQ ID NO 95
<211> LENGTH: 25
<212> TYPE: DNA
<213> ORGANISM: Artificial Sequence
<220> FEATURE:

<223> OTHER INFORMATION: synthetic primer

<400> SEQUENCE: 95
ggcaggatac tattctacca ctagg 25

<210> SEQ ID NO 96
<211> LENGTH: 21
<212> TYPE: DNA
<213> ORGANISM: Artificial Sequence
<220> FEATURE:
<223> OTHER INFORMATION: synthetic primer

<400> SEQUENCE: 96
cgcttcgatt ctgggaataa g 21

<210> SEQ ID NO 97
<211> LENGTH: 20
<212> TYPE: DNA
<213> ORGANISM: Artificial Sequence
<220> FEATURE:
<223> OTHER INFORMATION: synthetic primer

<400> SEQUENCE: 97
tacaggccta aatcagtcca 20

<210> SEQ ID NO 98
<211> LENGTH: 22
<212> TYPE: DNA
<213> ORGANISM: Artificial Sequence
<220> FEATURE:
<223> OTHER INFORMATION: synthetic primer

<400> SEQUENCE: 98
atgtgaagac aatgaattcc gc 22

<210> SEQ ID NO 99
<211> LENGTH: 23
<212> TYPE: DNA
<213> ORGANISM: Artificial Sequence
<220> FEATURE:
<223> OTHER INFORMATION: synthetic primer

<400> SEQUENCE: 99
gctctcctct gatacatggc tat 23

<210> SEQ ID NO 100
<211> LENGTH: 20
<212> TYPE: DNA
<213> ORGANISM: Artificial Sequence
<220> FEATURE:
<223> OTHER INFORMATION: synthetic primer

<400> SEQUENCE: 100
tgtttcagtc tcaaattcat 20

<210> SEQ ID NO 101
<211> LENGTH: 447
<212> TYPE: DNA
<213> ORGANISM: Artificial Sequence
<220> FEATURE:
<223> OTHER INFORMATION: synthetic

<400> SEQUENCE: 101
aattggtacc tttactttaa attttttctt atgcagcctg tgatggataa ctgaatcaaa 60
caaatggcgt ctgggtttaa gaagatctgt tttggctatg ttggacgaaa caagtgaact 120
tttaggatca acttcagttt atatatggag cttatatcga gcaataagat aagtgggctt 180
tttatgtaat ttaatgggct atcgtccata gattcactaa tacccatgcc cagtacccat 240
gtatgcgttt catataagct cctaatttct cccacatcgc tcaaatctaa acaaatcttg 300
ttgtatatat aacactgagg gagcaacatt ggtcacaatg atatcaagaa ttacgtttta 360
gagctagaaa tagcaagtta aaataaggct agtccgttat caacttgaaa aagtggcacc 420
gagtcggtgc ttttttgga tccaatt 447

<210> SEQ ID NO 102
<211> LENGTH: 4452
<212> TYPE: DNA
<213> ORGANISM: Artificial Sequence
<220> FEATURE:
<223> OTHER INFORMATION: Synthetic Cas 9

<400> SEQUENCE: 102
catatggatt acaaggatga tgatgataag gattacaagg atgatgatga taagatggct 60
ccaaagaaga agagaaaggt tggaatccac ggagttccag ctgctgataa gaagtactct 120
atcggacttg acatcggaac caactctgtt ggatgggctg ttatcaccga tgagtacaag 180
gttccatcta agaagttcaa ggttcttgga aacaccgata gacactctat caagaagaac 240
cttatcggtg ctcttctttt cgattctgga gagaccgctg aggctaccag attgaagaga 300
accgctagaa gaagatacac cagaagaaag aacagaatct gctaccttca ggaaatcttc 360
tctaacgaga tggctaaggt tgatgattct ttcttccaca gacttgagga gtctttcctt 420
gttgaggagg ataagaagca cgagagacac ccaatcttcg gaaacatcgt tgatgaggtt 480
gcttaccacg agaagtaccc aaccatctac caccttagaa agaagttggt tgattctacc 540
gataaggctg atcttagact tatctacctt gctcttgctc acatgatcaa gttcagagga 600
cacttcctta tcgagggaga ccttaaccca gataactctg atgttgataa gttgttcatc 660
cagcttgttc agacctacaa ccagcttttc gaggagaacc caatcaacgc ttctggagtt 720
gatgctaagg ctatcctttc tgctagactt tctaagtctc gtagacttga gaaccttatc 780
gctcagcttc caggagagaa gaagaacgga cttttcggaa accttatcgc tctttctctt 840
ggacttaccc caaacttcaa gtctaacttc gatcttgctg aggatgctaa gttgcagctt 900
tctaaggata cctacgatga tgatcttgat aaccttcttg ctcagatcgg agatcagtac 960
gctgatcttt tccttgctgc taagaacctt tctgatgcta tccttctttc tgacatcctt 1020
agagttaaca ccgagatcac caaggctcca ctttctgctt ctatgatcaa gagatacgat 1080
gagcaccacc aggatcttac ccttttgaag gctcttgtta gacagcagct tccagagaag 1140
tacaaggaaa tcttcttcga tcagtctaag aacggatacg ctggatacat cgatggagga 1200
gcttctcagg aggagttcta caagttcatc aagccaatcc ttgagaagat ggatggaacc 1260
gaggagcttc ttgttaagtt gaacagagag gatcttctta gaaagcagag aaccttcgat 1320
aacggatcta tcccacacca gatccacctt ggagagcttc acgctatcct tcgtagacag 1380
gaggatttct acccattctt gaaggataac agagagaaga tcgagaagat ccttaccttc 1440
agaatcccat actacgttgg accacttgct agaggaaact ctcgtttcgc ttggatgacc 1500
agaaagtctg aggagaccat caccccttgg aacttcgagg aggtaagttt ctgcttctac 1560
ctttgatata tatataataa ttatcattaa ttagtagtaa tataatattt caaatatttt 1620
tttcaaaata aaagaatgta gtatatagca attgcttttc tgtagtttat aagtgtgtat 1680

```
attttaattt ataacttttc taatatatga ccaaaatttg ttgatgtgca ggttgttgat   1740
aagggagctt ctgctcagtc tttcatcgag agaatgacca acttcgataa gaaccttcca   1800
aacgagaagg ttcttccaaa gcactctctt ctttacgagt acttcaccgt ttacaacgag   1860
cttaccaagg ttaagtacgt taccgaggga atgagaaagc cagctttcct tctggagag    1920
cagaagaagg ctatcgttga tcttcttttc aagaccaaca gaaaggttac cgttaagcag   1980
ttgaaggagg attacttcaa gaagatcgag tgcttcgatt ctgttgaaat ctctggagtt   2040
gaggatagat tcaacgcttc tcttggaacc taccacgatc ttttgaagat catcaaggat   2100
aaggatttcc ttgataacga ggagaacgag gacatccttg aggacatcgt tcttaccctt   2160
acccttttcg aggatagaga gatgatcgag gagagactca agacctacgc tcaccttttc   2220
gatgataagg ttatgaagca gttgaagaga agaagataca ccggatgggg tagactttct   2280
cgtaagttga tcaacggaat cagagataag cagtctggaa agaccatcct tgatttcttg   2340
aagtctgatg gattcgctaa cagaaacttc atgcagctta tccacgatga ttctcttacc   2400
ttcaaggagg acatccagaa ggctcaggtt tctggacagg gagattctct tcacgagcac   2460
atcgctaacc ttgctggatc tccagctatc aagaagggaa tccttcagac cgttaaggtt   2520
gttgatgagc ttgttaaggt tatgggtaga cacaagccag agaacatcgt tatcgagatg   2580
gctagagaga accagaccac ccagaaggga cagaagaact ctcgtgagag aatgaagaga   2640
atcgaggagg gaatcaagga gcttggatct caaatcttga aggagcaccc agttgagaac   2700
acccagcttc agaacgagaa gttgtacctt tactaccttc agaacggaag agatatgtac   2760
gttgatcagg agcttgacat caacagactt tctgattacg atgttgatca catcgttcca   2820
cagtctttct tgaaggatga ttctatcgat aacaaggttc ttacccgttc tgataagaac   2880
agaggaaagt ctgataacgt tccatctgag gaggttgtta agaagatgaa gaactactgg   2940
agacagcttc ttaacgctaa gttgatcacc cagagaaagt tcgataacct taccaaggct   3000
gagagaggag gactttctga gcttgataag gctggattca tcaagagaca gcttgttgag   3060
accagacaga tcaccaagca cgttgctcag atccttgatt ctcgtatgaa caccaagtac   3120
gatgagaacg ataagttgat cagagaggtt aaggttatca ccttgaagtc taagttggtt   3180
tctgatttca gaaaggattt ccagttctac aaggttagag agatcaacaa ctaccaccac   3240
gctcacgatg cttaccttaa cgctgttgtt ggaaccgctc ttatcaagaa gtacccaaag   3300
ttggagtctg agttcgttta cggagattac aaggtttacg atgttagaaa gatgatcgct   3360
aagtctgagc aggagatcgg aaaggctacc gctaagtact tcttctactc taacatcatg   3420
aacttcttca agaccgagat caccccttgct aacggagaga tcagaaagag accacttatc   3480
gagaccaacg gagagaccgg agagatcgtt tgggataagg gaagagattt cgctaccgtt   3540
agaaaggttc tttctatgcc acaggttaac atcgttaaga aaaccgaggt tcagaccgga   3600
ggattctcta aggagtctat ccttccaaag agaaactctg ataagttgat cgctagaaag   3660
aaggattggg acccaaagaa gtacggagga ttcgattctc caaccgttgc ttactctgtt   3720
cttgttgttg ctaaggttga gaagggaaag tctaagaagt tgaagtctgt taaggagctt   3780
cttggaatca ccatcatgga gcgttcttct ttcgagaaga acccaatcga tttccttgag   3840
gctaagggat acaaggaggt taagaaggat cttatcatca agttgccaaa gtactctctt   3900
ttcgagcttg agaacggaag aaagagaatg cttgcttctg ctggagagct tcagaaggga   3960
aacgagcttg ctcttccatc taagtacgtt aacttccttt accttgcttc tcactacgag   4020
aagttgaagg gatctccaga ggataacgag cagaagcagc ttttcgttga gcagcacaag   4080
```

```
cactaccttg atgagatcat cgagcaaatc tctgagttct ctaagagagt tatccttgct   4140

gatgctaacc ttgataaggt tctttctgct tacaacaagc acagagataa gccaatcaga   4200

gagcaggctg agaacatcat ccaccttttc acccttacca accttggtgc tccagctgct   4260

ttcaagtact tcgataccac catcgataga aaaagataca cctctaccaa ggaggttctt   4320

gatgctaccc ttatccacca gtctatcacc ggactttacg agaccagaat cgatctttct   4380

cagcttggag gagataagag accagctgct accaagaagg ctggacaggc taagaagaag   4440

aagtgagtcg ac                                                        4452
```

<210> SEQ ID NO 103
<211> LENGTH: 27
<212> TYPE: DNA
<213> ORGANISM: Artificial Sequence
<220> FEATURE:
<223> OTHER INFORMATION: synthetic primer

<400> SEQUENCE: 103

```
aagtattact actacaaaat tccaacg                                          27
```

<210> SEQ ID NO 104
<211> LENGTH: 23
<212> TYPE: DNA
<213> ORGANISM: Artificial Sequence
<220> FEATURE:
<223> OTHER INFORMATION: synthetic primer

<400> SEQUENCE: 104

```
ccatctgatg aagaacaact tgc                                              23
```

<210> SEQ ID NO 105
<211> LENGTH: 26
<212> TYPE: DNA
<213> ORGANISM: Artificial Sequence
<220> FEATURE:
<223> OTHER INFORMATION: synthetic primer

<400> SEQUENCE: 105

```
ttaaacacta gagagtgaga gagtgc                                           26
```

<210> SEQ ID NO 106
<211> LENGTH: 29
<212> TYPE: DNA
<213> ORGANISM: Artificial Sequence
<220> FEATURE:
<223> OTHER INFORMATION: synthetic primer

<400> SEQUENCE: 106

```
cagatgttta attattaaga caaagttcc                                        29
```

<210> SEQ ID NO 107
<211> LENGTH: 12
<212> TYPE: PRT
<213> ORGANISM: Nicotiana tabacum

<400> SEQUENCE: 107

```
Thr Gly Ile Leu Asn Ser Arg Lys Ser Leu Trp Asp
1               5                   10
```

<210> SEQ ID NO 108
<211> LENGTH: 11
<212> TYPE: PRT
<213> ORGANISM: Nicotiana tabacum

<400> SEQUENCE: 108

```
Glu Ile Leu Asn Ser Arg Lys Ser Leu Trp Asp
1               5                   10
```

<210> SEQ ID NO 109
<211> LENGTH: 20
<212> TYPE: DNA
<213> ORGANISM: Artificial Sequence
<220> FEATURE:
<223> OTHER INFORMATION: synthetic primer

<400> SEQUENCE: 109
ttcgtagaac cggagatcgt 20

<210> SEQ ID NO 110
<211> LENGTH: 21
<212> TYPE: DNA
<213> ORGANISM: Artificial Sequence
<220> FEATURE:
<223> OTHER INFORMATION: synthetic primer

<400> SEQUENCE: 110
gcaaagttgc ttccaatgaa t 21

<210> SEQ ID NO 111
<211> LENGTH: 26
<212> TYPE: DNA
<213> ORGANISM: Artificial Sequence
<220> FEATURE:
<223> OTHER INFORMATION: synthetic primer

<400> SEQUENCE: 111
ttggtttggg attttgaggt ttgagg 26

<210> SEQ ID NO 112
<211> LENGTH: 26
<212> TYPE: DNA
<213> ORGANISM: Artificial Sequence
<220> FEATURE:
<223> OTHER INFORMATION: synthetic primer

<400> SEQUENCE: 112
tttggaattg agggtgaaca ttgtgc 26

<210> SEQ ID NO 113
<211> LENGTH: 25
<212> TYPE: DNA
<213> ORGANISM: Artificial Sequence
<220> FEATURE:
<223> OTHER INFORMATION: synthetic primer

<400> SEQUENCE: 113
acgttaccat tcgtctacag taagc 25

<210> SEQ ID NO 114
<211> LENGTH: 25
<212> TYPE: DNA
<213> ORGANISM: Artificial Sequence
<220> FEATURE:
<223> OTHER INFORMATION: synthetic primer

<400> SEQUENCE: 114
ccaataaaca agaaacagat gatgg 25

<210> SEQ ID NO 115
<211> LENGTH: 25
<212> TYPE: DNA
<213> ORGANISM: Artificial Sequence
<220> FEATURE:
<223> OTHER INFORMATION: synthetic primer

<400> SEQUENCE: 115
gaatggacac catagacgga aagga 25

<210> SEQ ID NO 116
<211> LENGTH: 25
<212> TYPE: DNA
<213> ORGANISM: Artificial Sequence
<220> FEATURE:
<223> OTHER INFORMATION: synthetic primer

<400> SEQUENCE: 116
tttccgtcta tggtgtccat tctcc 25

<210> SEQ ID NO 117
<211> LENGTH: 25
<212> TYPE: DNA
<213> ORGANISM: Artificial Sequence
<220> FEATURE:
<223> OTHER INFORMATION: synthetic primer

<400> SEQUENCE: 117
gagacatggc aatactgaat tttca 25

<210> SEQ ID NO 118
<211> LENGTH: 25
<212> TYPE: DNA
<213> ORGANISM: Artificial Sequence
<220> FEATURE:
<223> OTHER INFORMATION: synthetic primer

<400> SEQUENCE: 118
agcctacgtg aagattgatg agaag 25

<210> SEQ ID NO 119
<211> LENGTH: 26
<212> TYPE: DNA
<213> ORGANISM: Artificial Sequence
<220> FEATURE:
<223> OTHER INFORMATION: synthetic primer

<400> SEQUENCE: 119
tcgattgggt tgtatgagtt aaccgt 26

<210> SEQ ID NO 120
<211> LENGTH: 26
<212> TYPE: DNA
<213> ORGANISM: Artificial Sequence
<220> FEATURE:
<223> OTHER INFORMATION: synthetic primer

<400> SEQUENCE: 120
gttaccataa gctgtggaat atcagg 26

<210> SEQ ID NO 121
<211> LENGTH: 26
<212> TYPE: DNA
<213> ORGANISM: Artificial Sequence
<220> FEATURE:
<223> OTHER INFORMATION: synthetic primer

<400> SEQUENCE: 121
aaccaatgga caagaaacgg atggca 26

<210> SEQ ID NO 122
<211> LENGTH: 26
<212> TYPE: DNA
<213> ORGANISM: Artificial Sequence
<220> FEATURE:
<223> OTHER INFORMATION: synthetic primer

<400> SEQUENCE: 122
tttagctatc cagtcaaaga ggcacg 26

<210> SEQ ID NO 123
<211> LENGTH: 25
<212> TYPE: DNA
<213> ORGANISM: Artificial Sequence
<220> FEATURE:
<223> OTHER INFORMATION: synthetic primer

<400> SEQUENCE: 123
agcctacgtg aagattgatg agaaa 25

<210> SEQ ID NO 124
<211> LENGTH: 20
<212> TYPE: DNA
<213> ORGANISM: Artificial Sequence
<220> FEATURE:
<223> OTHER INFORMATION: synthetic primer

<400> SEQUENCE: 124
cccagacccc cttttcctct 20

<210> SEQ ID NO 125
<211> LENGTH: 23
<212> TYPE: DNA
<213> ORGANISM: Artificial Sequence
<220> FEATURE:
<223> OTHER INFORMATION: synthetic primer

<400> SEQUENCE: 125
aatttccctt ataatttaac gcc 23

<210> SEQ ID NO 126
<211> LENGTH: 21
<212> TYPE: DNA
<213> ORGANISM: Artificial Sequence
<220> FEATURE:
<223> OTHER INFORMATION: synthetic primer

<400> SEQUENCE: 126
ccctagagag acccctttttt c 21

<210> SEQ ID NO 127
<211> LENGTH: 21
<212> TYPE: DNA
<213> ORGANISM: Artificial Sequence
<220> FEATURE:
<223> OTHER INFORMATION: synthetic primer

<400> SEQUENCE: 127
gggttttaaa tttaacgcca a 21

<210> SEQ ID NO 128
<211> LENGTH: 19

<212> TYPE: DNA
<213> ORGANISM: Artificial Sequence
<220> FEATURE:
<223> OTHER INFORMATION: synthetic primer

<400> SEQUENCE: 128
gtgaatgccc tattctgtc 19

<210> SEQ ID NO 129
<211> LENGTH: 23
<212> TYPE: DNA
<213> ORGANISM: Artificial Sequence
<220> FEATURE:
<223> OTHER INFORMATION: synthetic primer

<400> SEQUENCE: 129
atcactgatc taactaatcc aag 23

<210> SEQ ID NO 130
<211> LENGTH: 12
<212> TYPE: DNA
<213> ORGANISM: Artificial Sequence
<220> FEATURE:
<223> OTHER INFORMATION: synthetic probe

<400> SEQUENCE: 130
ctttgatcta ct 12

<210> SEQ ID NO 131
<211> LENGTH: 10
<212> TYPE: DNA
<213> ORGANISM: Artificial Sequence
<220> FEATURE:
<223> OTHER INFORMATION: synthetic probe

<400> SEQUENCE: 131
tgatctgctt 10

<210> SEQ ID NO 132
<211> LENGTH: 19
<212> TYPE: DNA
<213> ORGANISM: Artificial Sequence
<220> FEATURE:
<223> OTHER INFORMATION: synthetic primer

<400> SEQUENCE: 132
attgatggag gagaatgat 19

<210> SEQ ID NO 133
<211> LENGTH: 21
<212> TYPE: DNA
<213> ORGANISM: Artificial Sequence
<220> FEATURE:
<223> OTHER INFORMATION: synthetic primer

<400> SEQUENCE: 133
gacaagatac gttaagtgaa a 21

<210> SEQ ID NO 134
<211> LENGTH: 10
<212> TYPE: DNA
<213> ORGANISM: Artificial Sequence
<220> FEATURE:
<223> OTHER INFORMATION: synthetic probe

<400> SEQUENCE: 134
acaagctacg 10

<210> SEQ ID NO 135
<211> LENGTH: 17
<212> TYPE: DNA
<213> ORGANISM: Artificial Sequence
<220> FEATURE:
<223> OTHER INFORMATION: synthetic primer

<400> SEQUENCE: 135
ccatttcagg tgtcgag 17

<210> SEQ ID NO 136
<211> LENGTH: 20
<212> TYPE: DNA
<213> ORGANISM: Artificial Sequence
<220> FEATURE:
<223> OTHER INFORMATION: synthetic primer

<400> SEQUENCE: 136
acgttaccat tcgtctacag 20

<210> SEQ ID NO 137
<211> LENGTH: 10
<212> TYPE: DNA
<213> ORGANISM: Artificial Sequence
<220> FEATURE:
<223> OTHER INFORMATION: synthetic probe

<400> SEQUENCE: 137
ttacaagcga 10

<210> SEQ ID NO 138
<211> LENGTH: 10
<212> TYPE: DNA
<213> ORGANISM: Artificial Sequence
<220> FEATURE:
<223> OTHER INFORMATION: synthetic probe

<400> SEQUENCE: 138
gcaaaaacag 10

<210> SEQ ID NO 139
<211> LENGTH: 20
<212> TYPE: DNA
<213> ORGANISM: Artificial Sequence
<220> FEATURE:
<223> OTHER INFORMATION: synthetic primer

<400> SEQUENCE: 139
tccctaaacc aagtgactcc 20

<210> SEQ ID NO 140
<211> LENGTH: 20
<212> TYPE: DNA
<213> ORGANISM: Artificial Sequence
<220> FEATURE:
<223> OTHER INFORMATION: synthetic primer

<400> SEQUENCE: 140
ggtatcaagg tcatttccag 20

<210> SEQ ID NO 141
<211> LENGTH: 11
<212> TYPE: DNA
<213> ORGANISM: Artificial Sequence
<220> FEATURE:
<223> OTHER INFORMATION: synthetic probe

<400> SEQUENCE: 141
tgtaagcact a 11

<210> SEQ ID NO 142
<211> LENGTH: 20
<212> TYPE: DNA
<213> ORGANISM: Artificial Sequence
<220> FEATURE:
<223> OTHER INFORMATION: synthetic primer

<400> SEQUENCE: 142
agaggatgac agtggagcaa 20

<210> SEQ ID NO 143
<211> LENGTH: 21
<212> TYPE: DNA
<213> ORGANISM: Artificial Sequence
<220> FEATURE:
<223> OTHER INFORMATION: synthetic primer

<400> SEQUENCE: 143
taacgccaag aagatatgga a 21

<210> SEQ ID NO 144
<211> LENGTH: 12
<212> TYPE: DNA
<213> ORGANISM: Artificial Sequence
<220> FEATURE:
<223> OTHER INFORMATION: synthetic probe

<400> SEQUENCE: 144
ggtaaaatca ac 12

<210> SEQ ID NO 145
<211> LENGTH: 10
<212> TYPE: DNA
<213> ORGANISM: Artificial Sequence
<220> FEATURE:
<223> OTHER INFORMATION: synthetic probe

<400> SEQUENCE: 145
ggcaaaatca 10

<210> SEQ ID NO 146
<211> LENGTH: 22
<212> TYPE: DNA
<213> ORGANISM: Artificial Sequence
<220> FEATURE:
<223> OTHER INFORMATION: synthetic primer

<400> SEQUENCE: 146
gttgaaagtt caaatgattc ag 22

<210> SEQ ID NO 147
<211> LENGTH: 18
<212> TYPE: DNA
<213> ORGANISM: Artificial Sequence
<220> FEATURE:
<223> OTHER INFORMATION: synthetic primer

<400> SEQUENCE: 147
gaggagggta acgatcag 18

<210> SEQ ID NO 148
<211> LENGTH: 11
<212> TYPE: DNA
<213> ORGANISM: Artificial Sequence
<220> FEATURE:
<223> OTHER INFORMATION: synthetic probe

<400> SEQUENCE: 148
gcttgttagt t 11

<210> SEQ ID NO 149
<211> LENGTH: 11
<212> TYPE: DNA
<213> ORGANISM: Artificial Sequence
<220> FEATURE:
<223> OTHER INFORMATION: synthetic probe

<400> SEQUENCE: 149
cttgttggtt a 11

<210> SEQ ID NO 150
<211> LENGTH: 571
<212> TYPE: DNA
<213> ORGANISM: Artificial Sequence
<220> FEATURE:
<223> OTHER INFORMATION: Synthetic

<400> SEQUENCE: 150
aattggtacc aagcttcgtt gaacaacgga aactcgactt gccttccgca caatacatca 60
tttcttctta gcttttttc ttcttcttcg ttcatacagt tttttttgt ttatcagctt 120 acattttctt gaaccgtagc tttcgttttc ttctttttaa ctttccattc ggagtttttg 180
tatcttgttt catagtttgt cccaggatta gaatgattag gcatcgaacc ttcaagaatt 240
tgattgaata aaacatcttc attcttaaga tatgaagata atcttcaaaa ggcccctggg 300
aatctgaaag aagagaagca ggcccattta tatgggaaag aacaatagta tttcttatat 360
aggcccattt aagttgaaaa caatcttcaa aagtcccaca tcgcttagat aagaaaacga 420
agctgagttt atatacagct agagtcgaag tagtgattga gttcctttcc aaggctacgt 480
tttagagcta gaaatagcaa gttaaaataa ggctagtccg ttatcaactt gaaaaagtgg 540
caccgagtcg gtgcttttt tggatccaat t 571

<210> SEQ ID NO 151
<211> LENGTH: 571
<212> TYPE: DNA
<213> ORGANISM: Artificial Sequence
<220> FEATURE:
<223> OTHER INFORMATION: Synthetic

<400> SEQUENCE: 151
aattggtacc aagcttcgtt gaacaacgga aactcgactt gccttccgca caatacatca 60
tttcttctta gcttttttc ttcttcttcg ttcatacagt tttttttgt ttatcagctt 120 acattttctt gaaccgtagc tttcgttttc ttctttttaa ctttccattc ggagtttttg 180
tatcttgttt catagtttgt cccaggatta gaatgattag gcatcgaacc ttcaagaatt 240
tgattgaata aaacatcttc attcttaaga tatgaagata atcttcaaaa ggcccctggg 300
aatctgaaag aagagaagca ggcccattta tatgggaaag aacaatagta tttcttatat 360
aggcccattt aagttgaaaa caatcttcaa aagtcccaca tcgcttagat aagaaaacga 420
agctgagttt atatacagct agagtcgaag tagtgattgg agtggcagcc cgagcatggt 480
tttagagcta gaaatagcaa gttaaaataa ggctagtccg ttatcaactt gaaaaagtgg 540
caccgagtcg gtgctttttt tggatccaat t 571

<210> SEQ ID NO 152
<211> LENGTH: 23
<212> TYPE: DNA
<213> ORGANISM: Artificial Sequence
<220> FEATURE:
<223> OTHER INFORMATION: synthetic primer

<400> SEQUENCE: 152
cacctcaaga aaaagcttat ggg 23

<210> SEQ ID NO 153
<211> LENGTH: 20
<212> TYPE: DNA
<213> ORGANISM: Artificial Sequence
<220> FEATURE:
<223> OTHER INFORMATION: synthetic primer

<400> SEQUENCE: 153
gcagcagcta acaagttgta 20

<210> SEQ ID NO 154
<211> LENGTH: 20
<212> TYPE: DNA
<213> ORGANISM: Artificial Sequence
<220> FEATURE:
<223> OTHER INFORMATION: synthetic primer

<400> SEQUENCE: 154
cactgtagcc agagaccaca 20

<210> SEQ ID NO 155
<211> LENGTH: 565
<212> TYPE: DNA
<213> ORGANISM: Artificial Sequence
<220> FEATURE:
<223> OTHER INFORMATION: Synthetic

<400> SEQUENCE: 155
ctcaagaaaa agcttatggg attaatgcaa tcaacaaacc aaagaaaatc accatatttt 60
ccagctacta attctcttca agcccaaccc cagataaatt caagtctttt tagagactta 120
tattacaacc caaataatag gcctattatt acaggcctaa atcagtccat ttcttctgcc 180
caccagccaa attttctcta cactaatagt aacatgaatt ttcctaattt gggtgctaca 240
aatagtcaat atccttataa tattcaaagt cataatttac ttatgtttgg agaagcaagt 300
tgttcttcat cagatggaag ttgtagccaa atgagttttg gcaaagaaat caagagagag 360
gaaattatga gtaattgttt acaacaaggt caaatttcaa gtgttaatgc ttttgaagaa 420
aatcagaatt tcactcttga ttatggtaac agtagtagta attgggtgga tcaaaaacca 480
aatgtgtatt ttggaaatac tactactact actcaagtac ttcagtatga tgttgaagaa 540
gttaagcagc agctaacaag ttgta 565

<210> SEQ ID NO 156
<211> LENGTH: 364
<212> TYPE: DNA
<213> ORGANISM: Artificial Sequence
<220> FEATURE:
<223> OTHER INFORMATION: Synthetic

<400> SEQUENCE: 156

```
gaagaaactg atgatcaacg gcggagattc agttccactt cccctgcaat ccaaatccgg     60
caactactca ttagctgcgc ggagttaatc tcgcggtccg atttctcggc cgcaaacaga    120
ctcctcacca ttttatcaac taactcttcc ccttttggtg attcaactga aagattagtc    180
catcagttca ctcgcgcact ttctcttcgc ctcaaccgtt atatctcttc agccactaat    240
ttcttgacac catctaatgt tgttgaaagt tcaaatgatt cagctctact tcagtcatcc    300
tatctttccc taaaccaagt gactcctttc attagattta gtcagctgac tgctaatcaa    360
gcga                                                                 364
```

<210> SEQ ID NO 157
<211> LENGTH: 445
<212> TYPE: DNA
<213> ORGANISM: Artificial Sequence
<220> FEATURE:
<223> OTHER INFORMATION: Synthetic

<400> SEQUENCE: 157

```
gcctatgtag cttcgtcaat gaaatcttgt tcatatgcat atcctgggat gaggcctacc     60
agatttaccg gaagtcagat aataatgcca cttggccata caattgaaca tgaagagatg    120
cttgaggtta ttagattgga aggacactct attggccagg aagatacttt tatgccaaga    180
gatgttcacc ttctccagat gtgtagtgga actgatgaga atgctgtcgg agcttgttct    240
gaactagttt ttgctgcaat tgatgagatg tttccagatg atgcacccct gttgccctcc    300
gggtttcgta tcattcctct cgagtcaaaa tcaagcgatc cccaggatac atcgaatgct    360
catagaacac tggatctggc atcaagtctt gaagttggcc cagcaacaaa ccctgctact    420
ggagatgtgg tctctggcta cagtg                                          445
```

<210> SEQ ID NO 158
<211> LENGTH: 29
<212> TYPE: DNA
<213> ORGANISM: Artificial Sequence
<220> FEATURE:
<223> OTHER INFORMATION: synthetic primer

<400> SEQUENCE: 158

```
gagaaaacaa atgtaagtac accattagg                                       29
```

<210> SEQ ID NO 159
<211> LENGTH: 25
<212> TYPE: DNA
<213> ORGANISM: Artificial Sequence
<220> FEATURE:
<223> OTHER INFORMATION: synthetic primer

<400> SEQUENCE: 159

```
gaaaaagttt gaatcttctt gccaa                                           25
```

<210> SEQ ID NO 160
<211> LENGTH: 26
<212> TYPE: DNA
<213> ORGANISM: Artificial Sequence
<220> FEATURE:
<223> OTHER INFORMATION: synthetic primer

<400> SEQUENCE: 160

```
gatttgaaag ggcgtttggg tatggg                                          26
```

<210> SEQ ID NO 161
<211> LENGTH: 22
<212> TYPE: DNA
<213> ORGANISM: Artificial Sequence
<220> FEATURE:
<223> OTHER INFORMATION: synthetic primer

<400> SEQUENCE: 161
ccggtactgg aaatgacctt ga 22

<210> SEQ ID NO 162
<211> LENGTH: 29
<212> TYPE: DNA
<213> ORGANISM: Artificial Sequence
<220> FEATURE:
<223> OTHER INFORMATION: synthetic primer

<400> SEQUENCE: 162
cccttcgtag aaccggagat cgtttagct 29

<210> SEQ ID NO 163
<211> LENGTH: 19
<212> TYPE: DNA
<213> ORGANISM: Artificial Sequence
<220> FEATURE:
<223> OTHER INFORMATION: synthetic primer

<400> SEQUENCE: 163
tctccaggct cccctgaag 19

<210> SEQ ID NO 164
<211> LENGTH: 24
<212> TYPE: DNA
<213> ORGANISM: Artificial Sequence
<220> FEATURE:
<223> OTHER INFORMATION: synthetic primer

<400> SEQUENCE: 164
tgtccccatg tgataactgt agct 24

<210> SEQ ID NO 165
<211> LENGTH: 24
<212> TYPE: DNA
<213> ORGANISM: Artificial Sequence
<220> FEATURE:
<223> OTHER INFORMATION: synthetic primer

<400> SEQUENCE: 165
aacgttgtcg cactggatct gcca 24

<210> SEQ ID NO 166
<211> LENGTH: 4
<212> TYPE: PRT
<213> ORGANISM: Nicotiana tabacum

<400> SEQUENCE: 166

Lys Leu Glu Tyr
1